United States Patent
Gao et al.

(10) Patent No.: US 11,215,617 B2
(45) Date of Patent: Jan. 4, 2022

(54) TREATMENT OF METASTATIC PROSTATE CANCER

(71) Applicant: The Regents of the University of California, Oakland, CA (US)

(72) Inventors: Allen C. Gao, Davis, CA (US); Chengfei Liu, Sacramento, CA (US); Wei Lou, Davis, CA (US); Chong-xian Pan, Davis, CA (US)

(73) Assignees: The Regents of the University of California, Oakland, CA (US); U.S. Government Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 16/654,847

(22) Filed: Oct. 16, 2019

(65) Prior Publication Data

US 2020/0041516 A1    Feb. 6, 2020

Related U.S. Application Data

(60) Division of application No. 15/134,228, filed on Apr. 20, 2016, now abandoned, which is a continuation of application No. PCT/US2014/062455, filed on Oct. 27, 2014.

(60) Provisional application No. 61/914,389, filed on Dec. 11, 2013, provisional application No. 61/896,250, filed on Oct. 28, 2013.

(51) Int. Cl.
| | |
|---|---|
| *A61K 31/277* | (2006.01) |
| *G01N 33/574* | (2006.01) |
| *A61K 31/4166* | (2006.01) |
| *A61K 31/405* | (2006.01) |
| *A61K 45/06* | (2006.01) |
| *A61K 31/609* | (2006.01) |
| *A61K 31/337* | (2006.01) |
| *A61K 31/58* | (2006.01) |
| *A61K 47/68* | (2017.01) |
| *C12Q 1/6886* | (2018.01) |
| *A61K 38/00* | (2006.01) |

(52) U.S. Cl.
CPC ..... *G01N 33/57434* (2013.01); *A61K 31/277* (2013.01); *A61K 31/337* (2013.01); *A61K 31/405* (2013.01); *A61K 31/4166* (2013.01); *A61K 31/58* (2013.01); *A61K 31/609* (2013.01); *A61K 45/06* (2013.01); *A61K 47/6869* (2017.08); *C12Q 1/6886* (2013.01); *A61K 38/00* (2013.01); *C12Q 2600/178* (2013.01); *G01N 2800/52* (2013.01)

(58) Field of Classification Search
CPC .................................................. A61K 47/6869
See application file for complete search history.

(56) References Cited

U.S. PATENT DOCUMENTS

| | | |
|---|---|---|
| 5,512,570 A | 4/1996 | Dorn et al. |
| 7,547,804 B2 | 6/2009 | Bajii et al. |
| 2003/0139352 A1 | 7/2003 | Schoenhard et al. |
| 2004/0077601 A1 | 4/2004 | Adams et al. |
| 2005/0250709 A1 | 11/2005 | Khodadoust |
| 2007/0009533 A1 | 1/2007 | Sikic et al. |
| 2009/0035389 A1 | 2/2009 | Campion et al. |
| 2009/0208493 A1 | 8/2009 | Larson et al. |
| 2011/0110926 A1 | 5/2011 | Luo et al. |
| 2014/0199236 A1 | 7/2014 | Chen et al. |
| 2014/0221411 A1 | 8/2014 | Kim et al. |
| 2017/0315127 A1 | 11/2017 | Gao et al. |
| 2018/0153850 A1 | 6/2018 | Gao et al. |
| 2018/0346409 A1 | 12/2018 | Lu et al. |

FOREIGN PATENT DOCUMENTS

| | | |
|---|---|---|
| CN | 104771386 A | 7/2015 |
| CN | 105566147 A | 5/2016 |
| WO | 2004/006906 A2 | 1/2004 |
| WO | WO 2004/006906 * | 1/2004 |

(Continued)

OTHER PUBLICATIONS

Bono et al. (New England Journal of Medicine (May 2011) 364:1995-2005) (Year: 2011).*

(Continued)

*Primary Examiner* — Marcos L Sznaidman

(74) *Attorney, Agent, or Firm* — Kilpatrick Townsend & Stockton LLP

(57) ABSTRACT

The present invention provides new compositions and methods for treating prostate cancer, e.g., drug-resistant prostate cancer, such as anti-androgen drug (e.g., enzalutamide) resistant and/or castration resistant prostate cancer (CRPC). These new compositions include, but are not limited to, pharmaceutical compositions that include an AR-V7 inhibitor, such as niclosamide. Alternatively, these new compositions can include, but are not limited to, pharmaceutical compositions that include an AKR1C3 inhibitor, such as indomethacin. These new methods include, but are not limited to, methods of administering an AR-V7 inhibitor, such as niclosamide, and/or an AKR1C3 inhibitor, such as indomethacin, to treat patients having prostate cancer. The present invention also provides methods of inhibiting androgen receptor variant expression, e.g. AR-V7, and methods of killing cells expressing AR-V7. The present invention further provides methods of inhibiting AKR1C3 expression or activity, and methods of killing cells that express AKR1C3.

19 Claims, 56 Drawing Sheets

Specification includes a Sequence Listing.

(56) References Cited

FOREIGN PATENT DOCUMENTS

| WO | 2005/060951 | A2 | | 7/2005 |
|---|---|---|---|---|
| WO | 2012/142208 | A1 | | 10/2012 |
| WO | 2012/143377 | A1 | | 10/2012 |
| WO | 2013/059245 | A1 | | 4/2013 |
| WO | WO 2013/059245 | | * | 4/2013 |
| WO | 2013/142390 | A1 | | 9/2013 |
| WO | 2015/065919 | A1 | | 5/2015 |
| WO | 2016/077787 | A1 | | 5/2016 |
| WO | 2016/179002 | A1 | | 11/2016 |
| WO | 2018/136650 | A1 | | 7/2018 |

OTHER PUBLICATIONS

Antonarakis et al., "AR-V7 and Resistance to Enzalutamide and Abiraterone in Prostate Cancer", New England Journal of Medicine, vol. 371, No. 11, Sep. 2014, pp. 1028-1038.
Arora et al., "Glucocorticoid Receptor Confers Resistance to Antiandrogens by Bypassing Androgen Receptor Blockade," Cell 155, Dec. 5, 2013, pp. 1309-1322.
Bauman et al., "Identification of the Major Oxidative 3-Hydroxysteroid Dehydrogenase in Human Prostate That Converts 5α-Androstane-3α,17β-diol to 5α-Dihydrotestosterone: A Potential Therapeutic Target for Androgen-Dependent Disease," Mol Endocrinol, Feb. 2006, 20(2), pp. 444-458.
Berrieman et al., "Do β-tubulin mutations have a role in resistance to chemotherapy?" The Lancet Oncology, Mar. 2004, vol. 5, pp. 158-164.
Bhangal et al., "Expression of the multidrug resistance gene in human prostate cancer," Urologic Oncology, 2000, vol. 5, pp. 118-121.
Brooks et al., "Taxane-based reversal agents modulate drug resistance mediated by P-glycoprotein, multidrug resistance protein, and breast cancer resistance protein," Mol Cancer Ther., 2003, vol. 2, pp. 1195-1205.
Brunelli et al., "The non-steroidal anti-inflammatory drug indomethacin activates the eIF2α kinase PKR, causing a translational block in human colorectal cancer cells," Biochem. J., 2012, vol. 443, pp. 379-386.
Caceres et al., "HG-829 Is a Potent Noncompetitive Inhibitor of the ATP-Binding Cassette Multidrug Resistance Transporter ABCB1," Cancer Research, Aug. 15, 2012, vol. 72(16), pp. 4204-4213.
Cai et al., "Intratumoral De Novo Steroid Synthesis Activates Androgen Receptor in Castration-Resistant Prostate Cancer and Is Upregulated by Treatment with CYP17A1 Inhibitors," American Association for Cancer Research, 71(20), Oct. 15, 2011, pp. 6503-6513.
Chang et al., "A Gain-of-Function Mutation in DHT Synthesis in Castration-Resistant Prostate Cancer," Cell 154, Aug. 29, 2013, pp. 1074-1084.
Chang et al., "Androgen metabolism in prostate cancer: from molecular mechanisms to clinical consequences," British Journal of Cancer, 2014, vol. 111, pp. 1249-1254, doi: 10.1038/bjc.2014.268.
Cui et al., "Upregulation of glucose metabolism by NF-κB2/p52 mediates enzalutamide resistance in castration-resistant prostate cancer cells," Research, vol. 21, No. 3, Mar. 21, 2014, pp. 435-442.
De Bono et al., "Abiraterone and Increased Survival in Metastatic Prostate Cancer," New England Journal of Medicine, May 26, 2011, vol. 364, No. 21, pp. 1995-2005.
Dehm et al., "Splicing of a Novel Androgen Receptor Exon Generates a Constitutively Active Androgen Receptor that Mediates Prostate Cancer Therapy Resistance," Cancer Res, Jul. 1, 2008, vol. 68, No. 13, pp. 5469-5477.
Domingo-Domenech et al., "Suppression of acquired docetaxel resistance in prostate cancer through depletion of notch- and hedgehog-dependent tumor-initiating cells," Cancer Cell, Sep. 11, 2012, vol. 22, pp. 373-388.
Dutt et al., "Molecular mechanisms of castration-resistant prostate cancer progression," Future Oncology, 2009, vol. 5(9), pp. 1403-1413.
Efstathiou et al., "MDV3100 effects on androgen receptor (AR) signaling and bone marrow testosterone concentration modulation: Apreliminary report." Abstract, Journal of Clinical Oncology, vol. 29, No. 15-suppl, May 2011, pp. 4501-4501.
Efstathiou et al., "Molecular Characterization of Enzalutamide-treated Bone Metastatic Castration-resistant Prostate Cancer," European Urology, 2015, vol. 67, pp. 53-60.
European Application No. EP14857072.4 , "Partial Supplementary European Search Report", dated May 16, 2017, 3 pages.
European Application No. EP14857072.4 , "Extended European Search Report", dated Jul. 31, 2017, 5 pages.
Fankahauser et al., "Canonical Androstenedione Reduction Is the Predominant Source of Signaling Androgens in Hormone-Refractory Prostate Cancer," Clinical Cancer Research, Nov. 1, 2014, vol. 20, No. 21, pp. 5547-5557.
Fitzpatrick et al., "Taxane mechanisms of action: potential implications for treatment sequencing in metastatic castration-resistant prostate cancer," European Urology, 2014, vol. 65, pp. 1198-1204.
Flanagan et al., "Crystal Structures of Three Classes of Non-Steroidal Anti-Inflammatory Drugs in Complex with Aldo-Keto Reductase 1C3," PLOS ONE, Aug. 2012, vol. 7, No. 8, e439965, 16 pages.
Gaikwad et al., Ultra Performance Liquid Chromatography-Tandem Mass Spectrometry Method for Profiling of Steroid Metabolome in Human Tissue, Anal. Chem., 2013, vol. 85, pp. 4951-4960.
Galletti et al., "Paclitaxel and docetaxel resistance: molecular mechanisms and development of new generation taxanes," ChemMedChem, 2007, vol. 2, pp. 920-942.
Hara et al., "A mutation in β-tubulin and a sustained dependence on androgen receptor signalling in a newly established docetaxel-resistant prostate cancer cell line," CellBioInt., 2010, vol. 34, pp. 177-184.
Hari et al., "Paclitaxel-resistant cells have a mutation in the paclitaxel-binding region of β-tubulin (Asp26Glu) and less stable microtubules," Molecular Cancer Therapeutics, Feb. 2006, vol. 5(2), pp. 270-278.
Harris et al., "Montgomery B. Androgen deprivation therapy: progress in understanding mechanisms of resistance and optimizing androgen depletion," Nat Clin Pract Urol., Feb. 2009, vol. 6(2), pp. 76-85.
Herbst et al., "Mode of action of docetaxel—a basis for combination with novel anticancer agents," Cancer Treatment Reviews, 2003, vol. 29, pp. 407-415.
Ho et al., "Androgen regulation of multidrug resistance-associated protein 4 (MRP4/ABCC4) in prostate cancer", Prostate, Wiley-Liss, New York, NY, US, vol. 68, No. 13, Sep. 1, 2008, pp. 1421-1429.
Hörnberg et al., "Expression of androgen receptor splice variants in prostate cancer bone metastases is associated with castration-resistance and short survival", PLOS One vol. 6, No. 4, Apr. 2011, e19059, 9 pages.
Hu et al., "Distinct Transcriptional Programs Mediated by the Ligand-Dependent Full-Length Androgen Receptor and Its Splice Variants in Castration-Resistant Prostate Cancer," Cancer Res; Jul. 15, 2012, vol. 72, No. 14, pp. 3457-3462.
Huang et al., "Challenges to improved therapeutics for metastatic castrate resistant prostate cancer: from recent successes and failures," Journal of Hematology & Oncology, 2012, 5:35, 8 pages.
Ishizaki et al., "Androgen deprivation promotes intratumoral synthesis of dihydrotestosterone from androgen metabolites in prostate cancer," Mar. 25, 2013, Scientific Reports, 3:1528, 9 pages, DOI: 10.1038/srep01528.
Isikbay et al., "Glucocorticoid Receptor Activity Contributes to Resistance to Androgen-Targeted Therapy in Prostate Cancer," 2014, Horm Canc, No. 5, pp. 72-89, DOI 10.1007/s12672-014-0173-2.
James et al., "Celecoxib plus hormone therapy versus hormone therapy alone for hormone-sensitive prostate cancer: first results from the STAMPEDE multiarm, multistage, randomised controlled trial," Lancet Oncology, May 2012, vol. 13, pp. 549-558.
Joseph et al., "A Clinically Relevant Androgen Receptor Mutation Confers Resistance to Second-Generation Antiandrogens Enzalutamide

(56) References Cited

OTHER PUBLICATIONS and ARN-509," Cancer Discovery, Sep. 2013; vol. 3, pp. 1020-1029; DOI: 10.1158/2159-8290.CD-13-0226.
Kim et al., "Current treatment strategies for castration-resistant prostate cancer," Korean J Urol., 2011, vol. 52, pp. 157-165.
Kimchi-Sarfaty et al., "A "Silent" Polymorphism in the MDR1 Gene Changes Substrate Specificity," Science, Jan. 26, 2007, vol. 315, pp. 525-528.
Korpal et al. "An F876L Mutation in Androgen Receptor Confers Genetic and Phenotypic Resistance to MDV3100 (Enzalutamide)," Cancer Discovery, Sep. 2013, vol. 3, pp. 1030-1043, http://cancerdiscovery.aacrjournals.org/lookup/doi/10.1158/2159-8290.CD-13-0142.
Kosaka et al., "Long-Term Androgen Ablation and Docetaxel Up-Regulate Phosphorylated Akt in Castration Resistant Prostate Cancer," The Journal of Urology, Jun. 2011, vol. 185, pp. 2376-2381.
Labrie et al., "The key role of 17β-hydroxysteroid dehydrogenases in sex steroid biology," Steroids, Jan. 1997, vol. 62, pp. 148-158.
Li et al., "Androgen receptor splice variants mediate enzalutamide resistance in castration-resistant prostate cancer cell lines", American Association for Cancer Research, vol. 73, No. 2, Nov. 2012, pp. 483-489.
Liedtke et al., "Development of Potent and Selective Indomethacin Analogues for the Inhibition of AKR1C3 (Type 5 17β-Hydroxysteroid Dehydrogenase/Prostaglandin F Synthase) in Castrate-Resistant Prostate Cancer," J. Med. Chem., 2013, vol. 56, pp. 2429-2446, dx.doi.org/10.1021/jm3017656.
Liu et al., "Andrographolide Targets Androgen Receptor Pathway in Castration-Resistant Prostate Cancer," Genes & Cancer, 2011, vol. 2, No. 2, pp. 151-159.
Liu et al., "Inhibition of AKR1C3 Activation Overcomes Resistance to Abiraterone in Advanced Prostate Cancer," Jan. 2017, Mol Cancer Ther, 16(1); DOI: 10.1158/1535-7163.MCT-16-0186.
Liu et al., "Inhibition of Constitutively Active Stat3 Reverses Enzalutamide Resistance in LNCaP Derivative Prostate Cancer Cells," Prostate, 2014, vol. 74, pp. 201-209.
Liu et al., "Intracrine Androgens and AKR1C3 Activation Confer Resistance to Enzalutamide in Prostate Cancer," Apr. 1, 2015, Cancer Res; 75(7) 11 pages, doi: 10.1158/0008-5472.CAN-14-3080.
Liu et al., "Niclosamide enhances abiraterone treatment via inhibition of androgen receptor variants in castration resistant prostate cancer," Mar. 30, 2016, Oncotarget, 11 pages.
Liu et al., "Niclosamide inhibits androgen receptor variants expression and overcomes enzalutamide resistance in castration-resistant prostate cancer," Clinical Cancer Research, Jun. 15, 2014, vol. 20(12), pp. 3198-3210.
Liu et al., Functional p53 determines docetaxel sensitivity in prostate cancer cells, Prostate, Mar. 2013, vol. 73(4), pp. 418-427.
Locke et al., "Androgen Levels Increase by Intratumoral De novo Steroidogenesis during Progression of Castration-Resistant Prostate Cancer," Cancer Res, Aug. 1, 2008, vol. 68, pp. 6407-6415.
Lu et al., "Niclosamide suppresses cancer cell growth by inducing Wnt co-receptor LRP6 degradation and inhibiting the Wnt/β-catenin pathway", PLOS One, vol. 6, No. 12, Dec. 2011, p. e29290, 8 pages.
Malofeeva et al., "Modulation of the ATPase and transport activities of broad-acting multidrug resistance factor ABCC10 (MRP7)," Cancer Res., Dec. 15, 2012, vol. 72(24), pp. 6457-6467.
McKeage, K., "A Review of its Use for the First-Line Treatment of Advanced Castration-Resistant Prostate Cancer," Drugs, 2012, vol. 72, No. 11, pp. 1559-1577.
Mitsiades et al., "Distinct Patterns of Dysregulated Expression of Enzymes Involved in Androgen Synthesis and Metabolism in Metastatic Prostate Cancer Tumors," Cancer Res, Dec. 1, 2012, vol. 72, No. 23, pp. 6142-6152, DOI: 10.1158/0008-5472.CAN-12-1335.
Mohler et al., "Activation of the Androgen Receptor by Intratumoral Bioconversion of Androstanediol to Dihydrotestosterone in Prostate Cancer," Cancer Res, 2011, vol. 71, pp. 1486-1496, doi:10.1158/0008-5472.CAN-10-1343.
Montgomery et al., "Maintenance of Intratumoral Androgens in Metastatic Prostate Cancer: A Mechanism for Castration-Resistant Tumor Growth," Cancer Res., Jun. 1, 2008, vol. 68, No. 11, pp. 4447-4454.
Nadiminty et al., "NF-kB2/p52 Induces Resistance to Enzalutamide in Prostate Cancer: Role of Androgen Receptor and Its Variants," Mol Cancer Ther, Aug. 2013, vol. 12, No. 8, pp. 1629-1637, DOI: 10.1158/1535-7163.MCT-13-0027.
Nguyen et al., "Targeting autophagy overcomes Enzalutamide resistance in castration-resistant prostate cancer cells and improves therapeutic response in a xenograft model," Oncogene, 2014, vol. 33, pp. 4521-4530.
O'Neill et al., "Characterisation and manipulation of docetaxel-resistant prostate cancer cell lines," Molecular Cancer, 2011, 10:126, 13 pages.
Ren et al., "Identification of Niclosamide as a New Small-Molecule Inhibitor of the STAT3 Signaling Pathway", ACS Medicinal Chemistry Letters, vol. 1, No. 9, Dec. 2010, pp. 454-459.
Ryan et al., "Abiraterone in Metastatic Prostate Cancer without Previous Chemotherapy," N Engl J Med, Jan. 10, 2013; vol. 368, pp. 138-148, DOI: 10.1056/NEJMoa1209096.
Sanchez et al., "Chemotherapy sensitivity recovery of prostate cancer cells by functional inhibition and knock down of multidrug resistance proteins," The Prostate, 2011, vol. 71, pp. 1810-1817.
Scher et al. "Increased Survival with Enzalutamide in Prostate Cancer after Chemotherapy," New Engl J Med, Sep. 27, 2012, vol. 367, No. 13, pp. 1187-1197, DOI: 10.1056/NEJMoa1207506.
Scher et al., "Antitumour activity of MDV3100 in castration-resistant prostate cancer: a phase 1-2 study," www.thelancet.com, Articles, Apr. 24, 2010, vol. 375, pp. 1437-1446.
Scher et al., Increased Survival with Enzalutamide in Prostate Cancer after Chemotherapy, New England Journal of Medicine, Sep. 27, 2012, vol. 367, No. 13, pp. 1187-1197.
Seruga et al., "Drug resistance in metastatic castration-resistant prostate cancer," Nat Rev Clin Oncol., Jan. 2011, vol. 8, pp. 12-23.
Shalli et al., "Alterations of β-tubulin isotypes in breast cancer cells resistant to docetaxel," The FASEB Journal, published on Jun. 9, 2005, vol. 19, No. 10, pp. 1299-1301.
Sharom, F.J., "ABC multidrug transporters: structure, function and role in chemoresistance," Pharmacogenomics, 2008, 34 pages.
Sheu et al., "The Functional Influences of Common ABCB1 Genetic Variants on the Inhibition of P-glycoprotein by Antrodia cinnamomea Extracts," PLoS ONE, Feb. 2014, vol. 9, Issue 2, e89622.
Shi et al., "Sildenafil Reverses ABCB1- and ABCG2-Mediated Chemotherapeutic Drug Resistance," Cancer Research, Apr. 15, 2011, vol. 71(8), pp. 3029-3041.
Sowery et al. "Clusterin knockdown using the antisense oligonucleotide OGX-011 re-sensitizes docetaxel-refractory prostate cancer PC-3 cells to chemotherapy," BJU International., 2008, vol. 102, pp. 389-397.
Stanbrough et al., "Increased Expression of Genes Converting Adrenal Androgens to Testosterone in Androgen-Independent Prostate Cancer," Cancer Res, Mar. 1, 2006, vol. 66, No. 5, pp. 2815-2825.
Sternberg et al., "Docetaxel (Taxotere™), a novel taxoid, in the treatment of advanced colorectal carcinoma: an EORTC Early Clinical Trials Group Study," Br. J. Cancer, 1994, No. 70, pp. 376-379.
Szakacs et al., "Targeting multidrug resistance in cancer," Nature reviews of drug discovery, Mar. 2006, vol. 5, pp. 219-234.
Trapman et al., "Androgen-regulated gene expression in prostate cancer," Semin Cancer Biol., 1997; vol. 8, pp. 29-36.
Tse et al., "Indomethacin Sensitizes TRAIL-Resistant Melanoma Cells to TRAIL-Induced Apoptosis through ROS-Mediated Upregulation of Death Receptor 5 and Downregulation of Survivin," Journal of Investigative Dermatology, 2014, 134, pp. 1397-1407, http://dx.doi.org/10.1038/jid.2013.471.

(56) References Cited

OTHER PUBLICATIONS

Vidal et al., A targetable GATA2-IGF2 axis confers aggressiveness in lethal prostate cancer, Cancer Cell, Feb. 9, 2015, vol. 27(2), pp. 223-239.

Wako et al., "Expression of androgen receptor through androgen-converting enzymes is associated with biological aggressiveness in prostate cancer," J Clin Pathol, 2008, vol. 61, pp. 448-454, doi:10.1136/jcp.2007.050906.

Wilson et al., "New therapeutic options in metastatic castration-resistant prostate cancer: Can cost-effectiveness analysis help in treatment decisions?" Journal of Oncology Pharmacy Practice, 2014, vol. 20(6), pp. 417-425.

Yepuru et al., "Steroidogenic Enzyme AKR1C3 Is a Novel Androgen Receptor-Selective Coactivator that Promotes Prostate Cancer Growth," Clin Cancer Res, Oct. 15, 2013, vol. 19, No. 20, pp. 5613-5625, DOI: 10.1158/1078-0432.CCR-13-1151.

Yoshino et al., "Bcl-2 expression as a predictive marker of hormone-refractory prostate cancer treated with taxane-based chemotherapy," Clin Cancer Res., Oct. 15, 2006, vol. 12(20), pp. 6116-6124.

Zhong et al. "Induction of clusterin by AKT-Role in cytoprotection against docetaxel in prostate tumor cells," Mol Cancer Ther., Jun. 2010, vol. 9(6), pp. 1831-1841.

Zhu et al., "Anti-androgens inhibit ABCB1 efflux and ATPase activity and 'reverse docetaxel 1-4. 7, 20-27, 31-33, 39 resistance in advanced prostate cancer", American Association for Cancer Research, May 20, 2015, 35 pages.

Zhu et al., "Inhibition of ABCB1 Expression Overcomes Acquired Docetaxel Resistance in Prostate Cancer," Mol Cancer Ther, Sep. 2013, vol. 12, No. 9, pp. 1829-1836, DOI: 10.1158/1535-7163. MCT-13-0208.

Zhu et al., "Interleukin-6 induces neuroendocrine differentiation (NED) through suppression of RE-1 silencing transcription factor (REST)," The Prostate, 2014, vol. 74, pp. 1086-1094.

Zhu et al., RhoGDIα suppresses growth and survival of prostate cancer cells, The Prostate, Mar. 2012, vol. 72, Issue 4, pp. 392-398.

Zhu et al., Tubulin-targeting chemotherapy impairs androgen receptor activity in prostate cancer, Cancer Res., Oct. 15, 2010, vol. 70(20), pp. 7992-8002.

"Partial Supplementary European Search Report" dated Jun. 15, 2020 for EP Application No. 18742382.7, 13 pages.

"Extended European Search Report" dated Sep. 18, 2020 for European Application No. 18742382.7, 10 pages.

Chang et al., "Pharmacokinetics of Anti-SARS-CoV Agent Niclosamide and Its Analogs in Rats," Journal of Food and Drug Analysis, vol. 14, No. 4, 2006, pp. 329-333.

Liu et al., "Niclosamide Suppresses Cell Migration and Invasion in Enzalutamide Resistant Prostate Cancer Cells via Stat3-AR Axis Inhibition", The Prostate, vol. 75, No. 13, May 13, 2015, pp. 1341-1353.

Mook et al., "Structure-activity studies of Wnt/β-catenin inhibition in the Niclosamide chemotype: Identification of derivatives with improved drug exposure," Bioorg Med Chem., Sep. 1, 2015, vol. 23, No. 17, pp. 5829-5838.

"Pubchem CID 4477," Nicolsamide, $C_{13}H_8C_{12}N_2O_4$, Create Date: Mar. 25, 2005, 58 pages.

Bundgaard, Hans "Design and Application of Prodrugs", A Textbook of Drug Design and Development, Chapter 5, pp. 113-191.

Cochrane et al, "Role of the Androgen Receptor in Breast Cancer and Preclinical Analysis of Enzalutamide" Breast Cancer Research, Jan. 2014, vol. 16, No. 1, pp. 1-19.

\* cited by examiner

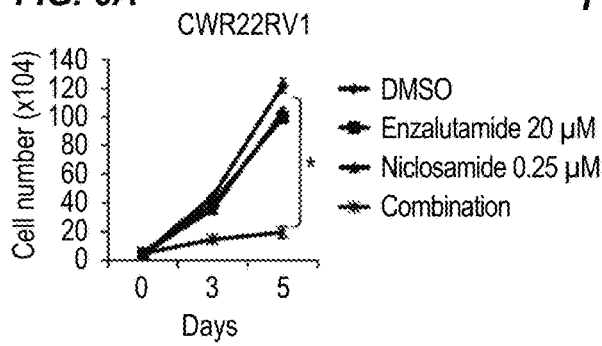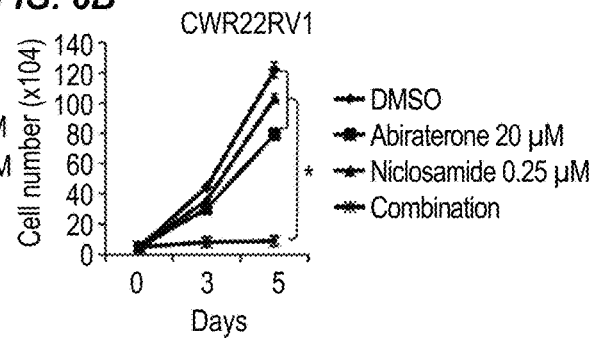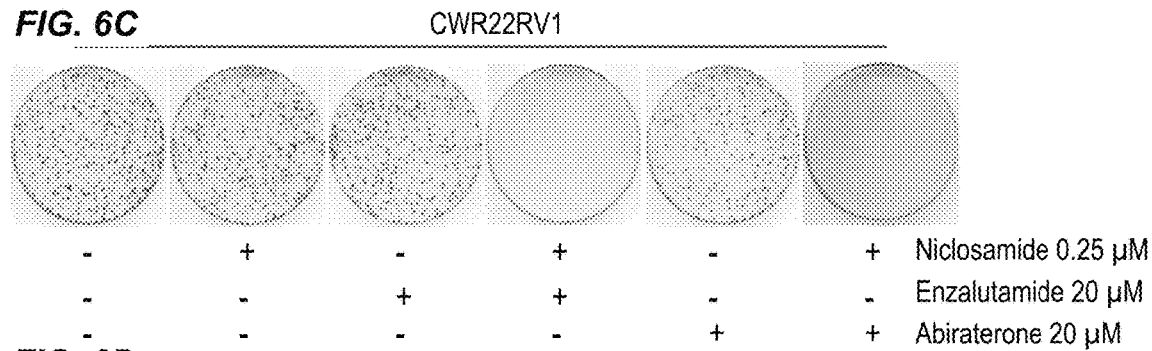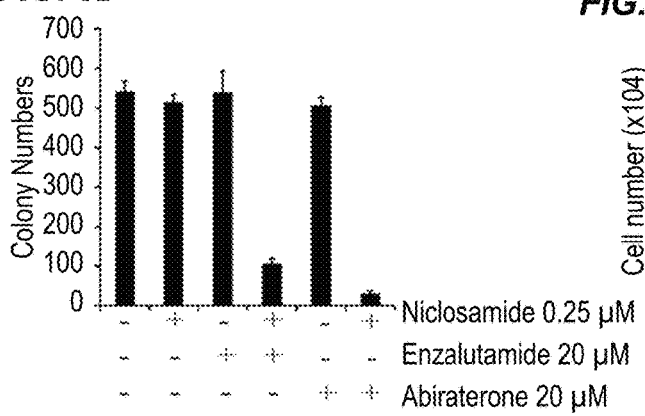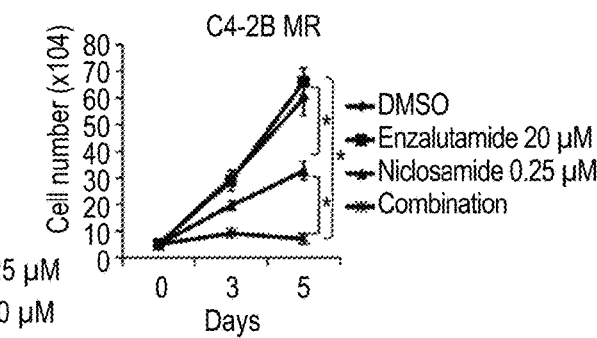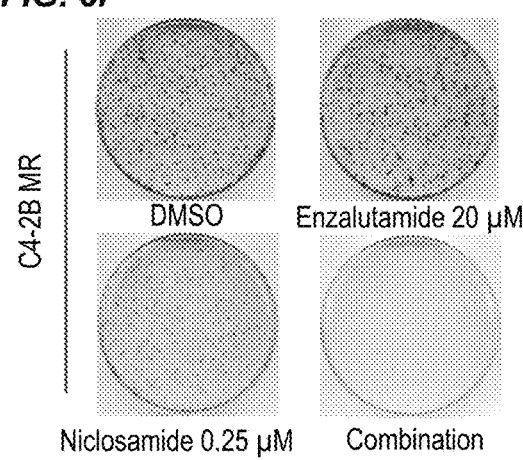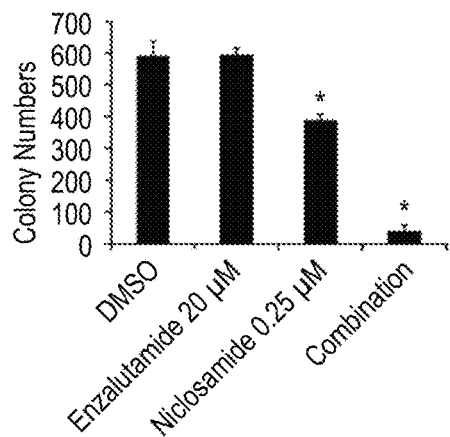

293 GFP AR-V7+ PSA E/P-LUC Stable cell line

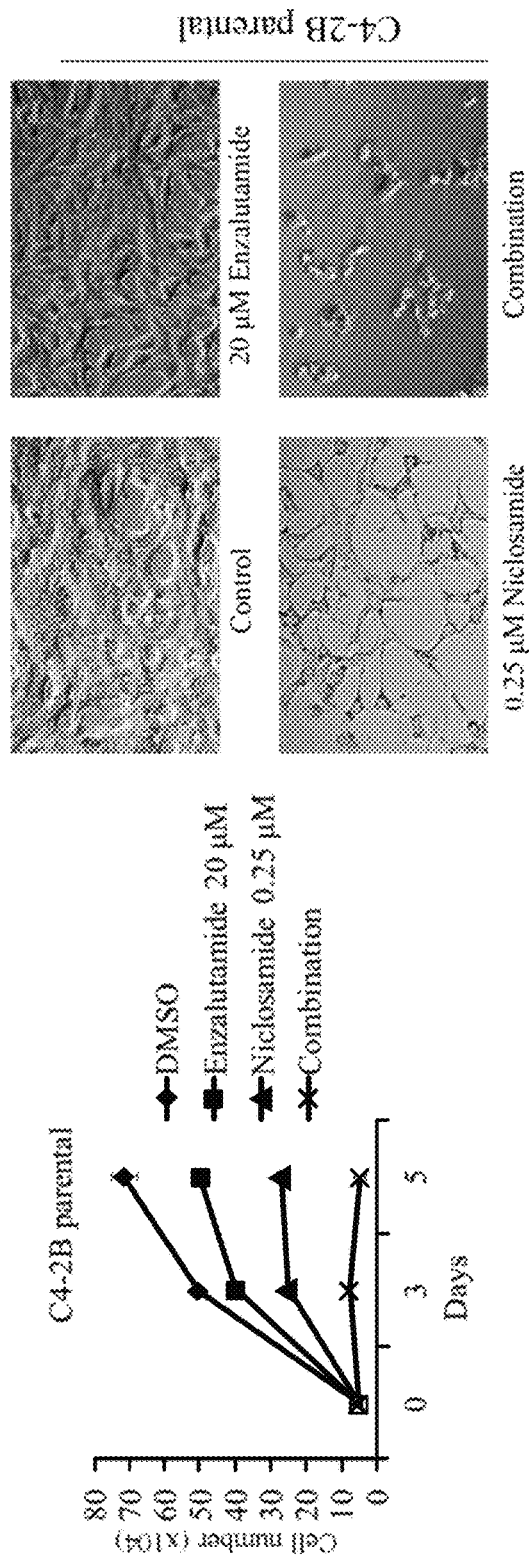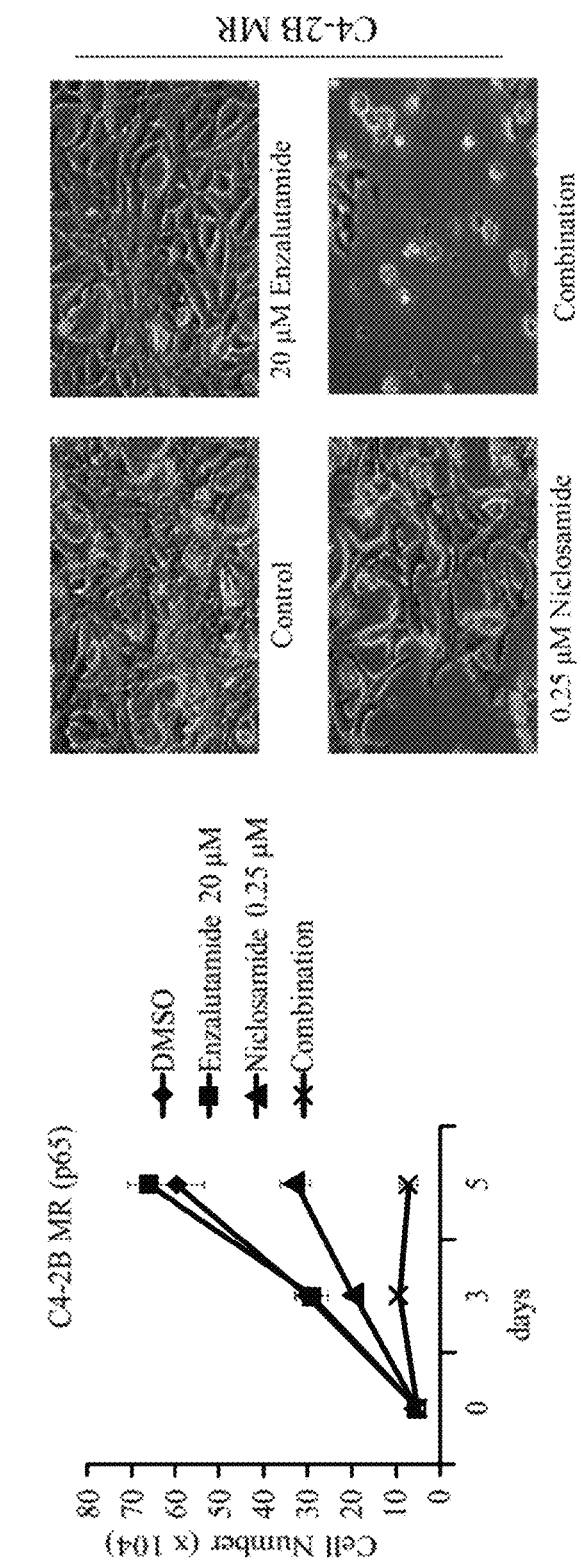
FIG. 22

5-chloro-N-(2-chloro-4-nitrophenyl)-2 hydroxybenzamide

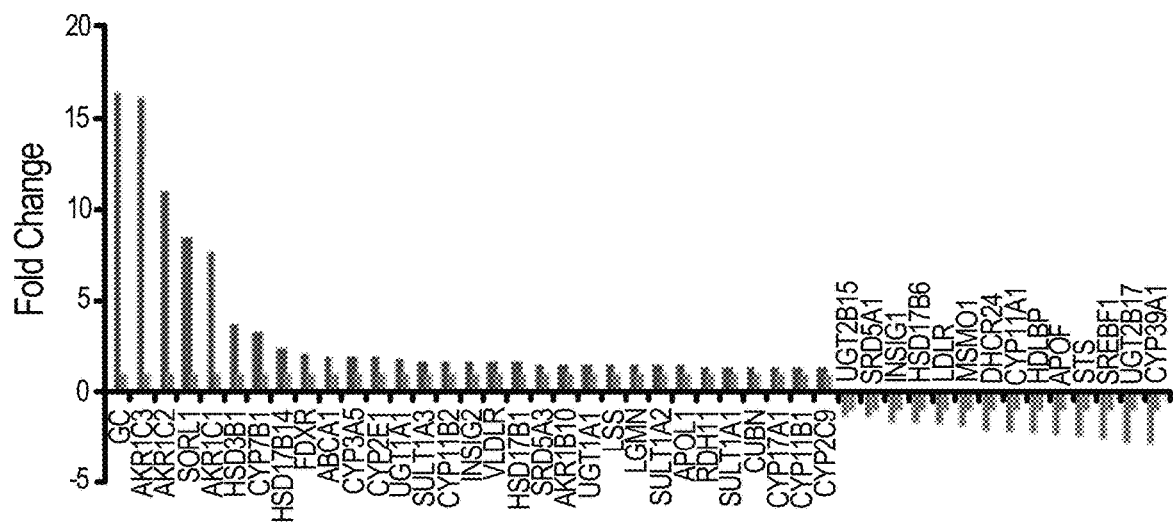
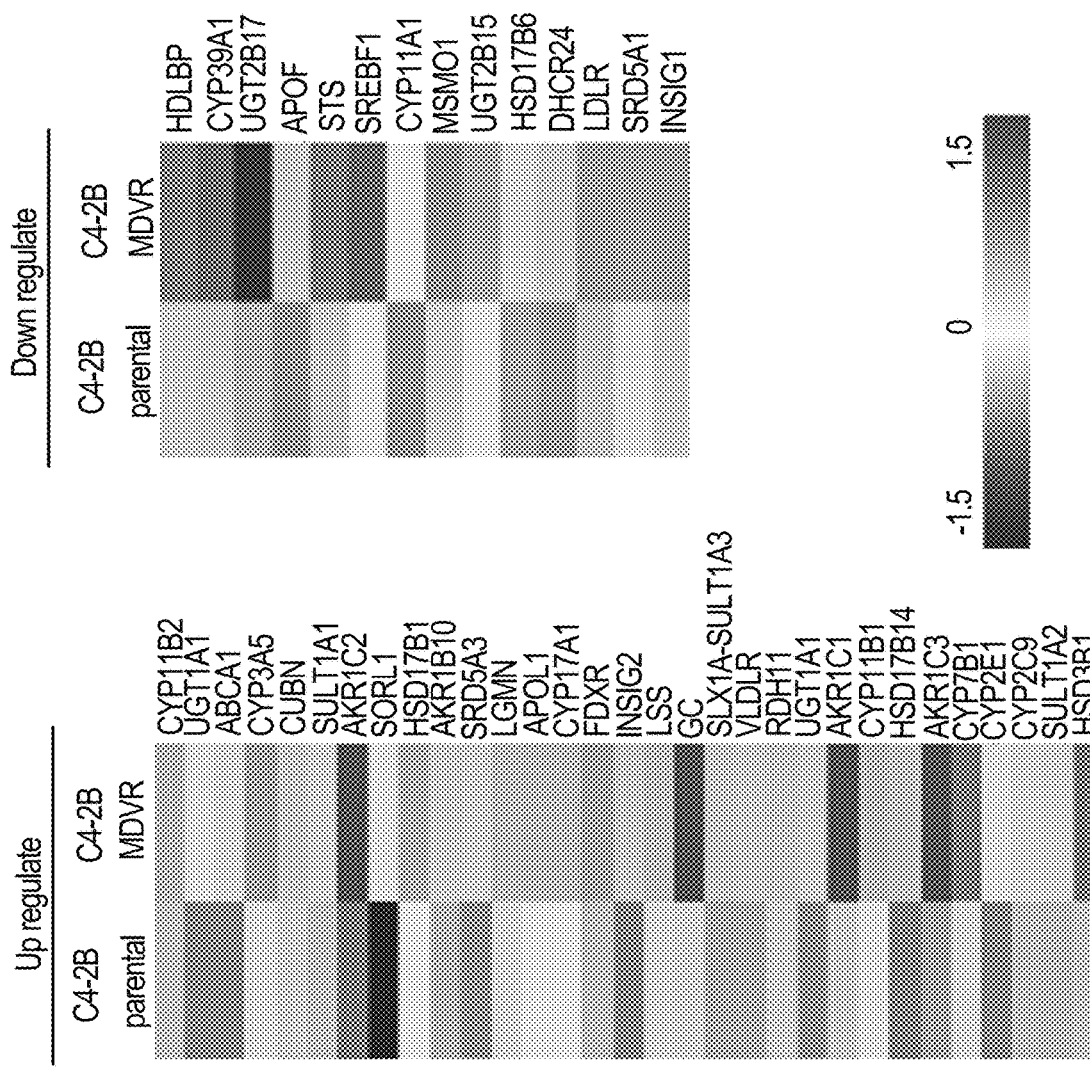
FIG. 44A

| Metabolites (pg/50 million cells) | C4-2B Pareneal | C4-2B MDVR |
|---|---|---|
| Cholesterol | 54094.35 | 777311.025 |
| 20-Hydroxypregnenolone | 1721.775 | 3802.875 |
| Progesterone | 41.85 | 164.325 |
| DHEA | 0 | 72.075 |
| 17β-Dihydroandrosterone | 247.65 | 339.225 |
| TESTOSTERONE | 0.15 | 131.025 |
| DIHYDROTESTOSTERONE | 0 | 17.55 |
| ESTRADIOL | 207.3 | 82.725 |
| 4-OH ESTRADIOL | 63.075 | 0 |
| 2-OH ESTRIOL | 18.375 | 11.325 |
| 6-KETOESTRIOL | 1667.7 | 917.1 |
| CORTEXONE | 0.825 | 9.975 |
| CORTICOSTERONE | 96.975 | 101.025 |

*FIG. 46C*

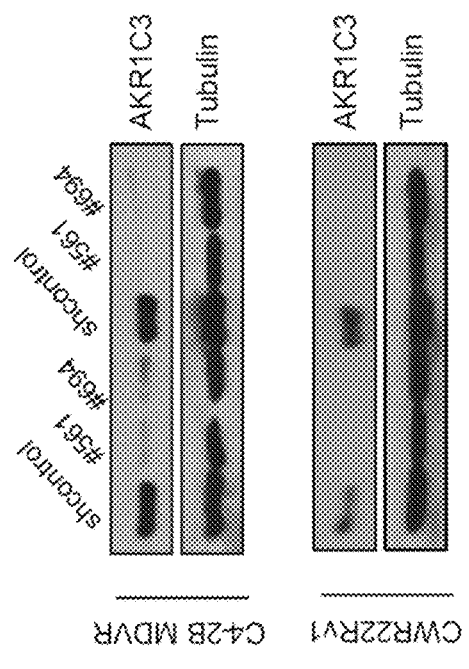
FIG. 47A
FIG. 47B
FIG. 47C
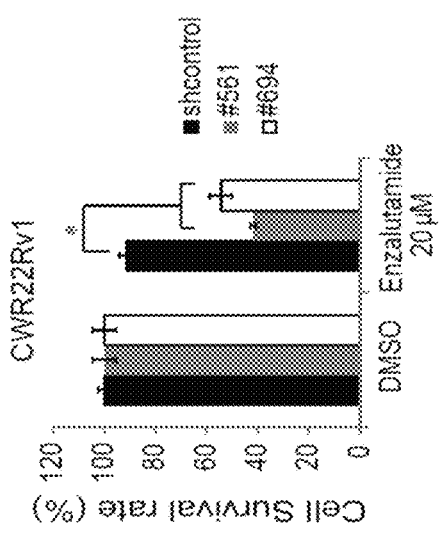
FIG. 47D
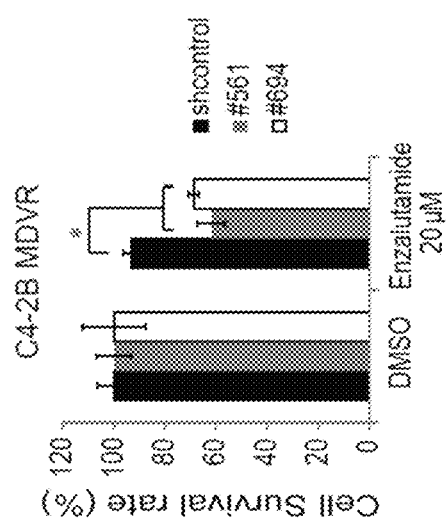
FIG. 47E
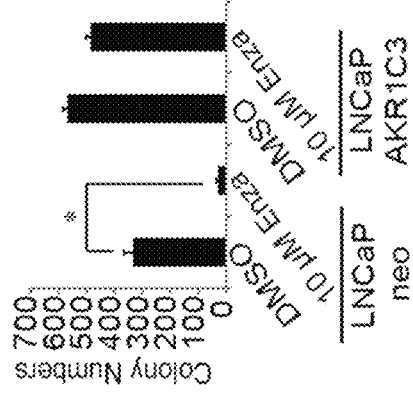
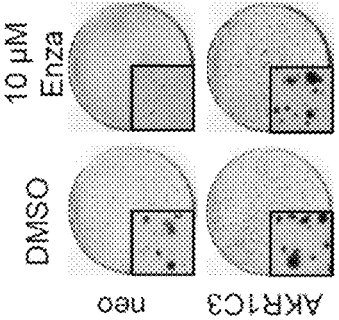
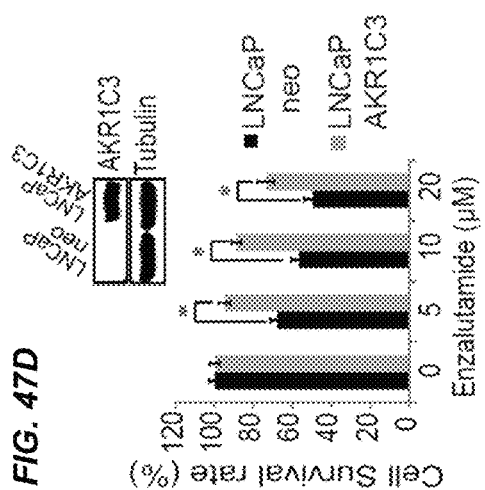
FIG. 47F

SEQUENCE LISTING

<160> NUMBER OF SEQ ID NOS: 31

<210> SEQ ID NO 1
<211> LENGTH: 19
<212> TYPE: RNA
<213> ORGANISM: Artificial Sequence
<220> FEATURE:
<223> OTHER INFORMATION: synthetic small interfering RNA (siRNA)
      targeting androgen receptor (AR) Exon7 sequence

<400> SEQUENCE: 1
ucaaggaacu cgaucguau                                                  19

<210> SEQ ID NO 2
<211> LENGTH: 19
<212> TYPE: RNA
<213> ORGANISM: Artificial Sequence
<220> FEATURE:
<223> OTHER INFORMATION: synthetic small interfering RNA (siRNA)
      targeting androgen receptor (AR) splice variant 7 (AR-V7) sequence

<400> SEQUENCE: 2
guaguuguaa guaucauga                                                  19

<210> SEQ ID NO 3
<211> LENGTH: 19
<212> TYPE: DNA

<213> ORGANISM: Artificial Sequence
<220> FEATURE:
<223> OTHER INFORMATION: synthetic small interfering RNA (siRNA) control
      sequence siControl targeting luciferase (Luc) gene

<400> SEQUENCE: 3
cttacgctga gtacttcga                                                    19

<210> SEQ ID NO 4
<211> LENGTH: 21
<212> TYPE: DNA
<213> ORGANISM: Artificial Sequence
<220> FEATURE:
<223> OTHER INFORMATION: synthetic androgen receptor (AR) full length
      primer for real-time PCR

<400> SEQUENCE: 4
aagccagagc tgtgcagatg a                                                 21

<210> SEQ ID NO 5
<211> LENGTH: 20
<212> TYPE: DNA
<213> ORGANISM: Artificial Sequence
<220> FEATURE:
<223> OTHER INFORMATION: synthetic androgen receptor (AR) full length
      primer for real-time PCR

<400> SEQUENCE: 5
cttggtcacc gacgtcctgt                                                   20

<210> SEQ ID NO 6
<211> LENGTH: 20
<212> TYPE: DNA
<213> ORGANISM: Artificial Sequence
<220> FEATURE:
<223> OTHER INFORMATION: synthetic androgen receptor (AR) splice variant
      1 (AR-V1) primer for real-time PCR

<400> SEQUENCE: 6
aacagaagta cctgtgcgcc                                                   20

<210> SEQ ID NO 7
<211> LENGTH: 20
<212> TYPE: DNA
<213> ORGANISM: Artificial Sequence
<220> FEATURE:
<223> OTHER INFORMATION: synthetic androgen receptor (AR) splice variant
      1 (AR-V1) primer for real-time PCR

<400> SEQUENCE: 7
actcccacaa acctcagagt                                                   20

<210> SEQ ID NO 8
<211> LENGTH: 20
<212> TYPE: DNA
<213> ORGANISM: Artificial Sequence
<220> FEATURE:
<223> OTHER INFORMATION: synthetic androgen receptor (AR) splice variant
      7 (AR-V7) primer for real-time PCR

<400> SEQUENCE: 8
aacagaagta cctgtgcgcc                                                   20

<210> SEQ ID NO 9
<211> LENGTH: 20
<212> TYPE: DNA
<213> ORGANISM: Artificial Sequence

```
<220> FEATURE:
<223> OTHER INFORMATION: synthetic androgen receptor (AR) splice variant
      7 (AR-V7) primer for real-time PCR

<400> SEQUENCE: 9
agttttactg gtctgggact                                               20

<210> SEQ ID NO 10
<211> LENGTH: 20
<212> TYPE: DNA
<213> ORGANISM: Artificial Sequence
<220> FEATURE:
<223> OTHER INFORMATION: synthetic androgen receptor (AR) splice variant
      1/2/2b (AR-V1/2/2b) primer for real-time PCR

<400> SEQUENCE: 10
tggatggata gctactccgg                                               20

<210> SEQ ID NO 11
<211> LENGTH: 24
<212> TYPE: DNA
<213> ORGANISM: Artificial Sequence
<220> FEATURE:
<223> OTHER INFORMATION: synthetic androgen receptor (AR) splice variant
      1/2/2b (AR-V1/2/2b) primer for real-time PCR

<400> SEQUENCE: 11
cgacttccta aaaagtctta cttg                                          24

<210> SEQ ID NO 12
<211> LENGTH: 20
<212> TYPE: DNA
<213> ORGANISM: Artificial Sequence
<220> FEATURE:
<223> OTHER INFORMATION: synthetic androgen receptor (AR) splice variant
      1/2/3/2b (AR-V1/2/3/2b) primer for real-time PCR

<400> SEQUENCE: 12
aacagaagta cctgtgcgcc                                               20

<210> SEQ ID NO 13
<211> LENGTH: 20
<212> TYPE: DNA
<213> ORGANISM: Artificial Sequence
<220> FEATURE:
<223> OTHER INFORMATION: synthetic androgen receptor (AR) splice variant
      1/2/3/2b (AR-V1/2/3/2b) primer for real-time PCR

<400> SEQUENCE: 13
gtggttaccc tgactgtctt                                               20

<210> SEQ ID NO 14
<211> LENGTH: 21
<212> TYPE: DNA
<213> ORGANISM: Artificial Sequence
<220> FEATURE:
<223> OTHER INFORMATION: synthetic actin primer for real-time PCR

<400> SEQUENCE: 14
agaactggcc cttcttggag g                                             21

<210> SEQ ID NO 15
<211> LENGTH: 21
<212> TYPE: DNA
<213> ORGANISM: Artificial Sequence
<220> FEATURE:
<223> OTHER INFORMATION: synthetic actin primer for real-time PCR
```

<400> SEQUENCE: 15
gggtatctcc ttgtattttt g                                              21

<210> SEQ ID NO 16
<211> LENGTH: 26
<212> TYPE: DNA
<213> ORGANISM: Artificial Sequence
<220> FEATURE:
<223> OTHER INFORMATION: synthetic prostate-specific antigen (PSA)
      promotor proximal binding site androgen response element
      (AREI/II) primer for ChIP assay

<400> SEQUENCE: 16
cctagatgaa gtctccatga gctaca                                         26

<210> SEQ ID NO 17
<211> LENGTH: 21
<212> TYPE: DNA
<213> ORGANISM: Artificial Sequence
<220> FEATURE:
<223> OTHER INFORMATION: synthetic prostate-specific antigen (PSA)
      promotor proximal binding site androgen response element
      (AREI/II) primer (proximal) for ChIP assay

<400> SEQUENCE: 17
gttcacgatc gagagggagg g                                              21

<210> SEQ ID NO 18
<211> LENGTH: 25
<212> TYPE: DNA
<213> ORGANISM: Artificial Sequence
<220> FEATURE:
<223> OTHER INFORMATION: synthetic aldo-keto reductase family 1 member
      C3 (AKR1C3, 17betaHSD5) forward primer for real-time PCR

<400> SEQUENCE: 18
gagaagtaaa gctttggagg tcaca                                          25

<210> SEQ ID NO 19
<211> LENGTH: 29
<212> TYPE: DNA
<213> ORGANISM: Artificial Sequence
<220> FEATURE:
<223> OTHER INFORMATION: synthetic aldo-keto reductase family 1 member
      C3 (AKR1C3, 17betaHSD5) reverse primer for real-time PCR

<400> SEQUENCE: 19
caacctgctc ctcattattg tataaatga                                      29

<210> SEQ ID NO 20
<211> LENGTH: 20
<212> TYPE: DNA
<213> ORGANISM: Artificial Sequence
<220> FEATURE:
<223> OTHER INFORMATION: synthetic aldo-keto reductase family 1 member
      1/2 (AKR1C1/2) forward primer for real-time PCR

<400> SEQUENCE: 20
ggtcacttca tgcctgtcct                                                20

<210> SEQ ID NO 21
<211> LENGTH: 20
<212> TYPE: DNA
<213> ORGANISM: Artificial Sequence
<220> FEATURE:
<223> OTHER INFORMATION: synthetic aldo-keto reductase family 1 member 1/2 (AKR1C1/2) reverse primer for real-time PCR

<400> SEQUENCE: 21
actctggtcg atgggaattg                                              20

<210> SEQ ID NO 22
<211> LENGTH: 30
<212> TYPE: DNA
<213> ORGANISM: Artificial Sequence
<220> FEATURE:
<223> OTHER INFORMATION: synthetic HSD3B1 forward primer for real-time
      PCR

<400> SEQUENCE: 22
agaatctaga ccactcttct gtccagcttt                                   30

<210> SEQ ID NO 23
<211> LENGTH: 30
<212> TYPE: DNA
<213> ORGANISM: Artificial Sequence
<220> FEATURE:
<223> OTHER INFORMATION: synthetic HSD3B1 reverse primer for real-time
      PCR

<400> SEQUENCE: 23
ctttgaattc aactatgtga aggaatggaa                                   30

<210> SEQ ID NO 24
<211> LENGTH: 19
<212> TYPE: DNA
<213> ORGANISM: Artificial Sequence
<220> FEATURE:
<223> OTHER INFORMATION: synthetic HSD3B2 forward primer for real-time
      PCR

<400> SEQUENCE: 24
cgggcccaac tcctacaag                                               19

<210> SEQ ID NO 25
<211> LENGTH: 22
<212> TYPE: DNA
<213> ORGANISM: Artificial Sequence
<220> FEATURE:
<223> OTHER INFORMATION: synthetic HSD3B2 reverse primer for real-time
      PCR

<400> SEQUENCE: 25
ttttccagag gctcttcttc gt                                           22

<210> SEQ ID NO 26
<211> LENGTH: 16
<212> TYPE: DNA
<213> ORGANISM: Artificial Sequence
<220> FEATURE:
<223> OTHER INFORMATION: synthetic CYP17A1 forward primer for real-time
      PCR

<400> SEQUENCE: 26
gggcggcctc aaatgg                                                  16

<210> SEQ ID NO 27
<211> LENGTH: 26
<212> TYPE: DNA
<213> ORGANISM: Artificial Sequence
<220> FEATURE:
<223> OTHER INFORMATION: synthetic CYP17A1 reverse primer for real-time
      PCR

```
<400> SEQUENCE: 27
cagcgaaggc gaaggcgata ccctta                                         26

<210> SEQ ID NO 28
<211> LENGTH: 18
<212> TYPE: DNA
<213> ORGANISM: Artificial Sequence
<220> FEATURE:
<223> OTHER INFORMATION: synthetic HSD17B3 forward primer for real-time
      PCR

<400> SEQUENCE: 28
tgggacagtg ggcagtga                                                  18

<210> SEQ ID NO 29
<211> LENGTH: 21
<212> TYPE: DNA
<213> ORGANISM: Artificial Sequence
<220> FEATURE:
<223> OTHER INFORMATION: synthetic HSD17B3 reverse primer for real-time
      PCR

<400> SEQUENCE: 29
cgagtacgct ttcccaattc c                                              21

<210> SEQ ID NO 30
<211> LENGTH: 19
<212> TYPE: DNA
<213> ORGANISM: Artificial Sequence
<220> FEATURE:
<223> OTHER INFORMATION: synthetic SRD5A1 forward primer for real-time
      PCR

<400> SEQUENCE: 30
acgggcatcg gtgcttaat                                                 19

<210> SEQ ID NO 31
<211> LENGTH: 21
<212> TYPE: DNA
<213> ORGANISM: Artificial Sequence
<220> FEATURE:
<223> OTHER INFORMATION: synthetic SRD5A1 reverse primer for real-time
      PCR

<400> SEQUENCE: 31
ccaacagtgg cataggcttt c                                              21
```

TREATMENT OF METASTATIC PROSTATE CANCER

CROSS-REFERENCE TO RELATED APPLICATIONS

This application is a divisional application of U.S. patent application Ser. No. 15/134,228, filed Apr. 20, 2016, which is a continuation of PCT/US2014/062455, filed Oct. 27, 2014, which application claims the benefit of and priority to U.S. Provisional Patent Application Nos. 61/896,250, filed Oct. 28, 2013; and 61/914,389, filed on Dec. 11, 2013, the contents of all of which are incorporated herein by reference in their entireties for all purposes.

STATEMENT AS TO RIGHTS TO INVENTIONS MADE UNDER FEDERALLY SPONSORED RESEARCH AND DEVELOPMENT

This invention was made with Government support under Grant No. CA140468, awarded by the National Institutes of Health. The Government has certain rights in the invention.

REFERENCE TO A "SEQUENCE LISTING"

The Sequence Listing written in file SequenceListing_070772-213621US-1161418.txt created on Oct. 14, 2019, 7,892 bytes, machine format IBM-PC, MS-Windows operating system, is hereby incorporated by reference in its entirety for all purposes.

BACKGROUND OF THE INVENTION

Current methods for treating prostate cancer include targeting androgen signaling and also androgen deprivation therapy by administering anti-androgen drugs and androgen antagonists to patients having prostate cancer. While these methods may be initially effective, they often become ineffective once a patient develops castration-resistant prostate cancer (CRPC). To date, CRPC is not curable.

Patients with CRPC and patients whose health does not improve with docetaxel treatments are often treated with drugs such as enzalutamide and abiraterone. However, drug resistance to enzalutamide and abiraterone often develops in patients that have prostate cancer.

Androgen receptor (AR) splice variants are often prevalent in advanced prostate cancer tissue, e.g., tissue from a patient having CRPC and advanced prostate cancer cell lines. These AR variants are generated by aberrant splicing, e.g., alternative mRNA splicing, and premature translation termination. Truncated AR variants drive androgen independent growth. AR also mediates gene expression. AR-V7, an AR variant that lacks the ligand binding domain (LBD) targeted by enzalutamide and abiraterone, is constitutively active in some prostate cancer cells. Because AR-V7 lacks the LBD, it is therefore resistant to LBD targeted treatments, e.g., enzalutamide and abiraterone.

AR variants have also been observed to be up-regulated in CRPC patient samples as compared to androgen sensitive patient samples. As such, AR variants are associated with prostate cancer progression and resistance to AR-targeted therapy. Certain AR variants were observed to induce ligand independent activation of ARE-driven reporters in the absence of androgen, which indicates that those variants may have a distinct transcription program as compared to full length AR. Certain AR variants may interact with the full length AR such that full length AR may mediate the activity of the AR variants.

Interleukin-6 (IL-6) is a pleiotropic cytokine that plays a central role in host defense mechanisms. The biological activities of IL-6 are mediated by the IL6 receptor, which is composed of an IL6-specific receptor subunit and a signal transducer, gp130. The binding of IL-6 to its receptor results in activation of several intracellular signaling cascades including JAK-STAT and MAPK pathways. IL-6 production correlates with tumor progression in certain human cancers, e.g., ovarian and prostate cancers. The serum levels of IL-6 are elevated in many men with advanced, hormone-refractory prostate cancer and are associated with progression and poor prognosis. IL-6 also regulates the expression of genes encoding many steroidogenic enzymes involved in androgen synthesis. Autocrine IL-6 promotes androgen independent growth in prostate cancer cells. Constitutively active STAT3 is a part of the positive autocrine IL-6 loop and STAT3 activation in human tumors is observed at the invasive front of tumors adjacent to inflammatory cells, which may mean that STAT3-dependent tumorigenesis is mediated by IL-6.

Some reports suggest that niclosamide is active against cancer cells but has minimal effects on the viability of normal cells (Pan J X, et al. *Chin J Cancer;* 31(4):178-184; Lu W, et al. *PLoS One;* 6(12):e29290; Park S J, et al. *BMB Rep;* 44(8):517-522; Osada T, et al. *Cancer Res;* 71(12): 4172-4182. 36; Jin Y, et al. *Cancer Res;* 70(6):2516-2527; Guo Z, et al. *Cancer Research* 2009; 69(6):2305-2313). Other reports suggest that niclosamide targets multiple signaling pathways such as STAT3, Nuclear factor-kappa B (NF-κB), Wnt/β-catenin, and Notch pathways (Yo Y T, et al. *Mol Cancer Ther;* 11(8):1703-1712). Niclosamide has also been reported to inhibit cancer cell metastasis and migration in vitro and in vivo (Helfman D M. *J Natl Cancer Inst;* 103(13):991-992; Sack U, et al. *J Natl Cancer Inst;* 103 (13):1018-1036).

There is currently a need for new compositions and methods for treating patients that have CRPC and patients that have anti-androgen drug resistant prostate cancer. Surprisingly, the present invention provides, in part, new compositions and methods for treating these patients as well as for inhibiting prostate cancer cell growth. Several other solutions to other problems in the field are also met by the present invention.

SUMMARY OF THE INVENTION

In one aspect, provided herein is a composition comprising an AR-V7 inhibitor and a compound selected from the group consisting of enzalutamide, abiraterone, docetaxel, bicalutamide, and combinations thereof. The composition can be a pharmaceutical composition and comprise a pharmaceutically acceptable excipient or diluent. In some embodiments, the amount of AR-V7 inhibitor is an amount effective to enhance the therapeutic benefit of a compound selected from the group consisting of bicalutamide, enzalutamide, abiraterone, docetaxel, and combinations thereof. In some embodiments, the composition further comprises an AKR1C3 inhibitor. In some embodiments, the composition is adapted for oral administration to a patient in need of prostate cancer treatment. In some embodiments, the AR-V7 inhibitor is niclosamide.

In a second aspect, the present invention provides a composition comprising an AKR1C3 inhibitor and a compound selected from the group consisting of enzalutamide, abiraterone, docetaxel, bicalutamide, and combinations thereof. The composition can be a pharmaceutical composition and comprise a pharmaceutically acceptable excipient or diluent. In some embodiments, the amount of AKR1C3 inhibitor is an amount effective to enhance the therapeutic benefit of a compound selected from the group consisting of bicalutamide, enzalutamide, abiraterone, docetaxel, and combinations thereof. In some embodiments, the composition further comprises an AR-V7 inhibitor. In some embodiments, the composition is adapted for oral administration to a patient in need of prostate cancer treatment. In some embodiments, the AKR1C3 inhibitor is indomethacin.

In a third aspect, provided herein is a method of treating prostate cancer in a patient, the method comprising administering to the patient an effective amount of an AR-V7 inhibitor, such as niclosamide. In some embodiments, the administration of the AR-V7 inhibitor comprises oral administration.

In a fourth aspect, provided herein is a method of reducing, reversing, or resensitizing prostate cancer cell resistance to anti-androgen drugs or docetaxel, comprising contacting prostate cancer cells with an AR-V7 inhibitor, such as niclosamide.

In a fifth aspect, provided herein is a method of enhancing the therapeutic effects of an anti-androgen drug or docetaxel in a patient having prostate cancer, comprising administering to a patient in need of an anti-androgen drug an effective amount of an AR-V7 inhibitor or an AKR1C3 inhibitor. In some embodiments, the method comprises co-administering to the patient an effective amount of the AR-V7 inhibitor and an effective amount of the AKR1C3 inhibitor. In some embodiments, the prostate cancer is selected from the group consisting of castration-resistant prostate cancer, metastatic castration-resistant prostate cancer, advanced stage prostate cancer, drug-resistant prostate cancer such as anti-androgen-resistant prostate cancer (e.g., enzalutamide-resistant prostate cancer, abiraterone-resistant prostate cancer, bicalutamide-resistant prostate cancer), docetaxel-resistant prostate cancer, AR-V7-induced drug-resistant prostate cancer such as AR-V7-induced enzalutamide-resistant prostate cancer, AKR1C3-induced drug-resistant prostate cancer such as AKR1C3-induced enzalutamide-resistant prostate cancer, and combinations thereof. In some embodiments, the AR-V7 inhibitor, such as niclosamide, or the AKR1C3 inhibitor, such as indomethacin, is administered orally. In some embodiments, the AR-V7 inhibitor, such as niclosamide, and the AKR1C3 inhibitor, such as indomethacin, are co-administered orally.

In some embodiments, the treating comprises reversing or reducing prostate cancer cell resistance to an anti-androgen drug or and/or resensitizing prostate cancer cells to an anti-anti-androgen drug. In some embodiments, the anti-androgen drug is a compound selected from the group consisting of enzalutamide, abiraterone, bicalutamide, and combinations thereof. In some embodiments, the treating comprises reversing or reducing prostate cancer cell resistance to docetaxel and/or resensitizing prostate cancer cells to docetaxel.

In some embodiments, the administering comprises co-administering the AR-V7 inhibitor with a compound selected from the group consisting of enzalutamide, abiraterone, docetaxel, bicalutamide and combinations thereof. In some embodiments, the administering comprises co-administering the AKR1C3 inhibitor with a compound selected from the group consisting of enzalutamide, abiraterone, docetaxel, bicalutamide, and combinations thereof. In some embodiments, the administering comprises co-administering the AR-V7 inhibitor and the AKR1C3 inhibitor. In some embodiments, the AR-V7 inhibitor is niclosamide. In some embodiments, the AKR1C3 inhibitor is indomethacin.

In a sixth aspect, provided herein is a method of inhibiting an androgen receptor (AR) variant, comprising contacting an AR variant with an amount of an AR variant inhibitor. In some embodiments, the AR variant inhibitor is an AR-V7 inhibitor, such as niclosamide. In certain embodiments, the present invention provides a method of inhibiting an AR variant in a cell, comprising contacting the cell with an effective amount of niclosamide. In some embodiments, the AR variant is AR-V7. In some embodiments, the inhibiting comprises inhibiting AR variant transactivation, inhibiting AR variant expression, inhibiting AR variant-induced cell migration, inhibiting AR variant-induced invasion by prostate cancer cells, inhibiting prostate cancer cell colony formation, inhibiting recruitment of an AR variant to a prostate-specific antigen (PSA) promoter, or combinations thereof. In some embodiments, the cell is a prostate cancer cell.

In a seventh aspect, provided herein is a kit comprising an AR variant inhibitor and a compound selected from the group consisting of enzalutamide, abiraterone, docetaxel, bicalutamide, and combinations thereof. In some embodiments, the AR variant inhibitor is an AR-V7 inhibitor. In some embodiments, the AR-V7 inhibitor is niclosamide.

In an eighth aspect, provided herein are methods of inhibiting STAT3, comprising contacting an AR-V7 inhibitor, such as niclosamide, with STAT3.

In a ninth aspect, the present invention provides a method of treating prostate cancer in a patient, the method comprising administering to the patient an effective amount of an AR-V7 inhibitor or an effective amount of an AKR1C3 inhibitor. In some embodiments, the method comprises co-administering to the patient an effective amount of the AR-V7 inhibitor and an effective amount of the AKR1C3 inhibitor. In some embodiments, the prostate cancer is selected from the group consisting of castration-resistant prostate cancer, metastatic castration-resistant prostate cancer, advanced stage prostate cancer, drug-resistant prostate cancer such as anti-androgen-resistant prostate cancer (e.g., enzalutamide-resistant prostate cancer, abiraterone-resistant prostate cancer, bicalutamide-resistant prostate cancer), docetaxel-resistant prostate cancer, AR-V7-induced drug-resistant prostate cancer such as AR-V7-induced enzalutamide-resistant prostate cancer, AKR1C3-induced drug-resistant prostate cancer such as AKR1C3-induced enzalutamide-resistant prostate cancer, and combinations thereof.

In some embodiments, the treating comprises reversing or reducing prostate cancer cell resistance to an anti-androgen drug and/or resensitizing prostate cancer cells to an anti-androgen drug. In some embodiments, the anti-androgen drug is a compound selected from the group consisting of enzalutamide, abiraterone, bicalutamide, and combinations thereof. In some embodiments, the treating comprises reversing or reducing prostate cancer cell resistance to docetaxel and/or resensitizing prostate cancer cells to docetaxel.

In some embodiments, the administering comprises co-administering the AR-V7 inhibitor with a compound selected from the group consisting of enzalutamide, abiraterone, docetaxel, bicalutamide, and combinations thereof. In some embodiments, the administering comprises co-administering the AKR1C3 inhibitor with a compound selected from the group consisting of enzalutamide, abiraterone, docetaxel, bicalutamide, and combinations thereof. In some embodiments, the AKR1C3 inhibitor is indomethacin. In some embodiments, the AR-V7 inhibitor is niclosamide. In some embodiments, the AR-V7 inhibitor, such as niclosamide, or the AKR1C3 inhibitor, such as indomethacin, is administered orally. In some embodiments, the AR-V7 inhibitor, such as niclosamide, and the AKR1C3 inhibitor, such as indomethacin, are co-administered orally.

In a tenth aspect, the present invention provides a method of reducing or reversing prostate cancer cell resistance to a prostate cancer drug, comprising contacting prostate cancer cells with an AR-V7 inhibitor or an AKR1C3 inhibitor. In some embodiments, the method comprises contacting prostate cancer cells with an AR-V7 inhibitor and an AKR1C3 inhibitor. In some embodiments, the prostate cancer drug is an anti-androgen drug. In some embodiments, the anti-androgen drug is a compound selected from the group consisting of enzalutamide, abiraterone, bicalutamide, and combinations thereof. In some embodiments, the prostate cancer drug is docetaxel. In some embodiments, the AKR1C3 inhibitor is indomethacin. In some embodiments, the AR-V7 inhibitor is niclosamide. In some embodiments, the reducing or reversing prostate cancer cell resistance to the prostate cancer drug comprises resensitizing the prostate cancer cells to the prostate cancer drug.

In some embodiments, the reducing or reversing prostate cancer cell resistance to the prostate cancer drug is in a patient having prostate cancer. In some embodiments, the AR-V7 inhibitor or the AKR1C3 inhibitor are contacted with the prostate cancer cells by orally administering the AR-V7 or the AKR1C3 inhibitor to the patient. In some embodiments, the AR-V7 inhibitor and the AKR1C3 inhibitor are co-administered orally. In some embodiments, the prostate cancer is selected from the group consisting of castration-resistant prostate cancer, metastatic castration-resistant prostate cancer, advanced stage prostate cancer, drug-resistant prostate cancer such as anti-androgen-resistant prostate cancer (e.g., enzalutamide-resistant prostate cancer, abiraterone-resistant prostate cancer, bicalutamide-resistant prostate cancer), docetaxel-resistant prostate cancer, AR-V7-induced drug-resistant prostate cancer such as AR-V7-induced enzalutamide-resistant prostate cancer, AKR1C3-induced drug-resistant prostate cancer such as AKR1C3-induced enzalutamide-resistant prostate cancer, and combinations thereof.

In an eleventh aspect, the present invention provides a method of enhancing the therapeutic effects of a prostate cancer drug in a patient having prostate cancer, comprising administering to a patient in need of prostate cancer treatment an effective amount of an AR-V7 inhibitor or an effective amount of an AKR1C3 inhibitor. In some embodiments, the method comprises co-administering to the patient in need of prostate cancer treatment an effective amount of AR-V7 inhibitor and an effective amount of an AKR1C3 inhibitor. In some embodiments, the prostate cancer drug that is enhanced is selected from the group consisting of enzalutamide, abiraterone, docetaxel, bicalutamide, and combinations thereof.

In some embodiments, the prostate cancer drug that is enhanced is an anti-androgen drug. In some embodiments, the anti-androgen drug is selected from the group consisting of enzalutamide, abiraterone, bicalutamide, and combinations thereof. In some embodiments, the AKR1C3 inhibitor is indomethacin. In some embodiments, the AR-V7 inhibitor is niclosamide. In some embodiments, the prostate cancer is selected from the group consisting of castration-resistant prostate cancer, metastatic castration-resistant prostate cancer, advanced stage prostate cancer, drug-resistant prostate cancer such as anti-androgen-resistant prostate cancer (e.g., enzalutamide-resistant prostate cancer, abiraterone-resistant prostate cancer, bicalutamide-resistant prostate cancer), docetaxel-resistant prostate cancer, AR-V7-induced drug-resistant prostate cancer such as AR-V7-induced enzalutamide-resistant prostate cancer, AKR1C3-induced drug-resistant prostate cancer such as AKR1C3-induced enzalutamide-resistant prostate cancer, and combinations thereof. In some embodiments, the AR-V7 inhibitor, such as niclosamide, or the AKR1C3 inhibitor, such as indomethacin, is administered orally. In some embodiments, the AR-V7 inhibitor, such as niclosamide, and the AKR1C3 inhibitor, such as indomethacin, are co-administered orally.

In a twelfth aspect, the present invention provides a kit comprising an AR-V7 inhibitor or an AKR1C3 inhibitor, and a compound selected from the group consisting of enzalutamide, abiraterone, docetaxel, bicalutamide, and combinations thereof. In some embodiments, the kit comprises a label describing a method of administering the AR-V7 inhibitor. For example, the label can describe oral administration of the AR-V7 inhibitor. In some embodiments, the kit comprises a label describing a method of administering the AKR1C3 inhibitor. For example, the label can describe oral administration of the AKR1C3 inhibitor. In some embodiments, the AKR1C3 inhibitor is indomethacin. In some embodiments, the AR-V7 inhibitor is niclosamide. In some embodiments, the AR-V7 inhibitor or the AKR1C3 inhibitor are adapted for oral administration to a patient in need of prostate cancer treatment. In some embodiments, both the AR-V7 inhibitor and the AKR1C3 inhibitor are adapted for oral administration to a patient in need of prostate cancer treatment.

In a thirteenth aspect, the present invention provides a composition comprising an AR-V7 inhibitor and an AKR1C3 inhibitor. In some embodiments, the composition further comprises an anti-androgen drug. For example, the anti-androgen drug can be a compound selected from the group consisting of enzalutamide, abiraterone, bicalutamide, and combinations thereof. In some embodiments, the composition further comprises a compound selected from the group consisting of enzalutamide, abiraterone, docetaxel, bicalutamide, and combinations thereof. In some embodiments, the AR-V7 inhibitor and AKR1C3 inhibitor are present in an amount effective to enhance the therapeutic benefit of one or more of the foregoing other compounds. In some embodiments, the AKR1C3 inhibitor is indomethacin. In some embodiments, the AR-V7 inhibitor is niclosamide. In some embodiments, the composition is adapted for oral administration. In some cases, the composition further comprises a pharmaceutically acceptable excipient.

In a fourteenth aspect, the present invention provides a method of treating prostate cancer, the method comprising administering an AR-V7 inhibitor to a patient having prostate cancer, and sequentially or simultaneously administering an AKR1C3 inhibitor to the patient. In some embodiments, the prostate cancer is selected from the group consisting of castration-resistant prostate cancer, metastatic castration-resistant prostate cancer, advanced stage prostate cancer, drug-resistant prostate cancer such as anti-androgen-resistant prostate cancer (e.g., enzalutamide-resistant prostate cancer, abiraterone-resistant prostate cancer, bicalutamide-resistant prostate cancer), docetaxel-resistant prostate cancer, AR-V7-induced drug-resistant prostate cancer such as AR-V7-induced enzalutamide-resistant prostate cancer, AKR1C3-induced drug-resistant prostate cancer such as AKR1C3-induced enzalutamide-resistant prostate cancer, and combinations thereof. In some embodiments, the AR-V7 inhibitor and AKR1C3 inhibitor are in the same composition. In some embodiments, the AR-V7 inhibitor and the AKR1C3 inhibitor are in different compositions. In some embodiments, the method further comprises administering an anti-androgen drug. For example, the anti-androgen drug can be a compound selected from the group consisting of enzalutamide, abiraterone, bicalutamide, and combinations thereof. In some embodiments, the method further comprises administering to the patient a drug selected from the group consisting of enzalutamide, abiraterone, docetaxel, bicalutamide, and combinations thereof. In some embodiments, the AR-V7 inhibitor or the AKR1C3 inhibitor is administered orally. In some embodiments, the AR-V7 inhibitor and the AKR1C3 inhibitor are co-administered orally. In some embodiments, the AR-V7 inhibitor is niclosamide. In some embodiments, the AKR1C3 inhibitor is indomethacin.

In a fifteenth aspect, the present invention provides a method of inhibiting an aldo-keto reductase 1C3 (AKR1C3) in a cell, comprising contacting the cell with an effective amount of indomethacin. In some embodiments, the inhibiting comprises inhibiting AKR1C3 expression, inhibiting AKR1C3 activity, or combinations thereof. In some embodiments, the cell is a prostate cancer cell.

Other objects, features, and advantages of the present invention will be apparent to one of skill in the art from the following detailed description and figures.

BRIEF DESCRIPTION OF THE DRAWINGS

FIG. 1A shows the results of LNCaP, C4-2, CWR22rv1, and VCaP cells that were cultured in CS-FBS condition for 3 days. AR-V7 mRNA level were analyzed by qRT-PCR. Results are presented as means±SD of 3 experiments performed in duplicate. FIG. 1B shows the results of LNCaP, C4-2, CWR22rv1 and VCaP cells that were cultured in CS-FBS condition for 3 days. Whole cell protein was extracted and immunoblotted with antibody indicated. FIG. 1C shows the results of C4-2 cells that were cultured in CS-FBS condition and transiently transfected with EGFP-AR-V7 plasmid for 3 days. The fluorescence intensity of individual cells were observed under microscope. FIG. 1D shows PC3 cells that were cultured in CS-FBS condition and transiently transfected with WT-AR or AR-V7 plasmid for 3 days followed by treatment with 10 nM DHT for another 24 hours. Whole cell lysates were subjected to luciferase assay. FIG. 1E shows the results of LNCaP cells that were cultured in CS-FBS condition and transiently transfected with vector or AR-V7 plasmid for 3 days followed by treatment with 10 nM DHT for another 24 hours. Whole cell lysates were subjected to luciferase assay. FIG. 1F shows the results of C4-2 neo and C4-2 AR-V7 stable clones that were cultured in CS-FBS condition. AR-V7 mRNA level was determined by qRT-PCR, the AR-V7 expression was detected by western blot (inside panel). FIG. 1G shows the results of C4-2 neo and C4-2 AR-V7 stable clones that were cultured in CS-FBS condition for 3 days. PSA mRNA levels were determined by qRT-PCR. FIG. 1H shows PSA protein levels as determined by PSA ELISA after culturing in CS-FBS for 3 days. Results are presented as means±SD of 3 experiments performed in duplicate. *P<0.05.

FIG. 2A: C4-2 neo, C4-2 AR-V7, CWR22rv1 and PZ-HPV7 cells were treated with 0.5 μM niclosamide in media containing FBS. Cell numbers were counted and cell survival rate was calculated after 48 hours. FIG. 2B: C4-2 neo, C4-2 AR-V7, CWR22rv1 and PZ-HPV7 cells were treated with 0.5 μM niclosamide in media containing FBS. Apoptosis was detected by Cell death ELISA after 48 hours. FIG. 2C: CWR22rv1 cells were treated with 0, 0.5 μM or 1.0 μM niclosamide and clonogenic assays were performed. FIG. 2D: colonies were counted and results are presented as means±SD of 2 experiments performed in duplicate. Niclosamide inhibited colony formation in a dose dependent manner. *P<0.05.

FIG. 3A: CWR22rv1 cells were treated with 0 μM, 0.5 μM or 1.0 μM niclosamide in RPMI 1640 media containing 10% FBS condition overnight and the whole cell lysates were immunoblotted with the indicated antibodies. FIG. 3B: CWR22rv1 cells were treated with 1.0 μM niclosamide in RPMI 1640 media containing 10% FBS condition, whole cell lysates were extracted at different time point and immunoblotted with the indicated antibodies. FIG. 3C: CWR22rv1 cells were treated with 0 μM, 0.5 μM or 1.0 μM niclosamide in RPMI 1640 media containing 10% FBS condition overnight, total RNAs were extracted and AR or AR-V7 mRNA levels were analyzed by qRT-PCR. FIG. 3D: the protein synthesis inhibitor 50 μg/mL cycloheximide (CHX) was added with or without 2 μM niclosamide (Nic) at time 0 hour. At specified time points, cells were harvested, and the levels of AR-V7 protein were measured by Western blot using antibodies specific against AR-V7. FIG. 3E illustrates the effect of MG132 on niclosamide-induced AR protein degradation. MG132 (5 μmol/L) was added to CWR22rv1 cells together with cycloheximide (50 μg/mL) in the presence and absence of 2 μM niclosamide. The cell lysates were prepared at 8 h. AR-V7 protein levels were determined by Western blot analysis using antibodies specifically against AR-V7 and tubulin as a control.

FIG. 4A: 293-AR-V7-PSA luciferase promoter stable clones were treated with 1.0 μM niclosamide or 20 μM enzalutamide overnight in media containing 10% FBS or 10% CS-FBS, whole cell lysates were subjected to luciferase assay. FIG. 4B: LNCaP cells were co-transfected with PSA luciferase promoter with AR-V7 plasmid in CS-FBS condition for 24 hours, followed by treatment with 1.0 μM niclosamide or 200 μM enzalutamide overnight, whole cell lysates were subjected to luciferase assay. FIG. 4C: C4-2 AR-V7 stable cells were transfected with PSA luciferase promoter in CS-FBS condition for 24 hours, followed by treatment with 0.5 μM, 1.0 μM niclosamide or 200 μM enzalutamide with or without 1 nM DHT overnight, whole cell lysates were subjected to luciferase assay. FIG. 4D: C4-2 neo and C4-2 AR-V7 cells were cultured in CS-FBS condition for 3 days, then treated with 1.0 μM niclosamide or 200 μM enzalutamide overnight, the supernatants were collected and subjected to PSA ELISA. Results are presented as means±SD of 3 experiments performed in duplicate. *P<0.05.

FIG. 5A: C4-2B parental cells were treated with 20 μM enzalutamide in RPMI 1640 media containing 10% FBS condition, total cell numbers were counted on different days indicated. FIG. 5B: C4-2B MR cells were treated with 20 μM enzalutamide in RPMI 1640 media containing 10% FBS condition, total cell numbers were counted on different days indicated. FIG. 5C: C4-2B parental cells and C4-2B MR cells were cultured in RPMI 1640 media containing 10% FBS for 3 days, total RNAs were extracted and AR-V1, AR-V7, AR1/2/2b, AR1/2/3/2b or AR full length mRNA level were analyzed by qRT-PCR. FIG. 5D: C4-2B parental cells and C4-2B MR cells were cultured in RPMI 1640 media containing 10% FBS for 3 days, whole cell lysates were immunoblotted with the indicated antibodies. FIG. 5E: C4-2B parental cells and C4-2B MR cells were cultured in media containing 10% CS-FBS for 3 days, the cells were harvested for preparation of cytosolic and nuclear fractions and analyzed by Western blotting using antibodies against AR-V7, AR, polymerase II, or Tubulin. The expression of polymerase II and tubulin were used as markers for the integrity of the nuclear and cytosolic fractions, respectively. FIG. 5F: C4-2B MR cells were cultured in media containing 10% FBS and treated with different concentrations of enzalutamide or niclosamide as indicated, after 48 hours, total cell numbers were counted. FIG. 5G: C4-2B MR cells were treated with 0, 0.5 µM or 1.0 µM niclosamide and clonogenic assays were performed. FIG. 5H: colonies were counted and the results are presented as means±SD of 2 experiments performed in duplicate. Niclosamide inhibited colony formation in a dose dependent manner. *P<0.05.

FIGS. 6A-6G show that niclosamide enhances enzalutamide and abiraterone effects in prostate cancer cells. FIG. 6A: CWR22rv1 cells were treated with 0.25 µM niclosamide with or without 20 µM enzalutamide in media containing FBS and cell numbers were counted after 3 and 5 days. FIG. 6B: CWR22rv1 cells were treated with 0.25 µM niclosamide with or without 20 µM abiraterone in media containing FBS and cell numbers were counted after 3 and 5 days. Results are presented as means±SD of 3 experiments performed in duplicate. FIG. 6C: CWR22rv1 cells were treated with 0.25 µM niclosamide with or without 20 µM enzalutamide or 20 µM abiraterone in media containing FBS and clonogenic assays were performed. FIG. 6D: colonies were counted and results are presented as means±SD of 2 experiments performed in duplicate. FIG. 6E: C4-2B MR cells were treated with 0.25 µM niclosamide with or without 20 µM enzalutamide in media containing FBS and cell numbers were counted after 3 and 5 days. FIG. 6F: C4-2B MR cells were treated with 0.25 µM niclosamide with or without 20 µM enzalutamide in media containing FBS and clonogenic assays were performed. FIG. 6G: colonies were counted and results are presented as means±SD of 2 experiments performed in duplicate. *P<0.05.

FIG. 7A: CWR22rv1 cells were treated with 0.25 µM niclosamide with or without 20 µM enzalutamide or 20 µM abiraterone in media containing FBS, 48 hours later whole cell lysates were extracted and subjected to western blot. FIG. 7B: C4-B MR cells were treated with 0.25 µM niclosamide with or without 20 µM enzalutamide in media containing FBS, 48 hours later, whole cell lysates were extracted and subjected to western blot.

FIG. 8A: CWR22rv1, 293 and 293 GFP AR-V7-PSA promoter luciferase stable clones were cultured in media containing 10% FBS for 2 days. Whole cell lysates were prepared and subjected to Western blot analysis using antibodies as indicated. FIG. 8B: 293 GFP AR-V7-PSA promoter luciferase stable clones were cultured in media containing 10% FBS for 2 days, the fluorescence intensity of individual cells were observed under microscope, the arrow shows an example of AR-V7 protein expression. FIG. 8C: 293 neo and 293 GFP AR-V7-PSA promoter luciferase stable clones were cultured in media containing 10% FBS for 2 days, total RNA was isolated, AR full length and AR-V7 mRNA levels were determined by qRT-PCR. FIG. 8D: different cell numbers of 293 neo and 293 GFP AR-V7-PSA promoter luciferase stable clones were cultured in media containing 10% FBS for 2 days, whole cell lysates were subjected to luciferase assay. Results are presented as means±SD of 3 experiments performed in duplicate. FIG. 8E shows a schematic of the compound screening procedure. *P<0.05.

FIG. 9A: LNCaP cells were co-transfected PSA-E/P-luc or AREI/II-luc with AR V7 plasmid in CS-FBS condition for 3 days followed by treatment with 10 nM DHT with or without 20 µM enzalutamide overnight, whole cell lysates were subjected to luciferase assay. FIG. 9B: C4-2 neo and C4-2 AR-V7 cells were cultured in CS-FBS condition for 3 days followed by treatment with 10 nM DHT with or without 20 µM enzalutamide overnight, whole cell lysates were subjected to ChIP assay. Results are presented as means±SD of 3 experiments performed in duplicate.

FIG. 10A: CWR22rv1 cells were transiently transfected with control siRNA, AR exon7 siRNA or AR V7 siRNA in CS-FBS condition, cell numbers were counted on different days. FIG. 10B: CWR22rv1 cells were transient transfected with control siRNA, AR exon7 siRNA or AR-V7 siRNA in CS-FBS condition for 3 days, the knock down effects were examined by western blot. Results are presented as means±SD of 3 experiments performed in duplicate. *P<0.05.

FIG. 11A CWR22rv1, C4-2B and LNCaP cells were cultured in RPMI 1640 media containing 10% FBS condition, then treated with different doses of abiraterone, total cell numbers were counted and cell survival rate was calculated after 48 hours. FIG. 11B: CWR22rv1 cells were transient transfected with control siRNA, AR exon7 siRNA, AR-V7 siRNA or AR exon7 siRNA plus AR-V7 siRNA in FBS, then treated with 10 µM abiraterone, total cell numbers were counted and cell survival rate were calculated after 48 hours. Results are presented as means±SD of 3 experiments performed in duplicate. *P<0.05.

FIG. 22 shows that niclosamide enhanced the effects of enzalutamide in C4-2B MR cells.

FIG. 26A: LNCaP cells stably expressing IL6 (LNCaP-S17) and control LNCaP cells (LNCaP-neo) were treated with different doses of enzalutamide in media containing complete FBS and cell numbers were counted after 48 h. Results are presented as means±SD of 3 experiments performed in duplicate. FIG. 26B: LNCaP-neo and LNCaP-S17 cells were treated with 0 or 20 µM enzalutamide and clonogenic assays were performed.

FIG. 26C: colonies were counted and presented as means±SD of 2 experiments performed in duplicate. LNCaP-S17 cells formed higher numbers of colonies compared to LNCaP-neo cells when treated with enzalutamide. FIG. 26D: LNCaP-IL6+ cells (continuous culture in medium containing 10% FBS and 5 ng/mL IL-6) and control LNCaP cells were treated with 0, 10 or 20 µM enzalutamide in media containing complete FBS and cell numbers were counted after 48 hours. Results are presented as means±SD of 3 experiments performed in duplicate. *P<0.05.

FIG. 27A: prostate cancer cells with autocrine IL-6 exhibit constitutive activation of STAT3. LNCaP cells and LNCaP-s17 cells were cultured in FBS condition for 24 hours and the lysates were immunoblotted with the indicated antibodies. LNCaP-s17 cells express high levels of c-Myc (FIG. 27B), Survivin (FIG. 27C), IL-6 mRNA (FIG. 27D) and protein (FIG. 27E) compared to LNCaP-neo cells. Total RNAs from LNCaP-neo and LNCaP-S17 cells were analyzed by qRT-PCR. Results are presented as means±SD of 3 experiments performed in duplicate. FIG. 27F: recruitment of AR to AREs in PSA promoter was analyzed by ChIP assay, LNCaP-S17 and LNCaP-STAT3C cells enhanced recruitment of AR to PSA promoter compared to LNCaP-neo cells.

FIG. 28A: downregulation of STAT3 expression increased sensitivity of LNCaP-S17 cells to enzalutamide. LNCaP-s17 cells were transfected with siRNAs specific to STAT3 or control siRNA and were treated with 0 or 20 µM enzalutamide. Cell numbers were counted after 3 days. FIG. 28B: whole cell lysates were collected and subjected to Western blot. Results are presented as means±SD of 3 experiments performed in duplicate. FIG. 28C: LNCaP-neo and LNCaP-STAT3C cells were treated with DMSO, 10 or 20 µM enzalutamide in media containing FBS for 48 hours and cell numbers were counted. Results are presented as means±SD of 3 experiments performed in duplicate. FIG. 28D: recruitment of AR to AREs in PSA promoter was analyzed by ChIP assay. LNCaP-neo, LNCaP-S17 and LNCaP-STAT3C cells were cultured in FBS condition with or without 20 µM enzalutamide overnight, cross-linked with 1% formaldehyde and the resultant DNA-protein complexes were subjected to ChIP assay. * P<0.05

FIG. 29A depicts the chemical structure of niclosamide. FIG. 29B: niclosamide inhibited constitutively active STAT3 in a dose dependent manner in LNCaP-s17 cells. FIG. 29C: LNCaP-s17 cells were treated with 0.25 µM, 0.5 µM niclosamide or 10 µM AG490 combined with or without 20 µM enzalutamide in media containing FBS, cell numbers were counted after 48 h. FIG. 29D: apoptosis was analyzed by Cell death ELISA. Results are presented as means±SD of 3 experiments performed in duplicate. FIG. 29E: LNCaP-s17 cells were treated with 0.25 µM niclosamide with or without 20 µM enzalutamide in media containing FBS and cell numbers were counted after 2, 4 and 7 days. Results are presented as means±SD of 3 experiments performed in duplicate. FIG. 29F: colony formation ability was examined by clonogenic assay, LNCaP-s17 cells were treated with 0.25 µM niclosamide with or without 20 µM enzalutamide, equal numbers of cells were plated in 10 cm plates, the colonies were stained with 0.5% crystal violet after 3 weeks, and colony numbers were counted.

FIG. 41A: niclosamide in combination with bicalutamide inhibits tumor growth in vitro in a dose-dependent manner. FIG. 41B: niclosamide in combination with bicalutamide inhibits tumor growth in vitro in a time-dependent manner. *P<0.05.

FIG. 43A: C4-2B parental and C4-2B MDVR cells were treated with different concentrations of enzalutamide for 48 hours, total cell numbers were counted and cell survival rate was calculated. FIG. 43B: the clonogenic ability of C4-2B parental and C4-2B MDVR cells treated with 10 µM or 20 µM enzalutamide was analyzed. Enzalutamide significantly inhibited clonogenic ability of C4-2B parental cells. FIG. 43C: C4-2B parental and C4-2B MDVR cells were injected orthotopically into the prostates of SCID mice and treated with 25 mg/Kg enzalutamide or vehicle control. Tumors were harvested and weighed at 3 weeks. FIG. 43D: LNCaP, LN-95 and CWR22Rv1 cells were treated with different concentrations of enzalutamide for 2 days, total cell numbers were counted and cell survival rate (%) was calculated. *p<0.05.

FIGS. 44A-44B show that the intracrine androgen synthesis pathway is activated in enzalutamide resistant prostate cancer cells. FIG. 44A: the expression of transcripts encoding genes involved in steroid hormone biosynthesis was analyzed by gene set enrichment. Genes that were regulated 1.3 fold between C4-2B parental cells and C4-2B MDVR cells were enriched and heat map was generated by the Subio platform. FIG. 44B: C4-2B parental cells and C4-2B MDVR cells were cultured in RPMI 1640 media containing 10% FBS for 3 days, total RNAs were extracted and CYP17A1, HSD3B1, HSD3B2, HSD17B3, SRD5A1, AKR1C1/2 or AKR1C3 mRNA levels were analyzed by qRT-PCR. AKR1C3, HSD3B and CYP17A1 protein levels were examined by western blot (right panel).

FIG. 45A: C4-2B parental, C4-2B MDVR, VCaP, CWR22Rv1, LNCaP and LN-95 cells were harvested and whole lysates were subjected to Western blotting. FIG. 45B: AKR1C3 expression level was analyzed by IHC staining in C4-2B parental, C4-2B MDVR and CWR22Rv1 xenografts. FIG. 45C: gene expression analysis using the Oncomine database showing the relative expression levels of AKR1C3 in two datasets comparing normal prostate tissue and prostate cancer. Vanaja: normal, n=8; cancer, n=32. Singh: normal, n=50; cancer, n=52. Data are presented as mean±S.E. of normalized expression units according to Oncomine output (upper). AKR1C3 gene expression analysis using the GEO database in two datasets comparing benign, primary or metastatic prostate cancer. GSE27616: Benign, n=4; primary prostate cancer, n=5; and metastatic prostate cancer, n=4; GSE32269: primary prostate cancer, n=22; and metastatic prostate cancer, n=29. Data were extracted and analyzed by the Subio platform (bottom). FIG. 45D: gene expression analysis using the Oncomine database showed that AKR1C3 expression was correlated with prostate cancer progression and recurrence in two independent datasets (Glinsky and Singh prostate).

FIGS. 46A-46D show that intracrine androgens are up regulated in enzalutamide resistant prostate cancer cells. FIG. 46A: C4-2B parental and C4-2B MDVR cells were cultured in serum free and phenol red free RPMI1640 medium for 5 days, and levels of steroids in the cell extracts were analyzed by LC-MS. Representative testosterone and estradiol chromatograms generated by MassLynx 4.1 software are shown. FIG. 46B: the difference between levels of androgen metabolites in C4-2B parental and C4-2B MDVR cells was analyzed and quantified. FIG. 46C: the represented steroid metabolites between C4-2B parental and C4-2B MDVR cells were quantified. FIG. 46D: the androgen metabolism pathway was up regulated in enzalutamide resistant prostate cancer cells.

FIGS. 47A-47F show that AKR1C3 confers resistance to enzalutamide in prostate cancer cells. FIG. 47A: CWR22Rv1 cells were transiently transfected with control shRNA or AKR1C3 shRNA (#561 and #694), following treatment with 20 µM enzalutamide and cell numbers were determined on 3 days. FIG. 47B: C4-2B MDVR cells were transiently transfected with control shRNA or AKR1C3 shRNA (#561 and #694), following treatment with 20 µM enzalutamide and cell numbers were determined on 3 days. FIG. 47C: CWR22Rv1 or C4-2B MDVR cells were transiently transfected with control shRNA or AKR1C3 shRNA (#561 and #694), cells were collected on 3 or 5 days, and whole cell lysates were subjected to Western blotting. FIG. 47D: LNCaP-neo or LNCaP-AKR1C3 cells were treated with different concentrations of enzalutamide for 2 days, total cell numbers were counted and cell survival rate (%) was calculated. FIG. 47E: LNCaP-neo or LNCaP-AKR1C3 cells were treated with 10 µM enzalutamide and a clonogenic assay was performed, the colony size pictures were taken under a microscope. FIG. 47F: colonies were counted and results are presented as means±SD of 2 experiments performed in duplicate. *p<0.05. Enza: Enzalutamide.

FIG. 48A: CWR22Rv1 cells were treated with 10 μM or 20 μM indomethacin with or without 20 μM enzalutamide for 2 days, total cell numbers were counted (left), and a clonogenic assay was performed, the colony size pictures were taken under a microscope (middle). Colonies were counted and results are presented as means±SD of 2 experiments performed in duplicate (right). FIG. 48B: C4-2B MDVR cells were treated with 10 μM or 20 μM indomethacin with or without 20 μM enzalutamide for 2 days, total cell numbers were counted (left), and a clonogenic assay was performed; the colony size pictures were taken under a microscope (middle). Colonies were counted and results are presented as means±SD of 2 experiments performed in duplicate (right). FIG. 48C: mice bearing CWR22Rv1 xenografts were treated with vehicle control, enzalutamide (25 mg/Kg p.o), Indomethacin (3 mg/Kg i.p) or their combination for 3 weeks, tumor volumes were measured twice weekly and the tumors were collected and weighed. FIG. 48D: IHC staining of Ki67 and H/E staining in each group was performed and quantified. *p<0.05. Enza: Enzalutamide. Indocin: Indomethacin.

DETAILED DESCRIPTION OF THE INVENTION

I. Introduction

Figure 1A:
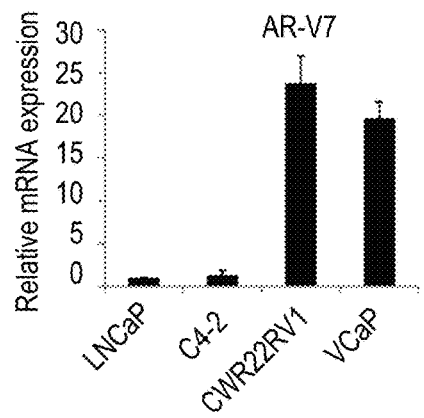
FIGS. 1A-1H show that AR-V7 is constitutively active in prostate cancer cells.

As described herein, the inventors have discovered two new mechanisms of prostate cancer cell growth, survival, or resistance to certain prostate cancer drugs, and methods and compositions for treatment of prostate cancer. In some embodiments, prostate cancer cell growth, survival, or drug resistance is mediated by expression or activity of androgen receptor (AR) variants, such as AR-V7. Accordingly, the present invention provides an inhibitor of AR variant expression or activity. For example, niclosamide is a novel AR variant inhibitor which inhibits prostate cancer cell growth and induces apoptosis. Niclosamide can inhibit drug-resistant prostate cancer cell or tumor growth, or survival. For example, niclosamide can inhibit anti-androgen (e.g., enzalutamide) resistant prostate cancer cell or tumor growth, or survival. Furthermore, niclosamide can exhibit synergistic effects with prostate cancer drugs. For example, niclosamide exhibits synergistic effects with anti-androgen compounds, such as enzalutamide, and can resensitize treatment resistant prostate cancer cells to prostate cancer therapies, such as anti-androgen (e.g., enzalutamide) therapy. Thus, AR-V7 inhibitors, such as niclosamide, are effective and orally bioavailable drugs either as monotherapy or in combination with current prostate cancer therapies, including anti-androgen therapies, for treatment of advanced stage prostate cancer, e.g., metastatic prostate cancer.

In some embodiments, prostate cancer cell growth, survival, or drug resistance is mediated by expression or activity of the enzyme aldo-keto reductase 1C3 (AKR1C3). Accordingly, the present invention provides an inhibitor of AKR1C3 expression or activity. For example, indomethacin is an AKR1C3 inhibitor which can inhibit prostate cancer cell growth or survival, or induce apoptosis. As described herein, AKR1C3 inhibitors can inhibit drug-resistant prostate cancer cell or tumor growth, or survival. For example, AKR1C3 inhibitors can inhibit anti-androgen (e.g., enzalutamide) resistant prostate cancer cell or tumor growth, or survival. Furthermore, AKR1C3 inhibitors can exhibit synergistic effects with other prostate cancer therapies. For example, AKR1C3 inhibitors can exhibit synergistic effects with anti-androgen compounds, such as enzalutamide, and can resensitize treatment resistant prostate cancer cells to anti-androgen (e.g., enzalutamide) therapy. Thus, AKR1C3 inhibitors, such as indomethacin, are effective and orally bioavailable drugs either as monotherapy or in combination with current prostate cancer therapies, including anti-androgen therapies, for treatment of advanced metastatic prostate cancer.

The present invention provides new compositions and methods for treating prostate cancer, e.g., anti-androgen drug-resistant prostate cancer, castration-resistant prostate cancer, or combinations thereof. These new compositions include, but are not limited to, pharmaceutical compositions that include an AR-V7 inhibitor, such as niclosamide, and/or an AKR1C3 inhibitor, such as indomethacin. These new methods include, but are not limited to, methods of administering effective amounts of an AR-V7 inhibitor, such as niclosamide, and/or an AKR1C3 inhibitor, such as indomethacin, to treat patients having prostate cancer. The present invention also provides methods of inhibiting androgen receptor variant expression, e.g. AR-V7, and methods of killing of cells expressing AR-V7. The present invention also provides methods of inhibiting AKR1C3 expression or activity, and methods of killing of cells expressing AKR1C3. The present invention also provides methods of enhancing the efficacy of prostate cancer drugs, including anti-androgen prostate cancer drugs.

II. Definitions

As used herein, the following terms have the meanings ascribed to them unless specified otherwise.

It is noted here that as used in this specification and the appended claims, the singular forms "a," "an," and "the" include plural reference unless the context clearly dictates otherwise.

As used herein, the term "effective amount" includes a dosage sufficient to produce a desired result with respect to the indicated disorder, condition, or mental state. The desired result may comprise a subjective or objective improvement in the recipient of the dosage. For example, an effective amount of an AR-V7 inhibitor (e.g., niclosamide) or an AKR1C3 inhibitor (e.g., indomethacin) includes an amount sufficient to alleviate the signs, symptoms, or causes of prostate cancer, e.g. CRPC. Thus, an effective amount can be an amount that slows or reverses tumor growth, increases mean time of survival, inhibits tumor progression or metastasis, or resensitizes a prostate cancer cell to a prostate cancer drug to which it has become or is resistant. Also, for example, an effective amount of an AR-V7 inhibitor (e.g., niclosamide) or an AKR1C3 inhibitor (e.g., indomethacin) includes an amount sufficient to cause a substantial improvement in a subject having prostate cancer when administered to the subject. The amount will vary with the type of prostate cancer being treated, the stage of advancement of the prostate cancer, the type and concentration of composition applied, and the amounts of anti-androgens drugs that are also administered to the subject. For example, an effective amount of an AR-V7 inhibitor (e.g., niclosamide) or an AKR1C3 inhibitor (e.g., indomethacin) can include an amount that is effective in enhancing the prostate cancer therapeutic activity of drugs such as enzalutamide, abiraterone, docetaxel, and bicalutamide.

As used herein, the term "treating" includes, but is not limited to, methods and manipulations to produce beneficial changes in a recipient's health status, e.g., a patient's prostate cancer status. The changes can be either subjective or objective and can relate to features such as symptoms or signs of the prostate cancer being treated. For example, if the patient notes decreased pain, then successful treatment of pain has occurred. For example, if a decrease in the amount of swelling has occurred, then a beneficial treatment of inflammation has occurred. Similarly, if the clinician notes objective changes, such as reducing the number of prostate cancer cells, the growth of the prostate cancer cells, the size of prostate cancer tumors, or the resistance of the prostate cancer cells to another prostate cancer drug, then treatment of prostate cancer has also been beneficial. Preventing the deterioration of a recipient's status is also included by the term. Treating, as used herein, also includes administering an AR-V7 inhibitor (e.g., niclosamide) or an AKR1C3 inhibitor (e.g., indomethacin) to a patient having prostate cancer.

As used herein, the term "administering" includes activities associated with providing a patient an amount of a compound described herein, e.g., an AR-V7 inhibitor (e.g., niclosamide) or an AKR1C3 inhibitor (e.g., indomethacin). Administering includes providing unit dosages of compositions set forth herein to a patient in need thereof. Administering includes providing effect amounts of compounds, e.g., an AR-V7 inhibitor (e.g., niclosamide) or an AKR1C3 inhibitor (e.g., indomethacin), for specified period of time, e.g., for about 1, 2, 3, 4, 5, 6, 7, 8, 9, 10, 12, 13, 14, 15, 16, 17, 18, 19, 20, 21, 22, 23, 24, 25, 26, 27, 28, 29, 30, or 31 days, or in a specified sequence, e.g., administration of an AR-V7 inhibitor (e.g., niclosamide) or an AKR1C3 inhibitor (e.g., indomethacin) followed by the administration of a compound selected from the group consisting of enzalutamide, abiraterone, docetaxel, bicalutamide, and combinations thereof, or vice versa.

As used herein, the term "co-administering" includes sequential or simultaneous administration of two or more structurally different compounds. For example, two or more structurally different pharmaceutically active compounds can be co-administered by administering a pharmaceutical composition adapted for oral administration that contains two or more structurally different active pharmaceutically active compounds. As another example, two or more structurally different compounds can be co-administered by administering one compound and then administering the other compound. In some instances, the co-administered compounds are administered by the same route. In other instances, the co-administered compounds are administered via different routes. For example, one compound can be administered orally, and the other compound can be administered, e.g., sequentially or simultaneously, via intravenous or intraperitoneal injection.

As used herein, the phrase "advanced stage prostate cancer" or "advanced prostate cancer" includes a class of prostate cancers that has progressed beyond early stages of the disease. Typically, advanced stage prostate cancers are associated with a poor prognosis. Types of advanced stage prostate cancers include, but are not limited to, metastatic prostate cancer, drug-resistant prostate cancer such as anti-androgen-resistant prostate cancer (e.g., enzalutamide-resistant prostate cancer, abiraterone-resistant prostate cancer, bicalutamide-resistant prostate cancer, and the like), hormone refractory prostate cancer, castration-resistant prostate cancer, metastatic castration-resistant prostate cancer, docetaxel-resistant prostate cancer, AR-V7-induced drug-resistant prostate cancer such as AR-V7-induced anti-androgen-resistant prostate cancer (e.g., AR-V7-induced enzalutamide-resistant prostate cancer), AKR1C3-induced drug-resistant prostate cancer such as AKR1C3-induced anti-androgen-resistant prostate cancer (e.g., AKR1C3-induced enzalutamide-resistant prostate cancer), and combinations thereof. In some instances, the advanced stage prostate cancers do not generally respond, or are resistant, to treatment with one or more of the following conventional prostate cancer therapies: enzalutamide, arbiraterone, bicalutamide, and docetaxel. Compounds, compositions, and methods of the present invention are provided for treating prostate cancer, such as advanced stage prostate cancer, including any one or more (e.g., two, three, four, five, six, seven, eight, nine, ten, or more) of the types of advanced stage prostate cancers disclosed herein.

As used herein, the phrase "ameliorating the symptoms of prostate cancer" includes aleviating or improving the symptoms or condition of a patient having prostate cancer. Ameliorating the symptoms includes reducing the pain or discomfort associated with prostate cancer. Amerliorating the symptoms also includes reducing the markers of prostate cancer, e.g., reducing the number of prostate cancer cells or reducing the size of prostate cancer tumors.

As used herein, the phrase "enhancing the therapeutic effects" includes any of a number of subjective or objective factors indicating a beneficial response or improvement of the condition being treated as discussed herein. For example, enhancing the therapeutic effects of an anti-androgen drug (e.g., enzalutamide, abiraterone, or bicalutamide) or docetaxel includes resensitizing anti-androgen drug or docetaxel resistant prostate cancer to anti-androgen or docetaxel therapy. Also, for example, enhancing the therapeutic effects of an anti-androgen drug or docetaxel includes altering anti-androgen drug or docetaxel resistant prostate cancer cells so that the cells are not resistant to anti-androgen drugs or docetaxel. Also, for example, enhancing the therapeutic effects of an anti-androgen drug or docetaxel includes additively or synergistically improving or increasing the activity of the anti-androgen drug or docetaxel. In some embodiments, the enhancement includes a one-fold, two-fold, three-fold, five-fold, ten-fold, twenty-fold, fifty-fold, hundred-fold, or thousand-fold increase in the therapeutic activity of an anti-androgen drug or docetaxel used to treat prostate cancer.

As used herein, the phrase "reversing prostate cancer cell resistance" includes altering or modifying a prostate cancer cell that is resistant to anti-androgen drug or docetaxel therapy so that the cell is no longer resistant to anti-androgen drug or docetaxel therapy.

As used herein, the phrase "reducing prostate cancer cell resistance" includes increasing the therapeutic activity of an anti-androgen drug or docetaxel towards prostate cancer cells that are, or previously were, resistant to anti-androgen drug or docetaxel therapy.

As used herein, the phrase "resensitizing prostate cancer cell resistance" includes inducing sensitization towards anti-androgen drug or docetaxel therapy in prostate cancer cells which are resistant to anti-androgen drug or docetaxel therapy. Sensitization as used herein includes inducing the ability of a prostate cancer cell to be effectively treated with anti-androgen drugs or docetaxel. Sensitization also includes reducing the dosage required to achieve a beneficial effect with anti-androgen drug or docetaxel therapy.

As used herein, the phrase "anti-androgen drug" includes anti-androgen compounds that alter the androgen pathway by blocking the androgen receptors, competing for binding sites on the cell's surface, or affecting or mediating androgen production. Anti-androgens are useful for treating several diseases including, but not limited to, prostate cancer. Anti-androgens include, but are not limited to, enzalutamide, abiraterone, and bicalutamide.

As used herein, the term "androgen receptor" or "AR" includes a nuclear receptor that binds androgenic hormones testosterone or dihydrotestosterone in the cytoplasm and translocates to the nucleus. AR modulates, inter alia, transcription of target genes by binding to Androgen Response Elements (AREs) in the promoters of such target genes.

As used herein, the term "AR variant" includes a splice variant of full-length AR. Various AR variants are known. See, Guo et al., Cancer Res. 2009 Mar. 15; 69(6):2305-13. Exemplary AR variants include, but are not limited to, variants lacking a functional ligand binding domain (LBD). An example of an AR variant that lacks an LBD is AR-V7. "AR-V7" includes androgen receptor splice variant 7, a contituitively active variant of an AR that lacks a functional ligand binding domain (LBD). See, e.g., Hu et al., Cancer Research, 69(1):16-22 (2009).

The term "individual," "subject," or "patient" typically includes humans, but also includes other animals such as, e.g., other primates, rodents, canines, felines, equines, ovines, porcines, and the like.

"Pharmaceutically acceptable" or "therapeutically acceptable" includes a substance which does not interfere with the effectiveness or the biological activity of the active ingredients and which is not toxic to the hosts in the amounts used, and which hosts may be either humans or animals to which it is to be administered.

III. Compositions a. AR-V7 Inhibitors

The present invention relates to AR-V7 inhibitors. In one aspect of this invention, it was suprisingly found that inhibition of AR-V7 can resensitize drug-resistant prostate cancer cells to prostate cancer drugs selected from the group consisting of docetaxel, an anti-androgen drug (e.g., bicalutamide, enzalutamide, and arbiraterone), and combinations thereof. In another aspect of this invention, it was surprisingly found that inhibition of AR-V7 can enhance the effectiveness of prostate cancer drugs selected from the group consisting of docetaxel, an anti-androgen drug (e.g., bicalutamide, enzalutamide, and arbiraterone), and combinations thereof. In yet another aspect of this invention, AR-V7 inhibitors can be administered in combination with AKR1C3 inhibitors.

AR-V7 inhibitors include, but are not limited to, compounds that inhibit AR-V7 transcription, translation, stability, or activity. Inhibition of AR-V7 activity can include inhibition of recruitment of AR-V7 to Androgen Response Elements (AREs). In some embodiments, inhibition of AR-V7 activity can include inhibition of recruitment of AR-V7 to the PSA promoter. In some embodiments, inhibition of AR-V7 activity can include inhibition of AR-V7-induced activation of the PSA promoter. In some embodiments, inhibition of AR-V7 activity can include inhibition of AR-V7-induced PSA production. For example, inhibition of AR-V7 can include inhibition of production of PSA in the absence of DHT.

The present invention also relates to compositions that include an AR-V7 inhibitor and a compound selected from the group consisting of enzalutamide (Xtandi), abiraterone (Zytiga), docetaxel (Taxotere), bicalutamide (Casodex, Cosudex, Calutide, Kalumid), indomethacin, and combinations thereof.

Exemplary AR-V7 inhibitors include, but are not limited to, nucleic acid-based inhibitors. Such nucleic acid based inhibitors of AR-V7 can include, but are not limited to, short hairpin RNAs (shRNAs) or small interfering RNAs (siRNAs) that target AR-V7 mRNA. In some embodiments, nucleic acid analogs can be utilized to target AR-V7 transcription, splicing, or translation. Such nucleic acid analogs include, but are not limited to, antisense phosphorodiamidate morpholino oligonucleotides, locked nucleic acids, or peptide nucleic acids. In some embodiments, exemplary AR-V7 inhibitors include, but are not limited to, LY294002, Wortmanin, and AKT inhibitor II. See, e.g., Mediwala et al., Prostate, 2013 Feb. 15; 73(3):267-77.

Over 1200 FDA approved small molecule drugs were assayed for potential inhibitory activity against AR variants, e.g., AR-V7. Surprisingly, niclosamide significantly down-regulated AR-V7 protein expression in a dose- and time-dependent manner by protein degradation and by way of a proteasome dependent pathway. Thus, AR-V7 inhibitors can include niclosamide.

Accordingly, the present invention provides compositions and methods for administering an AR-V7 inhibitor, such as niclosamide, to inhibit AR variant activity, such as AR-V7 transcription activity. The present invention also provides compositions and methods for reducing the recruitment of AR variants, such as AR-V7, to the PSA promoter. The present invention also provides compositions and methods for administering an AR-V7 inhibitor, such as niclosamide, to inhibit prostate cancer cell growth, or induce prostate cancer cell death, by targeting AR variant signaling.

The present invention also provides compositions and methods for administering an AR-V7 inhibitor, such as niclosamide, to inhibit prostate cancer cell growth, or induce prostate cancer cell death, by overcoming drug resistance, e.g., enzalutamide, bicalutamide, or abiraterone-resistance, in prostate cancer cells. The present invention further provides compositions comprising an AR-V7 inhibitor, such as niclosamide, alone or in combination with prostate cancer therapies, such as anti-androgen therapies, enzalutamide-based therapies, bicalutamide-based therapies, abiraterone-based therapies, docetaxel-based therapies, indomethacin-based therapies, or combinations thereof.

The present invention also provides such compositions which are tailored for patients having advanced stage prostate cancer, such as drug-resistant prostate cancer, metastatic prostate cancer, castration-resistant prostate cancer, or combinations thereof. The present invention additionally provides compositions including an AR-V7 inhibitor, such as niclosamide, which are tailored for patients with prostate cancer that is resistant to known prostate cancer treatments such as enzalutamide, bicalutamide, abiraterone, or docetaxel. The present invention additionally provides compositions containing an AR-V7 inhibitor, such as niclosamide, that provide an unexpected synergistic or additive effect on prostate cancer cells when used in combination with enzalutamide, bicalutamide, abiraterone, docetaxel, indomethacin, or combinations thereof.

Additionally, the present invention provides compositions and methods for inhibiting AR-V7 protein expression by protein degradation via the proteasome dependent pathway. Based on the assays set forth herein, AR variants such as AR-V7 were observed to induce enzalutamide and abiraterone resistance in prostate cancer cells. Furthermore, the compositions including an AR-V7 inhibitor, such as niclosamide, as well as the methods set forth herein are suitable for inhibiting AR activity, such as AR-V7 transcription activity. The compositions including an AR-V7 inhibitor, such as niclosamide, as well as the methods set forth herein are suitable for reducing AR variant, e.g., AR-V7, recruitment to the prostate specific antigen (PSA) promoter. By inhibiting AR-V7, for example, the compositions and methods set forth herein are suitable for treating enzalutamide- or abiraterone-resistant prostate cancer, or a combination thereof.

In some embodiments, the present invention provides a composition including an AR-V7 inhibitor, such as niclosamide, and a compound selected from the group consisting of enzalutamide, abiraterone, docetaxel, bicalutamide, indomethacin, and combinations thereof.

In some of the aforementioned embodiments, the amount of an AR-V7 inhibitor, such as niclosamide, is an amount effective to enhance the therapeutic benefit of a compound selected from the group consisting of bicalutamide, enzalutamide, abiraterone, docetaxel, and indomethacin. In certain embodiments, the compound is enzalutamide. In certain other embodiments, the compound is abiraterone. In certain other embodiments, the compound is docetaxel. In certain other embodiments, the compound is bicalutamide. In certain other embodiments, the compound is indomethacin.

In some of the compositions described herein, the composition includes both an AR-V7 inhibitor, such as niclosamide, and enzalutamide. In some other compositions described herein, the composition includes an AR-V7 inhibitor, such as niclosamide, and abiraterone. In some compositions described herein, the composition includes an AR-V7 inhibitor, such as niclosamide, and docetaxel. In yet other compositions described herein, the composition includes an AR-V7 inhibitor, such as niclosamide, and bicalutamide. In yet other compositions described herein, the composition includes both an AR-V7 inhibitor, such as niclosamide, and an AKR1C3 inhibitor, such as indomethacin.

Described herein is the AR-V7 inhibitor niclosamide. Niclosamide is a Food and Drug Administration (FDA) approved drug effective against human tapeworms. The chemical structure of niclosamide is set forth below:

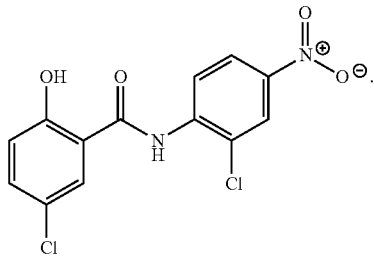 [SMILES: O=C(Nc1ccc([N+](=O)[O-])cc1Cl)c1cc(Cl)ccc1O]

The chemical name of niclosamide is (5-chloro-N-2chloro-4-nitro-phenyl)-2-hydroxybenzamide.

As used herein, the term "niclosamide" includes analogs and derivatives thereof, including pro-drugs that are converted to niclosamide or an analog or derivative thereof in a subject to which it is administered. See, e.g., Ulrike Sack et al., *J. Natl. Cancer Inst.*, July 6; 103(13):1018-36 (2011); and International Patent Publication No. WO 2012/143377. Exemplary niclosamide analogs include, but are not limited to, compounds 50643-F/1; 69360-X/1; 82020-K/D2; 111338-C/1; 164315-M/2; and 306664-O/1 as described in Sack et al., 2011. The term "niclosamide" also includes salts, such as pharmaceutically acceptable salts, of niclosamide. Niclosamide salts can include, but are not limited to, niclosamide ethanolamine salt, niclosamide methanol solvate, and niclosamide hydrate. The term "niclosamide" also includes nanoparticle packaged niclosamide formulations, such as those described in Ye et al., *Drug Dev. Ind. Pharm.*, September 10:1-9 (2014).

b. Aldo-keto Reductase 1C3 (AKR1C3) Inhibitors

The present invention also relates to compositions containing inhibitors of aldo-keto reductase 1C3 (AKR1C3), an enzyme that catalyzes the conversion of the weak androgen precursors 4-androstene-3,17-dione ($\Delta^4$-AD) and 5α-androstane-3,17-dione to the potent androgens testosterone and 5α-dihydrotestosterone (DHT), respectively. As described herein, AKR1C3 activation can confer resistance to therapeutic treatments commonly employed against prostate cancer cells. For example, AKR1C3 activation can confer resistance to bicalutamide, enzalutamide, or abiraterone. Accordingly, inhibitors of AKR1C3 transcription, translation, protein stability, or enzymatic activity can reduce, reverse, or eliminate drug resistance in prostate cancer cells.

Exemplary AKR1C3 inhibitors include, but are not limited to, nucleic acid-based inhibitors. Such nucleic acid based inhibitors of AKR1C3 include, but are not limited to, short hairpin RNAs (shRNAs) or small interfering RNAs (siRNAs) that target AKR1C3 mRNA. In some embodiments, nucleic acid analogs can be utilized to target AKR1C3 transcription, splicing, or translation. Such nucleic acid analogs include, but are not limited to, antisense phosphorodiamidate morpholino oligonucleotides, locked nucleic acids, or peptide nucleic acids.

In some embodiments, the inhibitor of AKR1C3 is indomethacin. Indomethacin is a Food and Drug Administration (FDA) approved Non-Steroidal Anti-Inflammatory Drug (NSAID) that can reduce fever, pain, stiffness, and swelling by inhibition of prostaglandin production. Indomethacin is also an inhibitor of androgen biosynthesis. In some embodiments, indomethacin inhibits AKR1C3.

The chemical structure of indomethacin, also known as indocin or indometacin, is set forth below:

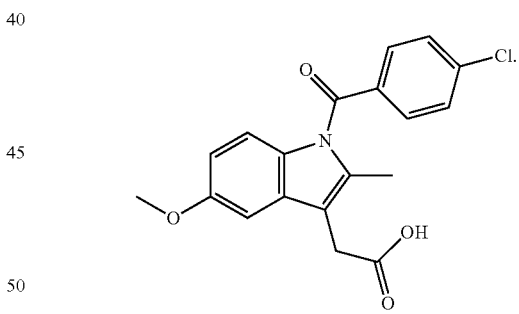

The chemical name of indomethacin is 2-{1-[(4-Chlorophenyl)carbonyl]-5-methoxy-2-methyl-1H-indol-3-yl}acetic acid. As used herein, the term "indomethacin" includes analogs and derivatives thereof, including pro-drugs that are converted to indomethacin or an analog or derivative thereof in a subject to which it is administered. In some embodiments, the indomethacin derivatives can include any of the derivatives described in Liedtke et al., *J Med Chem.*, 2013 Mar. 28; 56(6):2429-46.

Additional exemplary AKR1C3 inhibitors include, but are not limited to, ASP9521; 4-methyl(de-dimethylamine)-tetracycline; baccharin; stylopine; flufenamic acid; 3-((4'-(trifluoromethyl)phenyl)amino)benzoic acid; SN33638; N-(4-chlorobenzoyl)-melatonin; 3-(3,4-dihydroisoquinolin-2 (1H)-ylsulfonyl)benzoic acid, 3-(4'-(nitronaphthalen-1- amino))benzoic acid, and salts, analogs, or derivatives thereof. Exemplary AKR1C3 inhibitors can further include, but are not limited to, any of the AKR1C3 inhibitor compounds described in Khanim et al., Br J Cancer. 2014 Mar. 18; 110(6):1506-16; Liedtke et al., J Med Chem. 2013 Mar. 28; 56(6):2429-46; Adeniji et al., Endocr. Rev. 2012, 33, SAT-537; Adeniji et al., J Med Chem. 2012 Mar. 8; 55(5): 2311-23; Adeniji et al., Bioorg Med Chem Lett. 2011 Mar. 1; 21(5):1464-8; Chen et al., Bioorg Med Chem Lett. 2012 May 15; 22(10):3492-7; Endo et al., J Nat Prod. 2012 Apr. 27; 75(4):716-21; Jamieson et al., J Med Chem. 2012 Sep. 13; 55(17):7746-58; Sinreih et al., Bioorg Med Chem Lett. 2012 Sep. 15; 22(18):5948-51; Brožič et al., J Med Chem. 2012 Sep. 13; 55(17):7417-24; Bauman et al., Mol Pharmacol. 2005 January; 67(1):60-8; Yin et al. Front Oncol (2014) 4:159; Skarydova et al., J Steroid Biochem Mol Biol. 2014 September; 143:250-8; and International Patent Application Publication WO 2013/142390.

The present invention also relates to compositions that include an AKR1C3 inhibitor, such as indomethacin or a derivative thereof, and a compound selected from the group consisting of enzalutamide (Xtandi), abiraterone (Zytiga), docetaxel (Taxotere), bicalutamide (Casodex, Cosudex, Calutide, Kalumid), niclosamide, and combinations thereof.

The present invention also provides compositions and methods for administering an AKR1C3 inhibitor, such as indomethacin, to inhibit prostate cancer cell growth or induce prostate cancer cell death. The present invention also provides compositions and methods for administering indomethicin to inhibit prostate cancer cell growth by overcoming or reducing bicalutamide, enzalutamide, or abiraterone-resistance in prostate cancer cells. The present invention further provides compositions of indomethacin, alone or in combination with current anti-androgen therapies. The present invention also provides such compositions which are tailored for patients having advanced stage prostate cancer, such as drug-resistant prostate cancer, metastatic prostate cancer, castration-resistant prostate cancer, or combinations thereof. The present invention additionally provides compositions including an AKR1C3 inhibitor such as indomethacin which are tailored for patients with prostate cancer that is resistant to known prostate cancer treatments such as enzalutamide, abiraterone, or docetaxel. The present invention additionally provides compositions containing an AK1RC3 inhibitor, such as indomethacin, that provide an unexpected synergistic or additive effect on prostate cancer cells when used in combination with enzalutamide, bicalutamide, abiraterone, docetaxel, niclosamide, or combinations thereof. In some embodiments, the present invention provides a composition including an AKR1C3 inhibitor, such as indomethacin, and a compound selected from the group consisting of enzalutamide, abiraterone, docetaxel, bicalutamide, niclosamide, and combinations thereof.

In some of the aforementioned embodiments, the amount of AKR1C3 inhibitor, e.g., indomethacin, is an amount effective to enhance the therapeutic benefit of a compound selected from the group consisting of enzalutamide, abiraterone, bicalutamide, niclosamide, and docetaxel. In certain embodiments, the compound is enzalutamide. In certain other embodiments, the compound is abiraterone. In certain other embodiments, the compound is docetaxel. In certain other embodiments, the compound is bicalutamide. In certain other embodiments, the compound is niclosamide.

In some of the compositions described herein, the composition includes both an AKR1C3 inhibitor, such as indomethacin, and enzalutamide. In some other compositions described herein, the composition includes both an AKR1C3 inhibitor, such as indomethacin, and abiraterone. In some compositions described herein, the composition includes, both an AKR1C3 inhibitor, such as indomethacin, and docetaxel. In yet other compositions described herein, the composition includes both an AKR1C3 inhibitor, such as indomethacin, and bicalutamide. In yet other compositions described herein, the composition includes both an AKR1C3 inhibitor, such as indomethacin, and an AR-V7 inhibitor, such as niclosamide.

In any of the compositions described herein, the composition may further include a pharmaceutically acceptable excipient or diluent.

IV. Pharmaceutical Compositions

The pharmaceutical compositions of the present invention encompass compositions made by admixing an AR-V7 inhibitor, such as niclosamide, and a pharmaceutically acceptable carrier and/or excipient or diluent. Such compositions are suitable for pharmaceutical use in an animal or human.

The pharmaceutical compositions of the present invention also encompass compositions made by admixing an AKR1C3 inhibitor, such as indomethacin, and a pharmaceutically acceptable carrier and/or excipient or diluent. Such compositions are suitable for pharmaceutical use in an animal or human.

The pharmaceutical compositions of the present invention may be prepared by any of the methods well-known in the art of pharmacy. Pharmaceutically acceptable carriers suitable for use with the present invention include any of the standard pharmaceutical carriers, buffers and excipients, including phosphate-buffered saline solution, water, and emulsions (such as an oil/water or water/oil emulsion), and various types of wetting agents and/or adjuvants. Suitable pharmaceutical carriers and their formulations are described in Remington's Pharmaceutical Sciences (Mack Publishing Co., Easton, 19th ed. 1995). Preferred pharmaceutical carriers depend upon the intended mode of administration of the active agent.

The pharmaceutical compositions of the present invention can include drug, e.g., enzalutamide, abiraterone, docetaxel, bicalutamide, an AKR1C3 inhibitor (e.g., indomethacin), or an AR-V7 inhibitor (e.g., niclosamide), or any pharmaceutically acceptable salts thereof, as an active ingredient and a pharmaceutically acceptable carrier and/or excipient or diluent. In some embodiments, the pharmaceutical composition can include an AKR1C3 inhibitor, such as indomethacin, and an AR-V7 inhibitor, such as niclosamide. A pharmaceutical composition may optionally contain other therapeutic ingredients.

The compounds of the present invention can be combined as the active ingredient in intimate admixture with a suitable pharmaceutical carrier and/or excipient according to conventional pharmaceutical compounding techniques. Any carrier and/or excipient suitable for the form of preparation desired for administration is contemplated for use with the compounds disclosed herein.

The compositions include compositions suitable for topical, parenteral, pulmonary, nasal, rectal, or oral administration. The most suitable route of administration in any given case will depend in part on the nature and severity of the prostate cancer condition and also optionally the stage of the prostate cancer.

Other preferred compositions include compositions suitable for systemic (enteral or parenteral) administration. Systemic administration includes oral, rectal, sublingual, or sublabial administration. In some embodiments, the compositions may be administered via a syringe or intravenously.

Compositions for pulmonary administration include, but are not limited to, dry powder compositions consisting of the powder of a compound described herein, or a salt thereof, and the powder of a suitable carrier and/or lubricant. The compositions for pulmonary administration can be inhaled from any suitable dry powder inhaler device known to a person skilled in the art.

Compositions for systemic administration include, but are not limited to, dry powder compositions consisting of the composition as set forth herein and the powder of a suitable carrier and/or excipient. The compositions for systemic administration can be represented by, but not limited to, tablets, capsules, pills, syrups, solutions, and suspensions.

In some embodiments, the present invention provides compositions further including a pharmaceutical surfactant. In other embodiments, the present invention provides compositions further including a cryoprotectant. In some embodiments, the cryoprotectant is selected from the group consisting of glucose, sucrose, trehalose, lactose, sodium glutamate, PVP, HPβCD, CD, glycerol, maltose, mannitol, and saccharose.

In some embodiments, the present invention provides a pharmaceutical composition including an AR-V7 inhibitor, such as niclosamide, or an AKR1C3 inhibitor, such as indomethacin, and a pharmaceutically acceptable excipient. In some embodiments, the present invention provides a pharmaceutical composition including an AR-V7 inhibitor, such as niclosamide, and an AKR1C3 inhibitor, such as indomethacin, in combination with a pharmaceutically acceptable excipient. In some of these embodiments, the pharmaceutically acceptable excipient includes a salt or a diluent.

In some embodiments, the present invention provides compositions including an effective amount of an AR-V7 inhibitor, such as niclosamide, or an AKR1C3 inhibitor, such as indomethacin. In some embodiments, the composition is formulated for oral administration or intravenous administration and includes an AR-V7 inhibitor, such as niclosamide, or an AKR1C3 inhibitor, such as indomethacin, and at least one member selected from the group consisting of an aqueous solution and a buffer solution. In some embodiments, the composition can include both an AR-V7 inhibitor, such as niclosamide, and an AKR1C3 inhibitor, such as indomethacin.

Pharmaceutical compositions or medicaments for use in the present invention can be formulated by standard techniques using one or more physiologically acceptable carriers or excipients. Suitable pharmaceutical carriers are described herein and in Remington: The Science and Practice of Pharmacy, 21st Ed., University of the Sciences in Philadelphia, Lippencott Williams & Wilkins (2005).

Controlled release parenteral formulations of the compositions of the present invention can be made as implants, oily injections, or as particulate systems. For a broad overview of delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles.

Polymers can be used for ion-controlled release of compositions of the present invention. Various degradable and nondegradable polymeric matrices for use in controlled drug delivery are known in the art (Langer R., Accounts Chem. Res., 26:537-542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin 2 and urease (Johnston et al., Pharm. Res., 9:425-434 (1992); and Pec et al., J. Parent. Sci. Tech., 44(2):58 65 (1990)). Alternatively, hydroxyapatite has been used as a microcarrier for controlled release of proteins (Ijntema et al., Int. J. Pharm., 112:215-224 (1994)). In yet another aspect, liposomes are used for controlled release as well as drug targeting of the lipid-capsulated drug (Betageri et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

V. Methods of Treating Prostate Cancer

In some embodiments, the present invention provides a method of treating prostate cancer in a patient (e.g., advanced stage prostate cancer), wherein the method comprises administering to the patient an effective amount of an AR-V7 inhibitor, such as niclosamide, an AKR1C3 inhibitor, such as indomethacin, or a combination thereof. In some of these embodiments, the prostate cancer is advanced stage prostate cancer, such as any one or more of the types of advanced staged prostate cancers disclosed herein. In some of these embodiments, the prostate cancer is drug resistant. In some of these embodiments, the prostate cancer is anti-androgen drug resistant. In some of these embodiments, the prostate cancer is metastatic. In some of these embodiments, the prostate cancer is metastatic and drug resistant (e.g., anti-androgen drug resistant). In some of these embodiments, the prostate cancer is castration resistant. In some of these embodiments, the prostate cancer is metastatic and castration resistant. In some of these embodiments, the prostate cancer is enzalutamide resistant. In some of these embodiments, the prostate cancer is enzalutamide and arbiraterone resistant. In some of these embodiments, the prostate cancer is enzalutamide, arbiraterone, and bicalutamide resistant. In some of these embodiments, the prostate cancer is docetaxel resistant. In some of these embodiments, the prostate cancer is enzalutamide, arbiraterone, bicalutamide, and docetaxel resistant.

In some embodiments, the treating comprises inhibiting prostate cancer cell growth; inhibiting prostate cancer cell migration; inhibiting prostate cancer cell invasion; ameliorating the symptoms of prostate cancer; reducing the size of a prostate cancer tumor; reducing the number of prostate cancer tumors; reducing the number of prostate cancer cells; inducing prostate cancer cell necrosis, pyroptosis, oncosis, apoptosis, autophagy, or other cell death; or enhancing the therapeutic effects of a compound selected from the group consisting of enzalutamide, abiraterone, docetaxel, bicalutamide, and combinations thereof.

In some methods of treating prostate cancer, described herein, the treating comprises inhibiting prostate cancer cell growth. In some methods of treating prostate cancer, described herein, the treating comprises inhibiting prostate cancer cell migration. In some methods of treating prostate cancer, described herein, the treating comprises inhibiting prostate cancer cell invasion. In some methods of treating prostate cancer, described herein, the treating comprises ameliorating the symptoms of prostate cancer. In some methods of treating prostate cancer, described herein, the treating comprises reducing the size of a prostate cancer tumor. In some methods of treating prostate cancer, described herein, the treating comprises reducing the number of prostate cancer tumors. In some methods of treating prostate cancer, described herein, the treating comprises reducing the number of prostate cancer cells. In some methods of treating prostate cancer, described herein, the treating comprises inducing prostate cancer cell necrosis, pyroptosis, oncosis, apoptosis, autophagy, or other cell death.

In particular methods of treating prostate cancer, described herein, the treating comprises enhancing the therapeutic effects of a compound selected from the group consisting of enzalutamide, abiraterone, docetaxel, bicalutamide, and combinations thereof. In certain embodiments, the treating comprises enhancing the therapeutic effects of enzalutamide. In certain other embodiments, the treating comprises enhancing the therapeutic effects of abiraterone. In yet other embodiments, the treating comprises enhancing the therapeutic effects of docetaxel. In some other embodiments, the treating comprises enhancing the therapeutic effects of bicalutamide. The enhancement can be synergistic or additive.

In certain embodiments of the methods set forth herein, the treating comprises reversing, or reducing prostate cancer cell resistance to anti-androgen drugs. In certain embodiments of the methods set forth herein, the treating comprises resensitizing prostate cancer cells to anti-androgen drugs. In any of the methods described herein, the anti-androgen drug is a compound selected from the group consisting of enzalutamide, abiraterone, docetaxel, bicalutamide, and combinations thereof. In certain embodiments, the anti-androgen drug is enzalutamide.

In any of the aforementioned methods, the treating may comprise reversing prostate cancer cell resistance to enzalutamide; reducing prostate cancer cell resistance to enzalutamide; or resensitizing prostate cancer cells to enzalutamide. In some embodiments, the treating comprises reversing prostate cancer cell resistance to enzalutamide. In some other embodiments, the treating comprises reducing prostate cancer cell resistance to enzalutamide. In yet other embodiments of the present invention, the treating comprises resensitizing prostate cancer cells to enzalutamide.

In some embodiments set forth herein, the treating comprises reversing prostate cancer cell resistance to docetaxel. In some other embodiments, the treating comprises reducing prostate cancer cell resistance to docetaxel. In yet other embodiments, the treating comprises resensitizing prostate cancer cells to docetaxel.

In some embodiments set forth herein, the treating comprises reversing prostate cancer cell resistance to abiraterone. In some other embodiments set forth herein, the treating comprises reducing prostate cancer cell resistance to abiraterone. In yet other embodiments set forth herein, the treating comprises resensitizing prostate cancer cells to abiraterone.

In any of the methods described herein, the prostate cancer is selected from the group consisting of castration-resistant prostate cancer, metastatic castration-resistant prostate cancer, advanced stage prostate cancer, drug-resistant prostate cancer, anti-androgen-resistant prostate cancer, bicalutamide resistant prostate cancer, enzalutamide-resistant prostate cancer, abiraterone-resistant prostate cancer, docetaxel-resistant prostate cancer, AR-V7- or AKR1C3-induced drug-resistant prostate cancer, AR-V7- or AKR1C3-induced anti-androgen drug-resistant prostate cancer, AR-V7- or AKR1C3-induced enzalutamide-resistant prostate cancer, and combinations thereof.

In some embodiments of the present invention, the prostate cancer is castration-resistant prostate cancer. In other embodiments, the prostate cancer is metastatic castration-resistant prostate cancer. In still other embodiments, the prostate cancer is advanced stage prostate cancer. In other embodiments, the prostate cancer is anti-androgen-resistant prostate cancer. In some other embodiments, the prostate cancer is enzalutamide-resistant prostate cancer. In yet other embodiments, the prostate cancer is abiraterone-resistant prostate cancer. In some other embodiments, the prostate cancer is docetaxel-resistant prostate cancer. In certain other embodiments, the prostate cancer is AR-V7- or AKR1C3-induced enzalutamide-resistant prostate cancer. In some embodiments, the prostate cancer is a combination of one, two, three, four, five, six, seven, eight, nine, ten, or more of the foregoing types of prostate cancer.

The methods of treating prostate cancer may comprise co-administering an AR-V7 inhibitor, such as niclosamide, with a compound selected from the group consisting of enzalutamide, abiraterone, docetaxel, bicalutamide, an AKR1C3 inhibitor, such as indomethacin, and combinations thereof. The methods of treating prostate cancer may additionally or alternatively comprise co-administering an AKR1C3 inhibitor, such as indomethacin, with a compound selected from the group consisting of enzalutamide, abiraterone, docetaxel, bicalutamide, niclosamide, and combinations thereof.

Some embodiments of the present invention include methods for treating enzalutamide-resistant and abiraterone-resistant prostate cancer that comprise administering an AR-V7 inhibitor, such as niclosamide, an AKR1C3 inhibitor, such as indomethacin, or a combination thereof, to a patient having enzalutamide-resistant or abiraterone-resistant prostate cancer.

VI. Methods of Inhibiting Prostate Cancer Cells

In some embodiments, the present invention provides a method for inhibiting androgen receptor splice variants in a cell, wherein the method comprises contacting the cell or the androgen receptor splice variant with an amount of an AR variant inhibitor, such as niclosamide. In certain embodiments, the variants are AR-V7 splice variants. In certain embodiments, the amount is an effective amount. In certain embodiments, the cell is a prostate cancer cell, such as a castration-resistant prostate cancer cell, an anti-androgen-resistant (e.g., enzalutamide-resistant) prostate cancer cell, or a combination thereof.

In some embodiments, the present invention provides a method for inhibiting STAT3 activation in a cell, wherein the method comprises contacting the cell or STAT3 with an amount of an AR-V7 inhibitor. In some embodiments, the amount is an effective amount. In some embodiments, the AR-V7 inhibitor is niclosamide or an analog or derivative thereof. In certain embodiments, the cell is a prostate cancer cell, such as a castration-resistant prostate cancer cell, an anti-androgen-resistant (e.g., enzalutamide-resistant) prostate cancer cell, or a combination thereof.

In some embodiments, the present invention provides a method for inhibiting IL-6 signalling in a cell, wherein the method comprises contacting the cell or STAT3 with an amount of an AR-V7 inhibitor. In some embodiments, the amount is an effective amount. In some embodiments, the AR-V7 inhibitor is niclosamide or an analog or derivative thereof. In certain embodiments, the cell is a prostate cancer cell, such as a castration-resistant prostate cancer cell, an anti-androgen-resistant (e.g., enzalutamide-resistant) prostate cancer cell, or a combination thereof.

In some embodiments, the present invention provides a method for inhibiting AKR1C3 in a cell, wherein the method comprises contacting the cell or AKR1C3 with an amount of an AKR1C3 inhibitor. In some embodiments, the amount is an effective amount. In some embodiments, the AKR1C3 inhibitor is indomethacin or an analog or derivative thereof. In certain embodiments, the cell is a prostate cancer cell, such as a castration-resistant prostate cancer cell, an anti-androgen-resistant (e.g., enzalutamide-resistant) prostate cancer cell, or a combination thereof.

In some embodiments, the present invention provides a method for inhibiting prostate cancer cell growth, wherein the method comprises contacting prostate cancer cells with an AR-V7 inhibitor, such as niclosamide, or an AKR1C3 inhibitor, such as indomethacin, and optionally one or more compounds selected from the group consisting of enzalutamide, abiraterone, docetaxel, and bicalutamide.

In some other embodiments, the present invention provides a method for inhibiting prostate cancer cell migration, wherein the method comprises contacting prostate cancer cells with an AR-V7 inhibitor, such as niclosamide, or an AKR1C3 inhibitor, such as indomethacin, and optionally one or more compounds selected from the group consisting of enzalutamide, abiraterone, docetaxel, and bicalutamide.

In some embodiments, the present invention provides a method for inhibiting prostate cancer cell invasion, wherein the method comprises contacting prostate cancer cells with an AR-V7 inhibitor, such as niclosamide, or an AKR1C3 inhibitor, such as indomethacin, and optionally one or more compounds selected from the group consisting of enzalutamide, abiraterone, docetaxel, and bicalutamide.

In some embodiments, the present invention provides a method for reversing prostate cancer cell resistance to anti-androgen drugs, wherein the method comprises contacting prostate cancer cells with an AR-V7 inhibitor, such as niclosamide, or an AKR1C3 inhibitor, such as indomethacin. In some embodiments, the present invention provides a method for reversing prostate cancer cell resistance to anti-androgen drugs, wherein the method comprises contacting prostate cancer cells with an AR-V7 inhibitor, such as niclosamide, and an AKR1C3 inhibitor, such as indomethacin. In certain embodiments, the amount is an effective amount.

In some embodiments, the present invention provides a method for reversing prostate cancer cell resistance to enzalutamide, wherein the method comprises contacting prostate cancer cells with an AR-V7 inhibitor, such as niclosamide, or an AKR1C3 inhibitor, such as indomethacin. In some embodiments, the present invention provides a method for reversing prostate cancer cell resistance to enzalutamide, wherein the method comprises contacting prostate cancer cells with an AR-V7 inhibitor, such as niclosamide, and an AKR1C3 inhibitor, such as indomethacin. In certain embodiments, the amount is an effective amount.

In some embodiments, the present invention provides a method for reversing prostate cancer cell double resistance to enzalutamide and abiraterone, wherein the method comprises contacting prostate cancer cells with an AR-V7 inhibitor, such as niclosamide, or an AKR1C3 inhibitor, such as indomethacin. In some embodiments, the present invention provides a method for reversing prostate cancer cell double resistance to enzalutamide and abiraterone, wherein the method comprises contacting prostate cancer cells with an AR-V7 inhibitor, such as niclosamide, and an AKR1C3 inhibitor, such as indomethacin. In certain embodiments, the amount is an effective amount.

In some embodiments, the present invention provides a method for resensitizing prostate cancer cells to anti-androgen drugs, wherein the method comprises contacting prostate cancer cells with an AR-V7 inhibitor, such as niclosamide, or an AKR1C3 inhibitor, such as indomethacin. In some embodiments, the present invention provides a method for resensitizing prostate cancer cells to anti-androgen drugs, wherein the method comprises contacting prostate cancer cells with an AR-V7 inhibitor, such as niclosamide, and an AKR1C3 inhibitor, such as indomethacin. In certain embodiments, the amount is an effective amount.

In some embodiments, the present invention provides a method for resensitizing prostate cancer cells to enzalutamide, wherein the method comprises contacting prostate cancer cells with an AR-V7 inhibitor, such as niclosamide, or an AKR1C3 inhibitor, such as indomethacin. In some embodiments, the present invention provides a method for resensitizing prostate cancer cells to enzalutamide, wherein the method comprises contacting prostate cancer cells with an AR-V7 inhibitor, such as niclosamide, and an AKR1C3 inhibitor, such as indomethacin. In certain embodiments, the amount is an effective amount.

In some embodiments, the present invention provides a method for resensitizing prostate cancer cells to abiraterone, wherein the method comprises contacting prostate cancer cells with an AR-V7 inhibitor, such as niclosamide, or an AKR1C3 inhibitor, such as indomethacin. In some embodiments, the present invention provides for a method for resensitizing prostate cancer cells to abiraterone, wherein the method comprises contacting prostate cancer cells with an AR-V7 inhibitor, such as niclosamide, and an AKR1C3 inhibitor, such as indomethacin. In certain embodiments, the amount is an effective amount.

In some embodiments, the present invention provides a method for resensitizing prostate cancer cells to enzalutimide and abiraterone, wherein the method comprises contacting prostate cancer cells with an AR-V7 inhibitor, such as niclosamide, or an AKR1C3 inhibitor, such as indomethacin. In some embodiments, the present invention provides a method for resensitizing prostate cancer cells to enzalutimide and abiraterone, wherein the method comprises contacting prostate cancer cells with an AR-V7 inhibitor, such as niclosamide, and an AKR1C3 inhibitor, such as indomethacin. In certain embodiments, the amount is an effective amount.

In some embodiments, the present invention provides a method for resensitizing prostate cancer cells to bicalutamide, wherein the method comprises contacting prostate cancer cells with an AR-V7 inhibitor, such as niclosamide, or an AKR1C3 inhibitor, such as indomethacin. In some embodiments, the present invention provides a method for resensitizing prostate cancer cells to bicalutamide, wherein the method comprises contacting prostate cancer cells with an AR-V7 inhibitor, such as niclosamide, and an AKR1C3 inhibitor, such as indomethacin. In certain embodiments, the amount is an effective amount.

In some embodiments, the present invention provides a method for resensitizing prostate cancer cells to docetaxel, wherein the method comprises contacting prostate cancer cells with an AR-V7 inhibitor, such as niclosamide, or an AKR1C3 inhibitor, such as indomethacin. In some embodiments, the present invention provides a method for resensitizing prostate cancer cells to docetaxel, wherein the method comprises contacting prostate cancer cells with an AR-V7 inhibitor, such as niclosamide, and an AKR1C3 inhibitor, such as indomethacin. In certain embodiments, the amount is an effective amount.

In some embodiments, the present invention provides a method for reducing, reversing, or resensitizing prostate cancer cell resistance to anti-androgen drugs, wherein the method comprises contacting prostate cancer cells with an AR-V7 inhibitor, such as niclosamide, or an AKR1C3 inhibitor, such as indomethacin. In some embodiments, the present invention provides a method for reducing, reversing, or resensitizing prostate cancer cell resistance to anti-androgen drugs, wherein the method comprises contacting prostate cancer cells with an AR-V7 inhibitor, such as niclosamide, and an AKR1C3 inhibitor, such as indomethacin.

In any of the aforementioned methods, the anti-androgen drug may be a compound selected from the group consisting of enzalutamide, abiraterone, docetaxel, bicalutamide, and combinations thereof.

In some embodiments set forth herein, the reducing, reversing, or resensitizing prostate cancer cell resistance to anti-androgen drugs is in a patient having prostate cancer.

In some embodiments, the present invention also provides a method for enhancing the therapeutic effects of an anti-androgen drug in a patient having prostate cancer, wherein the method comprises administering to a patient in need of an anti-androgen drug an effective amount of an AR-V7 inhibitor, such as niclosamide, or an AKR1C3 inhibitor, such as indomethacin. In some embodiments, the present invention also provides a method for enhancing the therapeutic effects of an anti-androgen drug in a patient having prostate cancer, wherein the method comprises administering to a patient in need of an anti-androgen drug an effective amount of an AR-V7 inhibitor, such as niclosamide, and an AKR1C3 inhibitor, such as indomethacin.

In some other embodiments, the present invention provides a method for enhancing the therapeutic effects of enzalutamide, in a patient having prostate cancer, the method comprising co-administering to the patient an effective amount of enzalutamide in combination with an AR-V7 inhibitor, such as niclosamide, or an AKR1C3 inhibitor, such as indomethacin. In some embodiments, the method comprises co-administering to the patient an effective amount of enzalutamide in combination with an AR-V7 inhibitor, such as niclosamide, and an AKR1C3 inhibitor, such as indomethacin.

In yet other embodiments, the present invention provides a method for enhancing the therapeutic effects of docetaxel, in a patient having prostate cancer, the method comprising co-administering to the patient an effective amount of docetaxel in combination with an AR-V7 inhibitor, such as niclosamide, or an AKR1C3 inhibitor, such as indomethacin. In some embodiments, the method comprises co-administering to the patient an effective amount of docetaxel in combination with an AR-V7 inhibitor, such as niclosamide, and an AKR1C3 inhibitor, such as indomethacin.

In certain embodiments, the present invention provides a method for enhancing the therapeutic effects of abiraterone, in a patient having prostate cancer, the method comprising co-administering to the patient an effective amount of abiraterone in combination with an AR-V7 inhibitor, such as niclosamide, or an AKR1C3 inhibitor, such as indomethacin. In some embodiments, the method comprises co-administering to the patient an effective amount of abiraterone in combination with an AR-V7 inhibitor, such as niclosamide, or an AKR1C3 inhibitor, such as indomethacin.

In certain embodiments, the present invention provides a method for enhancing the therapeutic effects of bicalutamide, in a patient having prostate cancer, the method comprising co-administering to the patient an effective amount of bicalutamide in combination with an AR-V7 inhibitor, such as niclosamide, or an AKR1C3 inhibitor, such as indomethacin. In some embodiments, the method comprises co-administering to the patient an effective amount of bicalutamide in combination with an AR-V7 inhibitor, such as niclosamide, and an AKR1C3 inhibitor, such as indomethacin.

In certain embodiments, the present invention provides a method for enhancing the therapeutic effects of an AR-V7 inhibitor, such as niclosamide, in a patient having prostate cancer, the method comprising co-administering to the patient an effective amount of an AR-V7 inhibitor, such as niclosamide, in combination with an AKR1C3 inhibitor, such as indomethacin. In certain embodiments, the present invention provides a method of enhancing the therapeutic effects of an AR-V7 inhibitor, such as niclosamide, in a patient having prostate cancer, the method comprising co-administering to the patient an effective amount of an AR-V7 inhibitor, such as niclosamide, in combination with a drug selected from the group consisting of enzalutamide, abiraterone, docetaxel, and bicalutamide, and combinations thereof.

In certain embodiments, the present invention provides a method for enhancing the therapeutic effects of an AKR1C3 inhibitor, such as indomethacin, in a patient having prostate cancer, the method comprising co-administering to the patient an effective amount of the AKR1C3 inhibitor in combination with a drug selected from the group consisting of enzalutamide, abiraterone, docetaxel, and bicalutamide, and combinations thereof.

In other embodiments, the present invention provides a method for inhibiting an androgen receptor (AR) variant, comprising contacting an AR variant with an amount of an AR-V7 inhibitor, such as niclosamide. In some of these embodiments, the AR variant is AR-V7.

In certain other embodiments, the present invention provides a method for inhibiting AR transactivation, inhibiting AR expression, inhibiting AR-cell migration, inhibiting AR-cell invasion in prostate cancer cells, inhibiting prostate cancer cell colony formation, and inhibiting recruitment of an AR variant to a prostate-specific antigen (PSA) promoter. In certain instances, this method of inhibition comprises contacting prostate cancer cells with an AR-V7 inhibitor, such as niclosamide, and optionally one or more compounds selected from the group consisting of enzalutamide, abiraterone, docetaxel, and bicalutamide.

The present invention also provides a method for inhibiting AR full length and AR-V7 expression, wherein the method comprises contacting an AR or a prostate cancer cell with an AR-V7 inhibitor, such as niclosamide. The present invention further provides a method for inhibiting AR full length and AR-V7 expression, wherein the method comprises contacting a prostate cancer cell with an AR-V7 inhibitor, such as niclosamide.

In certain other embodiments, the present invention provides a method for inhibiting enzalutamide/abiraterone-resistant CRPC cell growth, migration or invasion, wherein the method comprises contacting a prostate cancer cell with an AR-V7 inhibitor, such as niclosamide, or an AKR1C3 inhibitor, such as indomethacin. In some embodiments, the method comprises contacting a prostate cancer cell with an AR-V7 inhibitor, such as niclosamide, and an AKR1C3 inhibitor, such as indomethacin. In some embodiments, the prostate cancer cell is a CRPC cell.

In some other embodiments, the present invention provides a method for synergisticly enhancing enzalutamide/abiraterone effects for treating prostate cancer, wherein the method comprises administering an effective amount of an AR-V7 inhibitor, such as niclosamide, or an AKR1C3 inhibitor, such as indomethacin, to a patient having prostate cancer. In some embodiments, the method comprises administering an effective amount of an AR-V7 inhibitor, such as niclosamide, and an AKR1C3 inhibitor, such as indomethacin, to a patient having prostate cancer.

The present invention also provides a method for inhibiting recruitment of AR to a PSA promoter, the method comprises contacting AR with an AR-V7 inhibitor, such as niclosamide.

In certain methods of administering an AR-V7 inhibitor, such as niclosamide, the AR-V7 inhibitor is administered orally, alone or in combination with enzalutamide, abiraterone, an AKR1C3 inhibitor, or combinations thereof. In certain methods of administering AKR1C3 inhibitors, such as indomethacin, the AKR1C3 inhibitor is administered orally, alone or in combination with enzalutamide, abiraterone, an AR-V7 inhibitor such as niclosamide, or combinations thereof. In certain methods of administering AKR1C3 inhibitors, such as indomethacin, the AKR1C3 inhibitor is administered orally in combination with an AR-V7 inhibitor, such as niclosamide.

The present invention also provides a method for synergisticly or additively enhanced anti-androgen (e.g., bicalutamide, enzalutamide, or abiraterone) effects in prostate cancer cells, wherein the method comprises contacting a prostate cancer cell with an AR-V7 inhibitor, such as niclosamide, or an AKR1C3 inhibitor, such as indomethacin, and optionally also one or more anti-androgen drugs such as bicalutamide, enzalutamide, or abiraterone. In some of these methods, the prostate cancer cells are resistant to one or more compounds selected from the group consisting of enzalutamide, abiraterone, docetaxel, and bicalutamide. In some embodiments, the compound is enzalutamide. In other embodiments, the compound is abiraterone. In some other embodiments, the compound is docetaxel. In yet other embodiments, the compound is bicalutamide.

In some embodiments, the present invention also provides a method for inhibiting STAT3, wherein the method comprises contacting STAT3 with an AR-V7 inhibitor (e.g., niclosamide).

In certain embodiments, the present invention also provides a method for reversing STAT3-mediated enzalutamide resistance in prostate cancer cells, wherein the method comprises contacting STAT3 with an AR-V7 inhibitor (e.g., niclosamide).

In certain other embodiments, the present invention provides a method for inhibiting STAT3, wherein the method comprises administering an AR-V7 inhibitor (e.g., niclosamide) to a patient having prostate cancer. In still other embodiments, the present invention provides a method for inhibiting STAT3, wherein the method comprises administering an AR-V7 inhibitor (e.g., niclosamide) to a patient having (e.g., enzalutamide resistant) prostate cancer.

In some embodiments, the present invention provides a method for inhibiting STAT3, wherein the method comprises contacting STAT3 with an AR-V7 inhibitor (e.g., niclosamide). In certain embodiments, the contacting is in, on, or near prostate cancer cells. In some embodiments, the method comprises contacting STAT3 with an AR-V7 inhibitor (e.g., niclosamide) and enzalutamide.

In some other embodiments, the present invention provides a method for inhibiting prostate cancer cell growth, wherein the method comprises contacting STAT3 with an AR-V7 inhibitor (e.g., niclosamide). In certain embodiments, the contacting is in, on, or near prostate cancer cells. In some embodiments, the method comprises contacting STAT3 with an AR-V7 inhibitor (e.g., niclosamide) and enzalutamide.

In some embodiments, the present invention provides a method for inducing prostate cancer cell apoptosis, wherein the method comprises contacting STAT3 with an AR-V7 inhibitor (e.g., niclosamide). In certain embodiments, the contacting is in, on, or near prostate cancer cells. In some embodiments, the method comprises contacting STAT3 with an AR-V7 inhibitor (e.g., niclosamide) enzalutamide.

In some embodiments, the present invention provides a method for inhibiting prostate cancer cell colony formation, wherein the method comprises contacting STAT3 with an AR-V7 inhibitor (e.g., niclosamide). In certain embodiments, the contacting is in, on, or near prostate cancer cells. In some embodiments, the method comprises contacting STAT3 with an AR-V7 inhibitor (e.g., niclosamide) and enzalutamide.

In some embodiments, the present invention provides a method for reversing enzalutamide resistance though inhibition of STAT3 expression, wherein the method comprises contacting STAT3 with an AR-V7 inhibitor (e.g., niclosamide). In certain embodiments, the contacting is in, on, or near prostate cancer cells. In some embodiments, the method comprises contacting STAT3 with an AR-V7 inhibitor (e.g., niclosamide) and enzalutamide.

VII. Administration

In some embodiments of the present invention, an AR-V7 inhibitor, such as niclosamide, is administered to a patient having prostate cancer.

In some embodiments of the present invention, an AR-V7 inhibitor, such as niclosamide, is administered in combination with enzalutamide.

In some embodiments of the present invention, an AR-V7 inhibitor, such as niclosamide, is administered in combination with abiraterone.

In some embodiments of the present invention, an AR-V7 inhibitor, such as niclosamide, is adminstered in combination with both enzalutamide and abiraterone.

In some embodiments of the present invention, an AR-V7 inhibitor, such as niclosamide, is adminstered in combination with docetaxel.

In some embodiments of the present invention, an AR-V7 inhibitor, such as niclosamide, is adminstered in combination with both enzalutamide and docetaxel.

In some embodiments of the present invention, an AR-V7 inhibitor, such as niclosamide, is adminstered in combination with both abiraterone and docetaxel.

In certain methods of treating prostate cancer, set forth herein, the methods comprise first administering an AR-V7 inhibitor, such as niclosamide, to a patient having prostate cancer, and then administering enzalutamide to the patient. In certain methods of treating prostate cancer, set forth herein, the methods comprise first administering enzalutamide to a patient having prostate cancer, and then administering an AR-V7 inhibitor, such as niclosamide, to the patient.

In some embodiments of the present invention, the methods of administration comprise administering an AR-V7 inhibitor, such as niclosamide, alone or in combination with enzalutamide to a patient in need thereof. In some other embodiments of the present invention, the methods of administration comprise administering an AR-V7 inhibitor, such as niclosamide, alone or in combination with abiraterone to a patient in need thereof. In yet other embodiments of the present invention, the methods comprise administering an AR-V7 inhibitor, such as niclosamide, alone or in combination with docetaxel to a patient in need thereof. In still other embodiments of the present invention, the methods comprise administering an AR-V7 inhibitor, such as niclosamide, alone or in combination with bicalutamide to a patient in need thereof.

In some embodiments, the present invention provides a method of delivering an effective amount of an AR-V7 inhibitor, such as niclosamide, to a patient having prostate cancer.

The AR-V7 inhibitor (e.g., niclosamide) formulations of the present invention are useful in the manufacture of a pharmaceutical composition or a medicament. A pharmaceutical composition or medicament can be administered to a subject in need thereof, e.g. a patient having prostate cancer.

In any of the aforementioned embodiments, the prostate cancer is selected from the group consisting of castration-resistant prostate cancer, metastatic castration-resistant prostate cancer, advanced stage prostate cancer, drug-resistant prostate cancer such as anti-androgen-resistant prostate cancer (e.g., enzalutamide-resistant prostate cancer, abiraterone-resistant prostate cancer, bicalutamide-resistant prostate cancer, and the like), docetaxel-resistant prostate cancer, AR-V7-induced anti-androgen-resistant prostate cancer such as AR-V7-induced enzalutamide-resistant prostate cancer, and combinations thereof.

In some embodiments of the present invention, an AKR1C3 inhibitor, such as indomethacin, is administered to a patient having prostate cancer.

In some embodiments of the present invention, an AKR1C3 inhibitor, such as indomethacin, is administered in combination with enzalutamide.

In some embodiments of the present invention, an AKR1C3 inhibitor, such as indomethacin, is administered in combination with abiraterone.

In some embodiments of the present invention, an AKR1C3 inhibitor, such as indomethacin, is adminstered in combination with both enzalutamide and abiraterone.

In some embodiments of the present invention, an AKR1C3 inhibitor, such as indomethacin, is administered in combination with docetaxel. In some other embodiments, an AKR1C3 inhibitor, such as indomethacin, is administered in combination with an AR-V7 inhibitor, such as niclosamide.

In some embodiments of the present invention, an AKR1C3 inhibitor, such as indomethacin, is administered in combination with both enzalutamide and docetaxel.

In some embodiments of the present invention, an AKR1C3 inhibitor, such as indomethacin, is adminstered in combination with both abiraterone and docetaxel.

In certain methods of treating prostate cancer, set forth herein, the methods comprise first administering an AKR1C3 inhibitor, such as indomethacin, to a patient having prostate cancer, and then administering enzalutamide to the patient. In certain methods of treating prostate cancer, set forth herein, the methods comprise first administering enzalutamide to a patient having prostate cancer, and then administering an AKR1C3 inhibitor, such as indomethacin, to the patient.

In some embodiments of the present invention, the methods of administration comprise administering an AKR1C3 inhibitor, such as indomethacin, alone or in combination with enzalutamide to a patient in need thereof. In some other embodiments of the present invention, the methods of administration comprise administering an AKR1C3 inhibitor, such as indomethacin, alone or in combination with abiraterone to a patient in need thereof. In yet other embodiments of the present invention, the methods comprise administering an AKR1C3 inhibitor, such as indomethacin, alone or in combination with docetaxel to a patient in need thereof. In still other embodiments of the present invention, the methods comprise administering an AKR1C3 inhibitor, such as indomethacin, alone or in combination with bicalutamide to a patient in need thereof.

In some embodiments, the present invention provides a method of delivering an effective amount of an AKR1C3 inhibitor, such as indomethacin, to a patient having prostate cancer.

The AKR1C3 inhibitor (e.g., indomethacin) formulations of the present invention are useful in the manufacture of a pharmaceutical composition or a medicament. A pharmaceutical composition or medicament can be administered to a subject in need thereof, e.g. a patient having prostate cancer.

In any of the aforementioned embodiments, the prostate cancer is selected from the group consisting of castration-resistant prostate cancer, metastatic castration-resistant prostate cancer, advanced stage prostate cancer, drug-resistant prostate cancer such as anti-androgen-resistant prostate cancer (e.g., enzalutamide-resistant prostate cancer, abiraterone-resistant prostate cancer, bicalutamide-resistant prostate cancer, and the like), docetaxel-resistant prostate cancer, AKR1C3-induced anti-androgen-resistant prostate cancer such as AKR1C3-induced enzalutamide-resistant prostate cancer, and combinations thereof.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E. W. Martin. Compounds and agents of the present invention and their physiologically acceptable salts and solvates can be formulated for administration by any suitable route, including via inhalation, topically, nasally, orally, intravenously, parenterally, or rectally.

a. Routes of Administration

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral or rectal administration is also contemplated.

Suitable formulations for transdermal application include an effective amount of one or more compounds described herein, optionally with a carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

For oral administration, a pharmaceutical composition or a medicament can take the form of, for example, a tablet or a capsule prepared by conventional means with a pharmaceutically acceptable excipient. The present invention provides tablets and gelatin capsules comprising an AKR1C3 inhibitor, such as indomethacin, and/or an AR-V7 inhibitor, such as niclosamide, alone or in combination with other compounds such as anti-androgen drugs and/or docetaxel, or a dried solid powder of these drugs, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound(s).

The compositions and formulations set forth herein can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient(s) can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient(s).

For administration by inhalation, the compositions of the present invention may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound(s) and a suitable powder base, for example, lactose or starch.

The compositions set forth herein can also be formulated in rectal compositions, for example, suppositories or retention enemas, for example, containing conventional suppository bases, for example, cocoa butter or other glycerides.

Furthermore, the active ingredient(s) can be formulated as a depot preparation. Such long-acting formulations can be administered by implantation (for example, subcutaneously or intramuscularly) or by intramuscular injection. Thus, for example, one or more of the compounds described herein can be formulated with suitable polymeric or hydrophobic materials (for example as an emulsion in an acceptable oil) or ion exchange resins, or as sparingly soluble derivatives, for example, as a sparingly soluble salt.

In particular embodiments, a pharmaceutical composition or medicament of the present invention can comprise (i) an effective amount of an AR-V7 inhibitor, such as niclosamide, and (ii) optionally a compound selected from the group consisting of enzalutamide, abiraterone, docetaxel, and combinations thereof. In particular embodiments, a pharmaceutical composition or medicament of the present invention can additionally or alternatively comprise (i) an effective amount of an AKR1C3 inhibitor such as indomethacin, and (ii) optionally a compound selected from the group consisting of enzalutamide, abiraterone, docetaxel, and combinations thereof. The therapeutic agent(s) may be used individually, sequentially, or in combination with one or more other such therapeutic agents (e.g., a first therapeutic agent, a second therapeutic agent, a compound of the present invention, etc.). Administration may be by the same or different route of administration or together in the same pharmaceutical formulation.

b. Dosage

Pharmaceutical compositions or medicaments can be administered to a subject at a therapeutically effective dose to prevent, treat, resensitize, or control prostate cancer as described herein. The pharmaceutical composition or medicament is administered to a subject in an amount sufficient to elicit an effective therapeutic response in the subject.

The dosage of active agents administered is dependent on the subject's body weight, age, individual condition, surface area or volume of the area to be treated and on the form of administration. The size of the dose also will be determined by the existence, nature, and extent of any adverse effects that accompany the administration of a particular formulation in a particular subject. A unit dosage for oral administration to a mammal of about 50 to about 70 kg may contain between about 5 and about 500 mg, about 25-200 mg, about 100 and about 1000 mg, about 200 and about 2000 mg, about 500 and about 5000 mg, or between about 1000 and about 2000 mg of the active ingredient. A unit dosage for oral administration to a mammal of about 50 to about 70 kg may contain about 10 mg, 20 mg, 25 mg, 50 mg, 75 mg, 100 mg, 200 mg, 300 mg, 400 mg, 500 mg, 600 mg, 700 mg, 800 mg, 900 mg, 1,000 mg, 1,250 mg, 1,500 mg, 2,000 mg, 2,500 mg, 3,000 mg, or more of the active ingredient.

Typically, a dosage of the active compound(s) of the present invention is a dosage that is sufficient to achieve the desired effect. Optimal dosing schedules can be calculated from measurements of active agent accumulation in the body of a subject. In general, dosage may be given once or more of daily, weekly, or monthly. Persons of ordinary skill in the art can easily determine optimum dosages, dosing methodologies and repetition rates.

Optimum dosages, toxicity, and therapeutic efficacy of the compositions of the present invention may vary depending on the relative potency of the administered composition and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Agents that exhibit large therapeutic indices are preferred. While agents that exhibit toxic side effects can be used, care should be taken to design a delivery system that targets such agents to the site of affected tissue to minimize potential damage to normal cells and, thereby, reduce side effects.

Optimal dosing schedules can be calculated from measurements of active ingredient accumulation in the body of a subject. In general, dosage is from about 1 ng to about 1,000 mg per kg of body weight and may be given once or more daily, weekly, monthly, or yearly. Persons of ordinary skill in the art can easily determine optimum dosages, dosing methodologies and repetition rates. One of skill in the art will be able to determine optimal dosing for administration of AR-V7 inhibitors, such as niclosamide, or AKR1C3 inhibitors, such as indomethacin, to a human being following established protocols known in the art and the disclosure herein.

The data obtained from, for example, animal studies (e.g. rodents and monkeys) can be used to formulate a dosage range for use in humans. The dosage of compounds of the present invention lies preferably within a range of circulating concentrations that include the $ED_{50}$ with little or no toxicity. The dosage can vary within this range depending upon the dosage form employed and the route of administration. For any composition for use in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a chimeric protein, preferably a composition is from about 1 ng/kg to about 100 mg/kg for a typical subject. In some embodiments, a single oral dose of 5 mg/kg niclosamide in rats can generate a maximal plasma concentration of 1.08 μmol/mL A typical composition of the present invention for oral or intravenous administration can be about 0.1 to about 10 mg of active ingredient per patient per day; about 1 to about 100 mg per patient per day; about 25 to about 200 mg per patient per day; about 50 to about 500 mg per patient per day; about 100 to about 1000 mg per patient per day; or about 1000 to about 2000 mg per patient per day. Exemplary dosages include, but are not limited to, about 10 mg, 20 mg, 25 mg, 50 mg, 75 mg, 100 mg, 200 mg, 300 mg, 400 mg, 500 mg, 600 mg, 700 mg, 800 mg, 900 mg, 1,000 mg, 1,250 mg, 1,500 mg, 2,000 mg, 2,500 mg, 3,000 mg, or more of the active ingredient per patient per day. Methods for preparing administrable compositions will be known or apparent to those skilled in the art and are described in more detail in such publications as *Remington: The Science and Practice of Pharmacy,* 21st Ed., University of the Sciences in Philadelphia, Lippencott Williams & Wilkins (2005).

Exemplary doses of the compositions described herein include milligram or microgram amounts of the composition per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a composition depend upon the potency of the composition with respect to the desired effect to be achieved. When one or more of these compositions is to be administered to a mammal, a physician, veterinarian, or researcher may, for example, prescribe a relatively low dose at first, subsequently increasing the dose until an appropriate response is obtained. In addition, it is understood that the specific dose level for any particular mammal subject will depend upon a variety of factors including the activity of the specific composition employed, the age, body weight, general health, gender, and diet of the subject, the time of administration, the route of administration, the rate of excretion, any drug combination, and the degree of expression or activity to be modulated.

In some embodiments, a pharmaceutical composition or medicament of the present invention is administered, e.g., in a daily dose in the range from about 1 mg of compound per kg of subject weight (1 mg/kg) to about 1 g/kg. In another embodiment, the dose is a dose in the range of about 5 mg/kg to about 500 mg/kg. In yet another embodiment, the dose is about 10 mg/kg to about 250 mg/kg. In another embodiment, the dose is about 25 mg/kg to about 150 mg/kg. A preferred dose is about 2, 3, 4, 5, 6, 7, 8, 9, 10, 12, 15, 18, 20, 25, 30, 40, or 50 mg/kg. The daily dose can be administered once per day or divided into subdoses and administered in multiple doses, e.g., twice, three times, or four times per day. However, as will be appreciated by a skilled artisan, compositions described herein may be administered in different amounts and at different times. The skilled artisan will also appreciate that certain factors may influence the dosage and timing required to effectively treat a subject, including but not limited to the severity of the disease or malignant condition, previous treatments, the general health and/or age of the subject, and other diseases present. Moreover, treatment of a subject with a therapeutically effective amount of a composition can include a single treatment or, preferably, can include a series of treatments.

To achieve the desired therapeutic effect, compounds or agents described herein may be administered for multiple days at the therapeutically effective daily dose. Thus, therapeutically effective administration of compounds to treat prostate cancer in a subject may require periodic (e.g., daily) administration that continues for a period ranging from three days to two weeks or longer. Compositions set forth herein may be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every other day, every third day, or, if higher dose ranges are employed and tolerated by the subject, once a week.

In some embodiments, the AR-V7 inhibitor niclosamide is orally administered. In some embodiments, the niclosamide is orally administered to a subject (e.g., an adult human) at a daily dose of approximately 100; 200; 300; 400; 500; 600; 700; 800; 900; 1,000; 1,250; 1,500; 1,750; 2,000; 2,500; 3,000; 3,500; 4,000; 4,500; 5,000; or more mg of niclosamide per day. In some embodiments, the niclosamide is orally administered to a subject (e.g., an adult human) at a daily dose of between 1,000 and 2,000 mg per day. In some embodiments, the AKR1C3 inhibitor indomethacin is orally administered. In some embodiments, the indomethacin is orally administered to a subject (e.g., an adult human) at a daily dose of approximately 10, 15, 20, 25, 30, 35, 40, 50, 60, 70, 80, 90, 100, 125, 150, 175, 200, 225, 250, 300, 350, 400, 500, or more mg of indomethacin per day. In some embodiments, the indomethacin is orally administered to a subject (e.g., an adult human) at a daily dose of between 25 and 200 mg per day. In some embodiments, the indomethacin and the niclosamide are orally co-administered. For example, the indomethacin can be co-administered at a daily oral dose of between 25 and 200 mg per day with niclosamide at a daily oral dose of between 1000 and 2000 mg per day.

In some embodiments, the methods comprise sequentially administering an AR-V7 inhibitor, such as niclosamide, followed by a compound selected from the group consisting of enzalutiade, abiraterone, bicalutamide, and docetaxel. In some embodiments, the methods comprise sequentially administering a compound selected from the group consisting of enzalutiade, abiraterone, bicalutamide, and docetaxel followed by an AR-V7 inhibitor, such as niclosamide.

In other embodiments, the methods comprise administering an AR-V7 inhibitor, such as niclosamide, in combination with a compound selected from the group consisting of bicalutamide, enzalutiade, abiraterone, and docetaxel. In some of these embodiments, the amount of bicalutamide, enzalutamide, aberiterarone, or docetaxel is less than the amount of bicalutamide, enzalutiade, aberiterarone, or docetaxel that would be administered to a patient having prostate cancer than would be adminstered if an AR-V7 inhibitor, such as niclosamide, were not adminstered to the patient.

In some embodiments, the methods comprise sequentially administering an AKR1C3 inhibitor, such as indomethacin, followed by a compound selected from the group consisting of enzalutiade, abiraterone, bicalutamide, and docetaxel. In some embodiments, the methods comprise sequentially administering a compound selected from the group consisting of enzalutiade, abiraterone, bicalutamide, and docetaxel followed by an AKR1C3 inhibitor, such as indomethacin.

In other embodiments, the methods comprise administering an AKR1C3 inhibitor, such as indomethacin, in combination with a compound selected from the group consisting of bicalutamide, enzalutamide, abiraterone, and docetaxel. In some of these embodiments, the amount of bicalutamide, enzalutiade, aberiterarone, or docetaxel is less than the amount of bicalutamide, enzalutiade, aberiterarone, or docetaxel that would be administered to a patient having prostate cancer than would be adminstered if the AKR1C3 inhibitor were not adminstered to the patient.

In some embodiments of the present invention, a pharmaceutical composition or medicament is administered to a patient at a therapeutically effective dose to prevent, treat, or control prostate cancer. The pharmaceutical composition or medicament is administered to a patient in an amount sufficient to elicit an effective therapeutic or diagnostic response in the patient. An effective therapeutic or diagnostic response is a response that at least partially arrests or slows the symptoms or complications of prostate cancer. An amount adequate to accomplish this is defined as "therapeutically effective dose."

Following successful treatment, it may be desirable to have the subject undergo maintenance therapy to prevent the recurrence of the prostate cancer.

Determination of an effective amount is well within the capability of those skilled in the art, especially in light of the detailed disclosure provided herein. Generally, an efficacious or effective amount of an composition is determined by first administering a low dose or small amount of the composition, and then incrementally increasing the administered dose or dosages, adding a second or third medication as needed, until a desired effect of is observed in the treated subject with minimal or no toxic side effects.

Single or multiple administrations of the compositions are administered depending on the dosage and frequency as required and tolerated by the patient. In any event, the composition should provide a sufficient quantity of the compositions of this invention to effectively treat the patient. Generally, the dose is sufficient to treat or ameliorate symptoms or signs of disease without producing unacceptable toxicity to the patient.

VIII. Kits, Containers, Devices, and Systems

A wide variety of kits, systems, and compositions can be prepared according to the present invention, depending upon the intended user of the kit and system and the particular needs of the user. In some embodiments, the present invention provides a kit that includes an AR-V7 inhibitor, such as niclosamide, and a compound selected from the group consisting of enzalutamide, abiraterone, docetaxel, bicalutamide, and combinations thereof. In certain embodiments, the kit includes an AR-V7 inhibitor, such as niclosamide, and enzalutamide. In certain other embodiments, the kit includes an AR-V7 inhibitor, such as niclosamide, and abiraterone. In other embodiments, the kit includes an AR-V7 inhibitor, such as niclosamide, and docetaxel. In some other embodiments, the kit includes an AR-V7 inhibitor, such as niclosamide, and bicalutamide. In some other embodiment, the kit includes an AR-V7 inhibitor, such as niclosamide, and an AKR1C3 inhibitor, such as indomethacin.

In some embodiments, the present invention provides a kit that includes an AKR1C3 inhibitor, such as indomethacin, and a compound selected from the group consisting of enzalutamide, abiraterone, docetaxel, bicalutamide, and combinations thereof. In certain embodiments, the kit includes the AKR1C3 inhibitor, such as indomethacin, and enzalutamide. In certain other embodiments, the kit includes the AKR1C3 inhibitor, such as indomethacin, and abiraterone. In other embodiments, the kit includes the AKR1C3 inhibitor, such as indomethacin, and docetaxel. In some other embodiments, the kit includes the AKR1C3 inhibitor, such as indomethacin, and bicalutamide. In other embodiments, the kit includes the AKR1C3 inhibitor, such as indomethacin, and an AR-V7 inhibitor, such as niclosamide.

Some of the kits described herein include a label describing a method of administering an AR-V7 inhibitor, such as niclosamide. For example, the label may describe oral administration of an AR-V7 inhibitor, such as niclosamide. Some of the kits described herein include a label describing a method of administering an AKR1C3 inhibitor, such as indomethacin. For example, the label may describe oral administration of an AKR1C3 inhibitor, such as indomethacin. Some of the kits described herein include a label describing a method of preventing, treating, or controlling prostate cancer, e.g., castration-resistant prostate cancer or anti-androgen-resistant prostate cancer.

The compositions of the present invention, including but not limited to compositions including an AR-V7 inhibitor, such as niclosamide, or compositions including an AKR1C3 inhibitor, such as indomethacin, may, if desired, be presented in a bottle, jar, vial, ampoule, tube, or other container-closure system approved by the Food and Drug Administration (FDA) or other regulatory body, which may provide one or more dosages containing the active ingredient. The package or dispenser may also be accompanied by a notice associated with the container in a form prescribed by a governmental agency regulating the manufacture, use, or sale of pharmaceuticals, the notice indicating approval by the agency. In certain aspects, the kit may include a formulation or composition as taught herein, a container closure system including the formulation or a dosage unit form including the formulation, and a notice or instructions describing a method of use as taught herein.

In some embodiments, the kit includes a container which is compartmentalized for holding the various elements of a formulation (e.g., the dry ingredients and the liquid ingredients) or composition, instructions for making the formulation or composition, and instructions for preventing, treating, or controlling prostate cancer, e.g., castration-resistant prostate cancer, anti-androgen-resistant prostate cancer, or a combination thereof. In certain embodiments, the kit may include the pharmaceutical preparation in dehydrated or dry form, with instructions for its rehydration (or reconstitution) and administration.

Kits with unit doses of the active composition, e.g. in oral, rectal, transdermal, or injectable doses (e.g., for intramuscular, intravenous, or subcutaneous injection), are provided. In such kits, in addition to the containers containing the unit doses will be an informational package insert describing the use and attendant benefits of the composition in preventing, treating, or controlling prostate cancer, e.g., castration-resistant prostate cancer, anti-androgen-resistant prostate cancer, or a combination thereof. Suitable active compositions and unit doses are those described herein.

Some embodiments of the present invention include packages that include an AR-V7 inhibitor, such as niclosamide, packaged together with a compound selected from the group consisting of bicalutamide, enzalutamide, aberiterarone, docetaxel, and combinations thereof. Some embodiments of the present invention include packages that include an AKR1C3 inhibitor, such as indomethacin, packaged together with a compound selected from the group consisting of bicalutamide, enzalutamide, aberiterarone, docetaxel, and combinations thereof. Some embodiments of the present invention include packages that include an AR-V7 inhibitor, such as niclosamide, and an AKR1C3 inhibitor, such as indomethacin, packaged together with a compound selected from the group consisting of bicalutamide, enzalutamide, aberiterarone, docetaxel, and combinations thereof.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

IX. EXAMPLES

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Figure 1B:
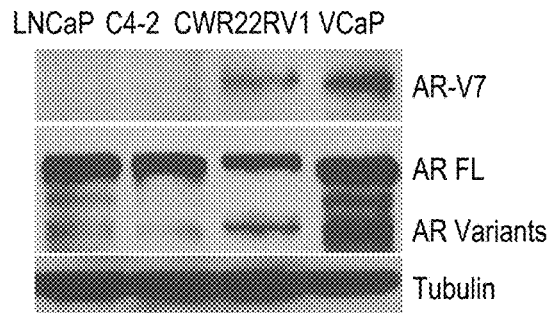
Figure 1C:
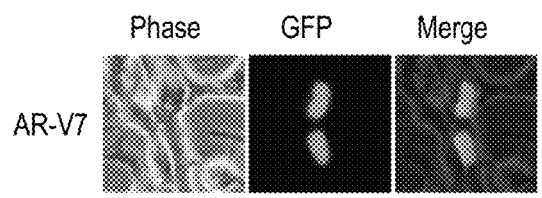
Figure 1D:
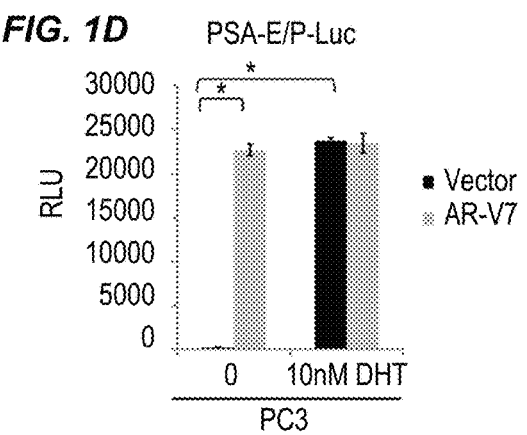
Figure 1E:
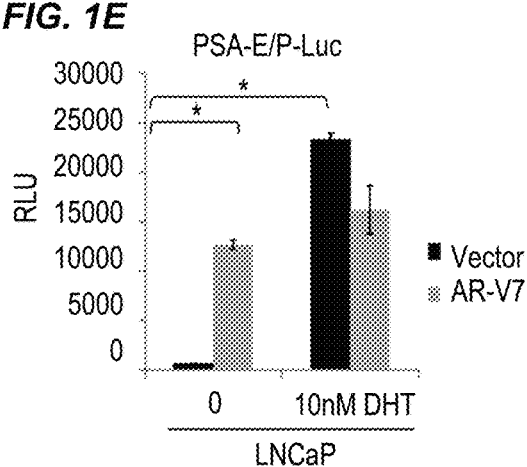
Figure 1F:
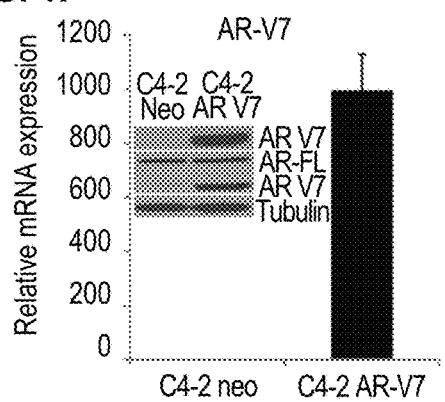
Figure 1G:
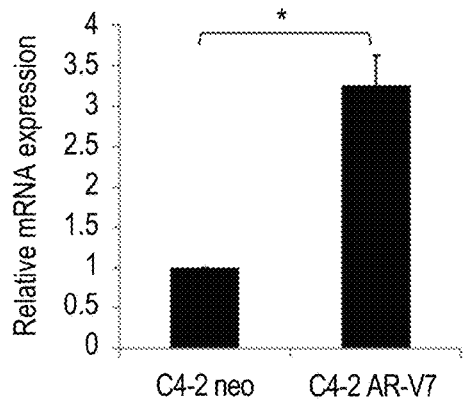
Figure 1H:
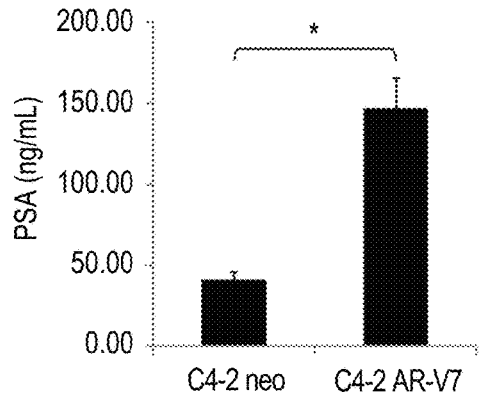

Example 1. AR-V7 Activity in Prostate Cancer Cells, Enzalutamide Resistance, and Compositions and Methods for Treatment of Prostate Cancer Cells a. Introduction The deletion of LBD results in constitutive activation of the AR in prostate cancer cells. AR-V7 mRNA expression in different cell lines was detected as shown in FIG. 1A. CWR22rv1 and VCaP cells expressed significantly higher AR-V7 than LNCaP and C4-2 cells; the expression level of AR-V7 in CWR22rv1 cells was 25 times higher than in LNCaP and C4-2 cells, whereas VCaP cells exhibited a 15 fold increase in comparison. The results were also confirmed by Western blot, as shown in FIG. 1B, in which CWR22rv1 and VCaP cells expressed higher protein expression levels of AR variants, especially AR-V7, than LNCaP and C4-2 cells. AR-V7 has been shown constitutively active in prostate cancer cells. To confirm these results, EGFP-AR-V7 was transiently transfected into C4-2 cells, and 48 hours later, as shown in FIG. 1C, AR-V7 was only expressed in the nucleus of C4-2 cells suggesting that AR-V7 which lacks the classic NLS (nuclear location sequence) is still capable of being translocated to the nucleus by mechanisms currently unknown. Next, the transcription activity of AR-V7 in the PC3 cell line was confirmed, which is void of AR, and LNCaP cells, which express mutant AR (T877A). As shown in FIGS. 1D and 1E, AR-V7 was constitutively activated in both PC3 and LNCaP cells and cannot be interrupted by androgen. To further understand the AR-V7 function in prostate cancer cells, AR-V7 was stably transfected into C4-2 cells, as shown in FIG. 1F. C4-2 AR-V7 stable clone expressed significantly higher AR-V7 mRNA compared with C4-2 neo cells. Furthermore, the AR-V7 functionally increased PSA mRNA and protein expression in C4-2 cells (FIGS. 1G and 1H). Collectively, these data confirmed AR-V7 is constitutively active in prostate cancer cells.

b. Reagents and Methods i. General Cell Culture

All cells were maintained at 37° C. in a humidified incubator with 5% carbon dioxide. LNCaP, C4-2, C4-2B, CWR22rv1, DU145, and 293 cells were maintained in RPMI 1640 supplemented with 10% fetal bovine serum (FBS), 100 units/ml penicillin and 0.1 mg/ml streptomycin. VCaP cells were maintained in DMEM supplemented with 10% fetal bovine serum (FBS), 100 units/ml penicillin and 0.1 mg/ml streptomycin. C4-2-neo and C4-2 AR-V7 cells were stably transfected with pc DNA3.1 or containing AR-V7 plasmid and maintained in 300 µg/mL G418 RPMI1640 medium. 293-AR-V7-PSA-E/P-LUC cells were stably transfected with AR-V7 plasmid and PSA-E/P-LUC reporter plasmid and maintained in 300 µg/mL G418 RPMI1640 medium. LNCaP-neo (LNCaP cells stably expressing pcDNA3.1 control vector), LNCaP-S17 (LNCaP cells stably expressingIL-6), and LNCaP-STAT3C cells (LNCaP cells stably expressing constitutively active STAT3) were prepared based on Lou W, Ni Z, Dyer K, Tweardy D J, Gao A C. *Interleukin-6 induces prostate cancer cell growth accompanied by activation of stat3 signaling pathway.* Prostate 2000; 42(3):239-242 and DeMiguel F, Lee S O, Lou W, Xiao X, Pflug B R, Nelson J B, Gao A C. *STAT3 enhances the growth of LNCaP human prostate cancer cells in intact and castrated male nude mice.* Prostate 2002; 52(2):123-129. Human recombinant IL-6 was obtained from R&D Systems (Minneapolis, Minn.).

C4-2B cells were incubated with increasing concentrations of enzalutamide (5 µM~40 µM) over 12 months in FBS and stored for further analysis. The resistant cells were isolated and referred to as C4-2B MR (i.e., C4-2B enzalutamide resistant). Parental C4-2B cells were passaged alongside the enzalutamide treated cells as an appropriate control. C4-2B MR cells were maintained in 20 µM enzalutamide containing medium. Niclosamide was purchased from Sigma.

ii. Plasmids and Cell Transfection

For small interfering RNA (siRNA) transfection, cells were seeded at a density of $1\times10^5$ cells per well in 12-well plates or $3\times10^5$ cells per well in 6-well plates and transfected with siRNA (Dharmacon) targeting the AR Exon7 sequence UCAAGGAACUCGAUCGUAU (SEQ ID NO: 1) or AR-V7 sequence GUAGUUGUAAGUAUCAUGA (SEQ ID NO: 2) or siRNA targeting STAT3 (Cell signaling #6582) using lipofectamine-RNAiMAX (invitrogen). A control sequence targeting the luciferase (Luc) gene, siControl CTTACGCTGAGTACTTCGA (SEQ ID NO: 3), using lipofectamine-RNAiMAX (invitrogen) was also transfected. Cells were transiently transfected with indicated expression plasmids, e.g., AR-V7 or EGFP-AR-V7, using Attractene (QIAGEN).

iii. Chromatin Immunoprecipitation Assay

C4-2 neo and C4-2 AR-V7 cells were treated as noted herein. DNA-AR protein complexes were cross-linked inside the cells by the addition of 1% formaldehyde. Whole-cell extracts were prepared by sonication, and an aliquot of the cross-linked DNA-protein complexes was immunoprecipitated by incubation with the AR-specific antibody (AR-441 obtained from Santa Cruz Biotechnology) overnight at 4° C. with rotation. Chromatin-antibody complexes were isolated from solution by incubation with protein A/G agarose beads for 1 hour at 4° C. with rotation. The bound DNA-protein complexes were washed and eluted from beads with elution buffer (1% SDS and 0.1 mol/L NaHCO$_3$), crosslinking was reversed, and DNA was extracted. The resulting chromatin preparations were analyzed by PCR using primers spanning either the proximal or the distal enhancer AREs of the PSA promoter. Isotype-matched IgG was used as control.

iv. Western Blot Analysis

Whole cell protein extracts were resolved on SDS-PAGE and proteins were transferred to nitrocellulose membranes. After blocking for 1 hour at room temperature in 5% milk in PBS/0.1% Tween-20, membranes were incubated overnight at 4° C. with the indicated primary antibodies [e.g., AR (441, sc-7305, Mouse monoclonal antibody, 1:1000 dilition, Santa Cruz Biotechnology, Santa Cruz, Calif.); AR-V7 (AG10008, Mouse monoclonal antibody, 1:1000 dilition, precision antibody); Tubulin (T5168, Monoclonal Anti-α-Tubulin antibody, 1:5000 dilution, Sigma-Aldrich, St. Louis, Mo.)]. Tubulin was used to monitor the amounts of samples applied. Following secondary antibody incubation, immunoreactive proteins were visualized with an enhanced chemiluminescence detection system (Millipore, Billerica, Mass.).

v. Luciferase Assay

LNCaP, C4-2 or 293 cells were transfected with pGL3-PSA6.0-Luc, pGL3-AREI/II-Luc reporters along with AR-V7, for example as indicated in the figures, in FBS or CS-FBS condition. Cell lysates were subjected to luciferase assays with the Luciferase Assay System (Promega).

vi. Cell Growth Assay

C4-2 neo, C4-2 AR-V7, CWR22rv1 or pzHPV7 cells were seeded on 12-well plates at a density of $1\times10^5$ cells/well in RPMI 1640 media containing 10% FBS and treated with 0.5 µM niclosamide for 48 hours. Total cell numbers were counted and the cell survival rate (%) was calculated. Cell survival rate (%)=(Treatment group cell number/Control group cell number)×100%. CWR22rv1 cells, C4-2B MR or C4-2B AbiR cells were seeded on 12-well plates at a density of $0.5\times10^5$ cells/well in RPMI 1640 media containing 10% FBS and treated 0.25 µM niclosamide with 20 µM enzalutamide or 20 µM abiraterone in media containing FBS. Total cell numbers were counted after 2, 4, and 7 days. LNCaP-neo, LNCaP-517, LNCaP-IL6+ or LNCaP-STAT3C cells were seeded in 12-well plates at a density of $1\times10^5$ cells/well in RPMI 1640 media containing 10% FBS. The cells were treated as indicated and total cell numbers were counted.

vii. Clonogenic Assay

C4-2 neo, C4-2 AR-V7, CWR22rv1 or C4-2B MR cells were treated with DMSO, 0.5 µM or 1.0 µM niclosamide in media containing 10% complete FBS. CWR22rv1 cells or C4-2B MR cells were treated with 0.25 µM niclosamide with or without 20 µM enzalutamide. Cells were plated at equal density in 100 mm dishes for 14 days; the medium was changed every 7 days. The colonies were rinsed with PBS before staining with 0.5% crystal violet/4% formaldehyde for 30 min and the number of colonies was counted. LNCaP-neo cells or LNCaP-S17 stable clone cells were treated with DMSO or enzalutamide in media containing 10% complete FBS. Cells were plated at equal density (1000 cells/dish) in 100 mm dishes for 14 days. The colonies were rinsed with PBS before staining with 0.5% crystal violet/4% formaldehyde for 30 min and the number of colonies was counted.

viii. Cell Death ELISA

C4-2 neo, C4-2 AR-V7, CWR22rv1 or pzHPV7 cells were seeded on 12-well plates ($1\times10^5$ cells/well) in RPMI 1640 media containing 10% FBS and treated with DMSO or 0.5 µM niclosamide for 48 hours. Mono- and oligonucleosomes in the cytoplasmic fraction were measured by the Cell Death Detection ELISA kit (Roche, Cat. NO. 11544675001) according to the manufacturer's instructions. Floating and attached cells were collected and homogenized in 400 µL of incubation buffer. The wells were coated with antihistone antibodies and incubated with the lysates, horseradish peroxidase-conjugated anti-DNA antibodies, and the substrate. Absorbance was measured at 405 nm.

ix. Real-Time Quantitative RT-PCR

Total RNAs were extracted using TriZOL reagent (Invitrogen). cDNAs were prepared after digestion with RNase-free RQ1 DNase (Promega). The cDNAs were subjected to real-time reverse transcription-PCR (RT-PCR) using Sso Fast Eva Green Supermix (Bio-Rad) according to the manufacturer's instructions or as described in Liu C, et al. *Andrographolide targets androgen receptor pathway in castrate-resistant prostate cancer*, Genes Cancer; 2: 151-9. Each reaction was normalized by co-amplification of actin. Triplicates of samples were run on default settings of Bio-Rad CFX-96 real-time cycler.

x. Measurement of PSA

PSA levels were measured in the culture supernatants using ELISA (United Biotech, Inc., Mountain View, Calif.) according to the manufacturer's instructions.

i. Measurement of IL-6

50 μl of cell culture supernatants were used to determine levels of IL-6 secretion. Secretion of IL-6 by LNCaP-neo and LNCaP-s17 cells was determined by ELISA according to the manufacturer's protocol (eBioscience, San Diego, Calif.).

xi. Statistical Analysis

Figure 2B:
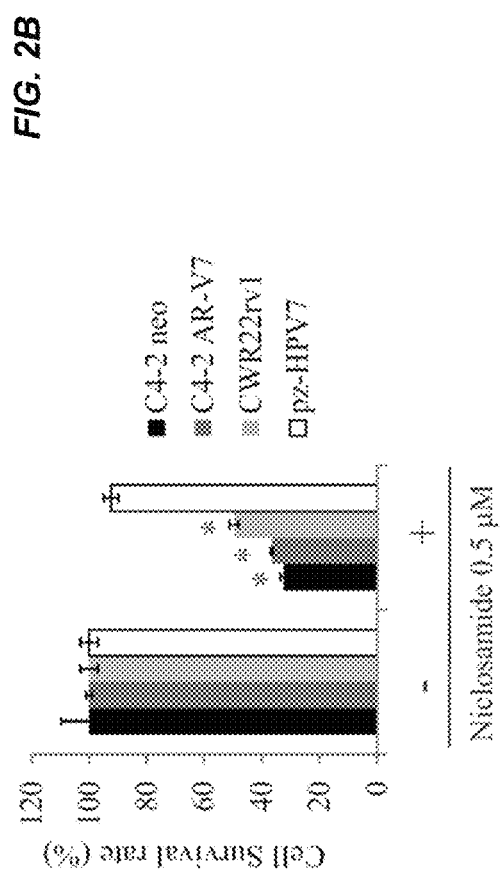
FIGS. 2A-2D show that niclosamide inhibited prostate cancer cell growth and induced cell apoptosis.
Figure 2D:
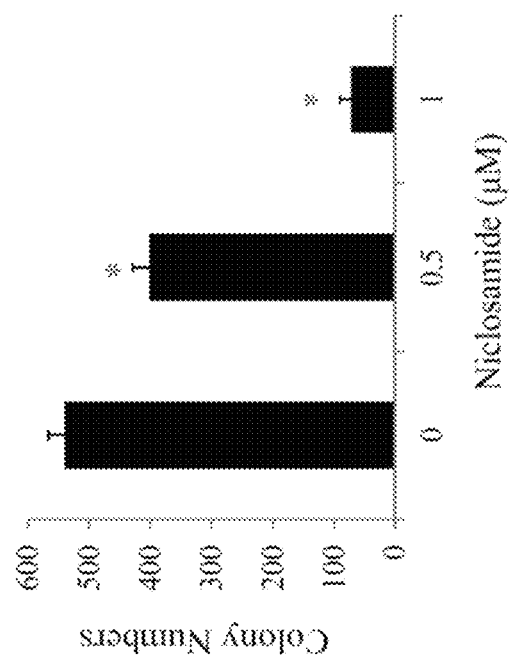
Figure 2A:
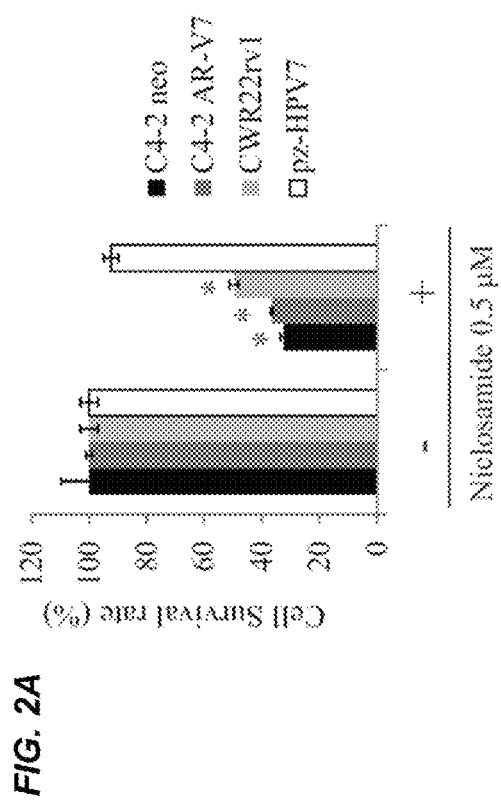
Figure 2C:
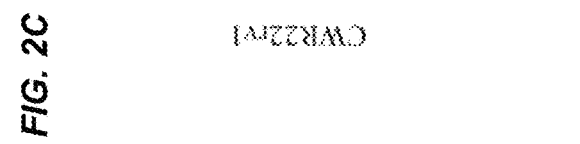
Figure 8A:
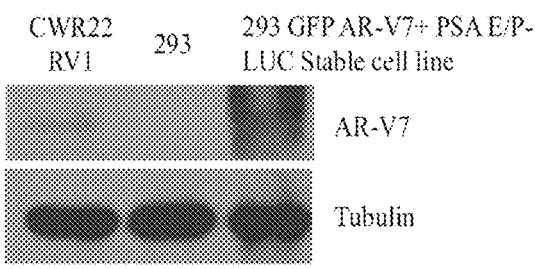
FIGS. 8A-8E show that 293 cells stably transfected with an AR-V7-PSA promoter luciferase construct were screened against candidate AR-V7 compounds form the Prestwick Chemical Library.
Figure 8B:
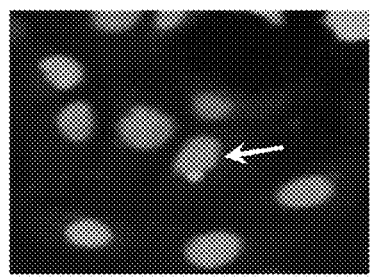
Figure 8C:
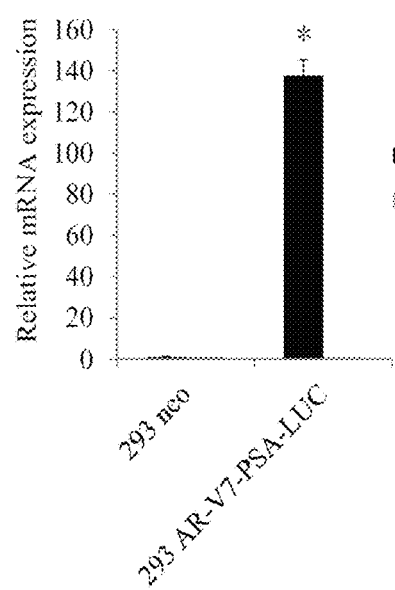
Figure 8D:
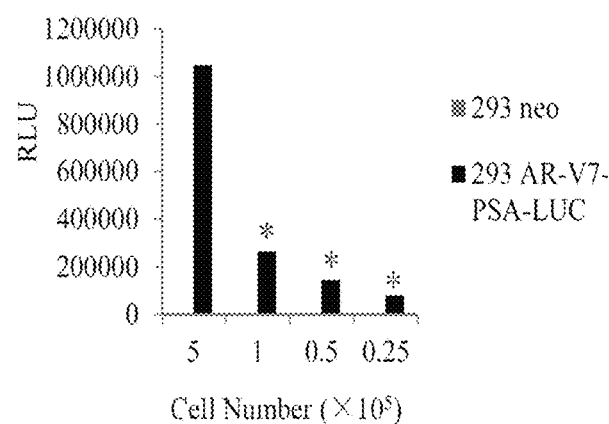
Figure 8E:
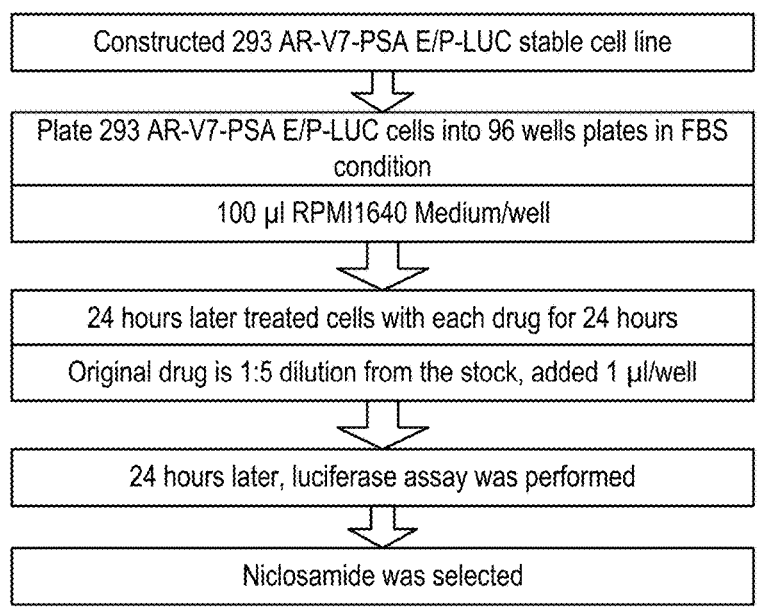

Data is presented as means±standard deviation of the mean (SD). STATistical analyses were performed with Microsoft Excel analysis tools. Differences between individual groups were analyzed by one-way analysis of variance (ANOVA) followed by the Scheffé procedure for comparison of means. $P<0.05$ was considered statistically significant.

c. Results i. Compound Screening for AR-V7 Inhibitors in the Prestwick Chemical Library The Prestwick Chemical Library® contains 1200 small molecules (FDA, EMEA and other agencies). The active compounds were selected for their high chemical and pharmacological diversity as well as for their known bioavailability and safety in humans. The present assay identified FDA-approved drugs that could target AR-V7 activity. The drug screening was conducted using luciferase activity assay to determine the AR-V7 activity 24 hours after treated with the library's compound. To avoid full length AR interruption, 293 cell line were used which were AR void. 293 cells were stable transfected with EGFP-AR-V7 plasmid and PSA-E/P-luciferase reporter plasmid, and stable clones were selected by G418, as shown in FIGS. 8A-8E and FIG. 12. 293 AR-V7-PSA-luc stable clones more greatly expressed AR-V7 protein compared with 293 neo cells. CWR22rv1 cells were used as a positive control. The nuclear translocation was examined under the fluorescence microscope. As shown in FIG. 8B, 293 AR-V7-PSA-luc stable clone highly expressed AR-V7 in the nucleus. The AR-V7 expression was also confirmed by qRT-PCR, where 293 AR-V7-PSA-luc stable clones expressed 140 fold higher AR-V7 mRNA level compared to 293 neo cells although both cells don't express full length AR (FIG. 8C). To confirm that 293 AR-V7-PSA-luc stable clones also stably express PSA-luc activities, cells were plated in CS-FBS condition in different cell numbers. Two days later, a luciferase assay was performed, as shown in FIG. 8D, and it was shown that 293 AR-V7-PSA-luc cells possess constitutive PSA promoter activity suggesting that the stable cells were successfully constructed in the 293 cell system. To conduct compound screening, the screen protocol was constructed, as shown in FIG. 8E. 293 AR-V7-PSA-luc stable clones were seeded in 96 well plates following treatment with each compound in the library over 24 hours. A luciferase assay was again performed and the compounds which significantly inhibited cell growth were excluded on the first round of screening. After the second round, high toxicity compounds were diluted further to screen again, and from this array of criteria, niclosamide was selected as a drug of interest.

ii. Niclosamide Inhibited Prostate Cancer Cell Growth and Induced Cell Apoptosis To examine niclosamide effects on prostate cancer cells, C4-2 neo, C4-2 AR-V7, CWR22rv1 and pz-HPV7 cells were treated with DMSO or 0.5 μM niclosamide for 48 hours, as shown in FIG. 2A. 0.5 μM niclosamide significantly inhibited cell growth in prostate cancer cells and had little effects on pz-HPV7 normal prostate epithelial cells. To further examine the anti-cancer effects by niclosamide, cell death ELISA was performed, as shown in FIG. 2B. 0.5 μM niclosamide significantly induced cell apoptosis in prostate cancer cells and had little effect on pz-HPV7 cells. The clonogenic ability inhibited by niclosamide was as examined and is shown in FIG. 2C and FIG. 2D. Niclosamide significantly inhibited prostate cancer cells clonogenic ability in a dose dependent manner which confirmed niclosamide has the great potential to be a candidate of prostate cancer therapy. Collectively, the results above revealed that niclosamide inhibited prostate cancer cell growth and induced cell apoptosis while inducing minimal effects on normal prostate epithelial cells.

Figure 33:
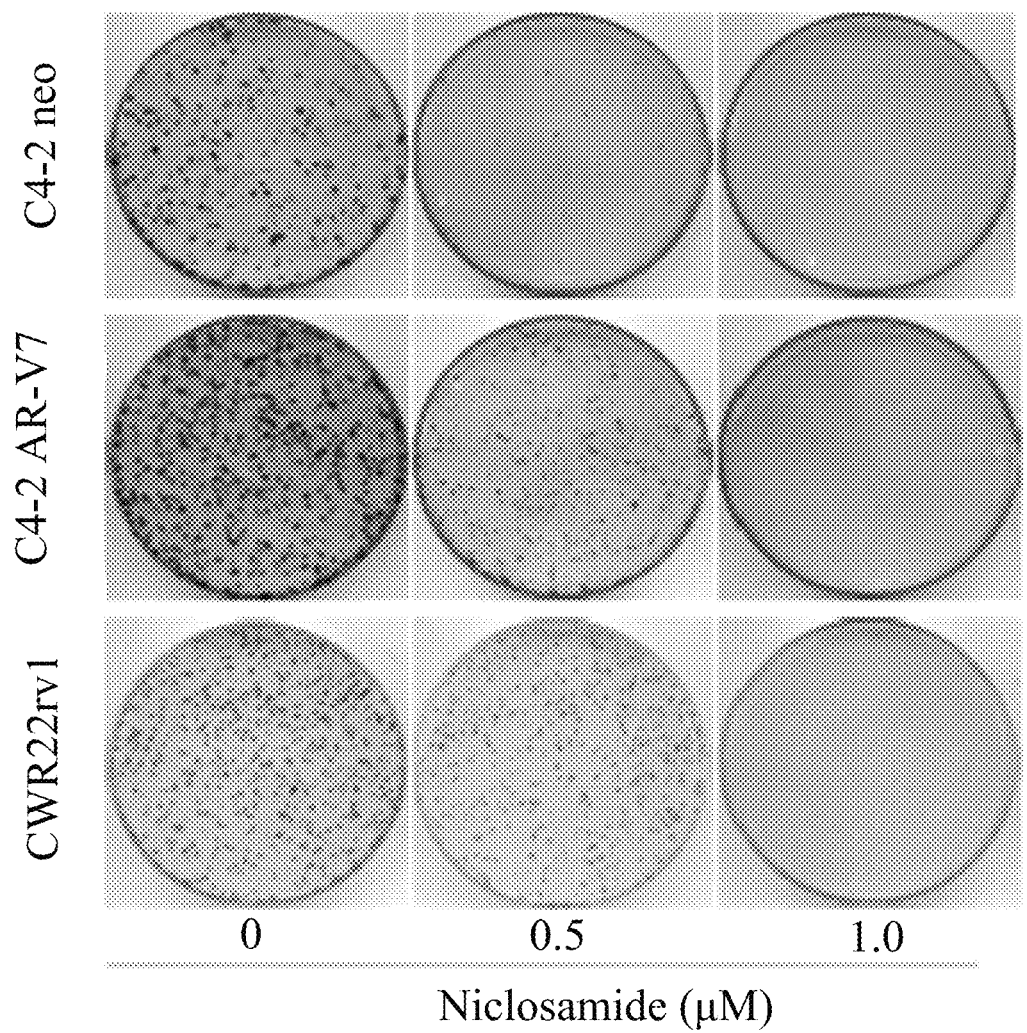
FIG. 33 shows CWR22rv1, C4-2R-V7, and C4-2 neo cells that were cultured with 0, 0.5, and 1.0 µM niclosamide. Niclosamide is shown in this figure to significantly inhibit clonogenic ability of prostate cancer cells in a dose dependent manner.
Figure 34:
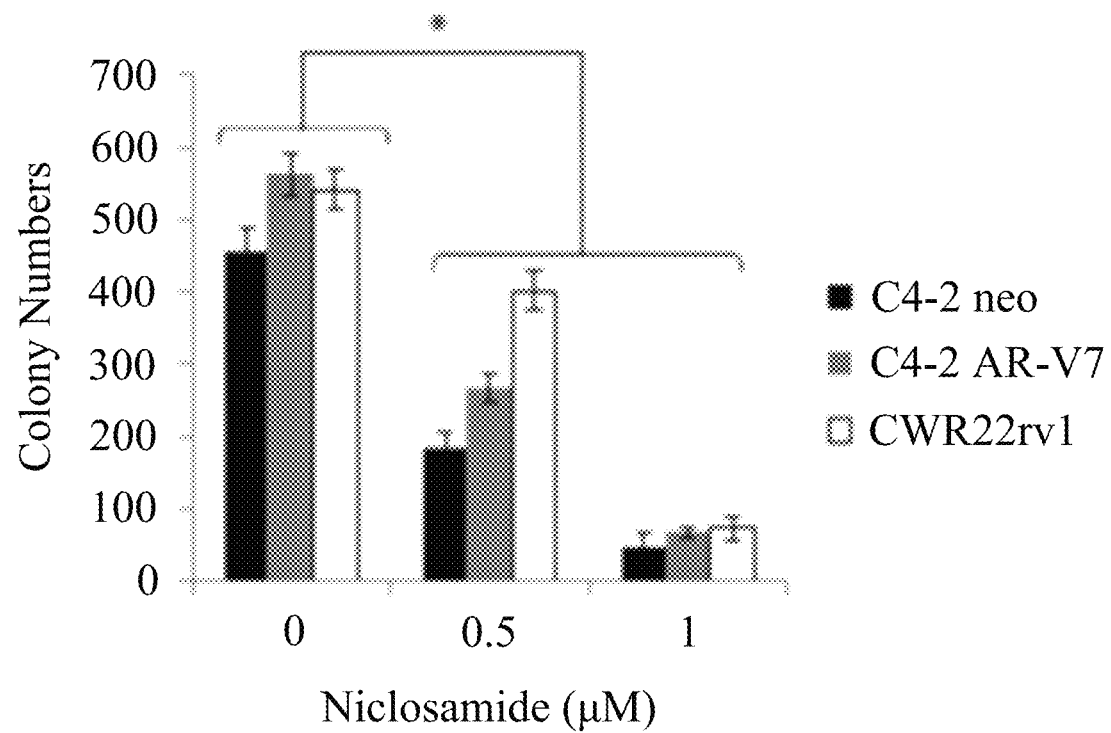
FIG. 34 shows a plot of colony numbers versus niclosamide concentration for CWR22rv1, C4-2R-V7, and C4-2 neo cells that were cultured with 0, 0.5, and 1.0 µM niclosamide. Colonies were counted and the results are presented as means±SD of 2 experiments performed in duplicate.
Figure 37:
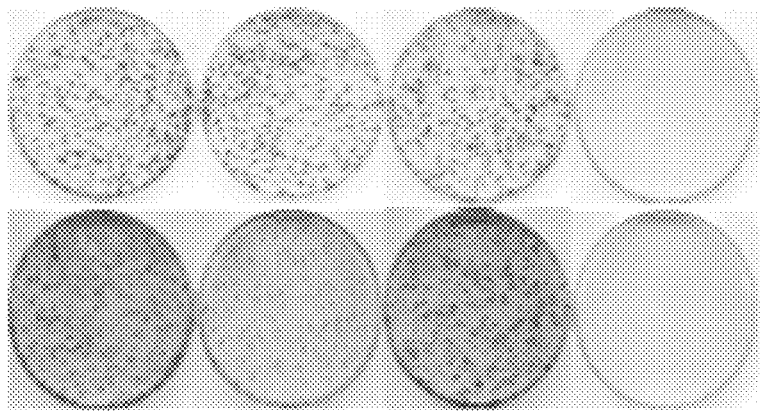
FIG. 37 shows the results of a clonogenic assay for CWR22rv1 cells treated with niclosamide with or without enzatulamide for 48 hours. CWR22rv1 cells or C4-2B MR cells were treated with 0.25 µM niclosamide with or without 20 µM enzalutamide in media containing FBS and clonogenic assays were performed.
Figure 38:
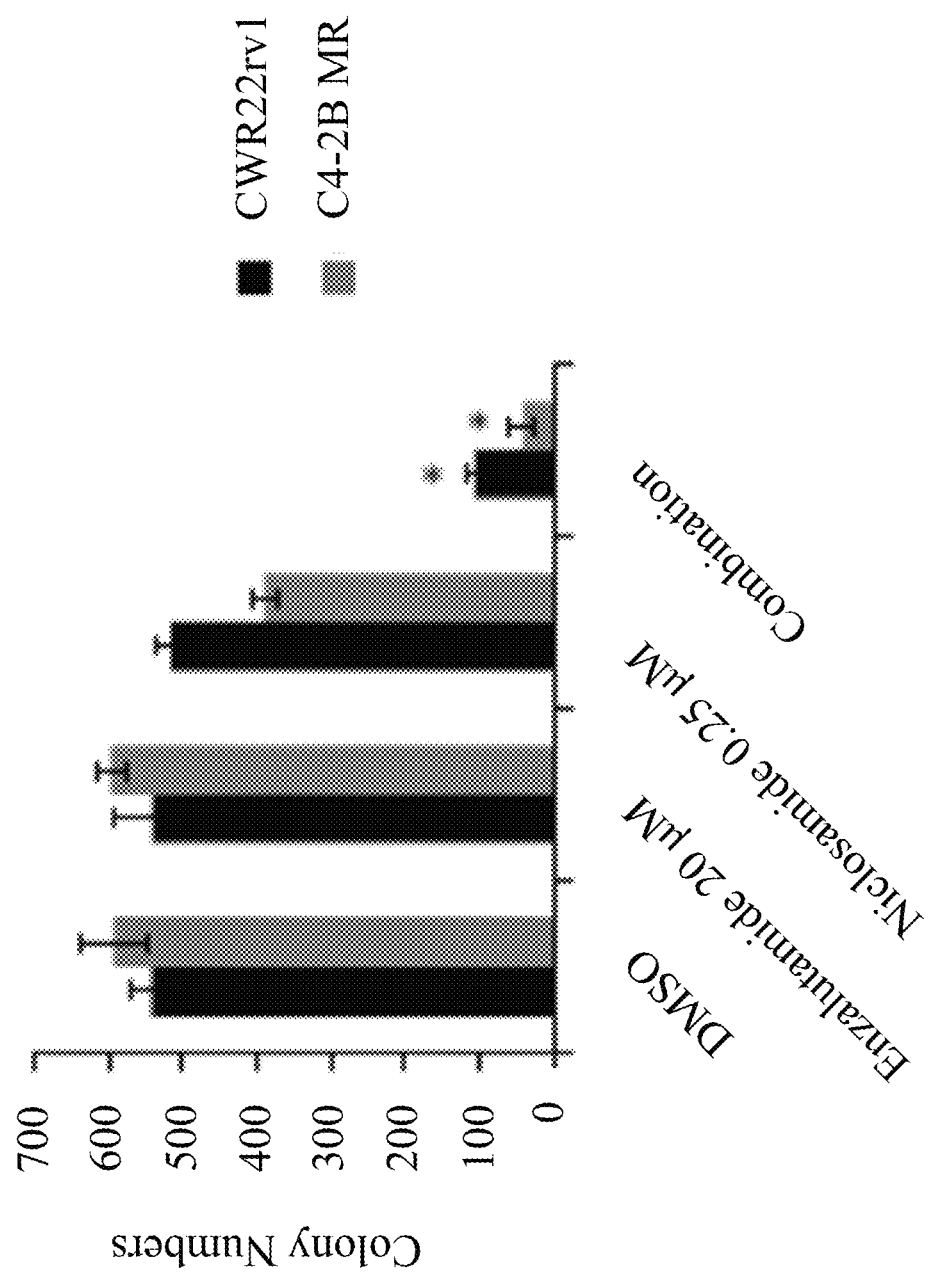
FIG. 38 shows the results of a clonogenic assay as a plot of colony numbers for CWR22rv1 cells treated with DMSO, enzalutamide, niclosamide, or a combination of niclosamide and enzalutamide. CWR22rv1 and C4-2B MR colonies were counted and results are presented as means±SD of 2 experiments performed in duplicate.

As shown in FIGS. 33 and 34, niclosamide significantly inhibited clonogenic ability of prostate cancer cells in a dose dependent manner. As shown in FIGS. 37 and 38, niclosamide significantly inhibits colony formation in C42B MR cells. Moreover, niclosamide significantly enhances enzalutamide inhibition of colony formation in C42B MR and CWR22rv1 cells. These results revealed that niclosamide inhibited prostate cancer cell growth and induced cell apoptosis with minimal effects on normal prostate epithelial cells.

Figure 3B:
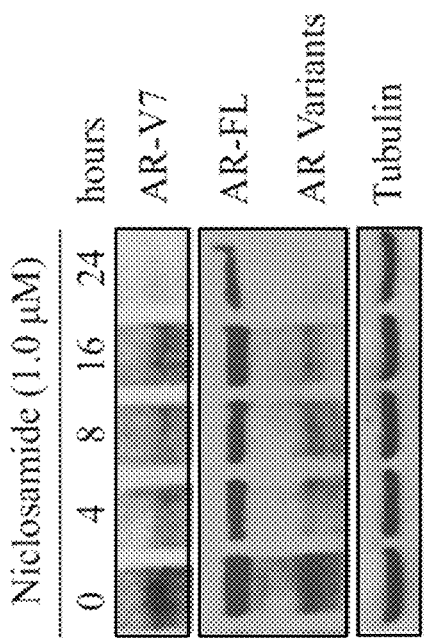
FIGS. 3A-3E show that niclosamide inhibited AR-V7 protein expression through enhancing protein degradation.
Figure 3A:
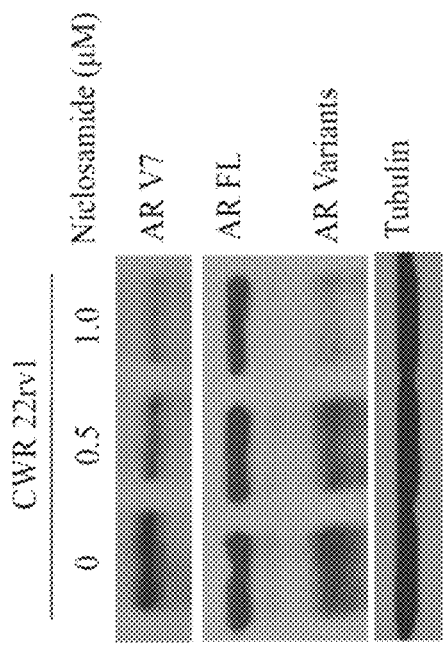
Figure 3E:
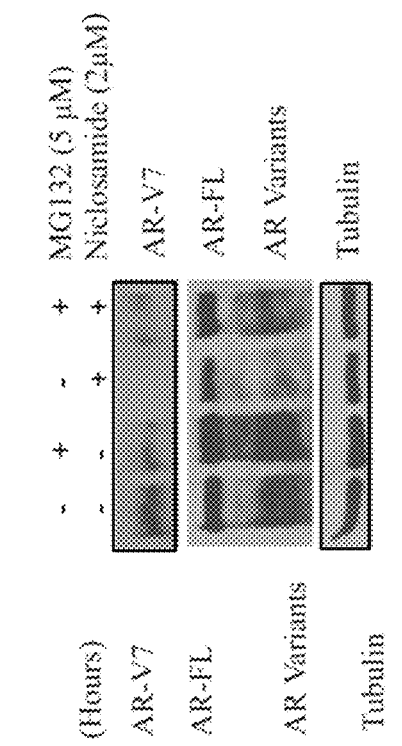
Figure 3D:
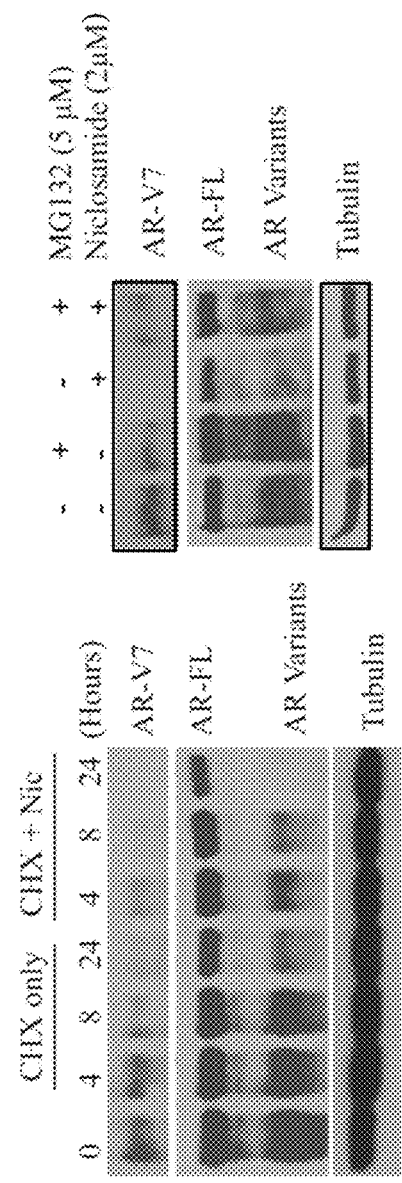
Figure 3C:
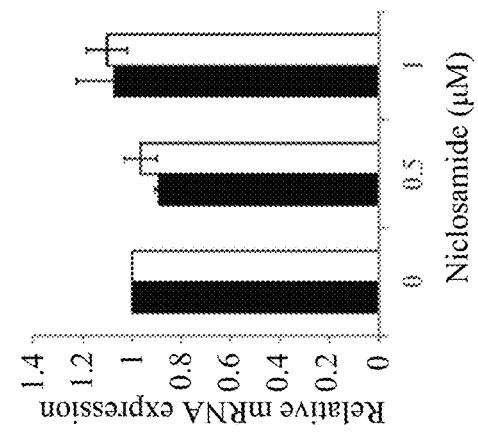
Figure 4B:
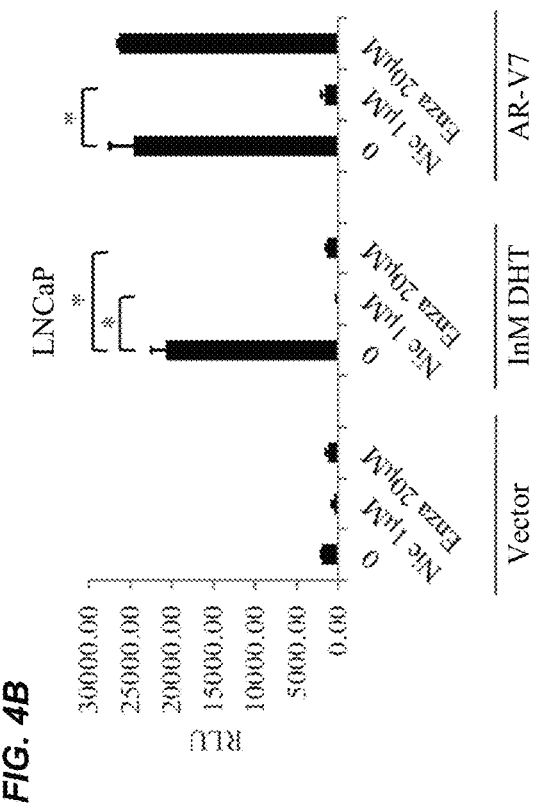
FIGS. 4A-4D show that niclosamide inhibits AR-V7 transcription activity.
Figure 4D:
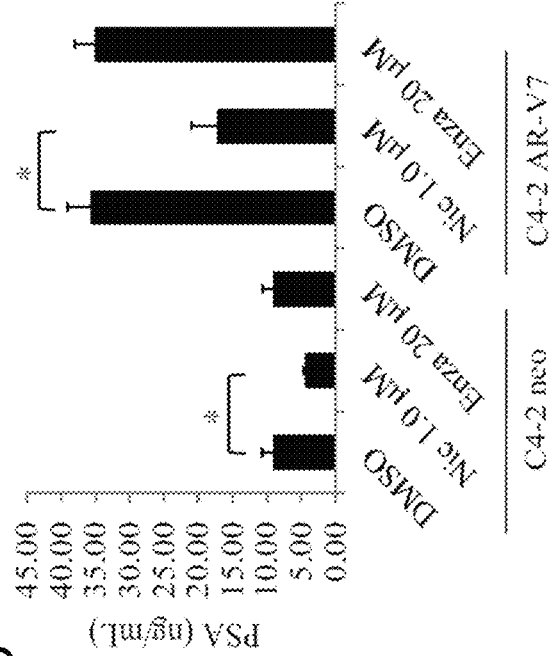
Figure 4A:
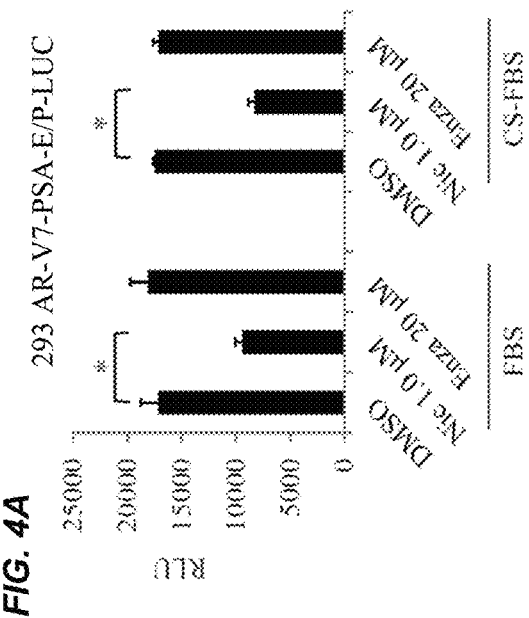
Figure 4C:
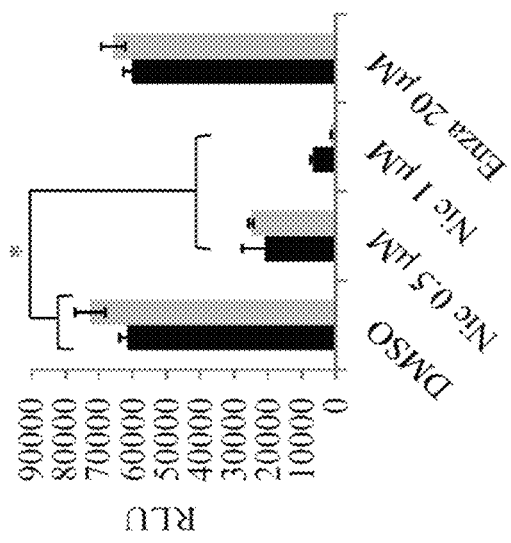
Figure 9A:
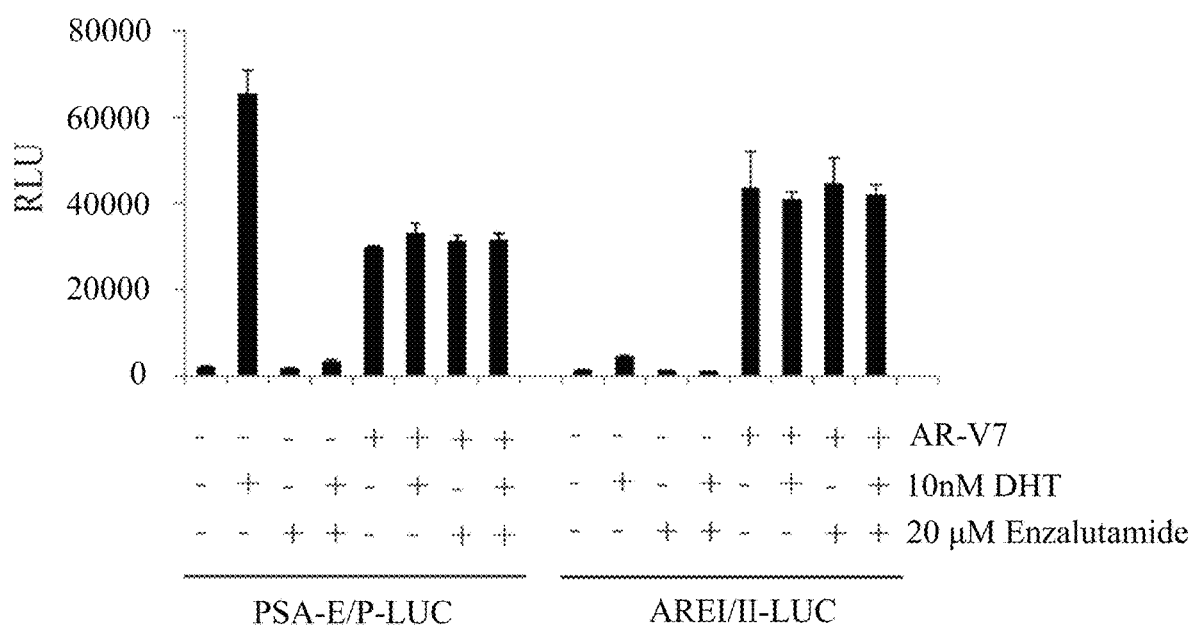
FIGS. 9A-9B show that the recruitment of AR-V7 to PSA promoter cannot be interrupted by enzalutamide.
Figure 9B:
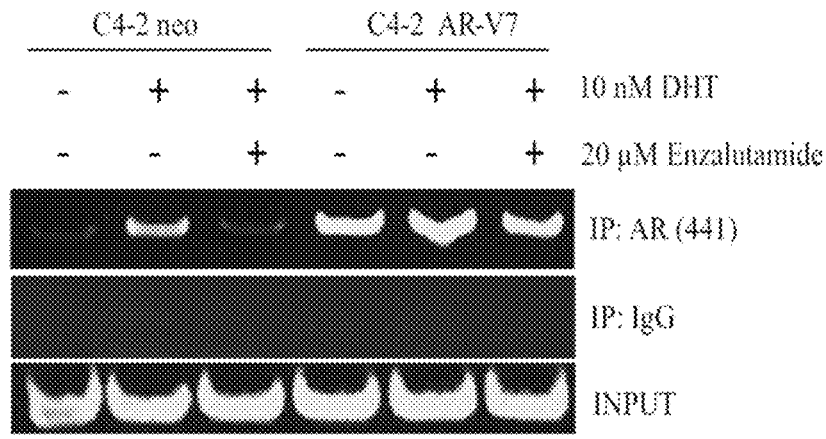
Figure 10B:
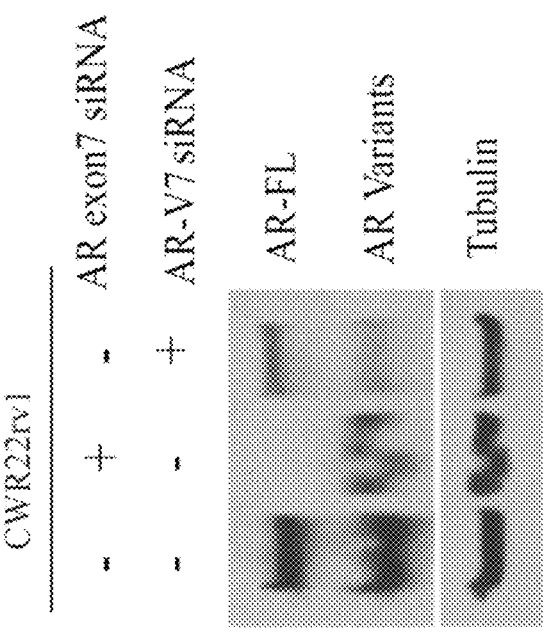
FIGS. 10A-10B show that AR-V7 mediates cell growth in CWR22rv1 cells.
Figure 10A:
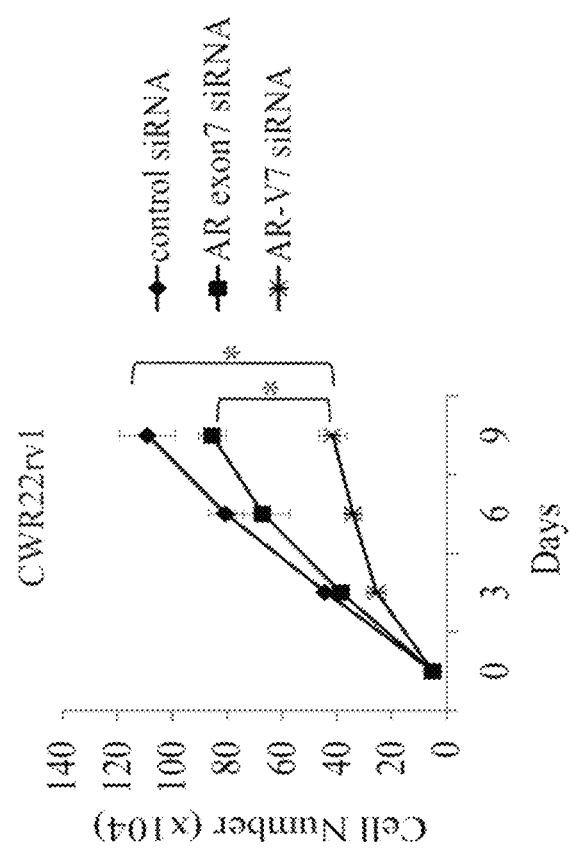
Figure 32:
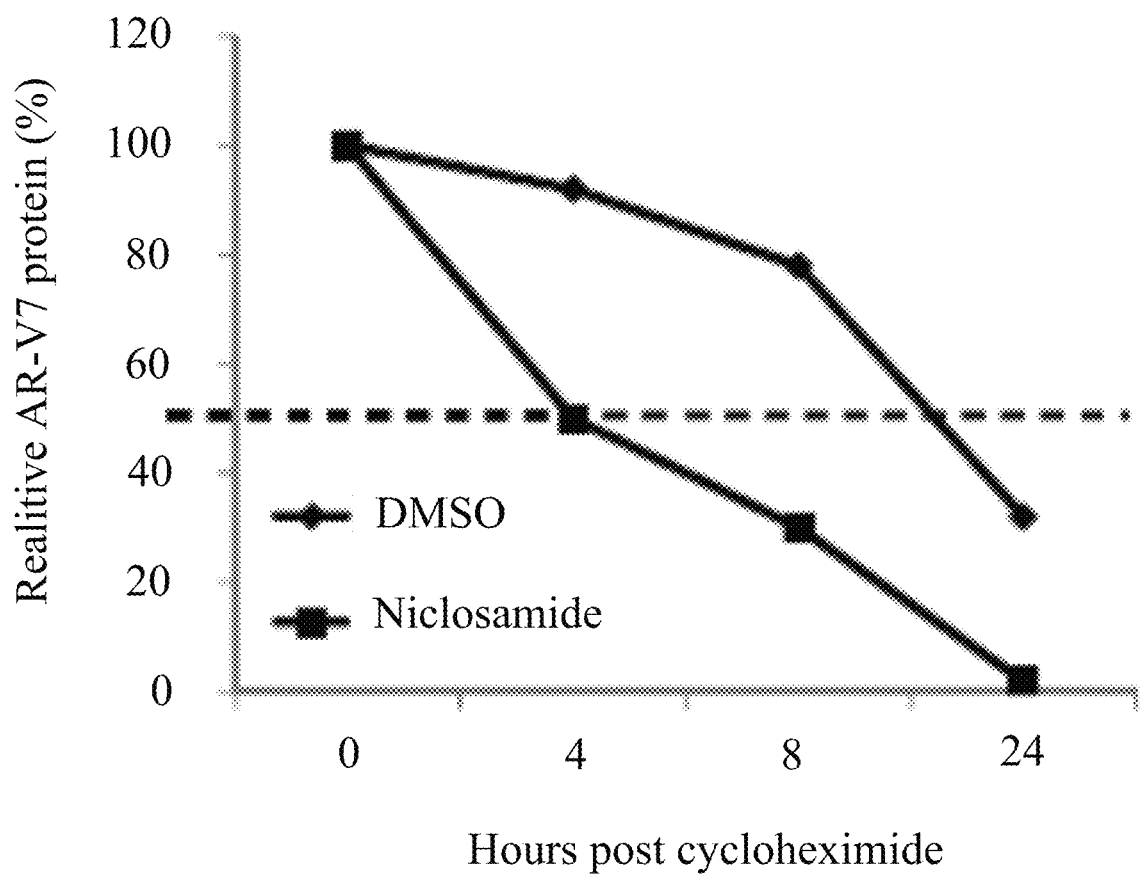
FIG. 32 shows that niclosamide increased AR-V7 protein degradation as compared to the untreated control cells. Relative amounts of AR-V7 protein are plotted on semilog scale. The amount of AR-V7 protein is normalized to 100% at time 0, the dashed line indicates 50% half-life.

To examine the cell growth function of AR-V7 in prostate cancer cells, CWR22rv1 cells were transiently transfected with AR exon7 siRNA or AR-V7 siRNA in CS-FBS condition. Cell numbers were counted on subsequent days, as shown in FIG. 10A, and knocked-down full length AR had moderate growth inhibition effects on CWR22rv1 cells while knocked-down AR-V7 significantly inhibited cell growth. The knock down effects were confirmed by Western blot (FIG. 10B) suggesting AR-V7 function is important to prostate cancer cell growth and targeting AR-V7 is an effective strategy to treat CRPC patients.

iii. Niclosamide Inhibited AR-V7 Protein Expression Through Enhancing Protein Degradation To determine whether niclosamide affects AR-V7 expression, CWR22rv1 cells, which express high endogenous AR-V7, were treated with different concentrations of niclosamide overnight; whole cell protein was extracted, as shown in FIG. 3A, niclosamide inhibited AR-V7 protein in a dose dependent manner. 0.5 μM niclosamide significantly inhibited AR-V7 expression but had little effects on full length AR (AR FL) expression, which suggested that niclosamide has a greater effect on truncated AR inhibition. Niclosamide also inhibited AR-V7 protein expression in a time dependent manner (FIG. 3B). To further clarify how niclosamide decreases AR-V7 protein expression, the effects of niclosamide on AR-V7 expression were determined at the transcriptional level. As shown in FIG. 3C, niclosamide did not affect AR-V7 or full length AR mRNA level, suggesting that niclosamide did not affect AR-V7 expression at the transcriptional level. Next, the effect of niclosamide on AR-V7 protein degradation was examined after new protein synthesis was blocked by cycloheximide as a potential mechanism for down regulation of AR-V7 protein level. The protein synthesis inhibitor cycloheximide (50 μg/mL) was added with or without 2 μM niclosamide at time 0 hour. At specified time points, cells were harvested, and the levels of AR-V7 protein were measured by Western blot using antibodies specific against AR-V7. As shown in FIGS. 3D and 32, in niclosamide treated cells, the half-life of AR-V7 protein was reduced to less than 4 hours from 8 hours in the control cells. Similar results are Systematic protein degradation by the ubiquitin-proteasome system plays an important role in the maintenance of protein stability. To examine whether niclosamide induced AR-V7 protein degradation via ubiquitin-proteasome system, the 26S proteasome inhibitor MG132 (5 μM) was added to the cells treated with niclosamide. MG132 was able to retard the niclosamide effect on AR-V7 protein levels (FIG. 3E), suggesting that niclosamide induced AR-V7 degradation via a proteasome-dependent pathway. As shown in FIG. 32, niclosamide increased AR-V7 protein degradation as compared to untreated controls.

iv. Niclosamide Inhibited AR-V7 Transcription Activity and Reduced Recruitment of AR-V7 to PSA Promoter This assay confirms that enzalutamide cannot inhibit AR-V7 transcriptional activity and also cannot reduce recruitment of AR-V7 to the PSA promoter in prostate cancer cells (FIG. 9). To examine whether niclosamide has an effect on AR-V7 transcriptional activity, the 293 AR-V7-PSA-E/P-LUC cell system was used, as shown in FIG. 4A, and niclosamide significantly inhibited AR-V7 transcription activity while enzalutamide had no effect. To further examine whether the effects could be translated into prostate cancer cell system, LNCaP cells were transiently transfected with AR-V7 following treatment with niclosamide or enzalutamide with or without DHT overnight, as shown in FIG. 4B. Both niclosamide and enzalutamide dramatically inhibited DHT induced AR transcriptional activity, but only niclosamide inhibited AR-V7 transcriptional activity. Similar to LNCaP cells, the AR-V7 transcription activity in C4-2 cells, which were stably transfected with AR-V7, was significantly inhibited by niclosamide but not enzalutamide (FIG. 4C). The results were also confirmed by PSA ELISA, as shown in FIG. 4D. C4-2 AR-V7 cells were cultured in CS-FBS condition and shown to express higher PSA levels than C4-2 neo cells. Niclosamide significantly inhibited PSA levels in C4-2 AR-V7 cells. The phenomenon was confirmed by Western blot. To further dissect the mechanism of AR-V7 inhibition effects by niclosamide, a ChIP assay was performed. C4-2 AR-V7 cells were cultured in CS-FBS condition for 3 days, following treatment with 1 μM niclosamide or 2004 enzalutamide overnight; whole cell lysis was subjected to ChIP assay, as shown in FIG. 4D, and niclosamide significantly reduced recruitment of AR-V7 to PSA promoter while enzalutamide had no effect. Collectively, the results confirmed niclosamide has the potential to be a new AR-V7 inhibitor on both the protein and mRNA level.

Figure 13:
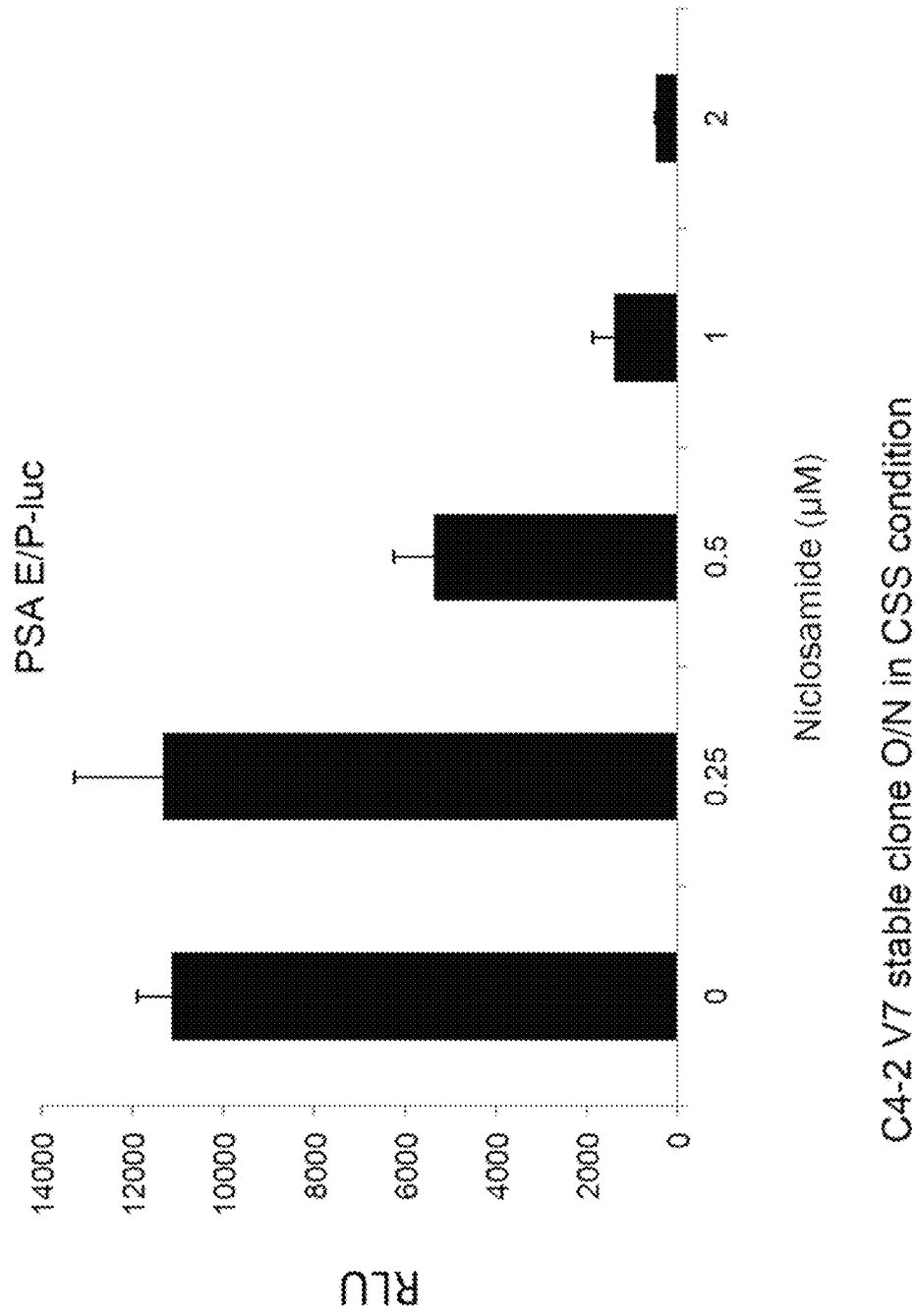
FIG. 13 shows a plot that demonstrates that niclosamide inhibits AR-V7 transactivation.
Figure 30:
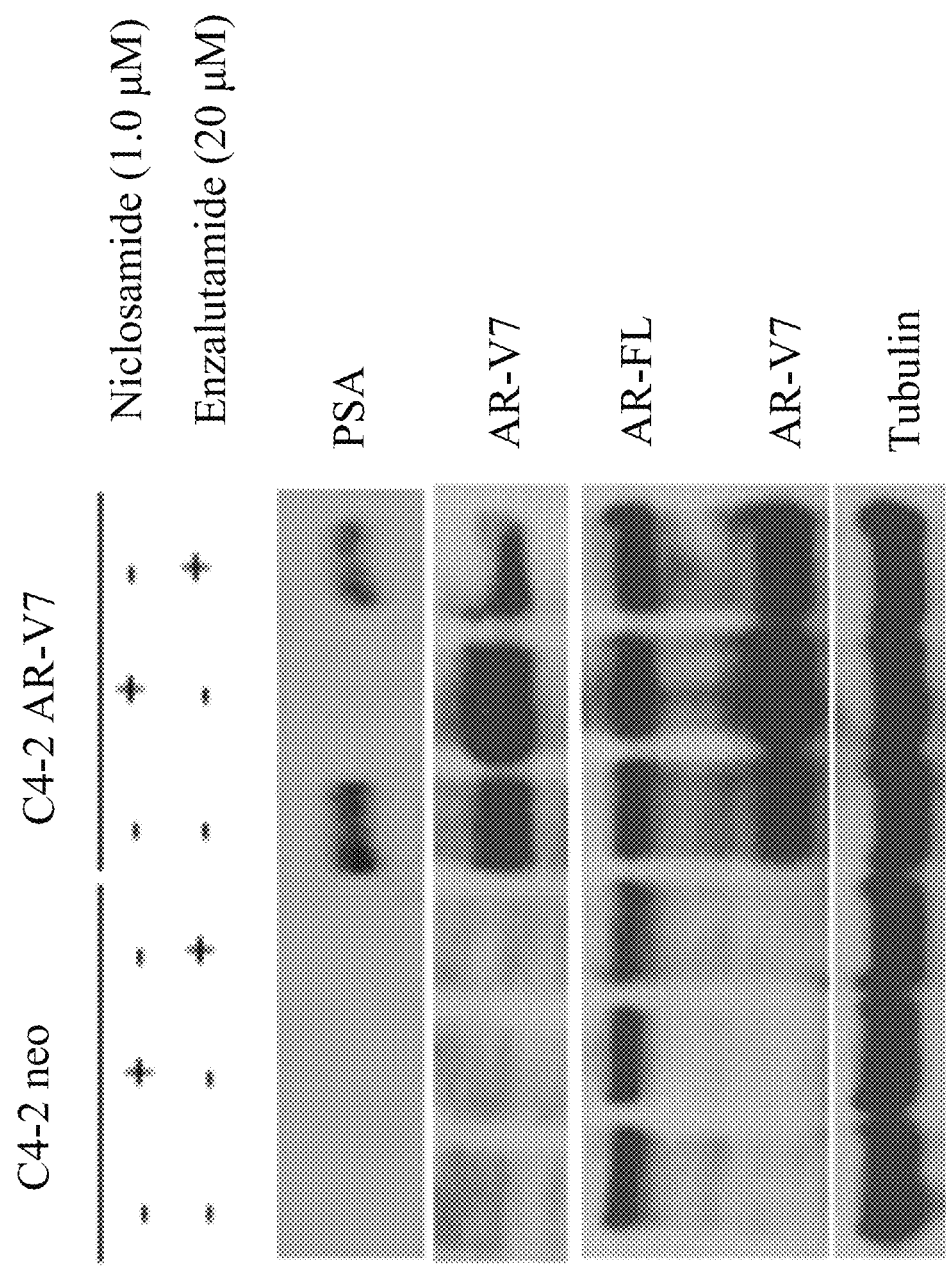
FIG. 30 shows that C4-2 neo and C4-2 AR-V7 cells were cultured in CS-FBS condition for 3 days, followed by treatment with 1.0 µM niclosamide or 20 µM enzalutamide overnight. Whole cell lysates were immunoblotted with the indicated antibodies.
Figure 31:
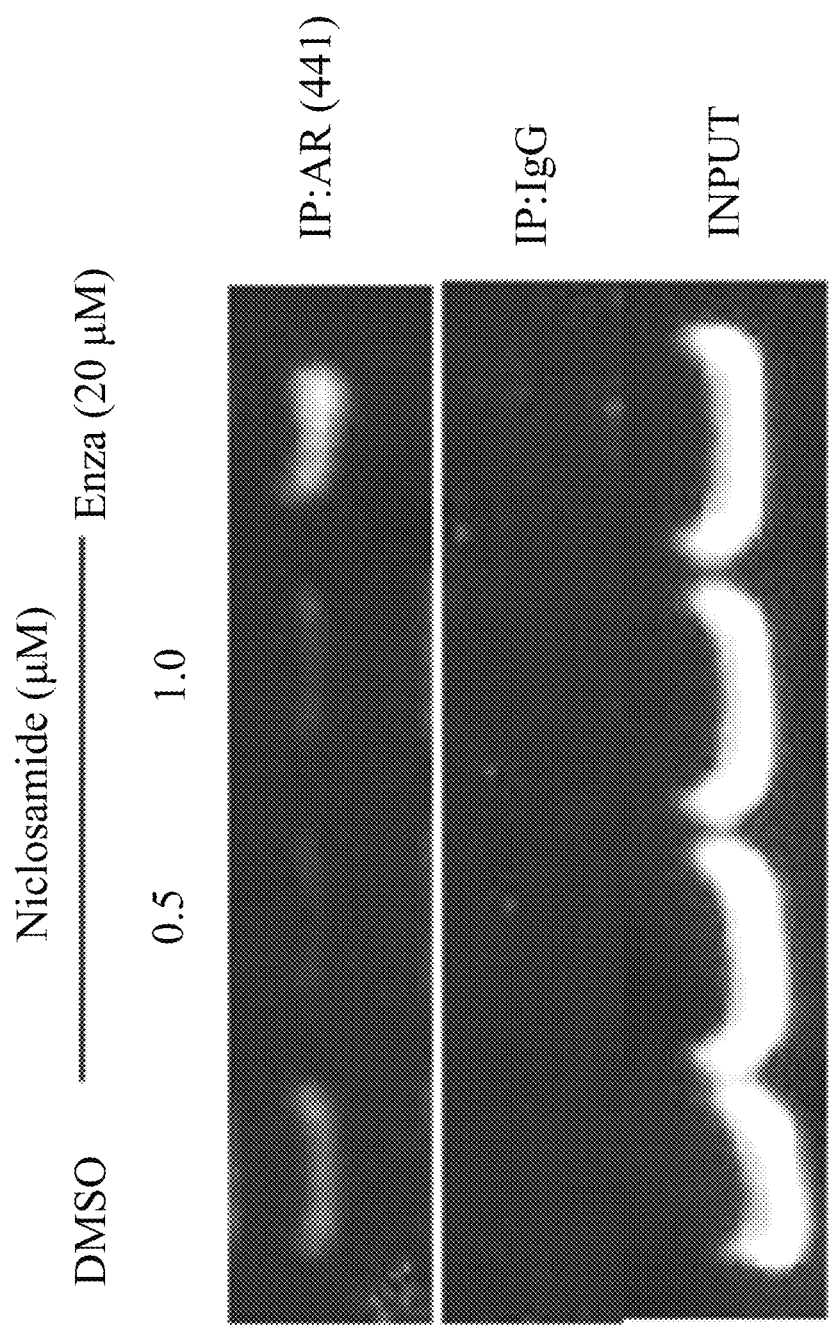
FIG. 31 shows C4-2 AR-V7 cells that were cultured in CS-FBS condition for 3 days, followed by treatment with 0.5 µM, 1.0 µM niclosamide or 20 µM enzalutamide overnight. Whole cell lysates were subjected to ChIP assay. Results are presented as means±SD of 3 experiments performed in duplicate. *P<0.05.

The results were also confirmed by western blot as shown in FIG. 30, niclosamide significantly inhibited PSA protein expression while enzalutamide had minimal effects. A ChIP assay was performed. C4-2 AR-V7 cells were cultured in CS-FBS condition for 3 days, followed by treatment with niclosamide (0.5 μM and 1 μM) or 20 μM enzalutamide overnight and whole cell lysates was subjected to ChIP assay. As shown in FIG. 31, niclosamide significantly reduced recruitment of AR-V7 to PSA promoter while enzalutamide had no effect. These results demonstrate that niclosamide but not enzalutamide was able to inhibit AR-V7 transactivation. Similar results were obtained after overnight incubation of C4-2 AR-V7 cells in charcoal stripped serum media with varying concentrations of niclosamide, as shown in FIG. 13.

Figure 5A:
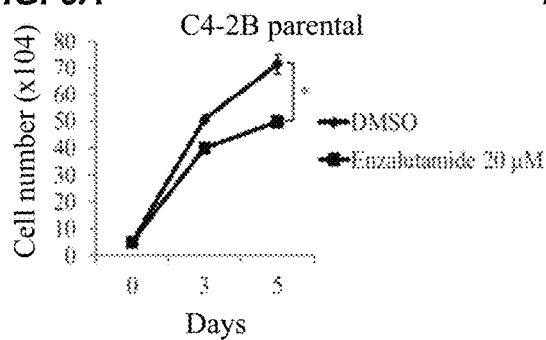
FIG. 5A-5H show that C4-2B cells that were chronically treated with enzalutamide express AR variants and are sensitive to niclosamide.
Figure 5B:
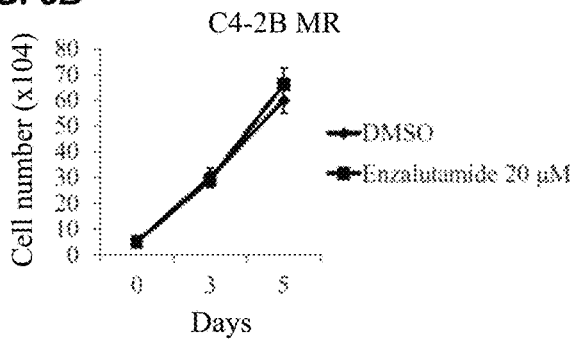
Figure 5C:
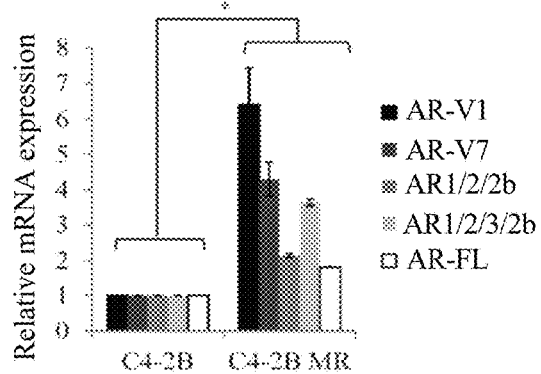
Figure 5D:
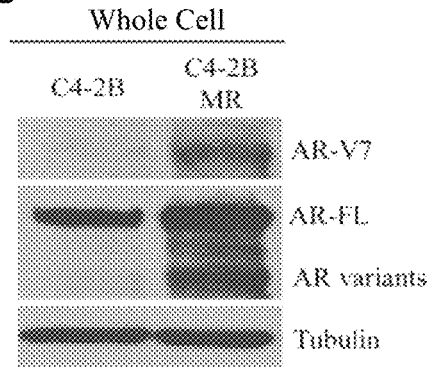
Figure 5E:
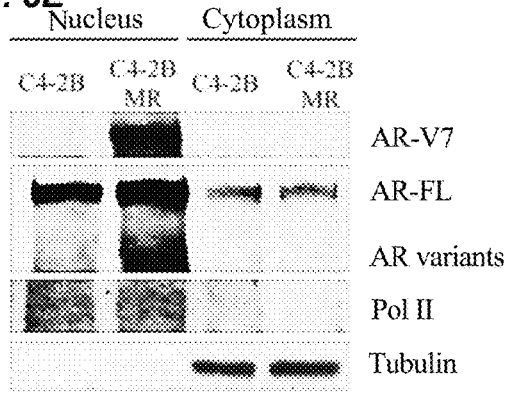
Figure 5F:
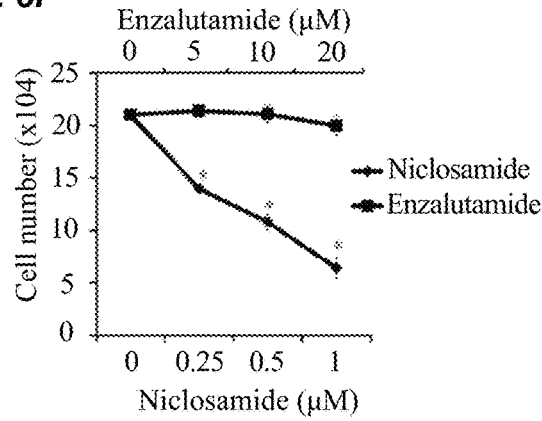
Figure 5G:
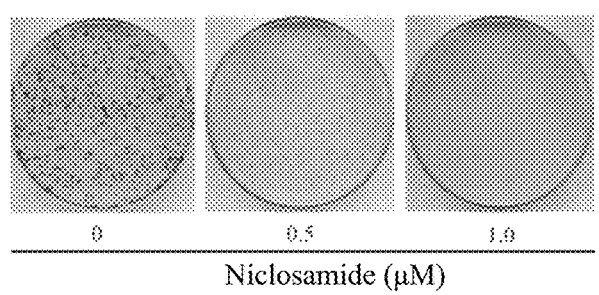
Figure 5H:
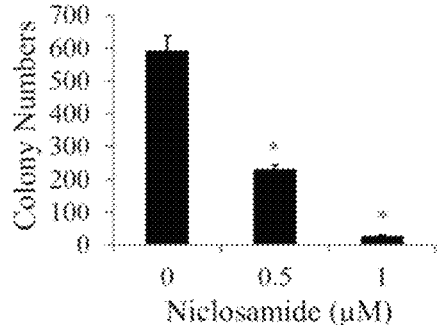
Figure 20:
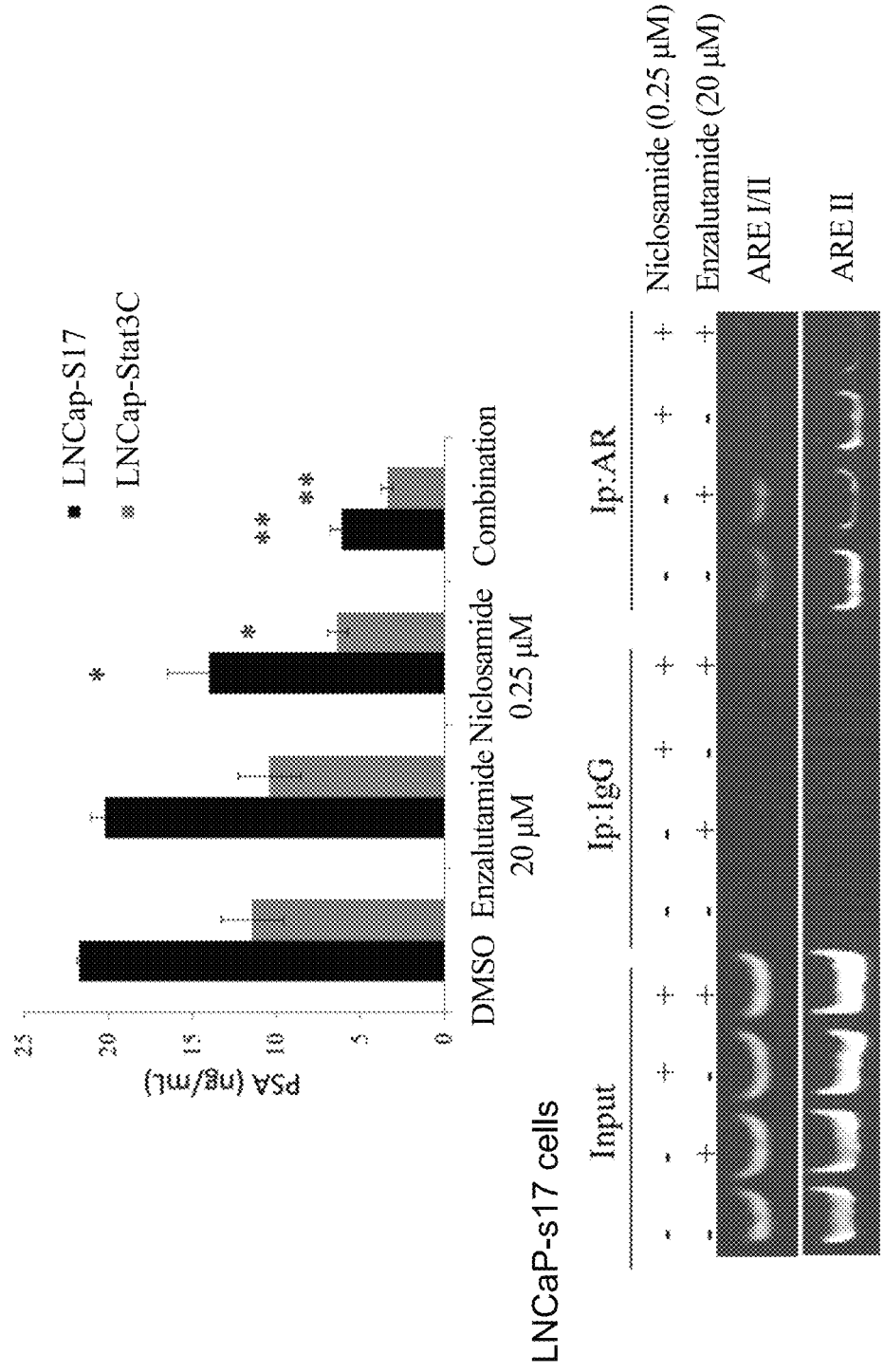
FIG. 20 shows that combination treatments inhibit recruitment of AR to PSA promoter.

Similar results were obtained with LNCap-Stat3C cells. As shown in FIG. 20, combination treatment with niclosamide and enzalutamide inhibits recruitment of AR to the PSA promoter.

v. C4-2B Cells Chronically Treated with Enzalutamide Express AR Variants and are Sensitive to Niclosamide AR variants have been shown to be one of the possible mechanisms to induce enzalutamide resistance, but to date, there is little evidence that enzalutamide induces AR variants in prostate cancer cells or patients. To address this issue, C4-2B cells were chronically treated with enzalutamide in FBS condition, as shown in FIGS. 5A and 5B. After 12 months being cultured in media containing enzalutamide, C4-2B MR (C4-2B enzalutamide resistant) cells exhibited more resistance than C4-2B parental cells. Next, we examined the AR variants level in C4-2B parental and C4-2B MR cells, as shown in FIG. 5C. C4-2B MR cells express higher AR variant mRNA level than C4-2B parental cells, including AR-V1, AR-V7, AR1/2/2b and AR1/2/3/2b. The results were also confirmed by Western blot, as shown in FIG. 5D. C4-2B MR cells expressed significantly higher AR-V7 in the nucleus compared to C4-2B parental cells. Full length AR was also up-regulated in C4-2B MR cells which suggested overexpression of AR signaling may be an important mechanisms of enzalutamide resistance. Knocked down AR-V7 significantly reversed enzalutamide resistance in C4-2B MR cells (FIG. 5E), suggesting AR-V7 is the major driver of enzalutamide resistance in C4-2B MR cells. Next, niclosamide effects were examined on C4-2B MR cells, as shown in FIG. 5F. C4-2B MR cells were resistant to enzalutamide but significantly inhibited by niclosamide in a dose dependent manner. The results were also confirmed by clonogenic assay, as shown in FIG. 5G, where 0.5 μM niclosamide significantly inhibited C4-2B MR cells colony formation and colony size. Collectively, the above data suggested that AR variants may be an important mechanisms of enzalutamide resistance and targeting AR signaling would be an effective strategy to treat advanced prostate cancer patients.

Figure 7B:
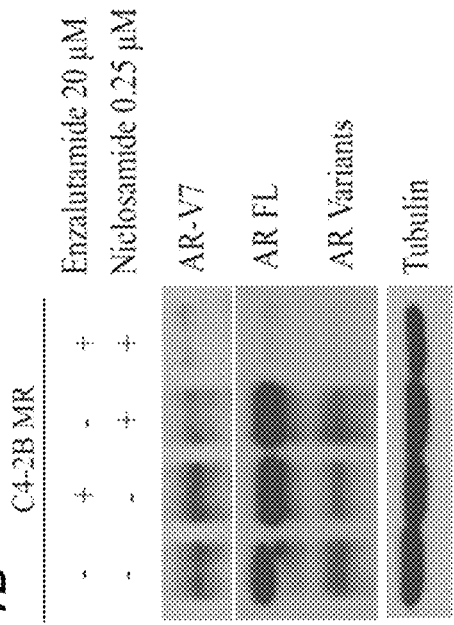
FIGS. 7A-7B show that niclosamide enhances enzalutamide and abiraterone effects through AR-V7 inhibition.
Figure 7A:
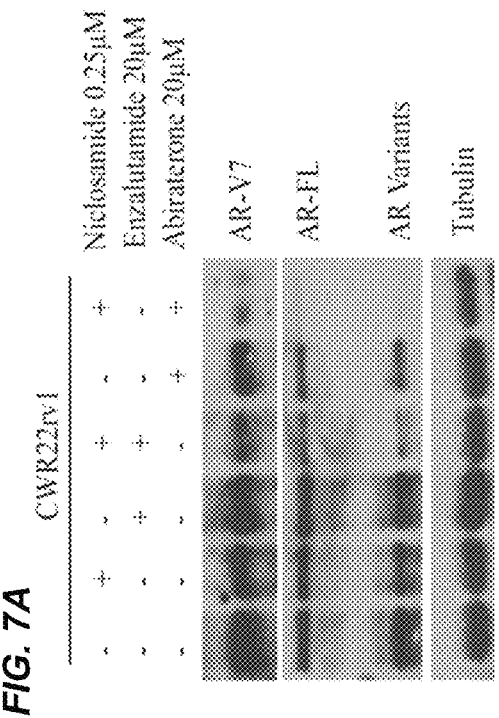
Figure 11A:
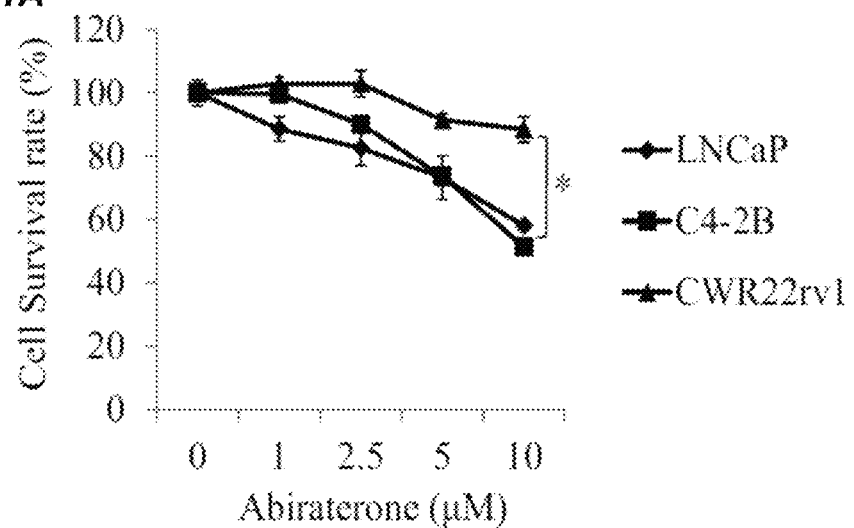
FIGS. 11A-11B show that AR-V7 induced abiraterone resistance in CWR22rv1 cells.
Figure 11B:
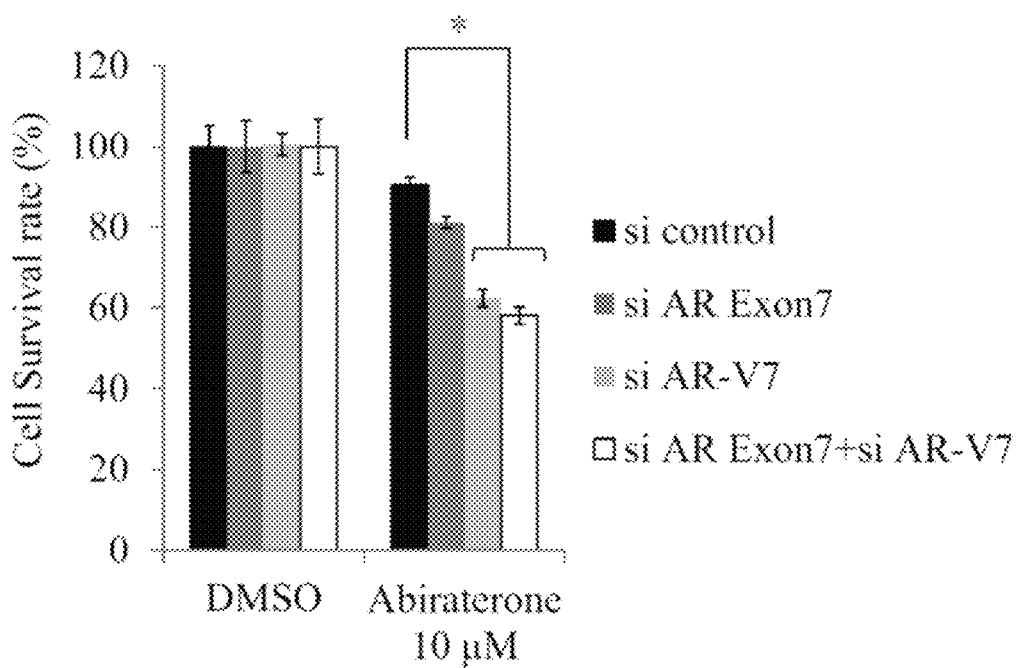
Figure 12:
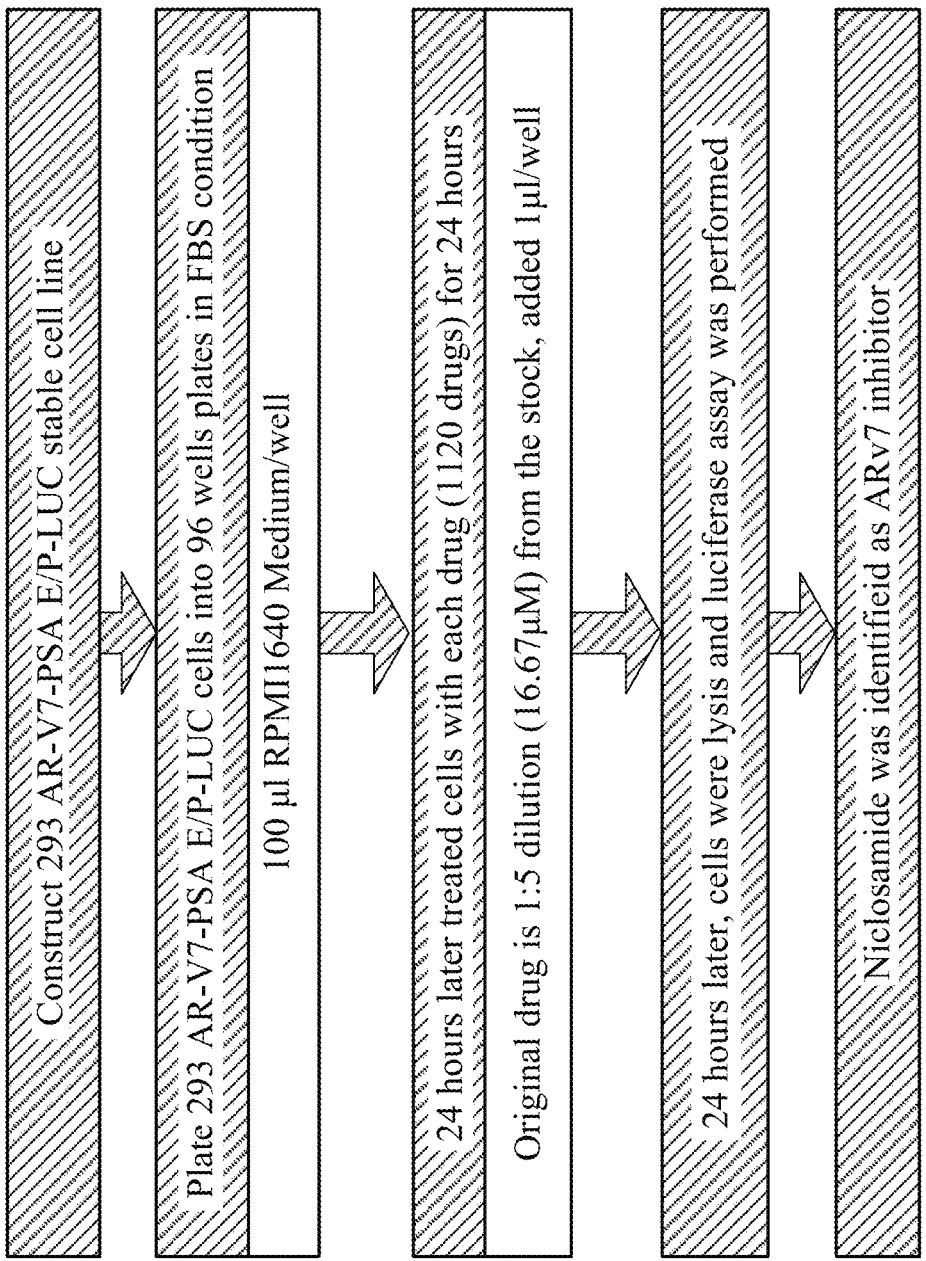
FIG. 12 shows a schematic of a drug screening procedure used to identify niclosamide as an AR-V7 inhibitor.
Figure 14:
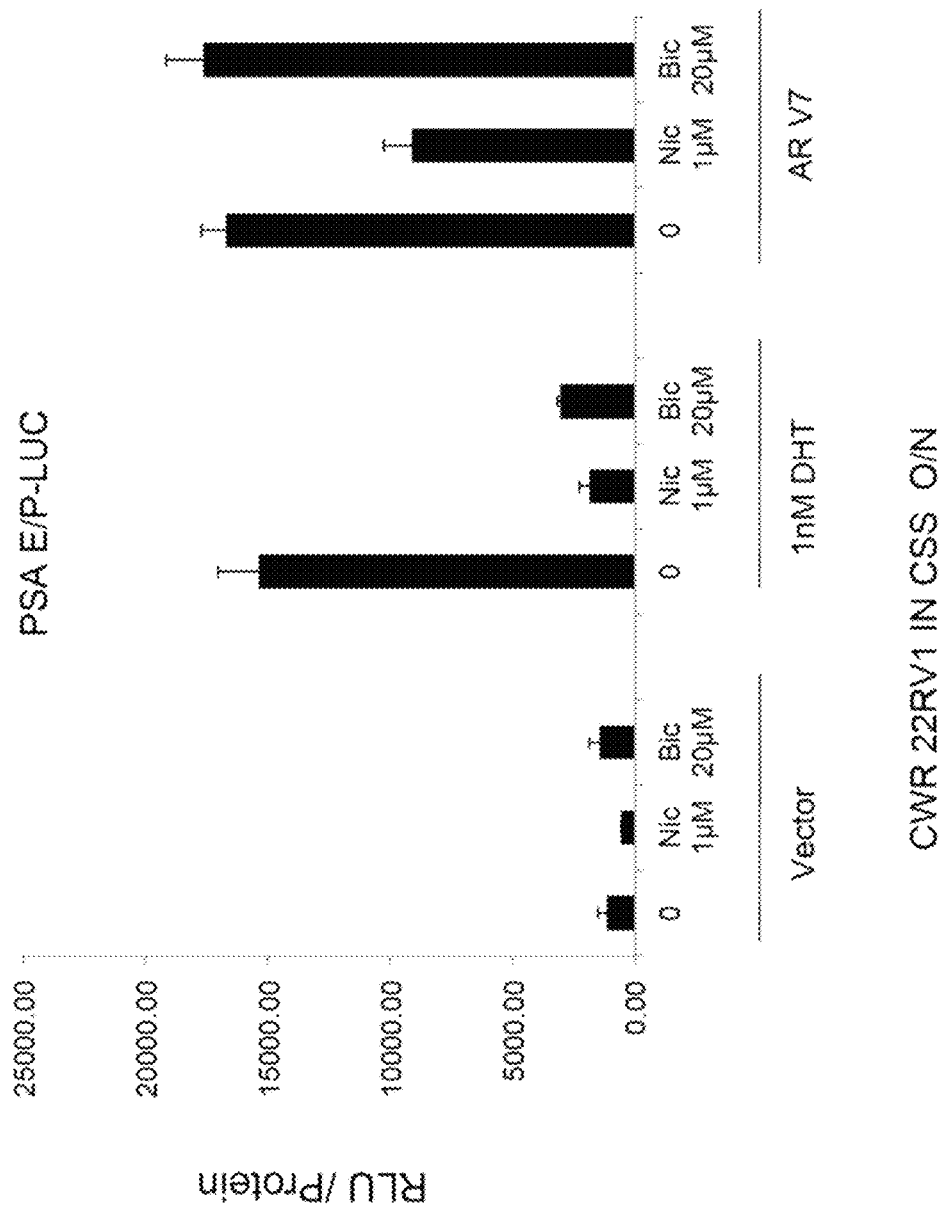
FIG. 14 shows a plot that demonstrates that niclosamide but not bicalutamide inhibits AR-V7 transactivation.
Figure 15:
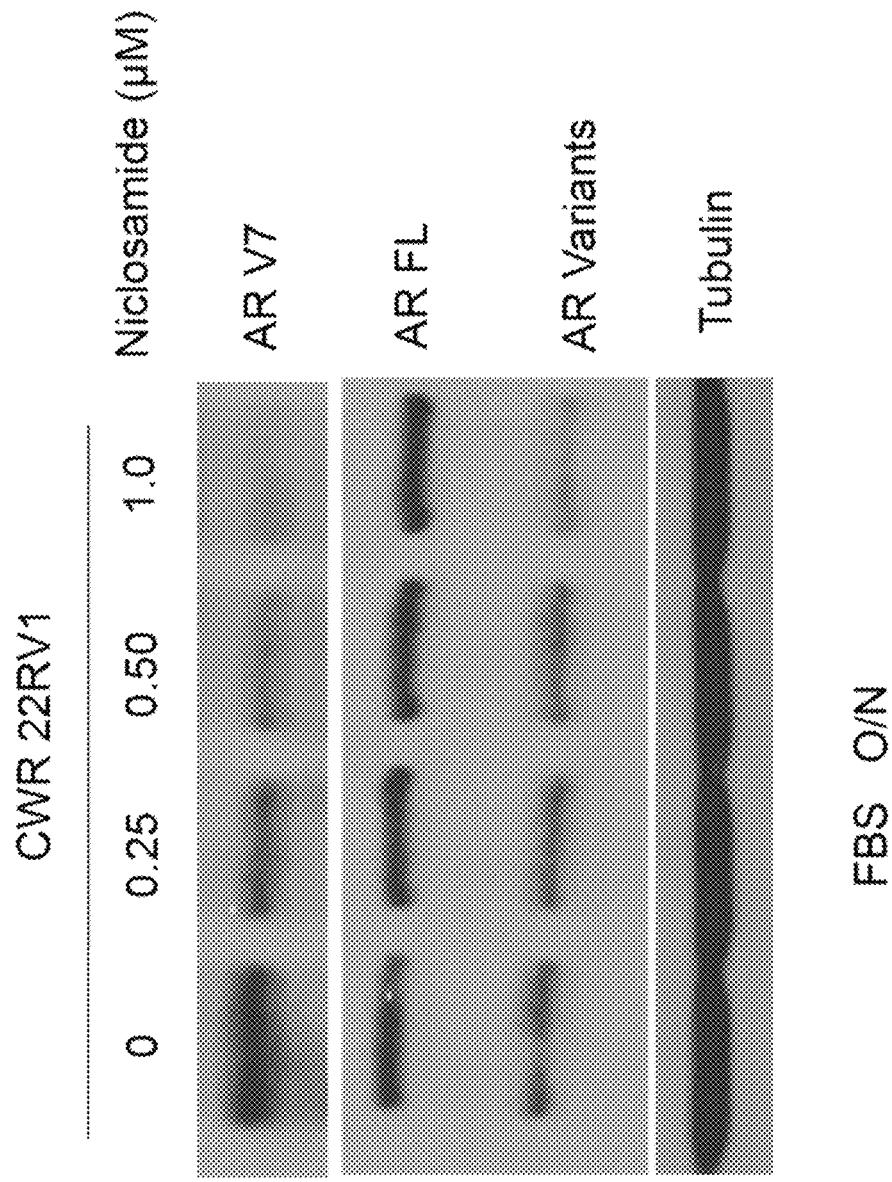
FIG. 15 shows a blot that demonstrates that niclosamide inhibits AR and AR-V7 expression.
Figure 16:
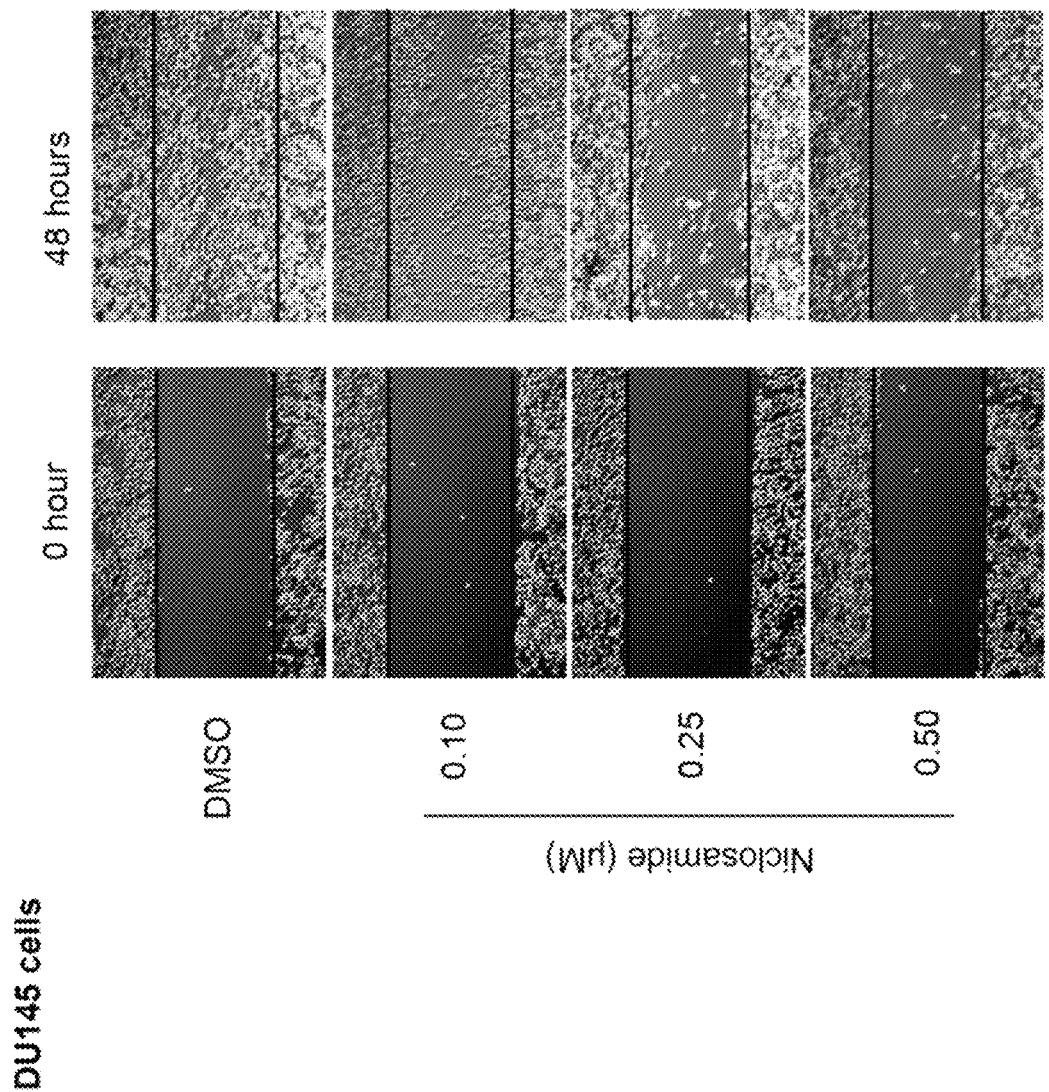
FIG. 16 illustrates niclosamide inhibition of cell migration and invasion in prostate cancer cells.
Figure 17:
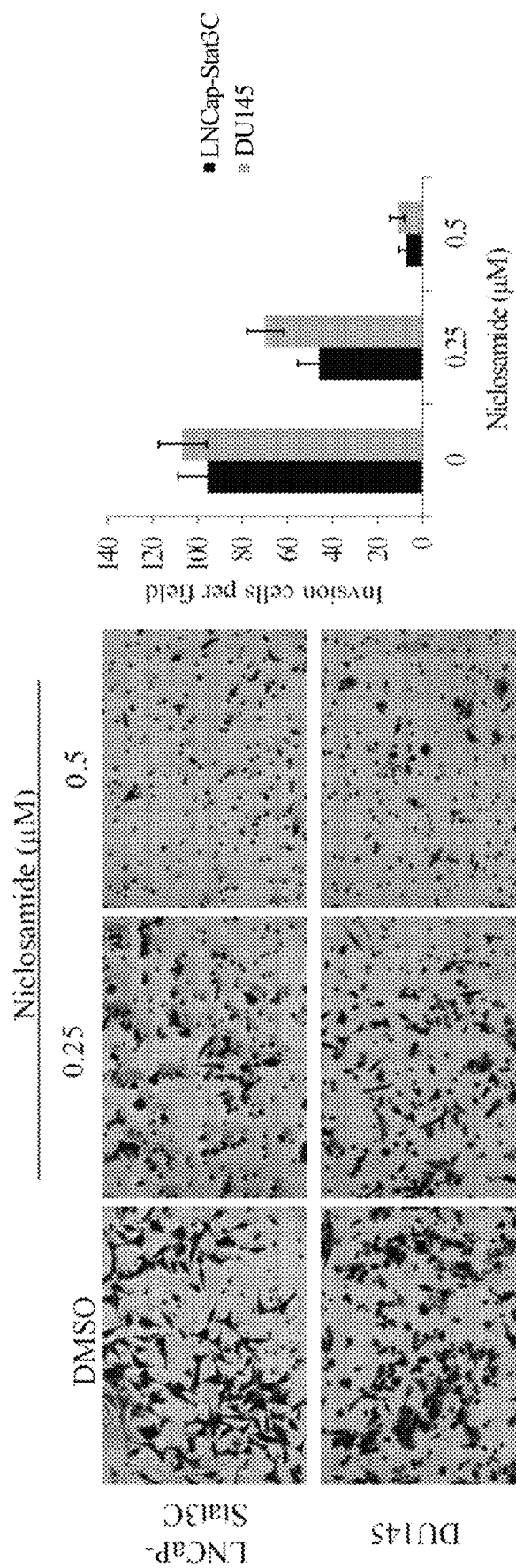
FIG. 17 illustrates niclosamide inhibition of cell invasion in prostate cancer cells.
Figure 18:
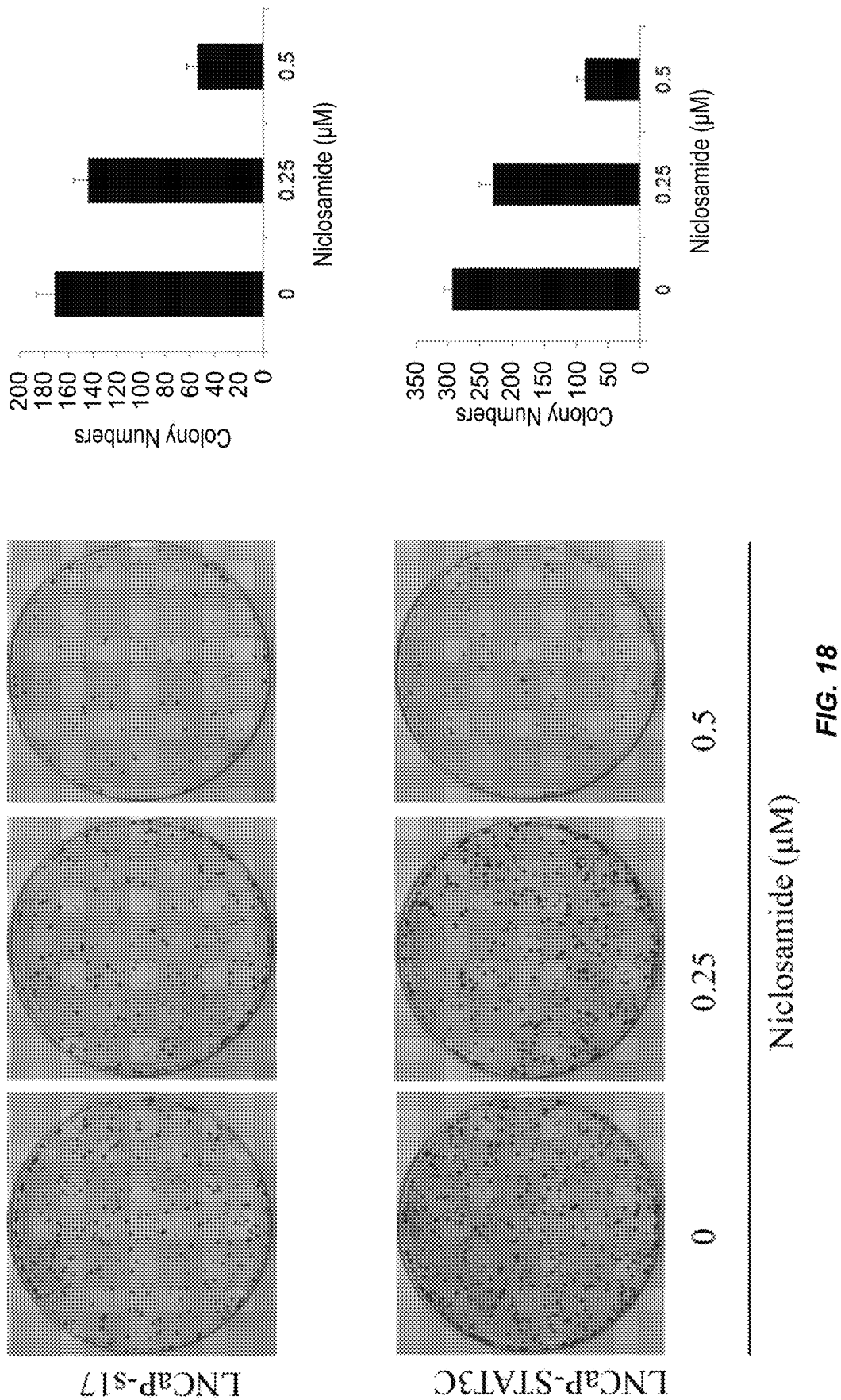
FIG. 18 illustrates niclosamide inhibition of colony formation in prostate cancer cells.
Figure 19:
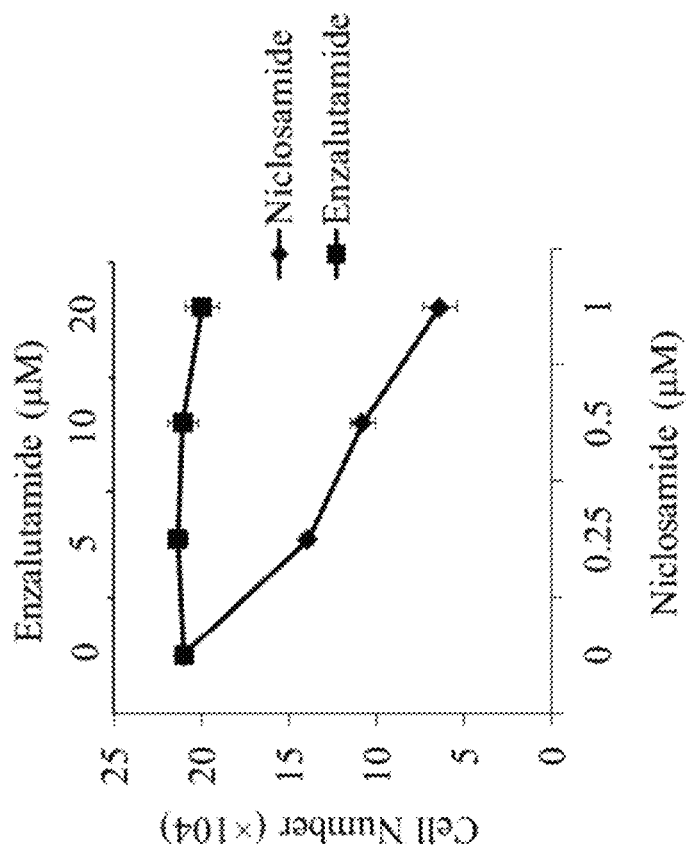
FIG. 19 shows that niclosamide inhibited C4-2B MR cell growth in a dose dependent manner.
Figure 21:
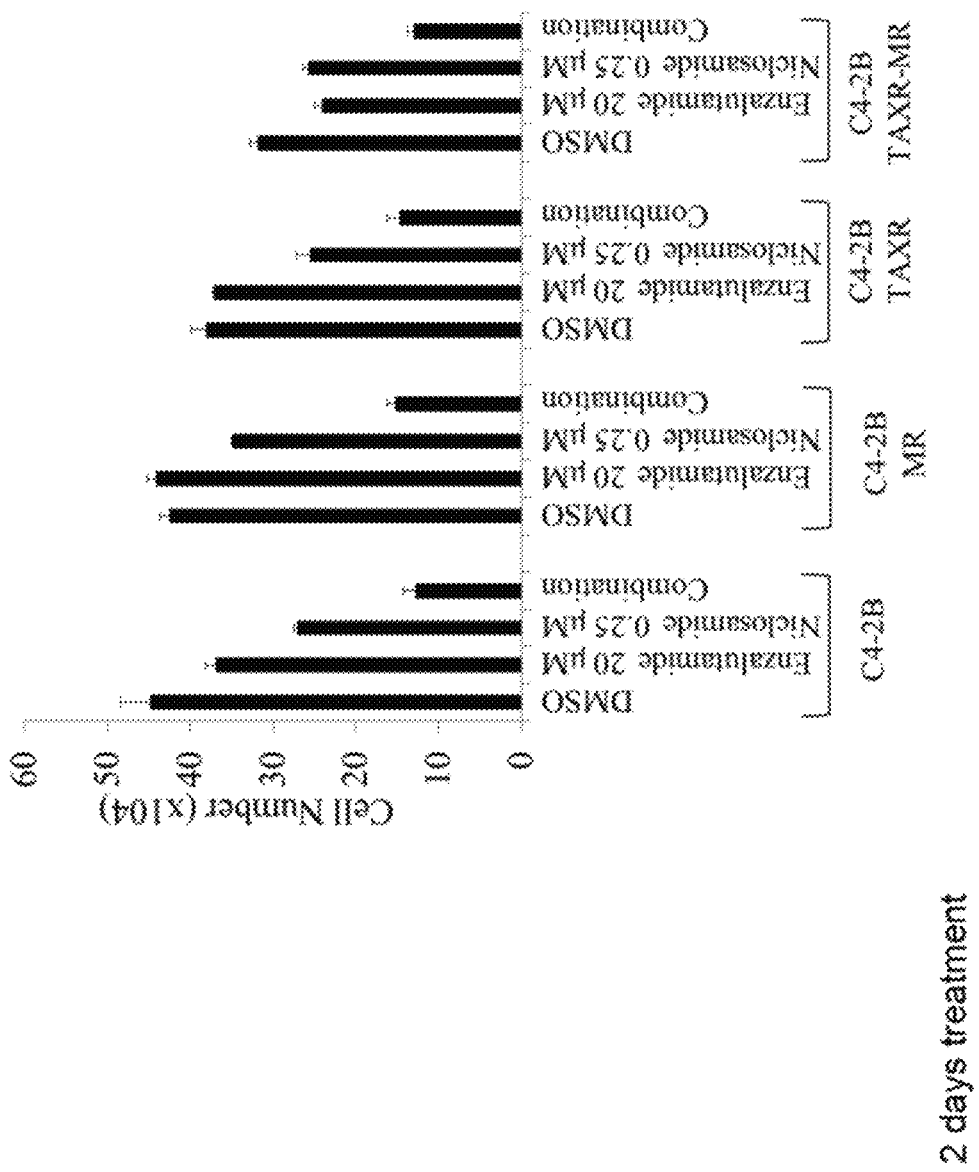
FIG. 21 shows that combination treatment inhibited C4-2B, C4-2B TAXR, C4-2B TAXR+MR, and C4-2B AbiR cell growth.
Figure 23:
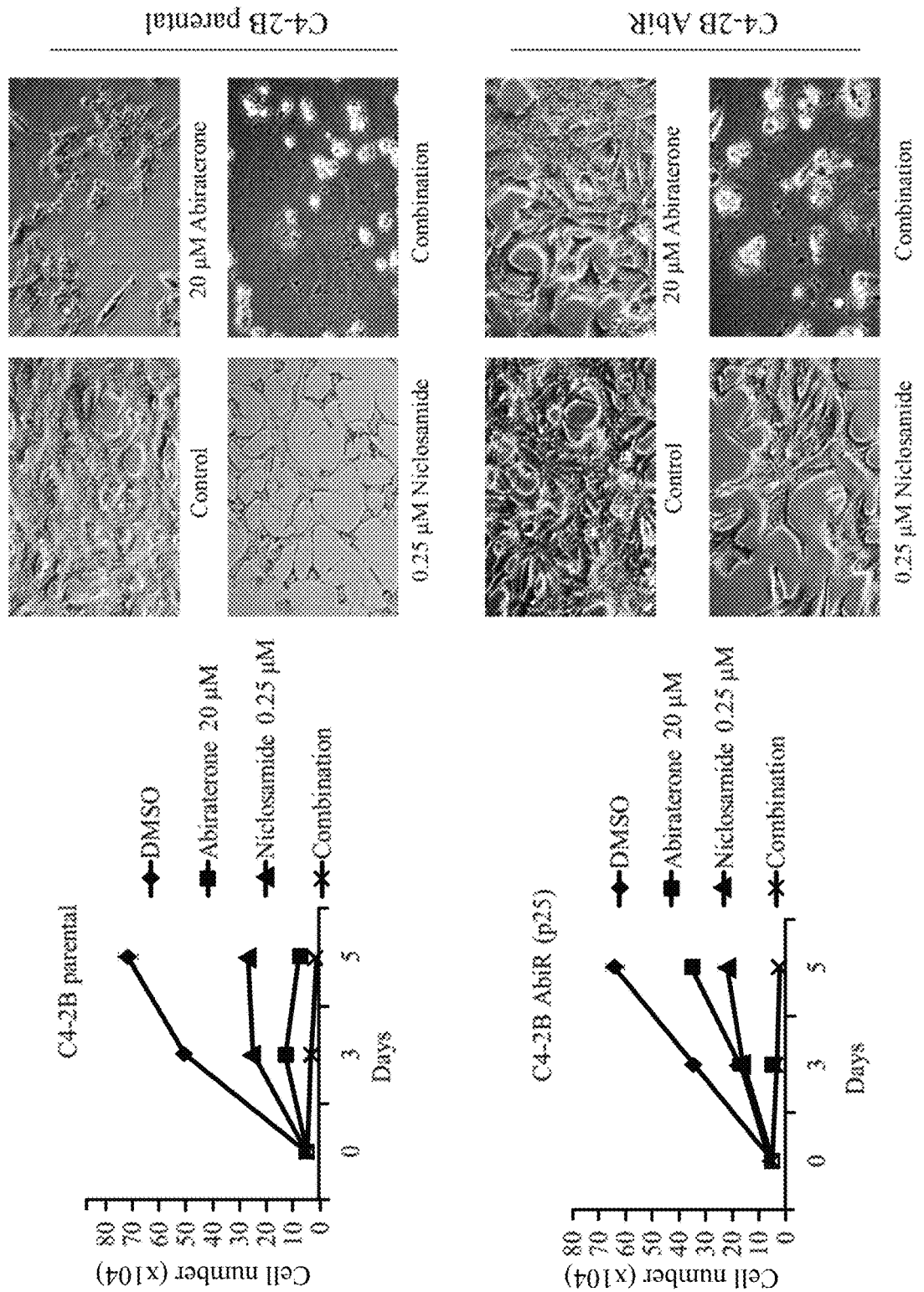
FIG. 23 shows that niclosamide enhanced the effects of abiraterone in C4-2B AbiR cells.
Figure 35:
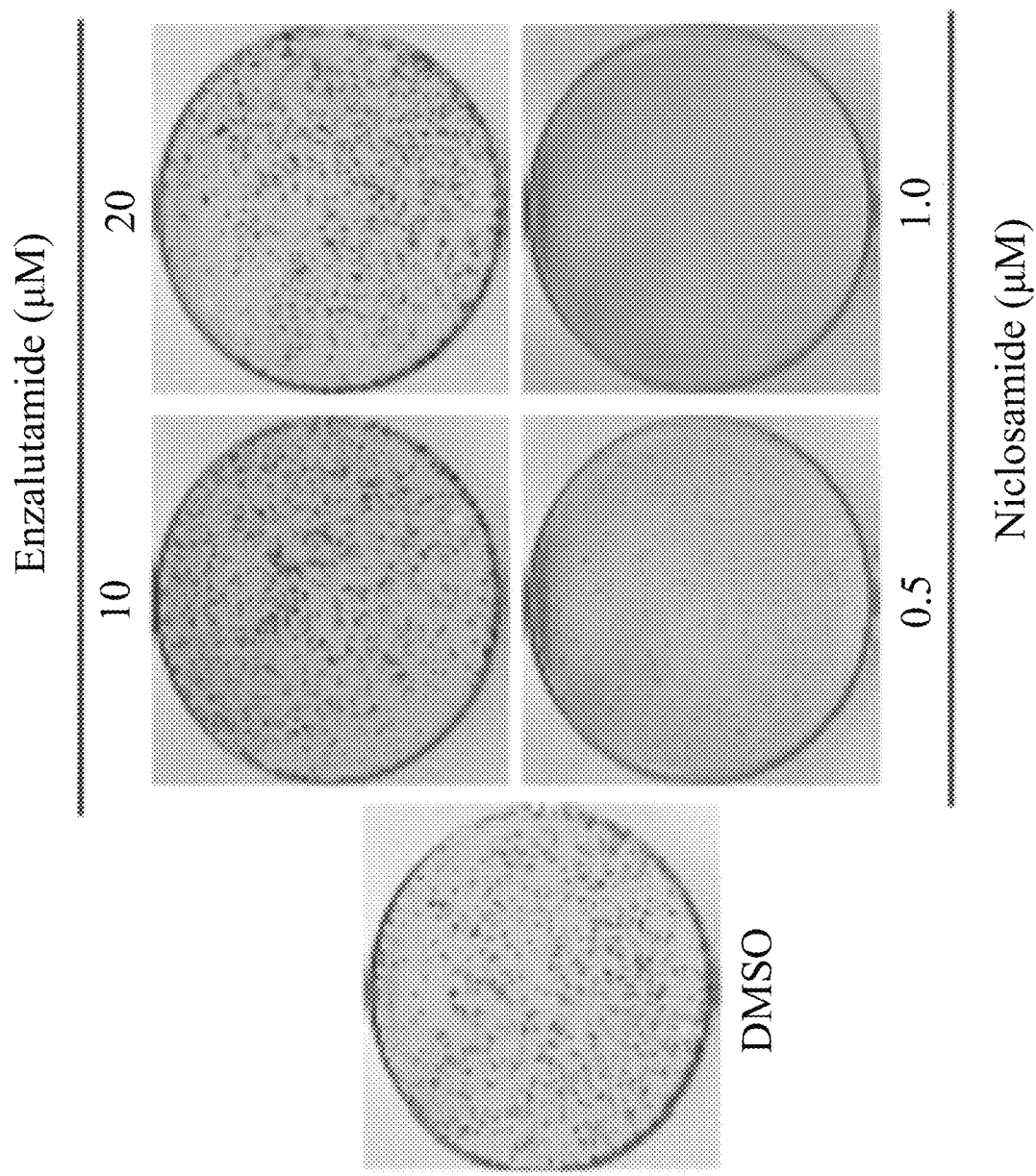
FIG. 35 shows that niclosamide but not enzalutamide inhibited colony formation, and also colony size, in C4-2B MR cells. C4-2B MR cells were treated with DMSO, 10 µM or 20 µM enzalutamide, 0.5 µM or 1.0 µM niclosamide and clonogenic assays were performed.
Figure 36:
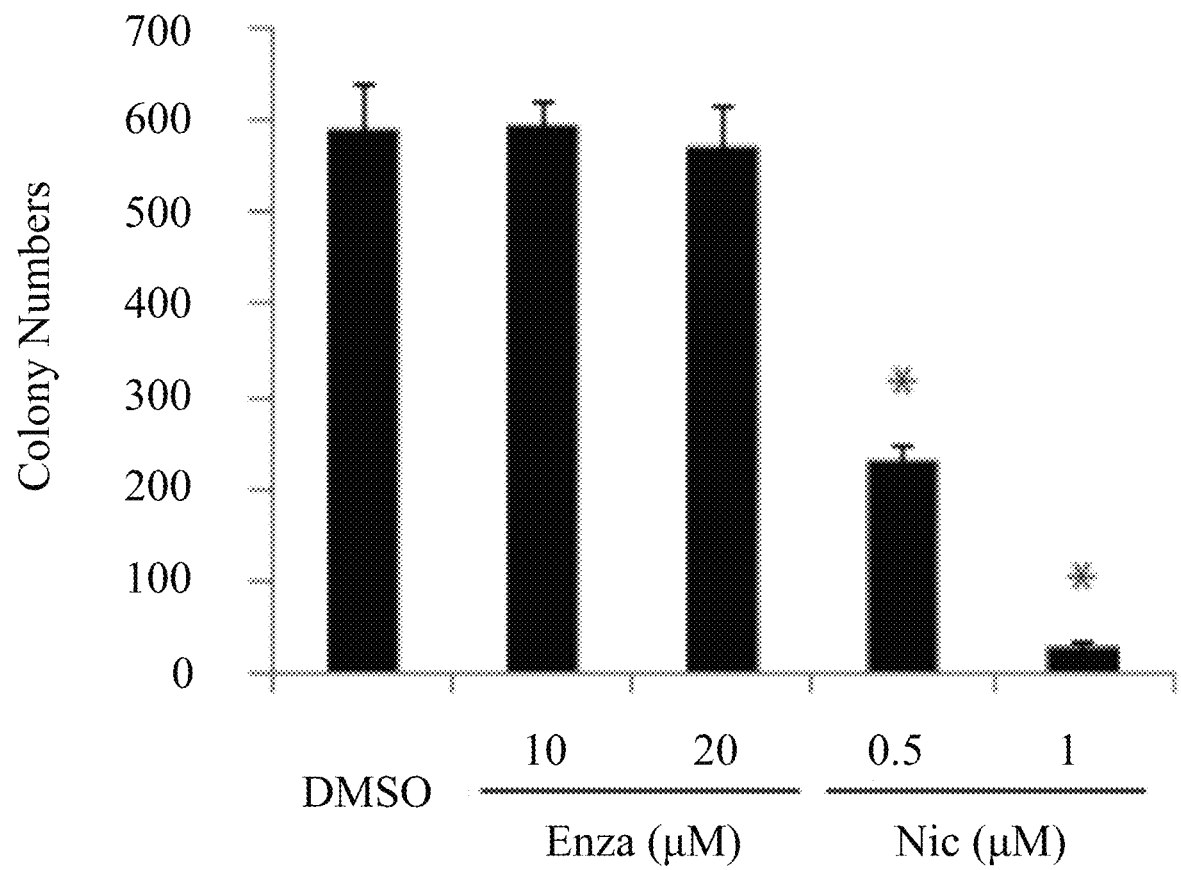
FIG. 36 shows a plot of colony numbers versus concentrations of enzalutamide, niclosamide, and control DMSO, which shows that niclosamide but not enzalutamide inhibited colony formation and colony size in C4-2B MR cells. Colonies were counted and results are presented as means±SD of 2 experiments performed in duplicate. Niclosamide inhibited colony formation in a dose dependent manner. *P<0.05.

As shown in FIGS. 35 and 36, niclosamide but not enzalutamide significantly inhibited colony formation by C4-2B MR cells. As shown in FIGS. 35 and 36, niclosamide but not enzalutamide significantly inhibited the colony size of the C4-2B MR cells. As shown in FIG. 21, combination treatment with niclosamide and enzalutamide significantly inhibits cell growth in C4-2B, C4-2B MR, CB-2B TAXR, and C4-2B TAXR-MR cells. As shown in FIG. 22, niclosamide enhances the effect of enzalutamide on growth or viability of C4-2B and C4-2B MR cells. As shown in FIG. 23, niclosamide enhances the effect of arbiraterone on growth or viability of C4-2B and C4-2B AbiR cells.

vi. Niclosamide Enhances Enzalutamide and Abiraterone Effects Through AR-V7 Inhibition AR variants have shown induced enzalutamide resistance in CWR22rv1 cells. This assay confirmed AR-V7 dominated cell growth in CWR22rv1 cells instead of full length AR, and CWR22rv1 cells were more resistant than LNCaP and C4-2B cells treated by abiraterone (FIG. 11A). To determine whether AR-V7 also induced abiraterone resistance in CWR22rv1 cells, AR-V7 specific siRNA or AR exon 7 siRNA were transiently transfected into CWR22rv1 cells following treatment with 10 μM abiraterone for 48 hours, as shown in FIG. 11B. Knocked-down AR-V7 significantly re-sensitized CWR22rv1 cells to abiraterone suggesting that AR-V7 may also induce abiraterone resistance in prostate cancer cells. To examine whether niclosamide, which was screened to be a AR-V7 inhibitor, could reverse the enzalutamide or abiraterone resistance in prostate cancer cells, CWR22rv1 cells were treated with niclosamide combined with or without enzalutamide and abiraterone for 48 hours, as shown in FIGS. 6A and 6B. Single treatments had moderate effects on CWR22rv1 cells while combination treatments significantly inhibited cell growth in a time dependent manner. Similar results are obtained after niclosamide treatment of CWR22rv1 cells with and without bicalutamide, as shown in FIG. 14. The effects in enzalutamide resistant and abiraterone resistant cell lines were also tested. Combination therapy of niclosamide with enzalutamide or abiraterone significantly inhibited C4-2B MR or C4-2B AbiR cell growth compared to the single treatment (FIG. 6C and FIG. 6D). The inhibition effects were also confirmed by clonogenic assay (FIG. 6E). Due to the AR-V7 function as enzalutamide and abiraterone resistant mechanism in prostate cancer cells, AR-V7 level in the CWR22rv1 cells treated with niclosamide and enzalutamide was examined, as shown in FIGS. 7A and 15. Single treatments with niclosamide reduced AR-V7 expression but when combined with enzalutamide or abiraterone the inhibition effects were significantly enhanced, suggesting inhibited AR-V7 expression could be a direct therapy strategy for enzalutamide or abiraterone resistance. The results were also confirmed in C4-2B MR cells (FIG. 7B). In summary, the results suggested niclosamide as a novel AR-V7 inhibitor could be a potent drug for advanced prostate cancer patients, especially to those who are resistant to enzalutamide or abiraterone.

vii. Inhibition of STAT3 and Reversing Enzalutamide Resistance

Sensitivity of prostate cancer cells to enzalutamide was tested using cell growth assays and clonogenic assays. Quantitative reverse transcription-PCR, ELISA and Western blotting were performed to detect expression levels of IL-6, c-Myc, survivin and AR. Expression of STAT3 was down-regulated using siRNA specific to STAT3. ChIP assay was performed to examine recruitment of AR to the PSA promoter.

The results demonstrate that prostate cancer cells expressing autocrine IL-6 are resistant to enzalutamide and that autocrine IL-6 leads to constitutive activation of STAT3 and its target genes. Down regulation of STAT3 led to an increase in sensitivity of prostate cancer cells to enzalutamide. Overexpression of constitutively active STAT3 in prostate cancer cells induced resistance to enzalutamide treatment. Constitutively active STAT3 also enhanced the recruitment of AR to PSA promoter which could not be disrupted by enzalutamide. The STAT3 inhibitor niclosamide reversed enzalutamide resistance in prostate cancer cells, while combination treatment with enzalutamide and niclosamide significantly inhibited cell growth, induced cell apoptosis and inhibited colony formation. The autocrine IL-6 pathway induces enzalutamide resistance in prostate cancer cells via the constitutive activation of STAT3.

Autocrine IL-6 in prostate cancer cells was observed herein to induce resistance to enzalutamide.

viii. Inhibition of STAT 3 and Reversing Enzalutamide Resistance

LNCaP-neo, LNCaP-s17 or LNCaP-STAT3C cells were treated as indicated. DNA-AR protein complexes were cross-linked inside the cells by the addition of 1% formaldehyde. Whole-cell extracts were prepared by sonication, and an aliquot of the cross-linked DNA-protein complexes was immunoprecipitated by incubation with the AR-specific antibody (AR-C19; Santa Cruz Biotechnology) overnight at 4° C. with rotation. Chromatin-antibody complexes were isolated from solution by incubation with protein A/G agarose beads for 1 hour at 4° C. with rotation. The bound DNA-protein complexes were washed and eluted from beads with elution buffer (1% SDS and 0.1 mol/L $NaHCO_3$), cross links were reversed, and DNA was extracted. The resulting chromatin preparations were analyzed by PCR using primers spanning either the proximal or the distal enhancer AREs of the PSA promoter. Isotype-matched IgG was used as control.

Figure 26A:
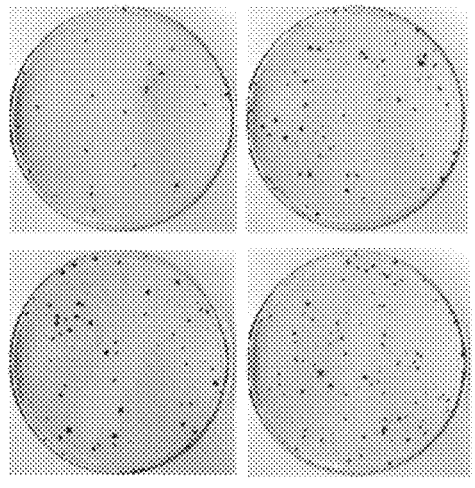
FIGS. 26A-26D show that overexpression of IL-6 increases LNCaP cell resistance to enzalutamide.
Figure 26B:
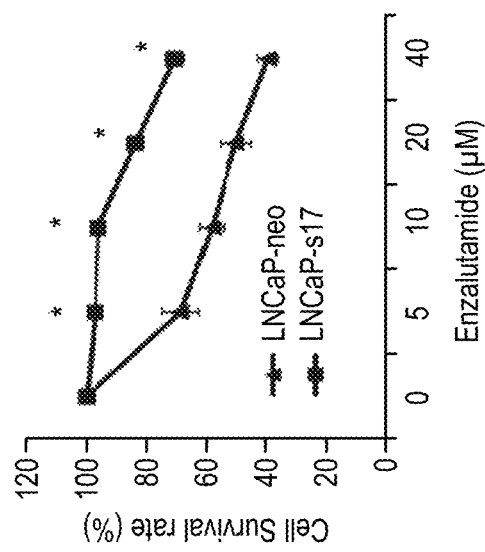
Figure 26C:
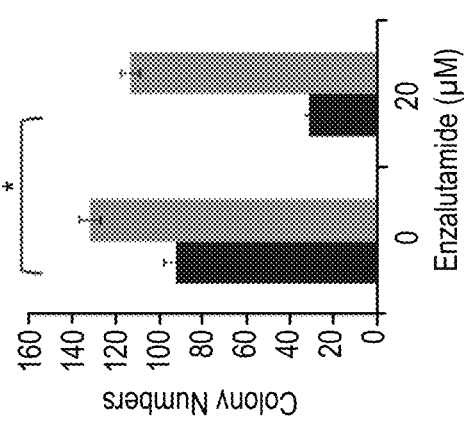

Overexpression of IL-6 increases LNCaP cell resistance to enzalutamide. Autocrine expression of IL-6 in LNCaP (LNCaP-s17) cells was observed to promote cell growth and increases resistance to bicalutamide treatment. This assay tested whether expression of IL-6 affects the response of prostate cancer cells to enzalutamide, LNCaP-s17 cells were treated with increasing doses of enzalutamide and cell numbers were counted. As shown in FIGS. 26A-26C, LNCaP-neo cells were highly sensitive to enzalutamide treatment compared to LNCaPs17 cells. Enzalutamide at a concentration of 5 µM reduced the growth of LNCaP-neo cells by more than 30%, while it had almost no effect on the growth of LNCaP-s17 cells. Even at a higher concentration of enzalutamide (40 µM), the growth of LNCaP-s17 cells was only reduced by about 30% compared to almost 60% reduction in LNCaP-neo cells.

A clonogenic assay was performed. LNCaP-neo cells and LNCaP-s17 cells were treated with 20 µM enzalutamide and clonogenic ability was determined. As shown in FIGS. 26A-26C, the colony formation ability was significantly inhibited in LNCaP-neo cells treated with 20 µM enzalutamide, while LNCaP-s17 cells continued to grow and form colonies.

Figure 26D:
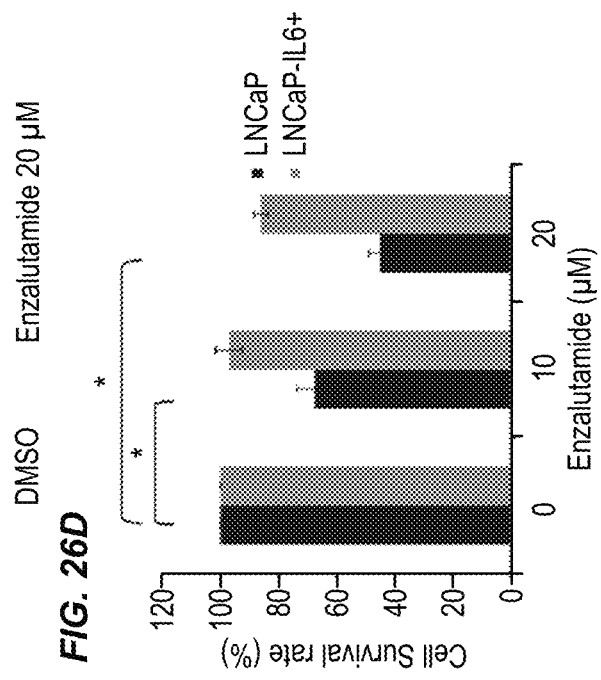

Overexpression of IL-6 involved in enzalutamide resistance was confirmed. LNCaP-IL6+ cells, LNCaP cells expressing IL-6 by long-term culture of LNCaP cells in media containing IL-6, were treated with 10 µM and 20 µM enzalutamide in media containing complete FBS for 48 hours. As shown in FIG. 26D, enzalutamide significantly inhibited growth of LNCaP cells. In contrast, enzalutamide had little effect on the growth of LNCaP-IL6+ cells. Collectively, these data shows that overexpression of IL-6 in prostate cancer cells is associated with enzalutamide resistance.

Autocrine IL-6 Constitutively Activates STAT3 Pathway and Enhances Androgen Receptor Transactivation in Prostate Cancer Cells:

Other reports have demonstrated that constitutive STAT3 activation is oncogenic and contributes to tumor progression and metastasis. Previous studies showed that STAT3 is constitutively activated in LNCaP-s17 cells. To test whether LNCaP-s17 cells exhibit elevated STAT3 signaling, this assay determined the levels of expression of several STAT3 target genes including c-Myc, survivin, and Bcl-2.

Figure 27A:
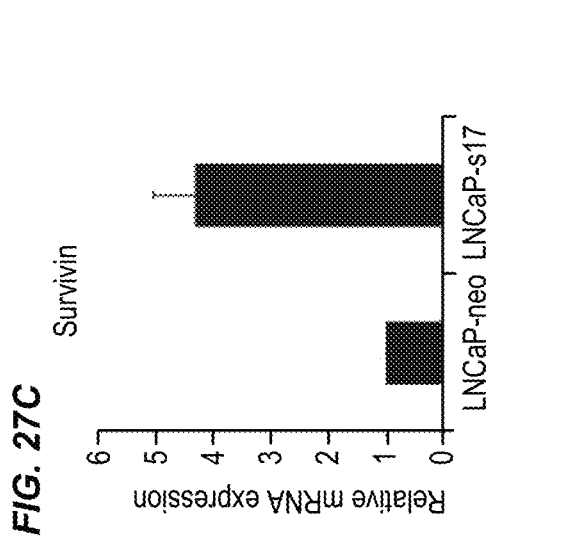
FIGS. 27A-27F show that autocrine IL-6 constitutively activates STAT3 pathway and enhances androgen receptor transactivation in prostate cancer cells.
Figure 27B:
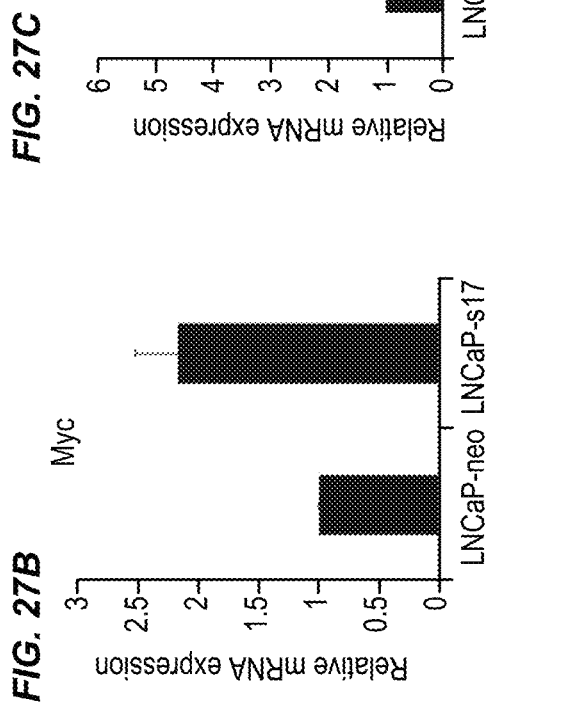
Figure 27C:
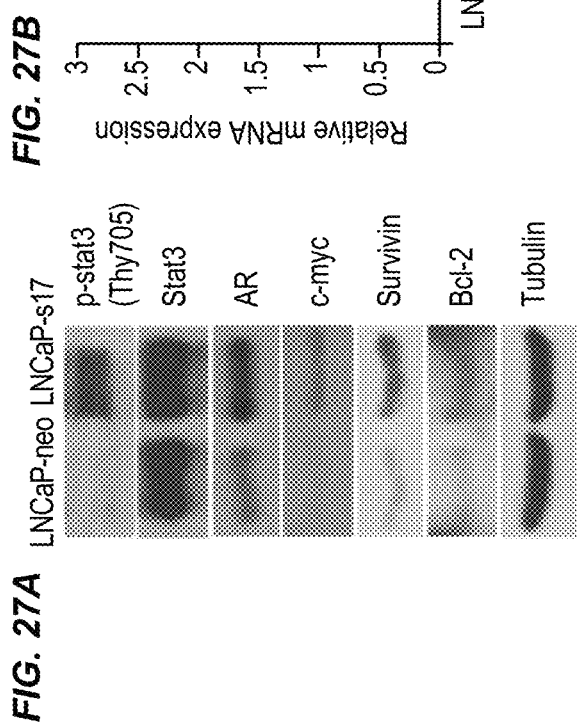

As shown in FIG. 27A, LNCaP-s17 cells express constitutively activated STAT3 (STAT3 phosphorylated at Tyr705) and express higher levels of AR, c-Myc, survivin, and Bcl-2 proteins than LNCaP-neo cells. Consistent with the protein levels, LNCaP-s17 cells express higher levels of c-Myc and survivin mRNA than LNCaP-neo cells (FIGS. 27B and 27C).

Figure 27D:
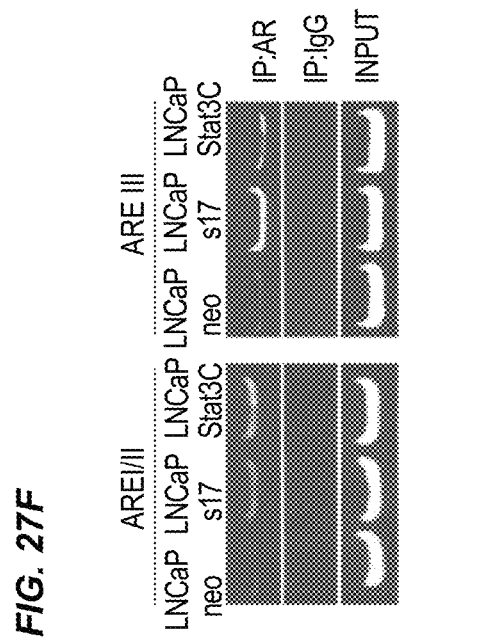
Figure 27E:
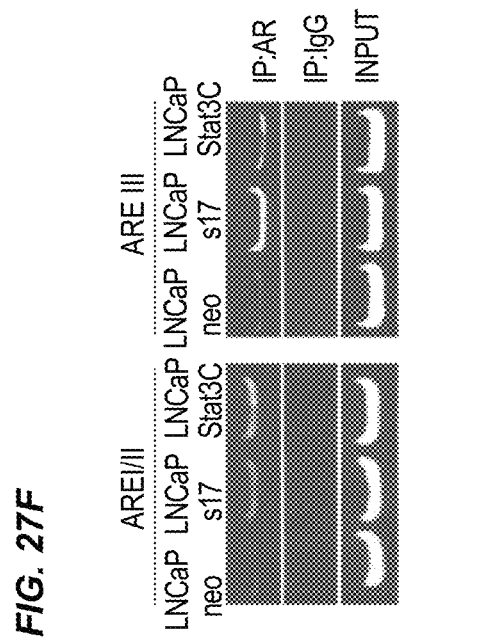

LNCaP-s17 cells expressed higher levels of IL-6 mRNA and protein than LNCaP-neo cells (FIGS. 27D and 27E).

Figure 27F:
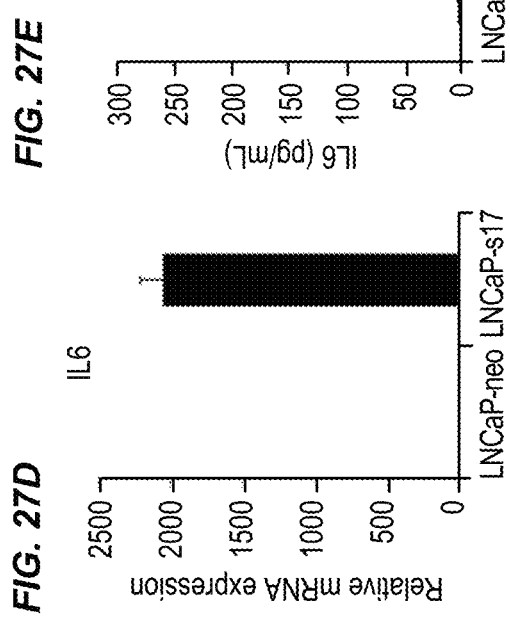

This assay also determined whether constitutively active STAT3 increases the recruitment of AR to the ARE sites, ChIP assay was performed in LNCaP, LNCaP-s17 and LNCaP-STAT3C cells. As shown in FIG. 27F, both LNCaP-s17 cells and LNCaP-STAT3C cells showed enhanced recruitment of AR to both the proximal binding site (AREI/II) and the distal enhancer binding site (AREIII) of the PSA promoter compared to LNCaP-neo cells.

Collectively, these data demonstrate that overexpression of IL-6 activates STAT3 and AR signaling pathways in prostate cancer cells.

Knockdown of STAT3 Expression Restores the Sensitivity of LNCaP-s17 Cells to Enzalutamide:

To determine whether STAT3 is involved in enzalutamide resistance in IL-6 expressing prostate cancer cells, LNCaP-neo and LNCaP-s17 cells were transfected with siRNA specific to STAT3.

Figure 28B:
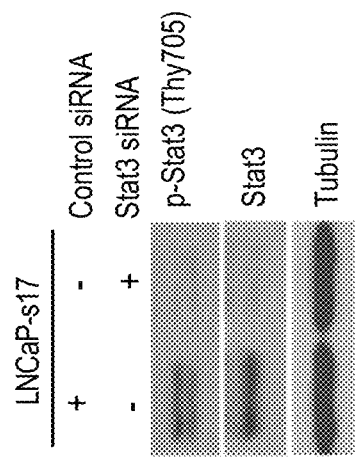
FIGS. 28A-28D show that downregulation of STAT3 expression restores the sensitivity of LNCaP-s17 cells to enzalutamide treatment.
Figure 28D:
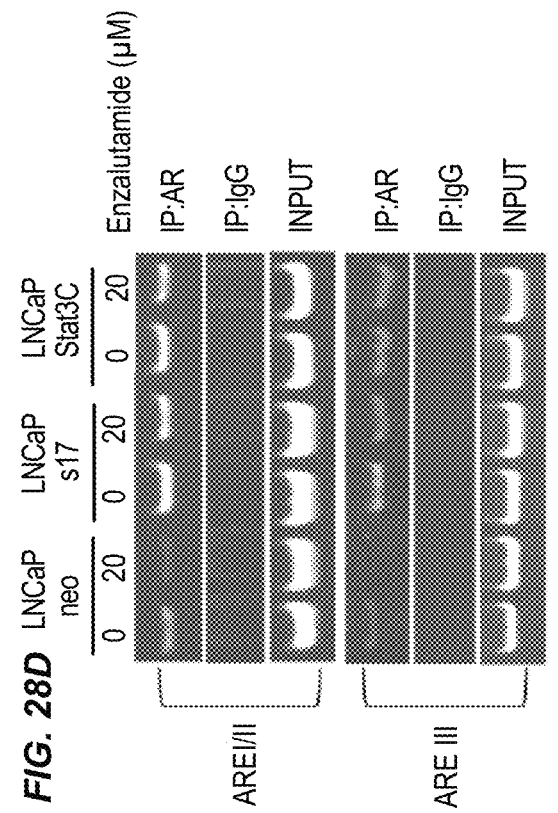
Figure 28A:
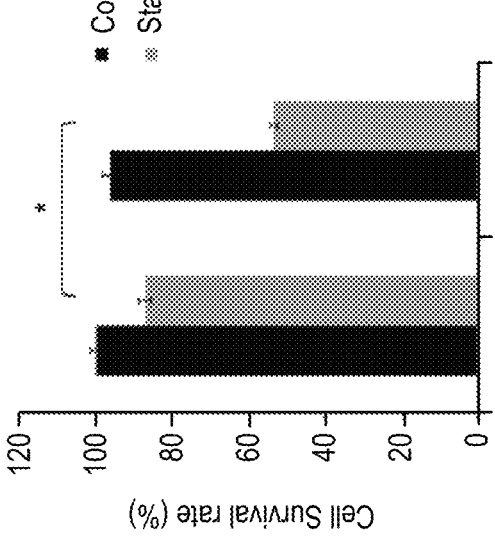
Figure 28C:
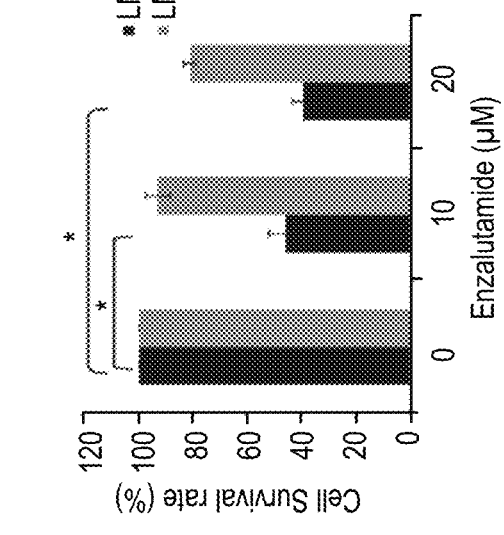

The cells were then treated with 20 µM enzalutamide for an additional 3 days and the cell numbers were determined. As shown in FIG. 28A, knockdown of STAT3 expression in LNCaP-s17 cells resensitized the cells to enzalutamide treatment. The knock down effects were confirmed by Western blotting using p-STAT3 (Tyr705) and STAT3 antibodies (FIG. 28B). In addition, LNCaP cells expressing constitutively active STAT3 (STAT3C) exhibited increased resistance to enzalutamide (FIG. 28C). These results suggest that stat3 activation is involved in enzalutamide resistance in prostate cancer cells.

One of the mechanisms of action of enzalutamide is to inhibit the recruitment of the AR to AREs in promoters of target genes. To test whether STAT3-mediated enzalutamide resistance affects the recruitment of AR to AREs, ChIP assay was performed. As shown in FIG. 28D, enzalutamide significantly inhibited recruitment of the AR to AREs in the PSA promoter (both proximal binding site and distal binding site) in LNCaP-neo cells. In contrast, enzalutamide had little effect on the recruitment of the AR to the AREs in LNCaP-s17 cells and LNCaP-STAT3C cells. These results show that STAT3-mediated enzalutamide resistance may be involved in affecting the recruitment of the AR to the AREs in the PSA promoter.

ix. Inhibition of STAT 3 and Reversing Enzalutamide Resistance

Figure 29A:
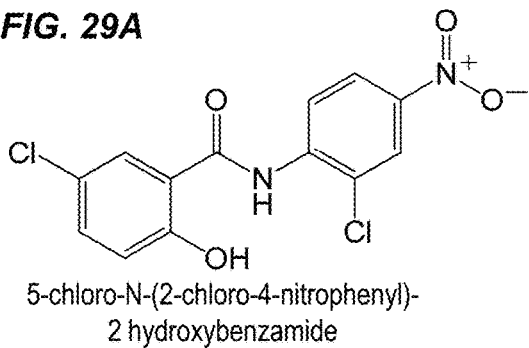
FIGS. 29A-29F show a novel STAT3 inhibitor, niclosamide, that reverses enzalutamide resistance in prostate cancer cells.

This assay tested whether a small non-peptide drug, niclosamide (FIG. 29A), which has been shown previously to be able to inhibit STAT3 expression in DU145 cells, is able to reverse enzalutamide resistance in prostate cancer cells.

Figure 29B:
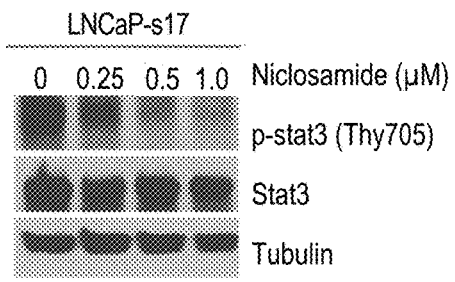

It was observed that niclosamide significantly inhibited STAT3 activation in prostate cancer cells (FIG. 29B).

Figure 29C:
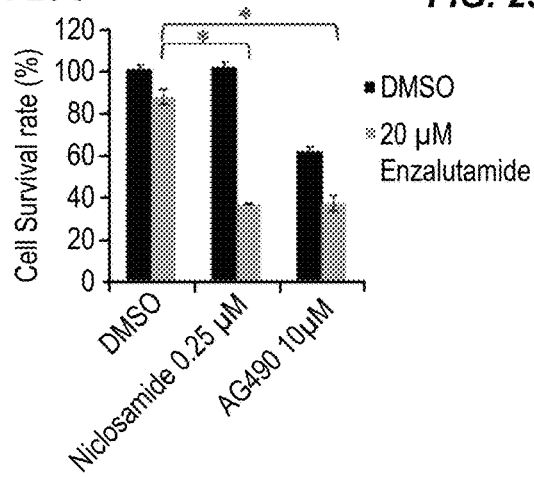
Figure 29D:
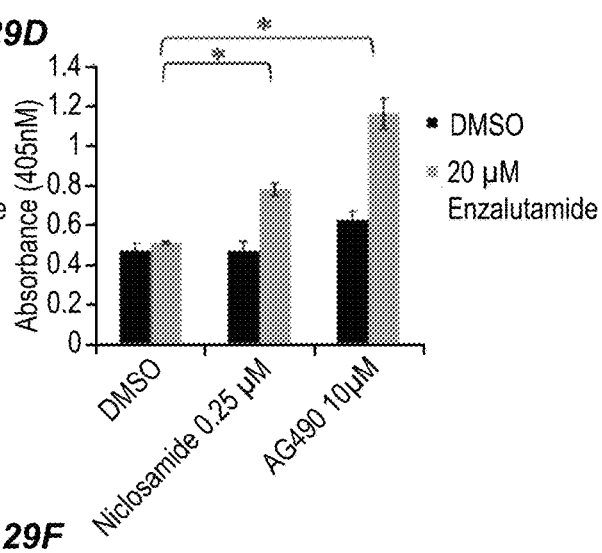

This assay tested whether inhibition of STAT3 activation by niclosamide can reverse enzalutamide resistance in LNCaP-s17 cells. As shown in FIG. 29C, enzalutamide treatment at 20 µM had minimal effect on LNCaP-s17 cell growth. However, enzalutamide significantly inhibited cell growth in the presence of 0.25 µM niclosamide (FIG. 29C), which may be due to induction of apoptotic cell death (FIG. 29D). AG490, a known Jak2-STAT3 inhibitor, was also observed to reverse enzalutamide resistance (FIGS. 29C and 29D).

Figure 29E:
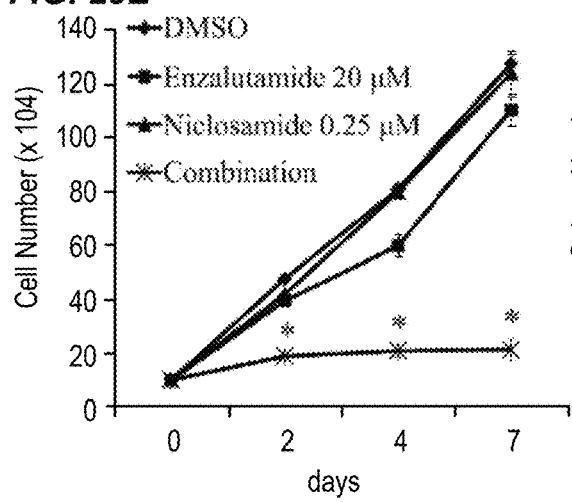
Figure 29F:
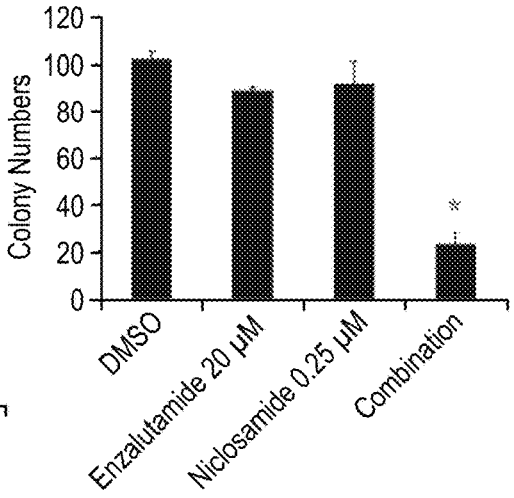

These results were also confirmed in a time dependent experiment. LNCaP-s17 cells were treated with 20 µM enzalutamide and 0.25 µM niclosamide individually or in combination for different time points. The growth of LNCaP-s17 cells was significantly inhibited by enzalutamide in the presence of niclosamide, while treatment with either enzalutamide or niclosamide alone had little effect on cell growth (FIG. 29E). Consistent with cell growth inhibition, the clonogenic ability of LNCaP-s17 cells was significantly inhibited by enzalutamide in the presence of niclosamide (FIG. 29F). Collectively, these data demonstrate that niclosamide can overcome, or reverse, enzalutamide resistance though inhibition of STAT3 expression.

This example shows that the axis between IL-6 and persistent STAT3 activation may be one of the critical mechanisms involved in enzalutamide resistance.

This example shows that autocrine IL-6 in LNCaP cells activates STAT3 pathway and enhances resistance to enzalutamide, while downregulation of STAT3 in LNCaP-s17 cells dramatically resensitized LNCaP-s17 cells to enzalutamide. In addition, transfection of constitutively active STAT3 into LNCaP cells induced resistance to enzalutamide which indicates that enzalutamide resistance may be driven by STAT3 activation in prostate cancer cells.

This example shows that in prostate cancer cell lines expressing constitutively active STAT3, enzalutamide treatment only slightly reduced recruitment of AR to the PSA promoter compared with LNCaP parental cells, which suggests that persistent STAT3 activation may counteract enzalutamide action in blocking the recruitment of AR to target gene promoters.

This example shows that niclosamide inhibited STAT3 activation and significantly reversed enzalutamide resistance in prostate cancer cells exhibiting constitutive activation of STAT3. Combination treatment with enzalutamide and niclosamide not only inhibited cell proliferation but also inhibited colony formation.

Figure 24:
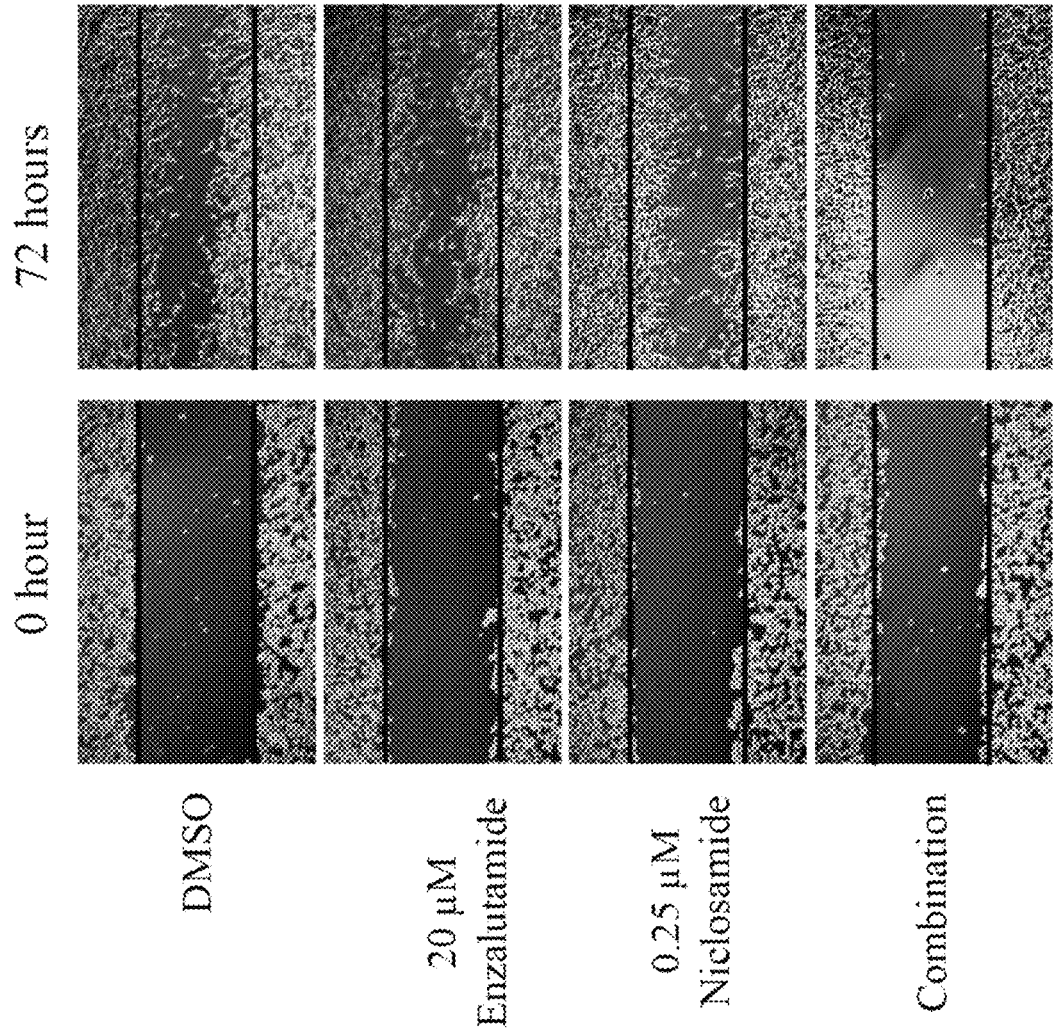
FIG. 24 shows the results of incubating LNCaP-s17 cells with DMSO, enzalutamide, niclosamide, and combinations of enzalutamide and niclosamide.
Figure 25:
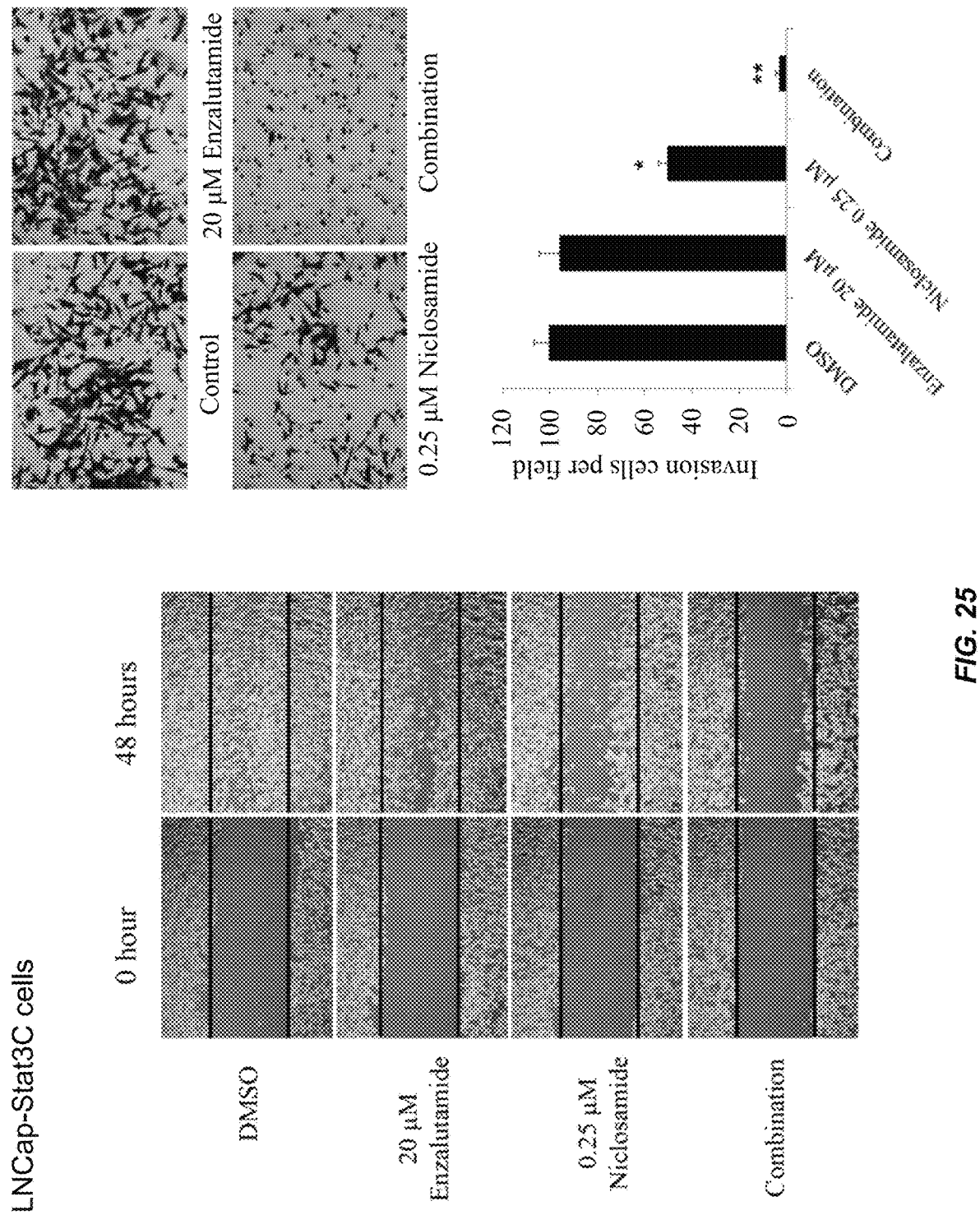
FIG. 25 shows the results of incubating LNCaP-STAT3C cells with DMSO, enzalutamide, niclosamide, and combinations of enzalutamide and niclosamide.

This example shows that the IL6-STAT3 axis is involved in the development of resistance to enzalutamide in prostate cancer. In addition, this example shows that targeting the IL-6-STAT3 axis may be a potential therapeutic strategy in patients resistant to enzalutamide.

x. Niclosamide Inhibits Cell Growth, Migration, Invasion and Colony Formation in Prostate Cancer Cells As shown in FIGS. 16-19, niclosamide inhibits cell growth, migration, invasion, and colony formation in prostate cancer cells. The effect appears to be dose dependent. As shown in FIG. 24, niclosamide inhibits cell migration or invasion in LNCap-s17 cells, and the effect is enhanced when niclosamide is used in combination with enzalutamide. As shown in FIG. 25, niclosamide inhibits cell migration or invasion in LNCap-Stat3C cells, and the effect is enhanced when niclosamide is used in combination with enzalutamide.

xi. In Vivo Tumorigenesis Assay

This assay tested whether niclosamide overcomes enzalutamide resistance of prostate cancer in vivo. In this assay, xenografts generated from CWR22rv1 cells were treated with vehicle, enzalutamide, niclosamide or their combination for 3 weeks.

CWR22rv1 cells (3 million) were mixed with matrigel (1:1) and injected subcutaneously into the flanks of 6-7 week male SCID mice. Tumor-bearing mice (tumor volume around 50-100 $mm_3$) were randomized into four groups and treated as follows: (1) vehicle control (5% Tween 80 and 5% ethanol in PBS, i.p.), (2) enzalutamide (25 mg/kg, p.o.), (3) niclosamide (25 mg/kg, i.p.), (4) enzalutamide (25 mg/kg, p.o.)+niclosamide (25 mg/kg, i.p.). Tumors were measured using calipers twice a week and tumor volumes were calculated using length×width2/2. Tumor tissues were harvested after 3 weeks of treatment.

Figure 39:
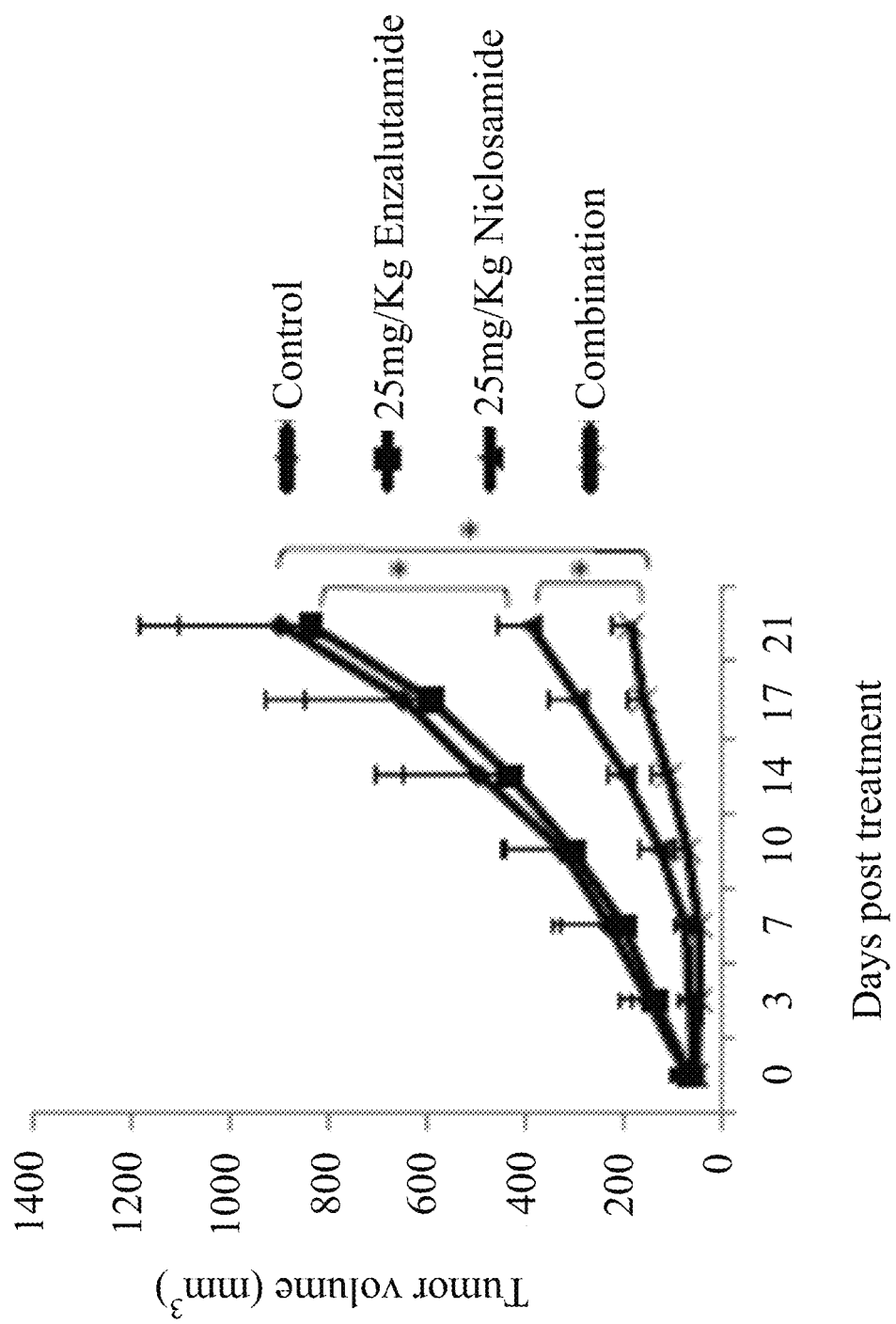
FIG. 39 shows a plot of tumor volume versus time (days) for an in vivo study using xenografts generated from CWR22rv1 cells treated with vehicle, enzalutamide, niclosamide, or a combination thereof. Mice bearing CWR22rv1 xenografts were treated with vehicle control, enzalutamide, niclosamide or a combination thereof for 3 weeks, tumor volumes were measured twice every week and the tumors were collected. *P<0.05.

As show in FIG. 39, CWR22rv1 cells that were resistant to enzalutamide treatment showed tumor volumes comparable to those in the vehicle treated control group. Niclosamide alone decreased the tumor volume while the combination of niclosamide and enzalutamide synergistically decreased CWR22rv1 tumors. This assay indicates that niclosamide can overcome enzalutamide resistance and restore sensitivity of CWR22rv1 xenografts to enzalutamide in vivo. In summary, these results demonstrate that niclosamide can improve enzalutamide treatment and overcome enzalutamide resistance.

Example 2. Niclosamide Effects on Enzalutamide-Resistant Cells

Figure 40A:
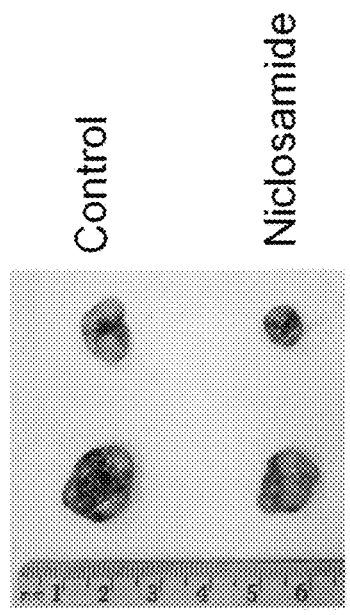
FIGS. 40A, 40B, 40C, and 40D show the effects of niclosamide on tumor growth of CWR22Rv1 xenograft model (niclosamide via oral administration). CWR22Rv1 cells (4 million) were mixed with matrigel (1:1) and injected subcutaneously into the flanks of male SCID mice. Tumor-bearing mice (tumor volume around 50-75 mm$^3$) were treated 5 days per week as follows: Control: (5% PGE8000 in H$_2$O p.o Bid), Niclosamide (200 mg/kg p.o Bid). Tumors were measured using calipers twice a week and tumor volumes were calculated using length×width2/2. Tumor tissues were harvested after 3 weeks of treatment. *P<0.05.
Figure 40B:
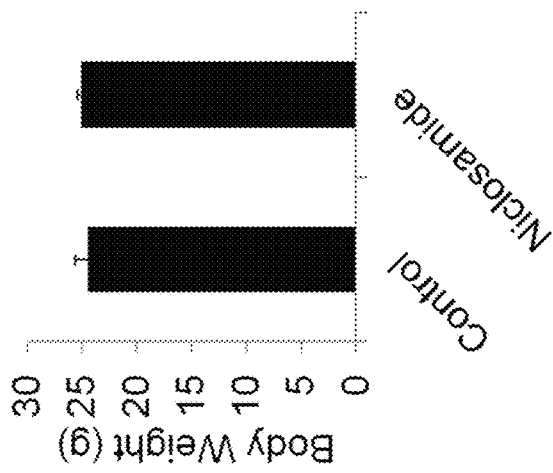
Figure 40C:
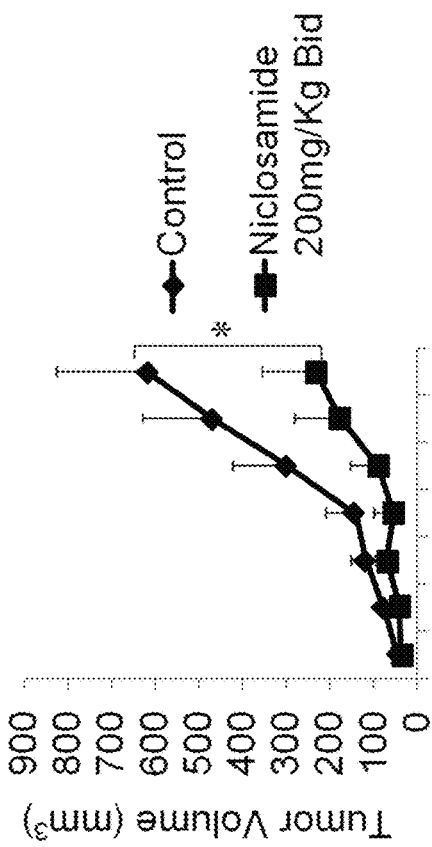
Figure 40D:
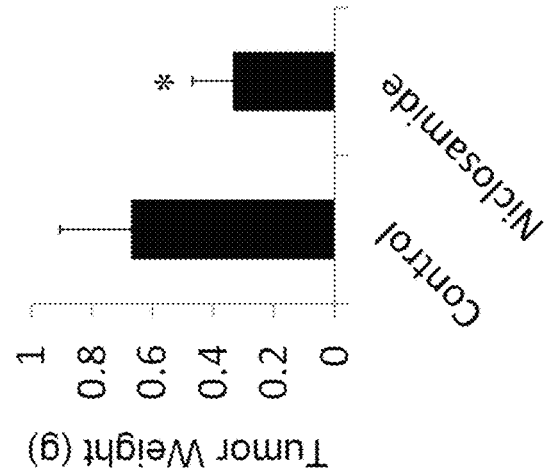

CWR22Rv1 cells (4 million) were mixed with matrigel (1:1) and injected subcutaneously into the flanks of male SCID mice, tumor-bearing mice (tumor volume around 50-75 mm$^3$) were treated 5 days per week as follows: Control: (5% PGE8000 in H$_2$O p.o B.I.D.), niclosamide (200 mg/kg p.o B.I.D.). Tumors were measured using calipers twice a week and tumor volumes were calculated using length×width2/2. Tumor tissues were harvested after 3 weeks of treatment. The results are depicted in FIGS. 40A-40D. As shown in FIGS. 40A-40C, niclosamide significantly inhibited Rv1 xenograft tumor growth when administered orally. As shown in FIG. 40D, the dosage of niclosamide was well-tolerated as illustrated by maintenance of body weight in comparison to control mice that did not receive niclosamide.

Figure 41A:
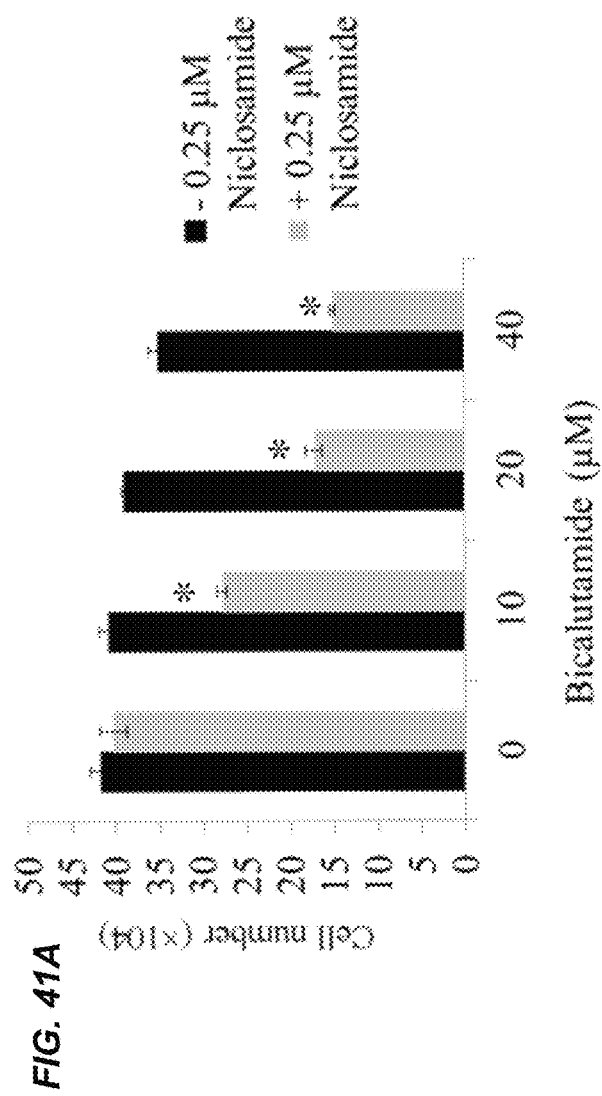
FIGS. 41A-41B show the combination of niclosamide with bicalutamide in CWR22Rv1 cells in vitro.
Figure 41B:
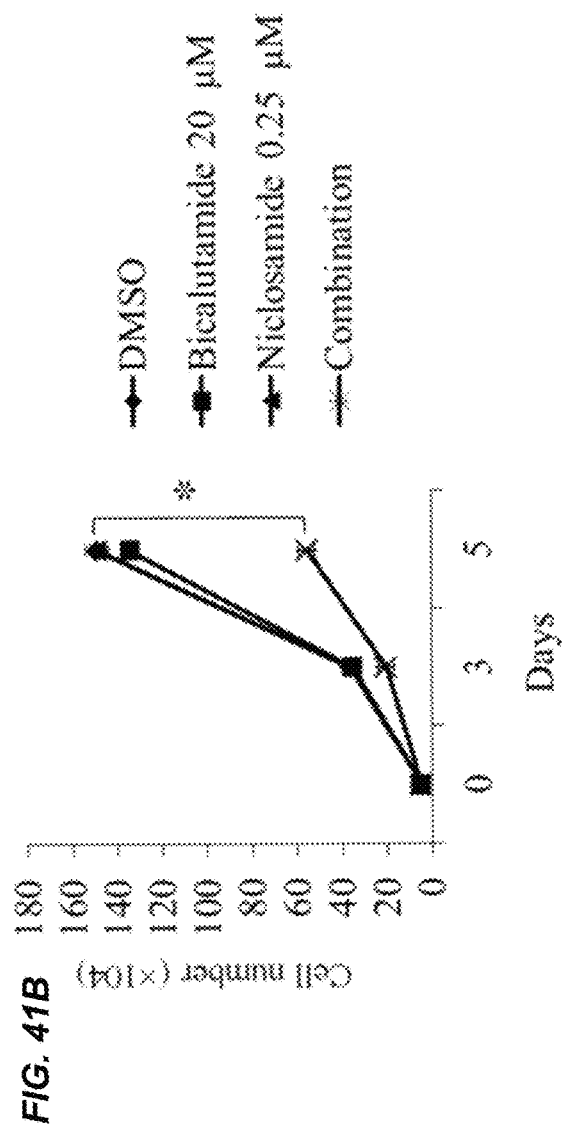

The effects of niclosamide in combination with bicalutamide were examined in vitro and in vivo. As shown in FIGS. 41A and 41B, niclosamide significantly enhanced bicalutamide effects in a dose (FIG. 41A) and time (FIG. 41B) dependent manner in CWR22Rv1 cells in vitro. Niclosamide also enhanced bicalutamide treatment of CWR22Rv1 cells in vivo in a mouse xenograft model.

Figure 42B:
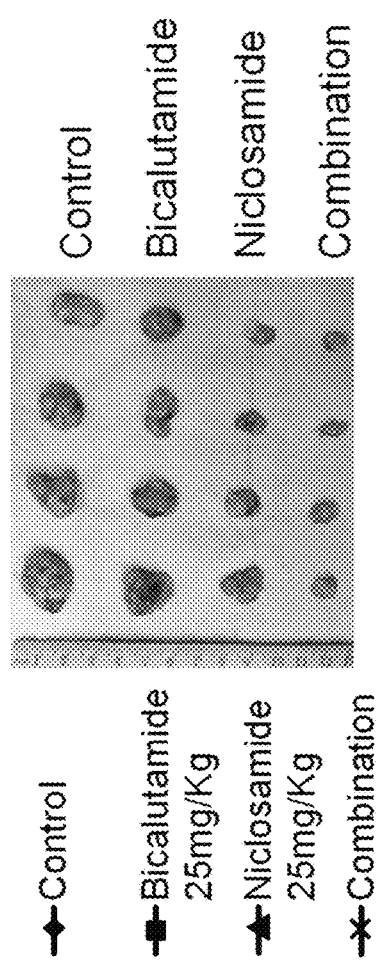
FIGS. 42A, 42B, 42C, and 42D show a CWR22Rv1 xenograft model of niclosamide combined with bicalutamide. CWR22Rv1 cells (4 million) were mixed with matrigel (1:1) and injected subcutaneously into the flanks of male SCID mice. Tumor-bearing mice (tumor volume around 50-75 mm$^3$) were treated 5 days per week as follows: Control: (0.5% weight/volume (w/v) Methocel A4M p.o and 5% Tween 80 and 5% ethanol in PBS, i.p.), Bicalutamide (25 mg/kg p.o), Niclosamide (25 mg/kg i.p.) and Combination (25 mg/kg Bicalutamide p.o+25 mg/kg Niclosamide i.p.). Tumors were measured using calipers twice a week and tumor volumes were calculated using length×width2/2. Tumor tissues were harvested after 3 weeks of treatment. *P<0.05.
Figure 42A:
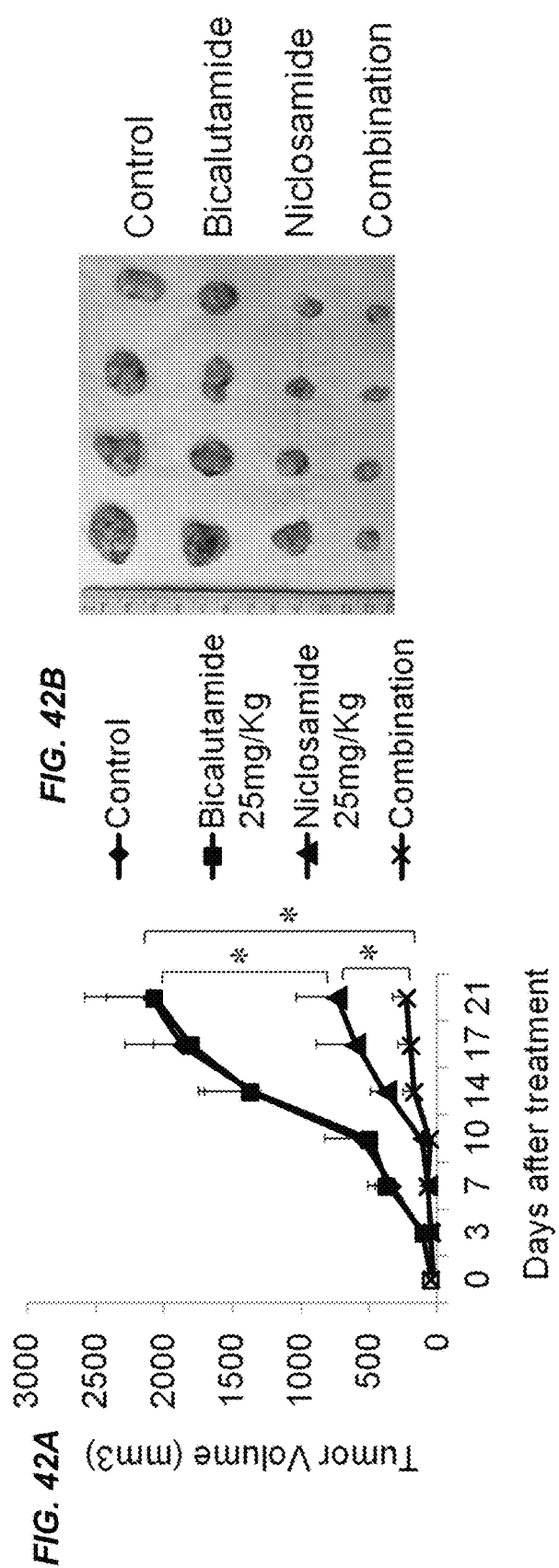
Figure 42D:
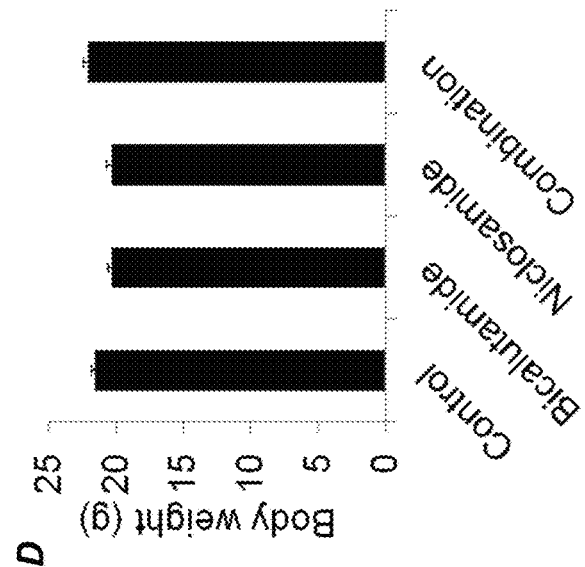
Figure 42C:
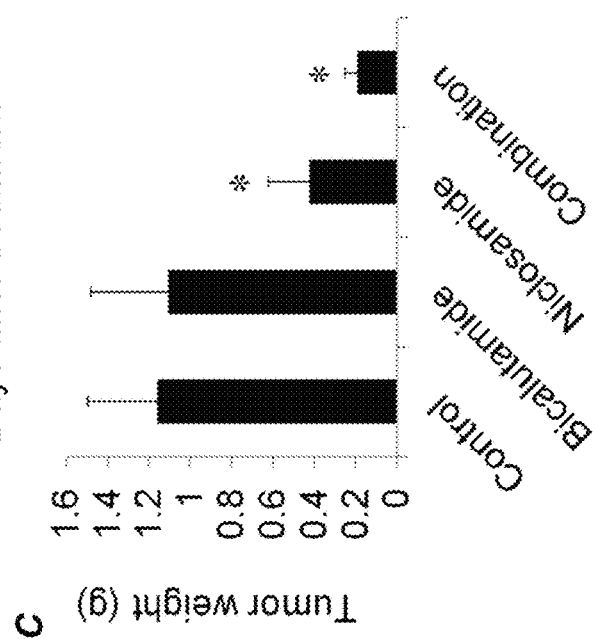

For the in vivo experiment, CWR22Rv1 cells (4 million) were mixed with matrigel (1:1) and injected subcutaneously into the flanks of male SCID mice. Tumor-bearing mice (tumor volume around 50-75 mm$^3$) were treated 5 days per week as follows: Control: (0.5% weight/volume (w/v) Methocel A4M p.o and 5% Tween 80 and 5% ethanol in PBS, i.p.), Bicalutamide (25 mg/kg p.o), Niclosamide (25 mg/kg i.p.) and Combination (25 mg/kg Bicalutamide p.o+ 25 mg/kg Niclosamide i.p.). Tumors were measured using calipers twice a week and tumor volumes were calculated using length×width2/2. Tumor tissues were harvested after 3 weeks of treatment. The results are depicted in FIGS. 42A-42D. As shown in FIGS. 42A-42C, niclosamide significantly enhanced bicalutamide effects on CWR22Rv1 cells in vivo in a mouse xenograft model. As shown in FIG. 42D, the dosage of niclosamide, whether alone or in combination with bicalutamide, was well-tolerated as illustrated by maintenance of body weight in comparison to control mice that did not receive niclosamide.

Example 3. AKR1C3 Activation and Intracrine Androgens Confer Resistance to Enzalutamide a. Introduction Targeting androgen signaling via androgen deprivation therapy has been the mainstay of clinical interventions in prostate cancer (PCa). While initially effective, the majority of men experience only transient benefit and relapse with castrate-resistant prostate cancer (CRPC), which is currently incurable. Enzalutamide, a second-generation antiandrogen, was recently approved for the treatment of castration resistant prostate cancer (CRPC) in patients. Despite these advances that provide temporary respite, resistance to enzalutamide occurs frequently. Several potential mechanisms of resistance have been revealed such as AR variants expression (Antonarakis et al., 2014; Li et al., 2013; Liu et al., 2014a), IL6-STAT3-AR axis activation (Liu et al., 2014b), AR F876L mutation (Joseph et al., 2013; Korpal et al., 2013) and glucocorticoid receptor (GR) overexpression (Arora et al., 2013; Isikbay et al., 2014).

Intratumoral androgen biosynthesis has been well characterized as a mechanism of CRPC (Cai et al., 2011; Ishizaki et al., 2013; Locke et al., 2008; Mohler et al., 2011), but its role in enzalutamide resistance is yet to be understood. Clinical reports have shown that patients treated with enzalutamide have elevated testosterone levels in the bone marrow (Efstathiou et al., 2014; Efstathiou E, 2011). A cascade of enzymes is involved in the biosynthesis of intratumoral androgens, including CYP17A1, HSD3B and AKR1C3. A gain of function mutation in HSD3B1 (N367T) has been identified in CRPC patients recently and was postulated to confer resistance to enzalutamide (Chang et al., 2014; Chang et al., 2013). Aldo-keto reductase family 1 member C3 (AKR1C3) is a multi-functional enzyme and is one of the most important genes involved in androgen synthesis and metabolism. AKR1C3 facilitates the conversion of weak androgens androstenedione (A' dione) and 5 α-androstanedione (5α-dione) to the more active androgens testosterone and DHT respectively (Bauman et al., 2006; Labrie et al., 1997). It catalyzes conversion of steroids and modulates trans-activation of steroid receptors. Elevated expression of AKR1C3 has been associated with PCa progression and aggressiveness (Stanbrough et al., 2006; Wako et al., 2008). The role of AKR1C3 in enzalutamide resistant prostate cancer is investigated herein.

Figure 43A:
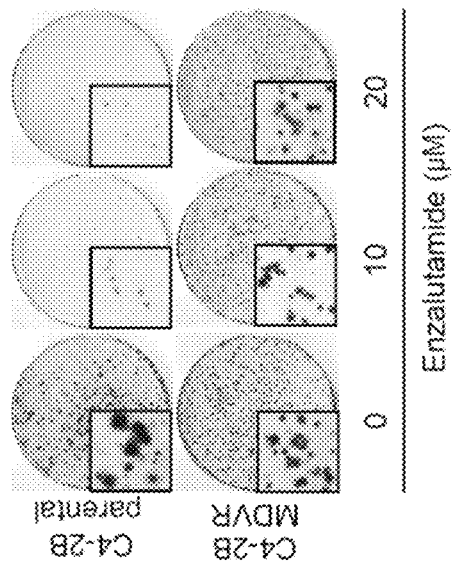
FIGS. 43A-43D show that C4-2B MDVR cells are resistant to enzalutamide in vitro and in vivo.
Figure 43B:
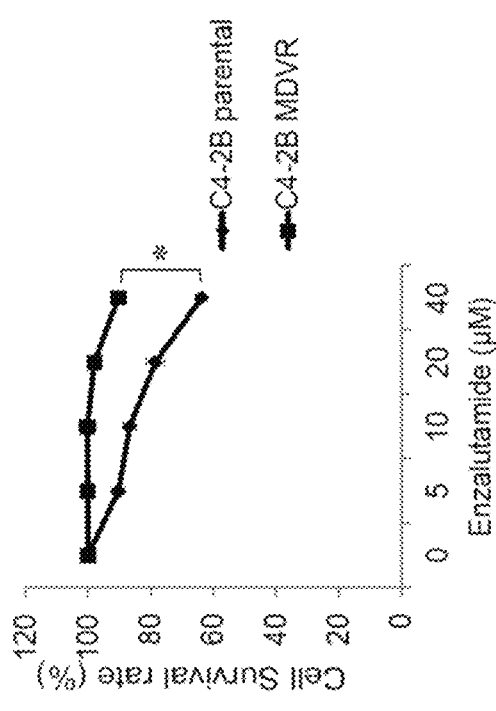
Figure 43D:
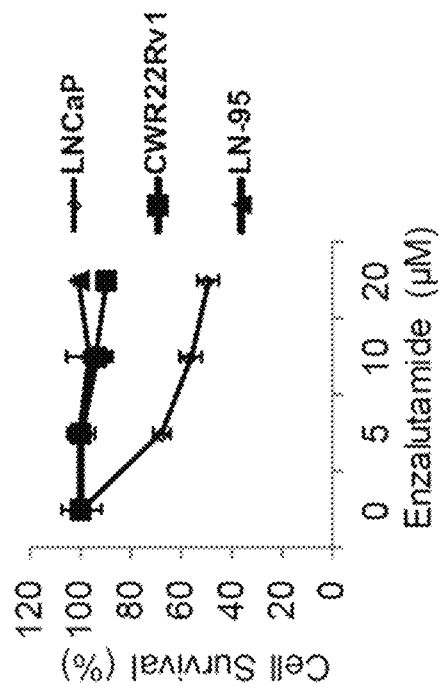
Figure 43C:
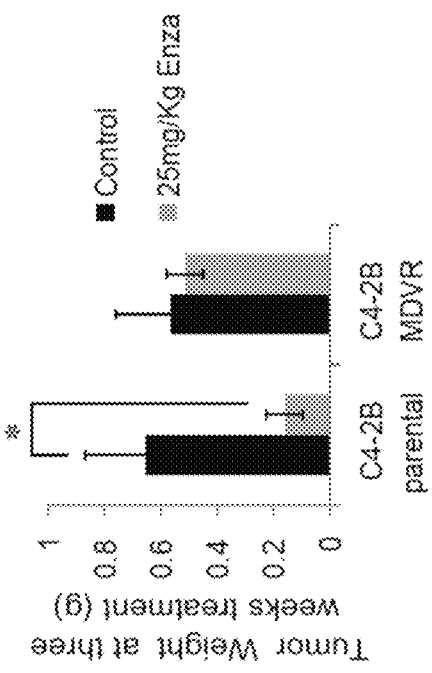

In the present study, PCa cell lines resistant to enzalutamide were developed and it was found that intracrine androgen synthesis is activated in enzalutamide resistant prostate cancer cells. Activation of one of the important steroidogenic enzymes, AKR1C3, was identified as a critical mechanism that confers resistance to enzalutamide. Inhibition of AKR1C3 activity using either shRNA or indomethacin resensitized enzalutamide resistant PCa cells to enzalutamide. Furthermore, the combination of indomethacin and enzalutamide resulted in significant inhibition of enzalutamide-resistant PCa xenograft tumor growth.

b. Results i. Identification of AKR1C3 Activation in Enzalutamide Resistant Prostate Cancer Cells Previously, enzalutamide resistant prostate cancer cells, named C4-2B MDVR, were generated by chronic culture of C4-2B cells in media containing enzalutamide (Liu et al., 2014a). As shown in FIGS. 43A and 43B, enzalutamide significantly inhibited proliferation and clonogenic ability of C4-2B parental cells but had little effect on C4-2B MDVR cells. The effects of enzalutamide treatment on C4-2B MDVR cells were also examined in vivo. As shown in FIG. 43C, C4-2B MDVR xenografts were resistant to enzalutamide. Tumor weights of C4-2B xenograft were significantly inhibited by enzalutamide after 3 weeks treatment with enzalutamide, while tumor weights of treated C4-2B MDVR group were comparable to those of non-treated control group. These results show that C4-2B-MDVR cells are resistant to enzalutamide both in vitro and in vivo. The responses of several other prostate cancer cell lines to enzalutamide treatment were also examined. As shown in FIG. 43D, LNCaP cells are sensitive to enzalutamide, while CWR22Rv1 and LN-95 cells are resistant to enzalutamide treatment, consistent with previously published studies (Dehm et al., 2008; Hu et al., 2013; Nadiminty et al., 2013).

Figure 44B:
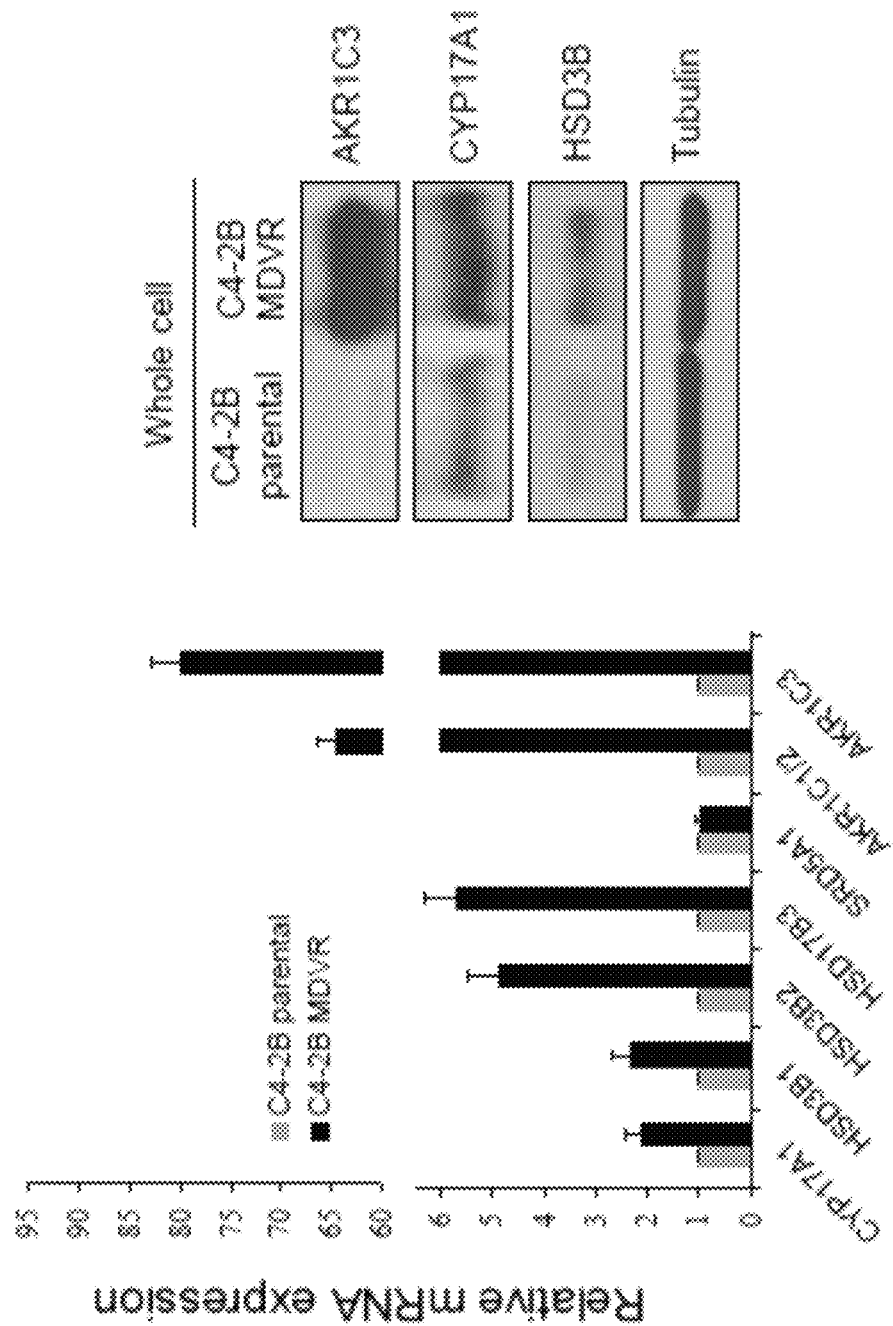
Figure 45A:
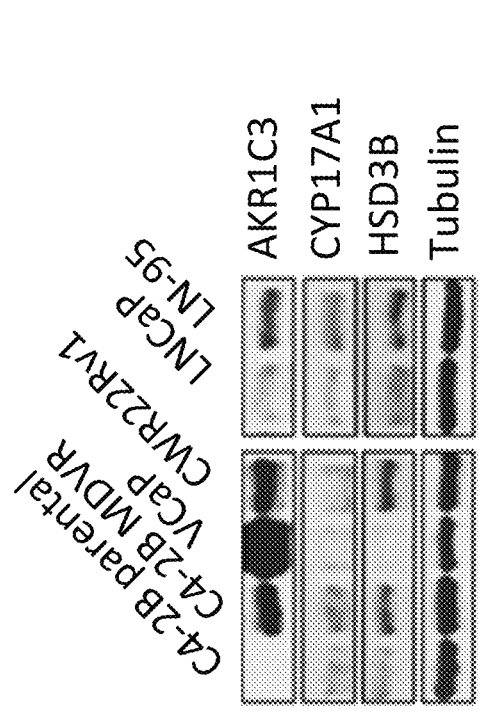
FIGS. 45A-45D show that AKR1C3 is highly expressed in metastatic prostate tumors and enzalutamide resistant xenografts.
Figure 45B:
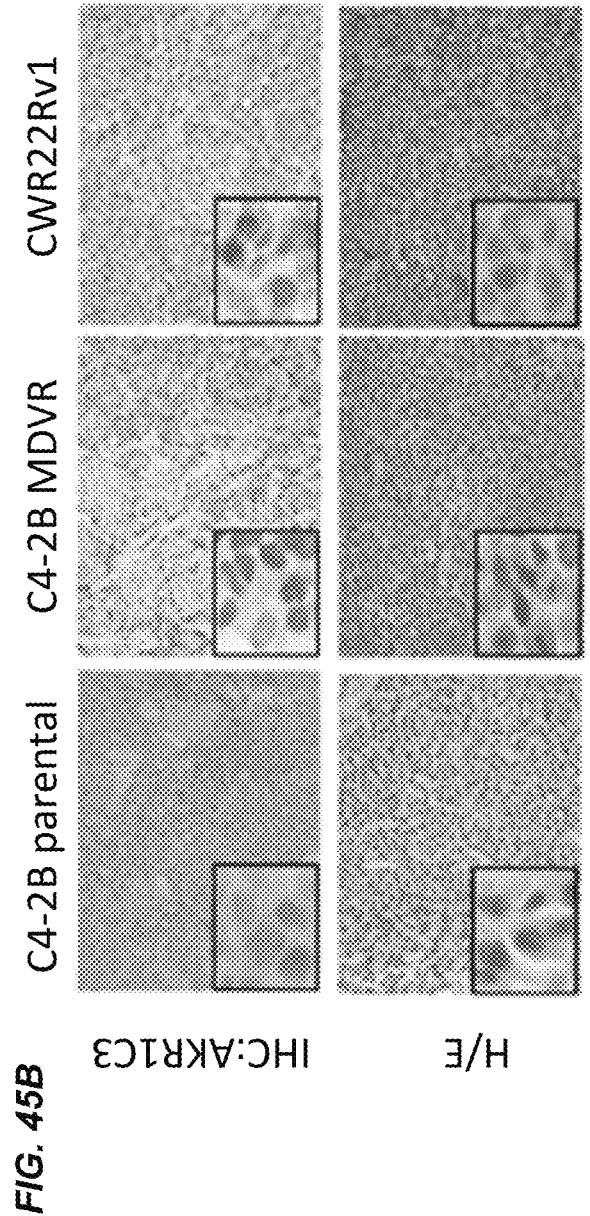
Figures 45C, 45D:
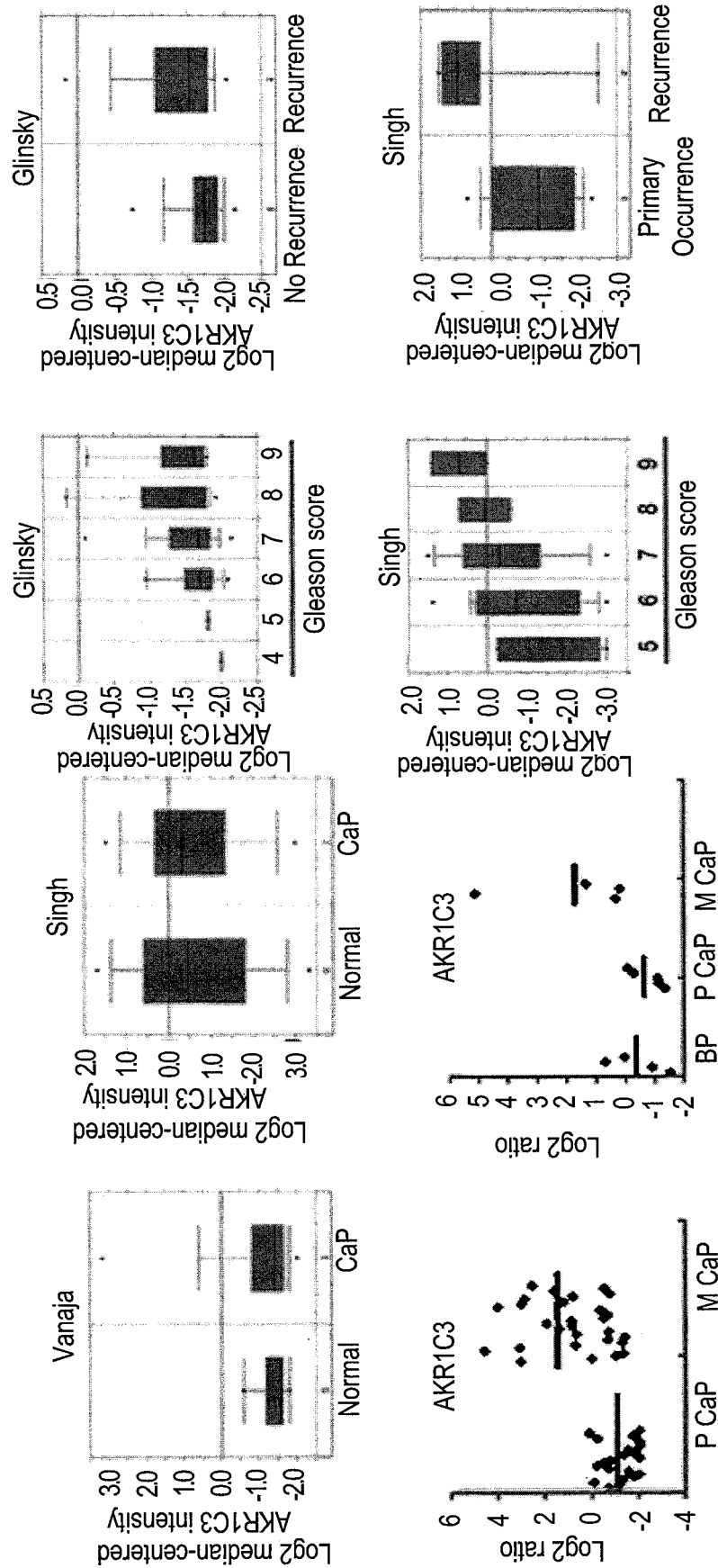
Figure 46A:
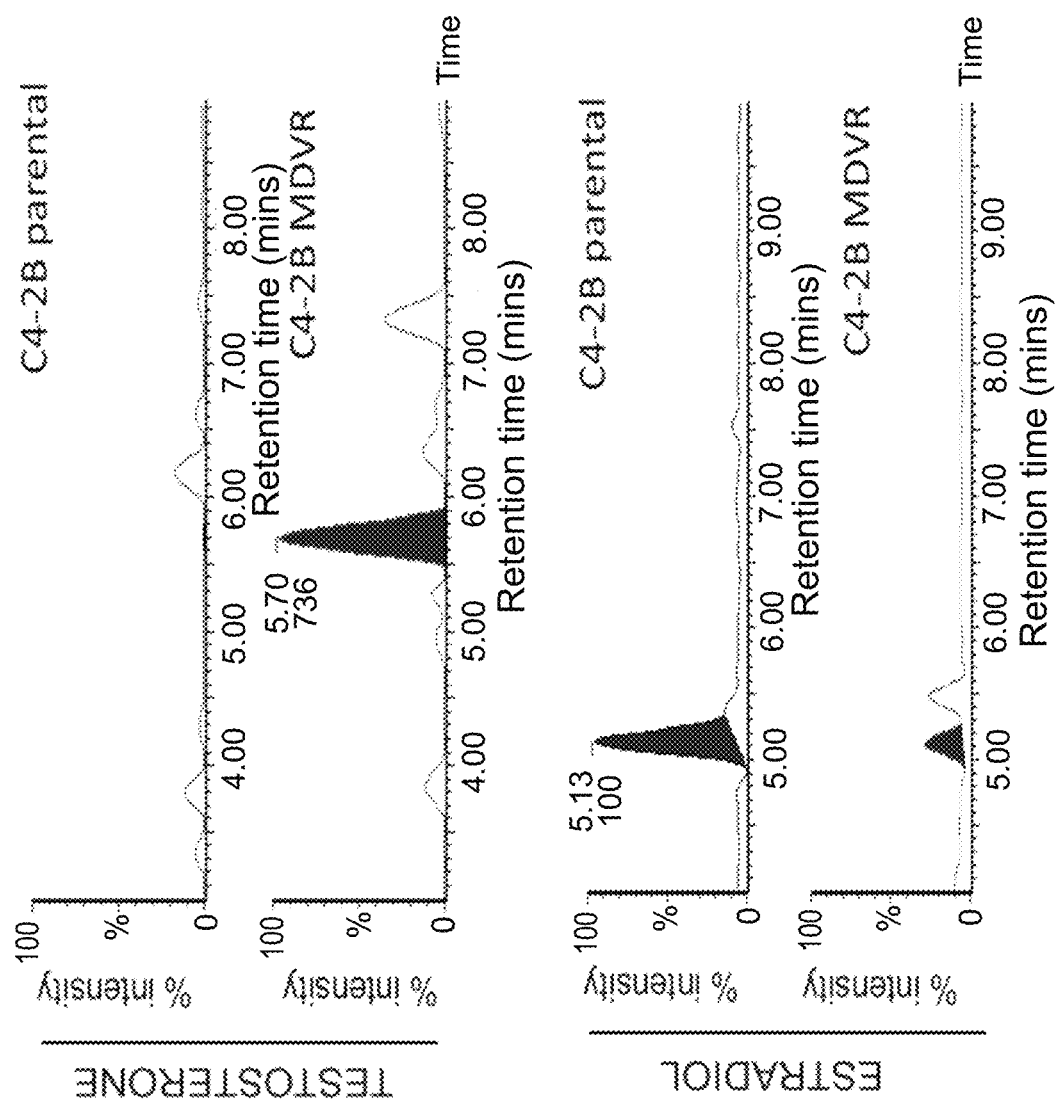
Figure 46B:
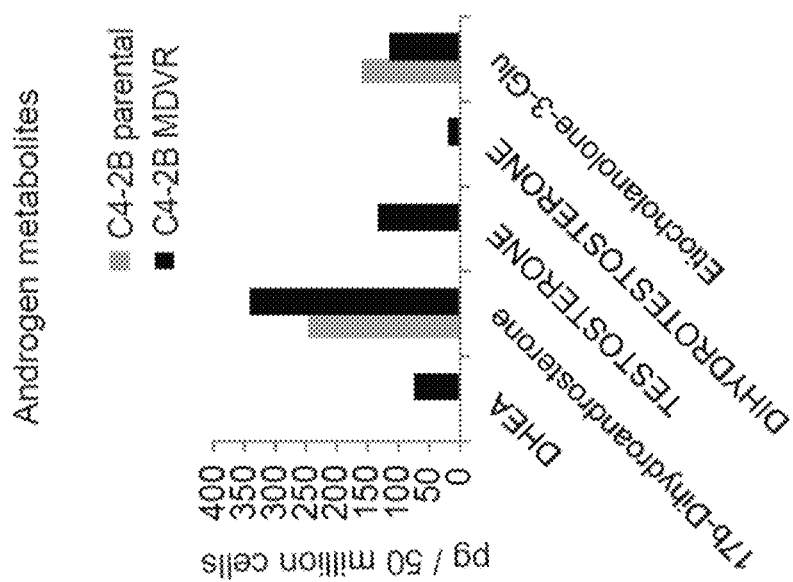
Figure 46D:
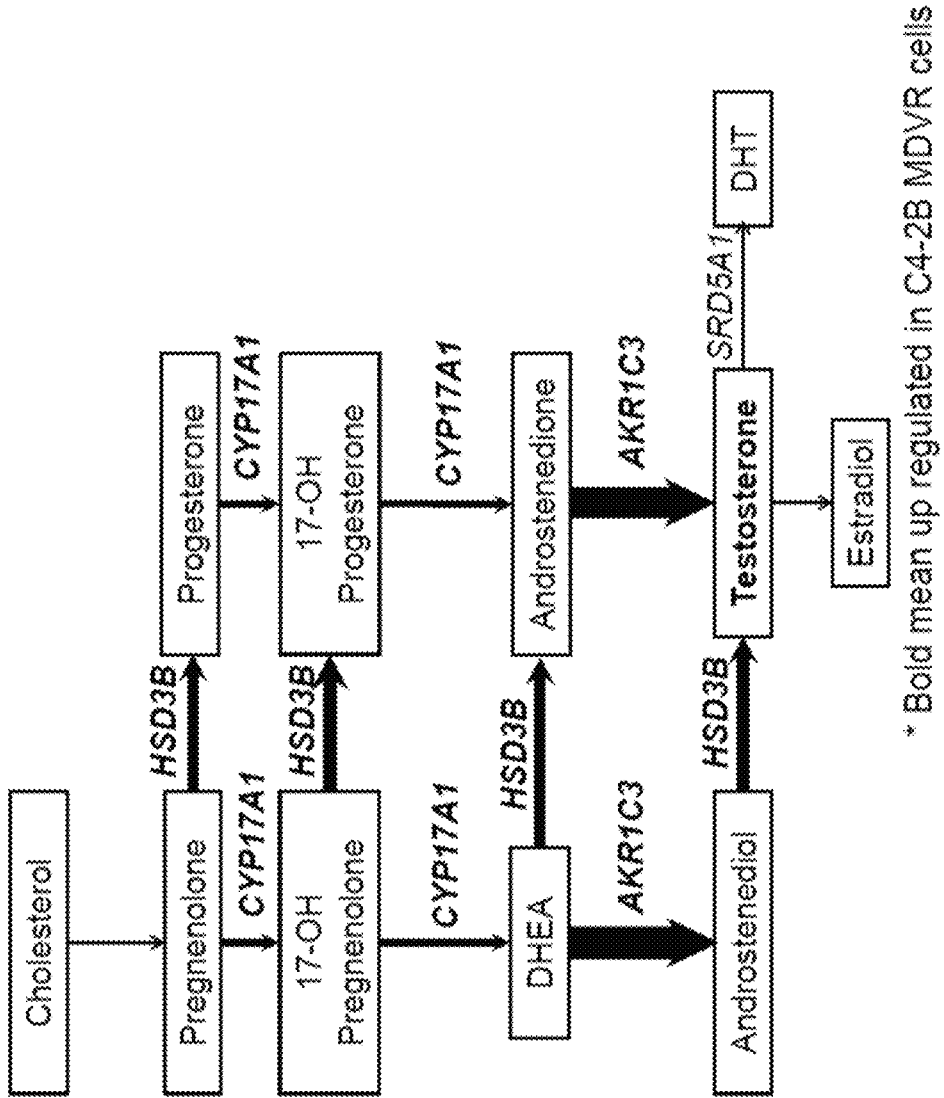

Intratumoral androgen biosynthesis has been well characterized as a mechanism of CRPC (Cai et al., 2011; Fankhauser et al., 2014; Ishizaki et al., 2013; Locke et al., 2008; Mohler et al., 2011), but its role in enzalutamide resistance has been unclear. To further understand potential mechanisms that underlie enzalutamide resistance, microarray analysis was performed on enzalutamide resistant C4-2B-MDVR cells and enzalutamide sensitive C4-2B parental cells. Expression of transcripts encoding for steroid hormone biosynthesis was analyzed by gene set enrichment. Among 45 genes involved in hormone biosynthesis, 31 genes were up regulated while 14 genes were down regulated in C4-2B MDVR cells. As shown in FIG. 44A, increased expression of AKR1C3, AKR1C1, AKR1C2, HSD3B1, CYP17A1 and SRD5A3, and decreased expression of UGT2B15, UGT2B17, CYP39A1, HSD17B6 and SRD5A1 was found in C4-2B MDVR cells as compared to C4-2B parental cells. To verify the gene expression data, CYP17A1, HSD3B1, HSD3B2, HSD17B3, SRD5A1, AKR1C1/2 and AKR1C3 mRNA levels were measured using specific primers by qRT-PCR. As shown in FIG. 44B left, the levels of mRNA expression were consistent with the microarray data. The results were also confirmed by western blot, as shown in FIG. 44B right, C4-2B MDVR cells express significantly higher levels of AKR1C3, HSD3B and CYP17A1 proteins compared to C4-2B parental cells. These results show that androgen synthesis signaling is upregulated in enzalutamide resistant prostate cancer cells.

ii. AKR1C3 is Highly Expressed in Metastatic and Recurrent Prostate Cancer and Enzalutamide Resistant Prostate Xenograft Tumors AKR1C3 was found to be up regulated by more than 16-fold in enzalutamide resistant C4-2B MDVR cells compared to the C4-2B parental cells. AKR1C3 expression was examined in the following different prostate cancer cell lines: VCaP, CWR22Rv1, LNCaP, LN-95, C4-2B and C4-2B-MDVR cells. C4-2B MDVR, CWR22Rv1, and LN-95 cells are resistant to enzalutamide while C4-2B and LNCaP cells are sensitive to enzalutamide. As shown in FIG. 45A, C4-2B MDVR, VCaP, CWR22Rv1 and LN-95 cells all express significantly higher levels of AKR1C3; C4-2B MDVR, CWR22Rv1 and LN-95 cells express higher levels of HSD3B; C4-2B MDVR and LN-95 cells also expressed higher levels of CYP17A1. AKR1C3 expression was also examined in tumor xenografts by IHC, as shown in FIG. 45B, C4-2B MDVR and CWR22Rv1 tumors express higher levels of AKR1C3 compared to C4-2B parental tumors. Data-mining was also performed using the Oncomine and GEO data bases to compare the expression of AKR1C3 in normal prostate and prostate cancer. Primary prostate cancer and normal prostate express similar AKR1C3 levels in two independent prostate datasets, while AKR1C3 was significantly elevated in metastatic prostate cancer in GEO datasets (FIG. 45C), which is consistent with the previous reports (Mitsiades et al., 2012; Montgomery et al., 2008). The correlation between AKR1C3 and prostate cancer disease progression was further explored. As shown in FIG. 45D, AKR1C3 was significantly correlated with Gleason score and recurrence status in prostate cancer patients in two independent prostate datasets in Oncomine. Collectively, these results demonstrate that AKR1C3 is highly expressed in late stage prostate cancer and in enzalutamide resistant prostate cancer xenografts.

iii. Intracrine Androgens are Elevated in Enzalutamide Resistant Prostate Cancer Cells AKR1C3 (also named 17βHSD5) is one of the most important genes involved in androgen synthesis and metabolism. AKR1C3 facilitates the conversion of weak androgens androstenedione (A' dione) and 5 α-androstanedione (5α-dione) to the more active androgens, testosterone and DHT respectively. To further confirm that intracellular androgen synthesis was acquired by C4-2B MDVR cells, steroid metabolism in C4-2B parental and C4-2B MDVR cells was analyzed by Liquid Chromatography-Mass Spectrometry (LC-MS). C4-2B parental and C4-2B MDVR cells were cultured in serum free and phenol red free medium for 5 days, and steroid metabolites were extracted from $50 \times 10^6$ cells and subjected to LC-MS analysis. As shown in FIGS. 46A-46C, C4-2B MDVR cells synthesize extremely high levels of testosterone (131.025 vs. 0.15 pg/50 million cells), dihydrotestosterone (17.55 vs. 0 pg/50 million cells), and DHEA (72.075 vs. 0 pg/50 million cells), compared to C4-2B parental cells. Intriguingly, the active estrogen metabolite estradiol was significantly reduced (82.725 vs. 207.3 pg/50 million cells) in C4-2B MDVR cells, suggesting that the biosynthesis of androgens was activated while transformation of estrogen from androgens was suppressed in C4-2B MDVR cells. Of note, the precursors involved in intracrine androgen synthesis such as cholesterol, DHEA and progesterone are also elevated in C4-2B MDVR cells compared to C4-2B parental cells (FIG. 46C). The steroidogenic enzymes involved in androgen synthesis and metabolism are illustrated in FIG. 46D, bold arrows and bold font indicate upregulation in enzalutamide resistant prostate cancer cells compared to C4-2B parental cells (FIG. 46D). Collectively, these results suggest that intracrine acquired androgen synthesis was elevated in prostate cancer cells resistant to enzalutamide.

iv. AKR1C3 Confers Resistance to Enzalutamide in Prostate Cancer Cells

Figure 48A:
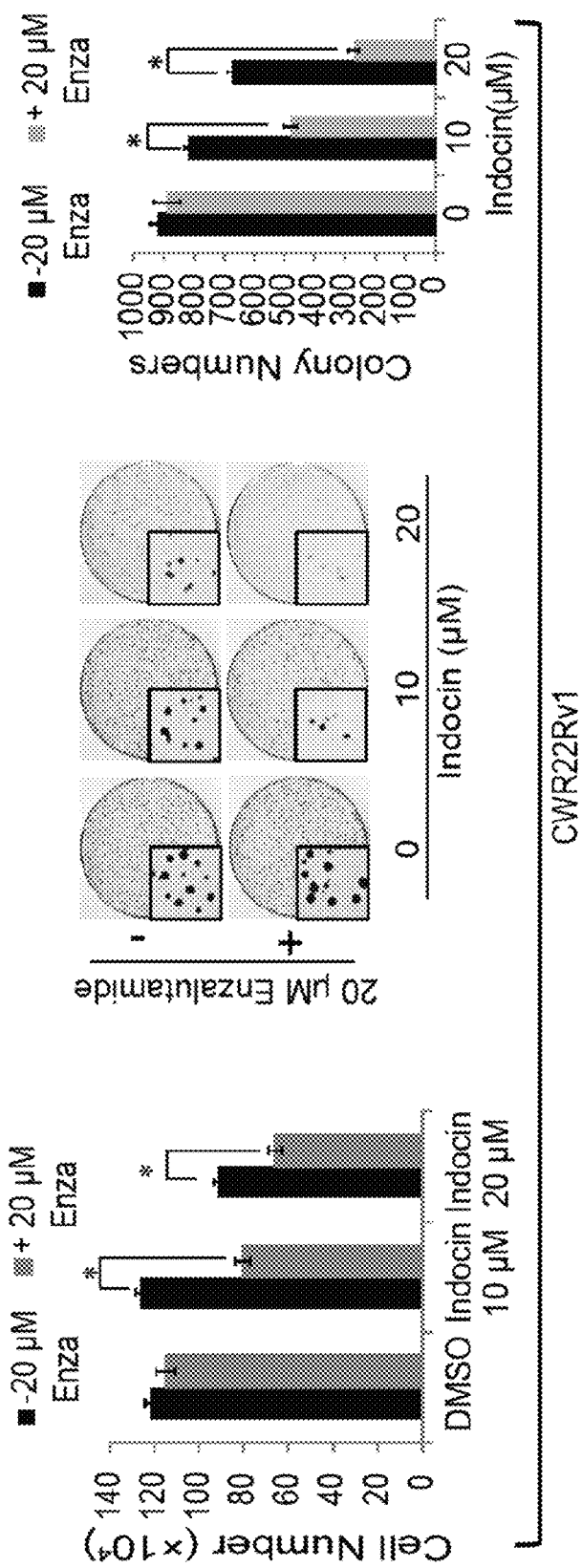
FIGS. 48A-48D show that indomethacin, an inhibitor of AKR1C3activity, overcomes enzalutamide resistance.
Figure 48B:
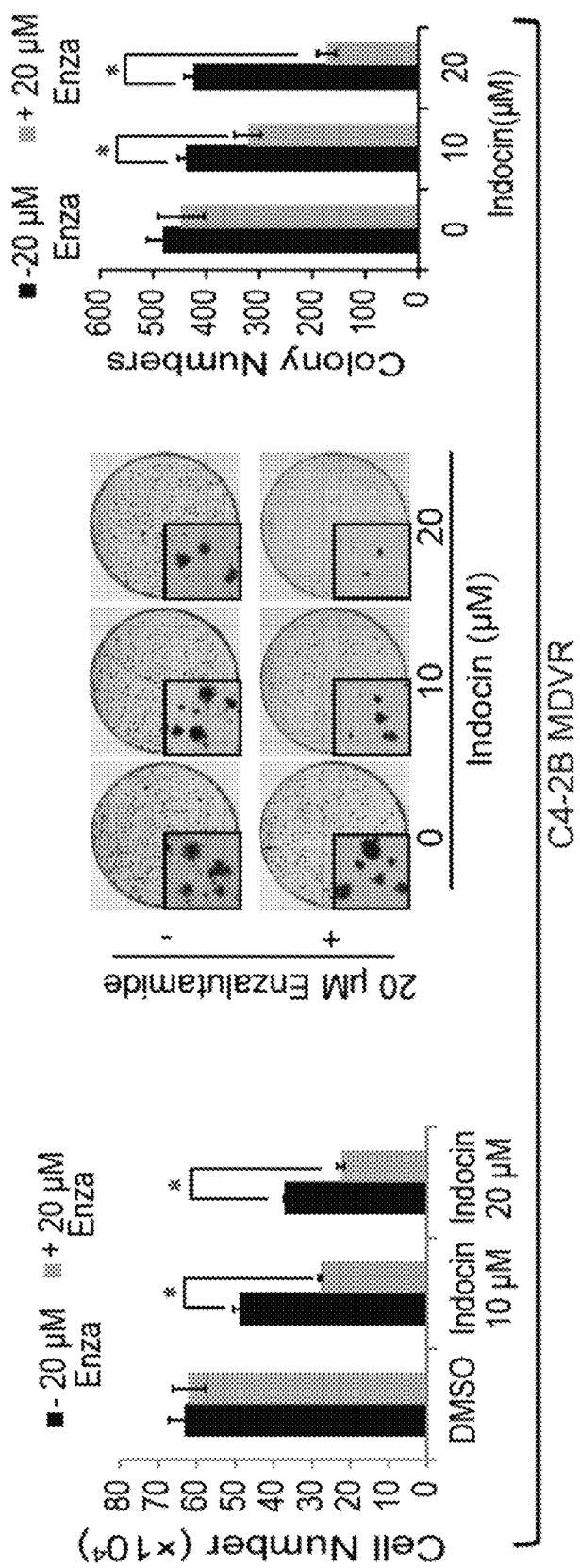
Figure 48C:
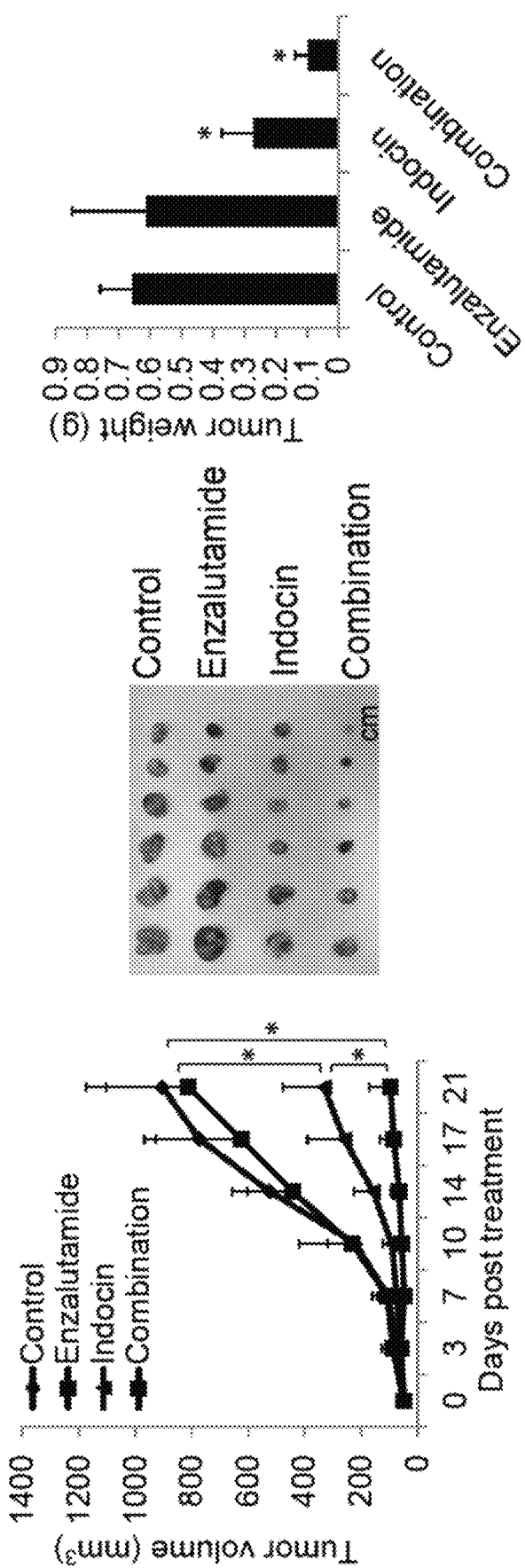
Figure 48D:
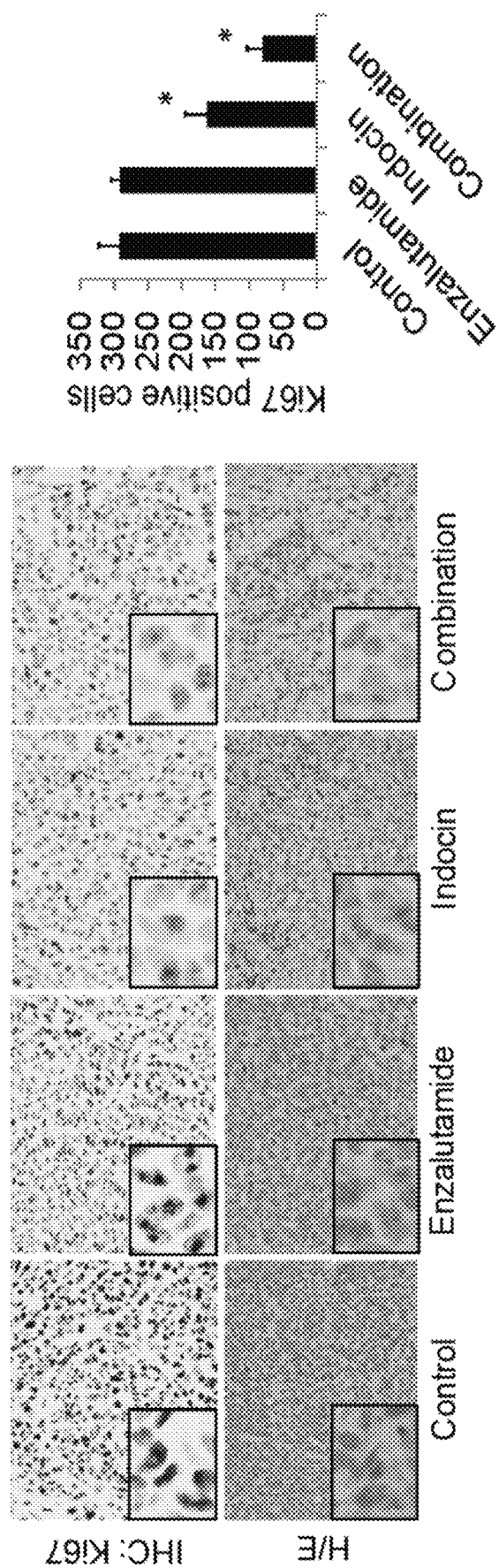

Having demonstrated that AKR1C3 is upregulated in enzalutamide resistant prostate cancer cells and in late stage prostate cancer patients, the inventors next examined whether AKR1C3 could confer resistance to enzalutamide. It was found that AKR1C3 was sufficient to confer resistance to enzalutamide in prostate cancer cells. CWR22Rv1 cells or C4-2B MDVR cells were transiently transfected with control shRNA or AKR1C3 shRNA following treatment with enzalutamide for three days. As shown in FIGS. 47A and 47B, CWR22Rv1 and C4-2B MDVR cells are resistant to enzalutamide, while knock down of AKR1C3 expression by two independent shRNAs (#561 and #694) restored their sensitivity to enzalutamide. The down regulation of AKR1C3 by shRNA was confirmed by western blot (FIG. 47C). LNCaP cells stably expressing AKR1C3 (LNCaP-AKR1C3) were also generated to test whether exogenous expression of AKR1C3 induces enzalutamide resistance. LNCaP-AKR1C3 and LNCaP-neo vector control cells were treated with different concentrations of enzalutamide for 48 hours and cell numbers were counted. As shown in FIG. 47D, LNCaP-AKR1C3 cells exhibited greater resistance to enzalutamide than LNCaP-neo cells. These results were also confirmed by clonogenic ability assay. LNCaP-AKR1C3 cells showed significantly more clonogenic ability than the control LNCaP-neo cells in response to enzalutamide treatment (FIGS. 47E and 47F). Collectively, these results demonstrate that overexpression of AKR1C3 confers resistance to enzalutamide, while down regulation of AKR1C3 resensitizes enzalutamide resistant prostate cancer cells to enzalutamide treatment.

v. Indomethacin, an Inhibitor of AKR1C3 Activity, Overcomes Enzalutamide Resistance Indomethacin, a non-steroidal anti-inflammatory drug (NSAID) used for reducing fever, pain and inflammation, has been shown to be able to inhibit AKR1C3 activity (Cai et al., 2011; Flanagan et al., 2012; Liedtke et al., 2013). To further examine the role of AKR1C3 in enzalutamide resistance, indomethacin was used to hinder AKR1C3 activation and the effects on the response of PCa cells to enzalutamide treatment were examined in vitro and in vivo. As shown in FIG. 48A left, indomethacin did not have an effect on CWR22Rv1 cell growth at 10 μM but inhibited cell growth marginally at 20 μM. However, combination of indomethacin with enzalutamide significantly inhibited the growth of enzalutamide resistant CWR22Rv1 cells. The results were also confirmed by clonogenic assay. As shown in FIG. 48A right, combination of indomethacin with enzalutamide significantly inhibited colony numbers and reduced colony size in CWR22Rv1 cells. Similar results were also obtained in C4-2B MDVR cells (FIG. 48B). To test whether inhibition of AKR1C3 by indomethacin overcomes resistance to enzalutamide treatment in vivo, CWR22Rv1 xenograft model was used. As shown in FIG. 48C, while CWR22Rv1 tumors were resistant to enzalutamide treatment, indomethacin significantly inhibited tumor growth. Combination of indomethacin with enzalutamide further inhibited tumor growth of CWR22Rv1 xenografts. Immunohistochemical staining of Ki67 showed that cell proliferation was significantly inhibited by indomethacin, and further inhibited by the combination treatment (FIG. 48D). Collectively, these results suggest that inhibition of AKR1C3 by indomethacin reduced enzalutamide-resistant tumor growth, and that combination of enzalutamide with indomethacin further reduced the tumor growth of enzalutamide-resistant prostate cancer. These results indicate that inhibition of AKR1C3 by indomethacin potentiates the cell killing effect of enzalutamide.

c. Discussion

The second generation androgen antagonist enzalutamide represents an improvement in therapy options for late stage metastatic CRPC (Scher et al., 2010; Scher et al., 2012). However, the initial responders develop resistance inevitably. The potential mechanisms associated with enzalutamide resistance have been the focus of intense investigation. Several novel mechanisms involved in enzalutamide resistance were previously identified, including activation of NF-κB2/p52 (Cui et al., 2014; Nadiminty et al., 2013), AR-V7 (Liu et al., 2014a; Nadiminty et al., 2013), STAT3 (Liu et al., 2014b), and induction of autophagy (Nguyen et al., 2014). In this study, AKR1C3 activation and elevated intracrine androgens were identified as potential mechanisms contributing to enzalutamide resistance. This study demonstrates that AKR1C3 is overexpressed in enzalutamide resistant prostate cancer cells. Moreover, this study shows that overexpression of AKR1C3 confers resistance to enzalutamide, while down regulation of AKR1C3 sensitizes PCa cells to enzalutamide treatment. In addition, overexpression of AKR1C3 is demonstrated in clinical metastatic prostate cancer and correlated with disease progression. It is also demonstrated that intracrine steroids including androgens are elevated in enzalutamide resistant cells, possibly through increased expression of steroidogenic enzymes such as AKR1C3. It is further demonstrated that indomethacin, a potent inhibitor of AKR1C3, can be used to overcome enzalutamide resistance. The discovery of elevated intracrine androgen synthesis and enhanced AKR1C3 activation in enzalutamide resistant cells reveals a novel mechanism for the development and progression of enzalutamide resistant CRPC. Co-targeting AKR1C3 is likely to overcome resistance and achieve durable responses in men with second-generation antiandrogen treatment.

Intracrine androgen biosynthesis has been well characterized as a mechanism of CRPC (Cai et al., 2011; Fankhauser et al., 2014; Ishizaki et al., 2013; Locke et al., 2008; Mohler et al., 2011). Many enzymes are involved in androgen synthesis, including CYP17A1, AKR1C3 and HSD3B. CYP17A1 can be inhibited by abiraterone in clinical treatments (de Bono et al., 2011; Ryan et al., 2013). AKR1C3 is a steroidogenic enzyme involved in steroid biosynthesis and mediates the last step of testosterone biosynthesis from androstenedione. It catalyzes conversion of steroids and modulates trans-activation of steroid receptors. Elevated expression of AKR1C3 has been associated with PCa progression and aggressiveness (Stanbrough et al., 2006; Wako et al., 2008). AKR1C3 has also been identified as an AR co-activator (Yepuru et al., 2013). In this study, gene enrichment analysis was used to compare enzalutamide resistant cells to enzalutamide sensitive cells. It was found that the steroid biosynthesis genes were highly enriched in C4-2B MDVR cells. Several important genes involved in androgen synthesis, such as AKR1C3, HSD3B and CYP17A1 were up regulated in enzalutamide resistant cells. In another de novo enzalutamide resistant cell line CWR22Rv1, AKR1C3 was highly expressed compared to C4-2B or LNCaP cells, suggesting that AKR1C3 plays a pivotal role in enzalutamide resistance. To further confirm that intracrine androgen synthesis was acquired by C4-2B MDVR cells, steroid levels in C4-2B parental and C4-2B MDVR cells were determined by Liquid Chromatography-Mass Spectrometry (LC-MS). In addition to the higher levels of testosterone and DHT in enzalutamide resistant cells, the levels of the precursors of testosterone such as cholesterol, DHEA and progesterone were all elevated in C4-2B-MDVR cells compared to C4-2B parental cells. These results demonstrate that AKR1C3 was significantly elevated in enzalutamide resistant prostate cancer cells which likely results in higher levels of testosterone and DHT in enzalutamide resistant cells.

Several inhibitors have been developed to target AKR1C3 activation including indomethacin (Flanagan et al., 2012). Indomethacin is a non-steroidal anti-inflammatory drug (NSAID) used for reducing fever, pain and inflammation. Several studies revealed indomethacin might have the potential to increase the sensitivity of cancer cells to anticancer agents, such as that of human melanoma cells to TRAIL-induced apoptosis (Tse et al., 2013), and of colon cancer cells to cisplatin (Brunelli et al., 2012). Indomethacin also has the ability to inhibit PSA and ERG protein expression and decreased testosterone and DHT levels in relapsed VCaP xenograft tumors (Cai et al., 2011). In the present study, it is shown that inhibition of AKR1C3 enzyme activity by indomethacin restored enzalutamide sensitivity in enzalutamide resistant prostate cancer cells both in vitro and in vivo. Furthermore, the combination of indomethacin and enzalutamide resulted in significantly greater inhibition of enzalutamide-resistant tumor growth. The data described herein demonstrate that inhibition of AKR1C3 can restore anti-tumor effects in patients resistant to enzalutamide.

Taken together, the present results show that AKR1C3 activation and the resultant intracrine androgen synthesis confers resistance to enzalutamide in prostate cancer cells. Inhibition of AKR1C3 by shRNA or indomethacin overcomes resistance to enzalutamide. Furthermore, the combination of indomethacin and enzalutamide resulted in significant inhibition of enzalutamide-resistant tumor growth. Targeting AKR1C3 thus provides an effective treatment strategy for patients resistant to enzalutamide.

d. Experimental Procedures i. Reagents and Cell Culture

LNCaP, CWR22Rv1, VCaP and HEK293T cells were obtained from the American Type Culture Collection (ATCC, Manassas, Va.). All experiments with cell lines were performed within 6 months of receipt from ATCC or resuscitation after cryopreservation. ATCC uses Short Tandem Repeat (STR) profiling for testing and authentication of cell lines. C4-2B cells were kindly provided and authenticated by Dr. Leland Chung, Cedars-Sinai Medical Center, Los Angeles, Calif. LN-95 cells were kindly provided and authenticated by Dr. Joel Nelson, University of Pittsburgh, Pa. The cells were maintained in RPMI 1640 supplemented with 10% fetal bovine serum (FBS), 100 units/ml penicillin and 0.1 mg/ml streptomycin. LNCaP-neo and LNCaP-AKR1C3 cells were generated by stable transfection of LNCaP cells with either empty vector pcDNA3.1 or pcDNA3.1 encoding AKR1C3 and were maintained in RPMI1640 medium containing 300 µg/mL G418. AKR1C3 shRNA (TRCN0000026561 and TRCN0000025694) were purchased from Sigma. Cells resistant to enzalutamide were referred to as C4-2B MDVR (C4-2B enzalutamide resistant) as described previously (Liu et al., 2014a). All cells were maintained at 37° C. in a humidified incubator with 5% carbon dioxide.

ii. Sample Preparation and Analysis of Steroids

The steroid extraction and analysis has been described previously (Gaikwad, 2013). Briefly, 50 million C4-2B parental and C4-2B MDVR cells were cultured in serum- and phenol red-free RPMI1640 medium for 5 days, then cells were suspended in 4 mL of a 1:1 water/methanol mixture. The suspension was homogenized, and the resulting homogenate was cooled on ice. The precipitated material was removed by centrifuging at high speed for 5 min, and the supernatant was removed and evaporated in a SpeedVac (Labconco Inc.) followed by lyophilizer (Labconco Inc.). The residue was suspended in 150 µL of CH3OH/H2O (1:1), filtered through a 0.2 µm ultracentrifuge filter (Millipore inc.) and subjected to UPLC/MS-MS analysis. Samples were run in duplicate during UPLC-MS/MS analysis. Samples were placed in an Acquity sample manager which was cooled to 8° C. to preserve the analytes. Pure standards were used to optimize the UPLC-MS/MS conditions prior to sample analysis. Also, the standard mixture was run before the first sample to prevent errors due to matrix effect and day-to-day instrument variations. In addition, immediately after the initial standard and before the first sample, two spiked samples were run to calibrate for the drift in the retention time of all analytes due to the matrix effect. After standard and spiked sample runs, blank was injected to wash the injector and remove carry over effect.

iii. UPLC-MS/MS Analysis of Steroid Metabolites

All mass spectrometry experiments were performed on a Waters Xevo-TQ triple quadruple mass spectrometer (Milford, Mass., USA) and MS and MS/MS spectra were recorded using Electro Spray Ionization (ESI) in positive ion (PI) and negative ion (NI) mode, capillary voltage of 3.0 kV, extractor cone voltage of 3 V and detector voltage of 650 V. Cone gas flow was set at 50 L/h and desolvation gas flow was maintained at 600 L/h. Source temperature and desolvation temperatures were set at 150 and 350° C., respectively. The collision energy was varied to optimize daughter ions. The acquisition range was 20-500 Da. Analytical separations were conducted on the UPLC system using an Acquity UPLC HSS T3 1.8 µm 1×150 mm analytical column kept at 50° C. and at a flow rate of 0.15 ml/min. The gradient started with 100% A (0.1% formic acid in H$_2$O) and 0% B (0.1% formic acid in CH3CN), after 2 min, changed to 80% A over 2 min, then 45% A over 5 min, followed by 20% A in 2 min. Finally it was changed over 1 min to original 100% A, resulting in a total separation time of 15 min. The elutions from the UPLC column were introduced to the mass spectrometer and resulting data were analyzed and processed using MassLynx 4.1 software.

iv. cDNA Microarray Analysis

The microarray analysis has been described previously (Zhu et al., 2013). Briefly, twenty-four hours after plating of 1×10$^5$ C4-2B parental and C4-2B MDVR cells, total RNA was isolated using TRIzol Reagent (Invitrogen) and purified with Eppendorf phase-lock-gel tube. RNA quality of all samples was tested by RNA electrophoresis to ensure RNA integrity. Samples were analyzed by the Genomics Shared Resource (UC Davis Medical Center, Sacramento, Calif.) using the Affymetrix Human Gene 1.0 ST array. The data was analyzed by Subio platform and Ingenuity Pathway Analysis (IPA).

v. Western Blot Analysis

Cellular protein extracts were resolved on SDS-PAGE and proteins were transferred to nitrocellulose membranes. After blocking for 1 hour at room temperature in 5% milk in PBS/0.1% Tween-20, membranes were incubated overnight at 4° C. with the indicated primary antibodies [AKR1C3 (A6229, Sigma); CYP17A1 (SC-66849, Santa Cruz Biotechnology, Santa Cruz, Calif.); HSD3B (SC-28206, Santa Cruz Biotechnology, Santa Cruz, Calif.); Tubulin (T5168, Sigma-Aldrich, St. Louis, Mo.)]. Tubulin was used as loading control. Following secondary antibody incubation, immunoreactive proteins were visualized with an enhanced chemiluminescence detection system (Millipore, Billerica, Mass.).

vi. Cell Growth Assay

C4-2B MDVR, CWR22Rv1 cells were seeded on 12-well plates at a density of 0.5×10$^5$ cells/well in RPMI 1640 media containing 10% FBS and transiently transfected with AKR1C3 shRNA or control shRNA following treatment with 20 µM enzalutamide. Total cell numbers were counted after 3 or 5 days. LNCaP-neo, LNCaP-AKR1C3 or LN-95 cells were treated with different concentrations of enzalutamide for 48 hours. Total cell numbers were counted or the cell survival rate (%) was calculated. Cell survival rate (%)=(Treatment group cell number/Control group cell number)×100%.

vii. Clonogenic Assay

C4-2 parental or C4-2B MDVR cells were treated with DMSO, 10 µM or 20 µM enzalutamide in media containing 10% FBS. CWR22Rv1 cells or C4-2B MDVR cells were treated with 10 µM or 20 µM indomethacin with or without 20 µM enzalutamide, cells were plated at equal density (1500 cells/dish) in 100 mm dishes for 14 days, the medium was changed every 3 days; LNCaP-neo or LNCaP-AKR1C3 cells were treated with DMSO or 10 enzalutamide in media containing 10% complete FBS, cells were plated at equal density (10000 cells/dish) in 100 mm dishes for 28 days, the colonies were rinsed with PBS before staining with 0.5% crystal violet/4% formaldehyde for 30 min and the numbers of colonies were counted.

viii. Real-Time Quantitative RT-PCR

Total RNAs were extracted using TriZOL reagent (Invitrogen). cDNAs were prepared after digestion with RNase-free RQ1 DNase (Promega). The cDNAs were subjected to real-time reverse transcription-PCR (RT-PCR) using Sso Fast Eva Green Supermix (Bio-Rad) according to the manufacturer's instructions and as described previously (Liu et al., 2011). Each reaction was normalized by co-amplification of actin. Triplicates of samples were run on default settings of Bio-Rad CFX-96 real-time cycler. Primers used for Real-time PCR are: AKR1C3, 5'-gagaagtaaagctttggaggt-caca-3' (forward) and 5'-caacctgctcctcattattgtataaatga-3' (reverse); AKR1C1/2, 5'-ggtcacttcatgcctgtcct-3' (forward) and 5'-actctggtcgatgggaattg-3' (reverse); HSD3B1, 5'-agaatcta-gaccactcttctgtccagatt-3' (forward) and 5'-ctttgaattcaactatgt-gaaggaatggaa-3' (reverse); HSD3B2, 5'-cgggcccaactccta-caag-3' (forward) and 5'-ttttccagaggctcttcttcgt-3' (reverse); CYP17A1, 5'-gggcggcctcaaatgg-3' (forward) and 5'-cagcgaaggcgaaggcgatacccta-3' (reverse); HSD17B3, 5'-tgggacagtgggcagtga-3' (forward) and 5'-cgagtacgctttcc-caattcc-3' (reverse); SRD5A1, 5'-acgggcatcggtgcttaat-3' (forward) and 5'-ccaacagtggcataggcttc-3' (reverse); and Actin, 5'-agaactggcccttcttggagg-3' (forward) and 5'-gttt-tatgttcctctatggg-3' (reverse).

ix. Measurement of PSA

PSA levels were measured in sera from C4-2B parental or C4-2B MDVR tumor bearing mice using PSA ELISA Kit (KA0208, Abnova, Inc., Walnut, Calif.) according to the manufacturer's instructions.

x. In Vivo Tumorigenic Assay

C4-2B parental or C4-2B MDVR cells (4 million) were mixed with matrigel (1:1) and injected into the prostates of 6-7 week male SCID mice. When the serum PSA level reached 5 ng/ml, mice were randomized into two groups (4 mice in each group) and treated as follows: (1) vehicle control (0.5% weight/volume (w/v) Methocel A4M p.o.), (2) enzalutamide (25 mg/kg, p.o.). Tumors were monitored by PSA level. All tumor tissues were harvested after 3 weeks of treatment.

CWR22Rv1 cells (4 million) were mixed with matrigel (1:1) and injected subcutaneously into the flanks of 6-7 week male SCID mice. Tumor-bearing mice (tumor volume around 50-100 mm3) were randomized into four groups (5 mice in each group) and treated as follows: (1) vehicle control (5% Tween 80 and 5% ethanol in PBS, i.p.), (2) enzalutamide (25 mg/kg, p.o.), (3) indomethacin (3 mg/kg, i.p.), (4) enzalutamide (25 mg/kg, p.o.)+indomethacin (3 mg/kg, i.p.). Tumors were measured using calipers twice a week and tumor volumes were calculated using length×width2/2. Tumor tissues were harvested after 3 weeks of treatment.

xi. Immunohistochemistry

Tumors were fixed by formalin and paraffin embedded tissue blocks were dewaxed, rehydrated, and blocked for endogenous peroxidase activity. Antigen retrieving was performed in sodium citrate buffer (0.01 mol/L, pH 6.0) in a microwave oven at 1,000 W for 3 min and then at 100 W for 20 min. Nonspecific antibody binding was blocked by incubating with 10% fetal bovine serum in PBS for 30 min at room temperature. Slides were then incubated with anti-Ki-67 (at 1:500; NeoMarker), anti-AKR1C3 (at 1:100; Sigma) at 4° C. overnight. Slides were then washed and incubated with biotin-conjugated secondary antibodies for 30 min, followed by incubation with avidin DH-biotinylated horseradish peroxidase complex for 30 min (Vectastain ABC Elite Kit, Vector Laboratories). The sections were developed with the diaminobenzidine substrate kit (Vector Laboratories) and counterstained with hematoxylin. Nuclear staining cells was scored and counted in 5 different vision areas. Images were taken with an Olympus BX51 microscope equipped with DP72 camera.

xii. Statistical Analysis

All data are presented as means±standard deviation of the mean (SD). STATistical analyses were performed with Microsoft Excel analysis tools. Differences between individual groups were analyzed by one-way analysis of variance (ANOVA) followed by the Scheffé procedure for comparison of means. $p<0.05$ was considered statistically significant.

e. References

Antonarakis, E. S., Lu, C., Wang, H., Luber, B., Nakazawa, M., Roeser, J. C., Chen, Y., Mohammad, T. A., Chen, Y., Fedor, H. L., et al. (2014). AR-V7 and resistance to enzalutamide and abiraterone in prostate cancer. The New England journal of medicine 371, 1028-1038.

Arora, V. K., Schenkein, E., Murali, R., Subudhi, S. K., Wongvipat, J., Balbas, M. D., Shah, N., Cai, L., Efstathiou, E., Logothetis, C., et al. (2013). Glucocorticoid receptor confers resistance to antiandrogens by bypassing androgen receptor blockade. Cell 155, 1309-1322.

Bauman, D. R., Steckelbroeck, S., Williams, M. V., Peehl, D. M., and Penning, T. M. (2006). Identification of the major oxidative 3alpha-hydroxysteroid dehydrogenase in human prostate that converts 5alpha-androstane-3alpha, 17beta-diol to 5alpha-dihydrotestosterone: a potential therapeutic target for androgen-dependent disease. Mol Endocrinol 20, 444-458.

Brunelli, C., Amici, C., Angelini, M., Fracassi, C., Belardo, G., and Santoro, M. G. (2012). The non-steroidal anti-inflammatory drug indomethacin activates the eIF2alpha kinase PKR, causing a translational block in human colorectal cancer cells. The Biochemical journal 443, 379-386.

Cai, C., Chen, S., Ng, P., Bubley, G. J., Nelson, P. S., Mostaghel, E. A., Marck, B., Matsumoto, A. M., Simon, N. I., Wang, H., et al. (2011). Intratumoral de novo steroid synthesis activates androgen receptor in castration-resistant prostate cancer and is unregulated by treatment with CYP17A1 inhibitors. Cancer research 71, 6503-6513.

Chang, K. H., Ercole, C. E., and Sharifi, N. (2014). Androgen metabolism in prostate cancer: from molecular mechanisms to clinical consequences. British journal of cancer 111, 1249-1254.

Chang, K. H., Li, R., Kuri, B., Lotan, Y., Roehrborn, C. G., Liu, J., Vessella, R., Nelson, P. S., Kapur, P., Guo, X., et al. (2013). A gain-of-function mutation in DHT synthesis in castration-resistant prostate cancer. Cell 154, 1074-1084.

Cui, Y., Nadiminty, N., Liu, C., Lou, W., Schwartz, C. T., and Gao, A. C. (2014). Upregulation of glucose metabolism by NF-kappaB2/p52 mediates enzalutamide resistance in castration-resistant prostate cancer cells. Endocrine-related cancer 21, 435-442.

de Bono, J. S., Logothetis, C. J., Molina, A., Fizazi, K., North, S., Chu, L., Chi, K. N., Jones, R. J., Goodman, O. B., Jr., Saad, F., et al. (2011). Abiraterone and increased survival in metastatic prostate cancer. The New England journal of medicine 364, 1995-2005.

Dehm, S. M., Schmidt, L. J., Heemers, H. V., Vessella, R. L., and Tindall, D. J. (2008). Splicing of a novel androgen receptor exon generates a constitutively active androgen receptor that mediates prostate cancer therapy resistance. Cancer Res 68, 5469-5477.

Efstathiou, E., Titus, M., Wen, S., Hoang, A., Karlou, M., Ashe, R., Tu, S. M., Aparicio, A., Troncoso, P., Mohler, J., and Logothetis, C. J. (2014). Molecular Characterization of Enzalutamide-treated Bone Metastatic Castration-resistant Prostate Cancer. European urology 10.1016/j.eururo.2014.05.005.

Efstathiou E, T. M., Tsavachidou D, Hoang A, Karlou M, Wen S, et al (2011). MDV3100 effects on androgen receptor (AR) signaling and bone marrow testosterone concentration modulation: Apreliminary report. ASCO Meeting Abstracts 29, 4501.

Fankhauser, M., Tan, Y., Macintyre, G., Haviv, I., Hong, M. K., Nguyen, T., Pedersen, J., Costello, A. J., Hovens, C. M., and Corcoran, N. M. (2014). Canonical Androstenedione Reduction is the Predominant Source of Signalling Androgens in Hormone Refractory Prostate Cancer. Clinical cancer research: an official journal of the American Association for Cancer Research doi: 10.1158/1078-0432. CCR-13-3483

Flanagan, J. U., Yosaatmadja, Y., Teague, R. M., Chai, M. Z., Turnbull, A. P., and Squire, C. J. (2012). Crystal structures of three classes of non-steroidal anti-inflammatory drugs in complex with aldo-keto reductase 1C3. PloS one 7, e43965.

Gaikwad, N. W. (2013). Ultra performance liquid chromatography-tandem mass spectrometry method for profiling of steroid metabolome in human tissue. Analytical chemistry 85, 4951-4960.

Hu, R., Lu, C., Mostaghel, E. A., Yegnasubramanian, S., Gurel, M., Tannahill, C., Edwards, J., Isaacs, W. B., Nelson, P. S., Bluemn, E., et al. (2013). Distinct transcriptional programs mediated by the ligand-dependent full-length androgen receptor and its splice variants in castration-resistant prostate cancer. Cancer Res 72, 3457-3462.

Ishizaki, F., Nishiyama, T., Kawasaki, T., Miyashiro, Y., Hara, N., Takizawa, I., Naito, M., and Takahashi, K. (2013). Androgen deprivation promotes intratumoral synthesis of dihydrotestosterone from androgen metabolites in prostate cancer. Scientific reports 3, 1528.

Isikbay, M., Otto, K., Kregel, S., Kach, J., Cai, Y., Vander Griend, D. J., Conzen, S. D., and Szmulewitz, R. Z. (2014). Glucocorticoid receptor activity contributes to resistance to androgen-targeted therapy in prostate cancer. Hormones & cancer 5, 72-89.

Joseph, J. D., Lu, N., Qian, J., Sensintaffar, J., Shao, G., Brigham, D., Moon, M., Maneval, E. C., Chen, I., Darimont, B., and Hager, J. H. (2013). A clinically relevant androgen receptor mutation confers resistance to second-generation antiandrogens enzalutamide and ARN-509. Cancer discovery 3, 1020-1029.

Korpal, M., Korn, J. M., Gao, X., Rakiec, D. P., Ruddy, D. A., Doshi, S., Yuan, J., Kovats, S. G., Kim, S., Cooke, V. G., et al. (2013). An F876L mutation in androgen receptor confers genetic and phenotypic resistance to MDV3100 (enzalutamide). Cancer discovery 3, 1030-1043.

Labrie, F., Luu-The, V., Lin, S. X., Labrie, C., Simard, J., Breton, R., and Belanger, A. (1997). The key role of 17 beta-hydroxysteroid dehydrogenases in sex steroid biology. Steroids 62, 148-158.

Li, Y., Chan, S. C., Brand, L. J., Hwang, T. H., Silverstein, K. A., and Dehm, S. M. (2013). Androgen receptor splice variants mediate enzalutamide resistance in castration-resistant prostate cancer cell lines. Cancer Res 73, 483-489.

Liedtke, A. J., Adeniji, A. O., Chen, M., Byrns, M. C., Jin, Y., Christianson, D. W., Marnett, L. J., and Penning, T. M. (2013). Development of potent and selective indomethacin analogues for the inhibition of AKR1C3 (Type 5 17beta-hydroxysteroid dehydrogenase/prostaglandin F synthase) in castrate-resistant prostate cancer. Journal of medicinal chemistry 56, 2429-2446.

Liu, C., Lou, W., Zhu, Y., Nadiminty, N., Schwartz, C. T., Evans, C. P., and Gao, A. C. (2014a). Niclosamide inhibits androgen receptor variants expression and overcomes enzalutamide resistance in castration-resistant prostate cancer. Clin Cancer Res 20, 3198-3210.

Liu, C., Nadiminty, N., Tummala, R., Chun, J. Y., Lou, W., Zhu, Y., Sun, M., Evans, C. P., Zhou, Q., and Gao, A. C. (2011). Andrographolide targets androgen receptor pathway in castration-resistant prostate cancer. Genes Cancer 2, 151-159.

Liu, C., Zhu, Y., Lou, W., Cui, Y., Evans, C. P., and Gao, A. C. (2014b). Inhibition of constitutively active STAT3 reverses enzalutamide resistance in LNCaP derivative prostate cancer cells. Prostate 74, 201-209.

Locke, J. A., Guns, E. S., Lubik, A. A., Adomat, H. H., Hendy, S. C., Wood, C. A., Ettinger, S. L., Gleave, M. E., and Nelson, C. C. (2008). Androgen levels increase by intratumoral de novo steroidogenesis during progression of castration-resistant prostate cancer. Cancer Res 68, 6407-6415.

Mitsiades, N., Sung, C. C., Schultz, N., Danila, D. C., He, B., Eedunuri, V. K., Fleisher, M., Sander, C., Sawyers, C. L., and Scher, H. I. (2012). Distinct patterns of dysregulated expression of enzymes involved in androgen synthesis and metabolism in metastatic prostate cancer tumors. Cancer research 72, 6142-6152.

Mohler, J. L., Titus, M. A., Bai, S., Kennerley, B. J., Lih, F. B., Tomer, K. B., and Wilson, E. M. (2011). Activation of the androgen receptor by intratumoral bioconversion of androstanediol to dihydrotestosterone in prostate cancer. Cancer research 71, 1486-1496.

Montgomery, R. B., Mostaghel, E. A., Vessella, R., Hess, D. L., Kalhorn, T. F., Higano, C. S., True, L. D., and Nelson, P. S. (2008). Maintenance of intratumoral androgens in metastatic prostate cancer: a mechanism for castration-resistant tumor growth. Cancer Res 68, 4447-4454.

Nadiminty, N., Tummala, R., Liu, C., Yang, J., Lou, W., Evans, C. P., and Gao, A. C. (2013). NF-kappaB2/p52 induces resistance to enzalutamide in prostate cancer: role of androgen receptor and its variants. Molecular cancer therapeutics 12, 1629-1637.

Nguyen, H. G., Yang, J. C., Kung, H. J., Shi, X. B., Tilki, D., Lara, P. N., Jr., DeVere White, R. W., Gao, A. C., and Evans, C. P. (2014). Targeting autophagy overcomes Enzalutamide resistance in castration-resistant prostate cancer cells and improves therapeutic response in a xenograft model. Oncogene 33, 4521-4530.

Ryan, C. J., Smith, M. R., de Bono, J. S., Molina, A., Logothetis, C. J., de Souza, P., Fizazi, K., Mainwaring, P., Piulats, J. M., Ng, S., et al. (2013). Abiraterone in metastatic prostate cancer without previous chemotherapy. The New England journal of medicine 368, 138-148.

Scher, H. I., Beer, T. M., Higano, C. S., Anand, A., Taplin, M. E., Efstathiou, E., Rathkopf, D., Shelkey, J., Yu, E. Y., Alumkal, J., et al. (2010). Antitumour activity of MDV3100 in castration-resistant prostate cancer: a phase 1-2 study. Lancet 375, 1437-1446.

Scher, H. I., Fizazi, K., Saad, F., Taplin, M. E., Sternberg, C. N., Miller, K., de Wit, R., Mulders, P., Chi, K. N., Shore, N. D., et al. (2012). Increased survival with enzalutamide in prostate cancer after chemotherapy. N Engl J Med 367, 1187-1197.

Stanbrough, M., Bubley, G. J., Ross, K., Golub, T. R., Rubin, M. A., Penning, T. M., Febbo, P. G., and Balk, S. P. (2006). Increased expression of genes converting adrenal androgens to testosterone in androgen-independent prostate cancer. Cancer Res 66, 2815-2825.

Tse, A. K., Cao, H. H., Cheng, C. Y., Kwan, H. Y., Yu, H., Fong, W. F., and Yu, Z. L. (2013). Indomethacin Sensitizes TRAIL-Resistant Melanoma Cells to TRAIL-Induced Apoptosis through ROS-Mediated Upregulation of Death Receptor 5 and Downregulation of Survivin. The Journal of investigative dermatology 134, 1397-1407.

Wako, K., Kawasaki, T., Yamana, K., Suzuki, K., Jiang, S., Umezu, H., Nishiyama, T., Takahashi, K., Hamakubo, T., Kodama, T., and Naito, M. (2008). Expression of androgen receptor through androgen-converting enzymes is associated with biological aggressiveness in prostate cancer. Journal of clinical pathology 61, 448-454.

Yepuru, M., Wu, Z., Kulkarni, A., Yin, F., Barrett, C. M., Kim, J., Steiner, M. S., Miller, D. D., Dalton, J. T., and Narayanan, R. (2013). Steroidogenic enzyme AKR1C3 is a novel androgen receptor-selective coactivator that promotes prostate cancer growth. Clinical cancer research: an official journal of the American Association for Cancer Research 19, 5613-5625.

Zhu, Y., Liu, C., Nadiminty, N., Lou, W., Tummala, R., Evans, C. P., and Gao, A. C. (2013). Inhibition of ABCB1 expression overcomes acquired docetaxel resistance in prostate cancer. Molecular cancer therapeutics 12, 1829-1836.

Although the forgoing invention has been described in some detail by way of illustration and example for clarity and understanding, it will be readily apparent to one of ordinary skill in the art in light of the teachings of this invention that certain variations, changes, modifications and substitutions of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results. It is also to be understood that the terminology used herein is for the purpose of describing particular embodiments only, and is not intended to be limiting, since the scope of the present invention will be limited only by the appended claims. In addition, each reference provided herein is incorporated by reference in its entirety to the same extent as if each reference was individually incorporated by reference. Where a conflict exists between the instant application and a reference provided herein, the instant application shall dominate.

---

X. INFORMAL SEQUENCE LISTING

UCAAGGAACUCGAUCGUAU (SEQ ID NO: 1)
GUAGUUGUAAGUAUCAUGA (SEQ ID NO: 2).
CTTACGCTGAGTACTTCGA (SEQ ID NO: 3)

Primer sequences
Primers used for Real-time PCR were:
AR-full length: 5'-AAG CCA GAG CTG TGC AGA TGA (SEQ ID NO: 4)
3'-TGT CCT GCA GCC ACT GGT TC (SEQ ID NO: 5)
AR-V1: 5'-AAC AGA AGT ACC TGT GCG CC (SEQ ID NO: 6)
3'-TGA GAC TCC AAA CAC CCT CA (SEQ ID NO: 7)
AR-V7: 5'-AAC AGA AGT ACC TGT GCG CC (SEQ ID NO: 8)
3'-TCA GGG TCT GGT CAT TTT GA (SEQ ID NO: 9)
AR V1/2/2b: 5'-TGG ATG GAT AGC TAC TCC GG (SEQ ID NO: 10)
3'-GTT CAT TCT GAA AAA TCC TTC AGC (SEQ ID NO: 11)
AR1/2/3/2b: 5'-AAC AGA AGT ACC TGT GCG CC (SEQ ID NO: 12)
3'-TTC TGT CAG TCC CAT TGG TG (SEQ ID NO: 13)
Actin: 5'-AGA ACT GGC CCT TCT TGG AGG (SEQ ID NO: 14)
3'-GTT TTT ATG TTC CTC TAT GGG (SEQ ID NO: 15)

Primers used for ChIP assay were:
PSA promoter: AREI/II -5'-CCTAGATGAAGTCTCCATGAGCTACA (SEQ ID NO: 16)
AREI/II-3'-GGGAGGGAGAGCTAGCACTTG (PROXIMAL) (SEQ ID NO: 17)

---

What is claimed is:

1. A method of enhancing the therapeutic effects of a prostate cancer drug in a patient having a prostate cancer that is resistant to the prostate cancer drug, the method comprising:
administering to the patient (i) the prostate cancer drug and (ii) an amount of an AR-V7 inhibitor that synergistically increases the therapeutic activity of the prostate cancer drug by reversing or reducing prostate cancer cell resistance to the prostate cancer drug,
wherein the prostate cancer drug is selected from the group consisting of enzalutamide, abiraterone, bicalutamide, and combinations thereof,
thereby enhancing the therapeutic effects of the prostate cancer drug in the patient.

2. The method of claim 1, wherein the prostate cancer is selected from the group consisting of castration-resistant prostate cancer, metastatic castration-resistant prostate cancer, advanced stage prostate cancer, AR-V7-induced drug-resistant prostate cancer, and combinations thereof.

3. The method of claim 1, wherein the AR-V7 inhibitor is orally administered.

4. The method of claim 1, wherein the AR-V7 inhibitor is niclosamide.

5. The method of claim 4, wherein a daily dose of about 500 mg or more of niclosamide is administered to the patient per day.

6. The method of claim 5, wherein the daily dose of niclosamide is administered once per day.

7. The method of claim 5, wherein the daily dose of niclosamide is divided into subdoses and administered in multiple doses.

8. The method of claim 7, wherein the multiple doses of niclosamide are administered twice, three times, or four times per day.

9. The method of claim 5, wherein the daily dose of niclosamide is orally administered.

10. The method of claim 1, wherein a daily dose of about 5,000 mg of niclosamide is administered to the patient per day.

11. The method of claim 10, wherein the daily dose of niclosamide is divided into subdoses and administered three times per day.

12. The method of claim 10, wherein the daily dose of niclosamide is orally administered.

13. The method of claim 1, wherein the method further comprises administering to the patient an effective amount of an AKR1C3 inhibitor.

14. The method of claim 13, wherein the AKR1C3 inhibitor is indomethacin.

15. The method of claim 1, wherein the prostate cancer drug is enzalutamide.

16. The method of claim 1, wherein the prostate cancer drug is abiraterone.

17. The method of claim 1, wherein the prostate cancer drug is bicalutamide.

18. The method of claim 1, comprising administering to the patient an amount of the AR-V7 inhibitor that increases the therapeutic activity of the prostate cancer drug by at least 5-fold.

19. The method of claim 1, comprising administering to the patient an amount of the AR-V7 inhibitor that increases the therapeutic activity of the prostate cancer drug by at least 10-fold.

* * * * *